United States Patent
Petit et al.

(10) Patent No.: US 10,900,044 B2
(45) Date of Patent: Jan. 26, 2021

(54) LISTERIA-BASED COMPOSITIONS COMPRISING A PEPTIDE MINIGENE EXPRESSION SYSTEM AND METHODS OF USE THEREOF

(71) Applicant: Advaxis, Inc., Princeton, NJ (US)

(72) Inventors: Robert Petit, Newton, PA (US); Michael F. Princiotta, Hightstown, NJ (US)

(73) Assignee: ADVAXIS, INC., Princeton, NJ (US)

( * ) Notice: Subject to any disclaimer, the term of this patent is extended or adjusted under 35 U.S.C. 154(b) by 0 days.

(21) Appl. No.: 15/553,507

(22) PCT Filed: Mar. 3, 2016

(86) PCT No.: PCT/US2016/020571
§ 371 (c)(1),
(2) Date: Aug. 24, 2017

(87) PCT Pub. No.: WO2016/141121
PCT Pub. Date: Sep. 9, 2016

(65) Prior Publication Data
US 2019/0002891 A1    Jan. 3, 2019

Related U.S. Application Data

(60) Provisional application No. 62/127,614, filed on Mar. 3, 2015.

(51) Int. Cl.
| | | |
|---|---|---|
| *C12N 15/74* | (2006.01) | |
| *A61P 35/00* | (2006.01) | |
| *A61K 39/00* | (2006.01) | |
| *A61K 35/74* | (2015.01) | |
| *C07K 14/00* | (2006.01) | |
| *C12P 21/02* | (2006.01) | |
| *C07K 14/195* | (2006.01) | |
| *C07K 14/82* | (2006.01) | |
| *A61K 38/00* | (2006.01) | |
| *A61K 39/12* | (2006.01) | |

(52) U.S. Cl.
CPC ............. *C12N 15/74* (2013.01); *A61K 35/74* (2013.01); *A61K 39/001106* (2018.08); *A61P 35/00* (2018.01); *C07K 14/00* (2013.01); *C07K 14/195* (2013.01); *C07K 14/82* (2013.01); *C12P 21/02* (2013.01); *A61K 38/00* (2013.01); *A61K 39/12* (2013.01); *A61K 2039/522* (2013.01); *A61K 2039/523* (2013.01); *A61K 2039/572* (2013.01); *A61K 2039/585* (2013.01); *C07K 2319/02* (2013.01); *C07K 2319/036* (2013.01); *C12N 2710/20034* (2013.01); *C12N 2710/20071* (2013.01)

(58) Field of Classification Search
None
See application file for complete search history.

(56) References Cited

U.S. PATENT DOCUMENTS

| | | |
|---|---|---|
| 5,830,702 A | 11/1998 | Portnoy et al. |
| 6,051,237 A | 4/2000 | Paterson |
| 6,099,848 A | 8/2000 | Frankel et al. |
| 6,504,020 B1 | 1/2003 | Frankel et al. |
| 6,565,852 B1 | 5/2003 | Paterson |
| 6,635,749 B2 | 10/2003 | Frankel et al. |
| 6,767,542 B2 | 7/2004 | Paterson et al. |
| 6,855,320 B2 | 2/2005 | Paterson et al. |
| 7,135,188 B2 | 11/2006 | Paterson |
| 7,488,487 B2 | 2/2009 | Frankel et al. |
| 7,588,930 B2 | 9/2009 | Paterson et al. |
| 7,635,479 B2 | 12/2009 | Paterson et al. |
| 7,655,238 B2 | 2/2010 | Paterson et al. |
| 7,662,396 B2 | 2/2010 | Paterson et al. |
| 7,700,344 B2 | 4/2010 | Paterson et al. |
| 7,794,729 B2 | 9/2010 | Paterson et al. |
| 7,820,180 B2 | 10/2010 | Paterson et al. |
| 7,855,064 B2 | 12/2010 | Paterson et al. |
| 7,858,097 B2 | 12/2010 | Paterson et al. |
| 8,114,414 B2 | 2/2012 | Paterson et al. |
| 8,241,636 B2 | 8/2012 | Paterson et al. |
| 8,268,326 B2 | 9/2012 | Paterson et al. |
| 8,337,861 B2 | 12/2012 | Paterson et al. |
| 8,771,702 B2 | 7/2014 | Paterson et al. |
| 8,778,329 B2 | 7/2014 | Seavey et al. |
| 8,791,237 B2 | 7/2014 | Paterson et al. |

(Continued)

FOREIGN PATENT DOCUMENTS

| | | |
|---|---|---|
| KR | 1020140134695 A | 11/2014 |
| WO | WO 1996/014087 A1 | 5/1996 |

(Continued)

OTHER PUBLICATIONS

Wood et al. 2014 (Attenuated Listeria monocytogenes: a powerful and versatile vector for the future of tumor immunotherapy; Frontiers in Cellular and Infection Microbiology; vol. 4; Article 51; pp. 1-22) (Year: 2014).*

Michalek et al. 1993 (A role for the ubiquitin-dependent proteolytic pathway in MHC class I-restricted antigen presentation; Nature 363: 552-554). (Year: 1993).*

Rodriguez et al. 1997 (DNA immunization: Ubiquitination of a viral protein enhances cytotoxic T-lymphocyte induction and antiviral protection but abrogates antibody induction; Journal of Virology 71(11): 8497-8503). (Year: 1997).*

Paal et al. 2009 (A novel Ecotin-Ubiquitin-Tag (ECUT) for efficient, soluble peptide production in the periplasm of *Escherichia coli*; Microbial Cell Factories 8:7; 9 pages). (Year: 2009)*

(Continued)

*Primary Examiner* — Mary Maille Lyons
(74) *Attorney, Agent, or Firm* — Alston & Bird LLP

(57) ABSTRACT

This disclosure provides compositions, including *Listeria* delivery vectors comprising minigene expression constructs, and methods of using the same for inducing an immune response against an antigen-expressing tumor and for treating the same, and vaccinating against the same in subjects bearing the tumors.

30 Claims, 19 Drawing Sheets

Specification includes a Sequence Listing.

(56) References Cited

U.S. PATENT DOCUMENTS

| | | |
|---|---|---|
| 8,906,664 B2 | 12/2014 | Paterson et al. |
| 8,956,621 B2 | 2/2015 | Paterson et al. |
| 9,012,141 B2 | 4/2015 | Paterson et al. |
| 9,017,660 B2 | 4/2015 | Shahabi et al. |
| 9,084,747 B2 | 7/2015 | Shahabi et al. |
| 9,226,958 B2 | 1/2016 | Harn et al. |
| 9,408,898 B2 | 8/2016 | Seavey et al. |
| 9,463,227 B2 | 10/2016 | Rothman et al. |
| 9,492,527 B2 | 11/2016 | Paterson et al. |
| 9,499,602 B2 | 11/2016 | Paterson et al. |
| 9,549,973 B2 | 1/2017 | Paterson et al. |
| 9,644,212 B2 | 5/2017 | Maciag et al. |
| 9,650,639 B2 | 5/2017 | Maciag et al. |
| 9,700,608 B2 | 7/2017 | Paterson et al. |
| 9,919,038 B2 | 3/2018 | Seavey et al. |
| 9,943,590 B2 | 4/2018 | Harn et al. |
| 9,981,024 B2 | 5/2018 | Seavey et al. |
| 10,010,593 B2 | 7/2018 | Paterson |
| 10,016,617 B2 | 7/2018 | Mason et al. |
| 10,058,599 B2 | 8/2018 | Singh et al. |
| 10,064,898 B2 | 9/2018 | Rothman et al. |
| 10,143,734 B2 | 12/2018 | Petit |
| 10,166,276 B2 | 1/2019 | Paterson et al. |
| 10,189,885 B2 | 1/2019 | Paterson et al. |
| 10,258,679 B2 | 4/2019 | Wallecha et al. |
| 2002/0025323 A1 | 2/2002 | Paterson et al. |
| 2002/0028206 A1 | 3/2002 | Paterson |
| 2002/0136737 A1 | 9/2002 | Frankel et al. |
| 2003/0138808 A1* | 7/2003 | Simard ............. A61K 39/0011 435/6.16 |
| 2003/0202985 A1 | 10/2003 | Paterson |
| 2004/0241177 A1* | 12/2004 | Frazer ................... A61K 39/00 424/184.1 |
| 2005/0048081 A1 | 3/2005 | Frankel et al. |
| 2005/0118184 A1 | 6/2005 | Paterson et al. |
| 2005/0129715 A1 | 6/2005 | Paterson et al. |
| 2006/0093582 A1 | 5/2006 | Paterson et al. |
| 2006/0104991 A1 | 5/2006 | Paterson et al. |
| 2006/0204516 A1 | 9/2006 | Paterson et al. |
| 2006/0205067 A1 | 9/2006 | Paterson et al. |
| 2006/0210540 A1 | 9/2006 | Paterson et al. |
| 2006/0233835 A1 | 10/2006 | Paterson et al. |
| 2006/0269561 A1 | 11/2006 | Paterson et al. |
| 2007/0003567 A1 | 1/2007 | Paterson et al. |
| 2007/0207170 A1* | 9/2007 | Dubensky ............ C07K 14/195 424/234.1 |
| 2007/0253976 A1 | 11/2007 | Paterson et al. |
| 2007/0264279 A1 | 11/2007 | Paterson et al. |
| 2008/0020465 A1 | 1/2008 | Padidam |
| 2008/0131456 A1 | 6/2008 | Paterson et al. |
| 2009/0081248 A1 | 3/2009 | Paterson et al. |
| 2009/0081250 A1 | 3/2009 | Paterson et al. |
| 2009/0186051 A1 | 7/2009 | Paterson et al. |
| 2009/0202587 A1 | 8/2009 | Paterson et al. |
| 2010/0189739 A1 | 7/2010 | Frankel et al. |
| 2010/0291140 A1 | 11/2010 | Paterson et al. |
| 2011/0129499 A1 | 6/2011 | Maciag et al. |
| 2011/0142791 A1 | 6/2011 | Shahabi et al. |
| 2011/0305724 A1 | 12/2011 | Paterson et al. |
| 2012/0014984 A1 | 1/2012 | Shahabi et al. |
| 2012/0114685 A1 | 5/2012 | Sewell |
| 2012/0135033 A1 | 5/2012 | Wallecha |
| 2012/0177678 A1 | 7/2012 | Paterson et al. |
| 2013/0259891 A1 | 10/2013 | Harn et al. |
| 2014/0199258 A1 | 7/2014 | Rothman |
| 2014/0234370 A1 | 8/2014 | Shahabi |
| 2014/0248304 A1 | 9/2014 | Paterson et al. |
| 2014/0314708 A1 | 10/2014 | Maciag et al. |
| 2014/0335120 A1 | 11/2014 | Maciag et al. |
| 2015/0079034 A1 | 3/2015 | Seavey et al. |
| 2015/0098964 A1 | 4/2015 | Singh et al. |
| 2015/0125480 A1 | 5/2015 | Paterson et al. |
| 2015/0196628 A1 | 7/2015 | Mason et al. |
| 2015/0238584 A1 | 8/2015 | Shahabi et al. |
| 2015/0297702 A1 | 10/2015 | Shahabi |
| 2015/0335721 A1 | 11/2015 | Paterson et al. |
| 2015/0343047 A1 | 12/2015 | Paterson et al. |
| 2015/0366955 A9 | 12/2015 | Shahabi et al. |
| 2016/0022814 A1 | 1/2016 | Petit et al. |
| 2016/0024173 A1 | 1/2016 | Paterson et al. |
| 2016/0158331 A1 | 6/2016 | Paterson et al. |
| 2016/0206716 A1 | 7/2016 | Seavey et al. |
| 2016/0220652 A1 | 8/2016 | Petit et al. |
| 2016/0228530 A1 | 8/2016 | Paterson |
| 2016/0256538 A1 | 9/2016 | Harn et al. |
| 2016/0324903 A1 | 11/2016 | Rothman et al. |
| 2016/0361401 A1 | 12/2016 | Shahabi et al. |
| 2016/0367650 A1 | 12/2016 | Paterson |
| 2017/0028045 A1 | 2/2017 | Paterson et al. |
| 2017/0042996 A1 | 2/2017 | Wallecha et al. |
| 2017/0049867 A1 | 2/2017 | Seavey et al. |
| 2017/0080064 A1 | 3/2017 | Petit et al. |
| 2017/0100469 A1 | 4/2017 | Paterson et al. |
| 2017/0106072 A1 | 4/2017 | Petit |
| 2017/0204361 A1 | 7/2017 | Eapen et al. |
| 2017/0246273 A1 | 8/2017 | Wallecha et al. |
| 2017/0281691 A1 | 10/2017 | Paterson et al. |
| 2017/0368157 A1 | 12/2017 | Khleif et al. |
| 2018/0064765 A1 | 3/2018 | Petit et al. |
| 2018/0104284 A1 | 4/2018 | Wallecha et al. |
| 2018/0153974 A1 | 6/2018 | Petit et al. |
| 2018/0265879 A1 | 9/2018 | Wallecha et al. |
| 2018/0280487 A1 | 10/2018 | Petit et al. |
| 2018/0305702 A1 | 10/2018 | Petit et al. |
| 2018/0325964 A1 | 11/2018 | Eapen et al. |
| 2018/0360940 A1 | 12/2018 | Petit et al. |
| 2019/0002891 A1 | 1/2019 | Petit et al. |
| 2019/0032064 A1 | 1/2019 | Petit et al. |
| 2019/0240303 A1 | 8/2019 | Wallecha et al. |
| 2019/0248856 A1 | 8/2019 | Princiotta et al. |
| 2019/0322714 A1 | 10/2019 | Petit et al. |
| 2020/0061167 A1 | 2/2020 | Hayes et al. |
| 2020/0069785 A1 | 3/2020 | Paterson et al. |

FOREIGN PATENT DOCUMENTS

| | | |
|---|---|---|
| WO | WO 1999/025376 A1 | 5/1999 |
| WO | WO 2001/072329 A1 | 10/2001 |
| WO | WO 2004/062597 A2 | 7/2004 |
| WO | WO 2006/017856 A2 | 2/2006 |
| WO | WO 2006/036550 A2 | 4/2006 |
| WO | WO 2007/106476 A2 | 9/2007 |
| WO | WO 2007/130455 A2 | 11/2007 |
| WO | WO 2008/079172 A2 | 7/2008 |
| WO | WO 2008/109155 A2 | 9/2008 |
| WO | WO 2008/130551 A2 | 10/2008 |
| WO | WO 2008/140812 A2 | 11/2008 |
| WO | WO 2009/143167 A2 | 11/2009 |
| WO | WO 2010/008782 A1 | 1/2010 |
| WO | WO 2010/040135 A1 | 4/2010 |
| WO | WO 2010/102140 A1 | 9/2010 |
| WO | WO 2011/060260 A2 | 5/2011 |
| WO | WO 2011/100754 A1 | 8/2011 |
| WO | WO 2012/125551 A1 | 9/2012 |
| WO | WO 2012/138377 A2 | 10/2012 |
| WO | WO 2013/025925 A1 | 2/2013 |
| WO | WO 2013/138337 A1 | 9/2013 |
| WO | WO 2015/126921 A1 | 8/2015 |
| WO | WO 2015/130810 A2 | 9/2015 |
| WO | WO 2015/134722 A2 | 9/2015 |
| WO | WO 2015/164121 A1 | 10/2015 |
| WO | WO 2015/167748 A1 | 11/2015 |
| WO | WO 2016/011320 A1 | 1/2016 |
| WO | WO 2016/011353 A1 | 1/2016 |
| WO | WO 2016/011357 A1 | 1/2016 |
| WO | WO 2016/011362 A1 | 1/2016 |
| WO | WO 2016/061182 A1 | 4/2016 |
| WO | WO 2016/061277 A1 | 4/2016 |
| WO | WO 2016/100924 A1 | 6/2016 |
| WO | WO 2016/100929 A1 | 6/2016 |
| WO | WO 2016/126876 A2 | 8/2016 |
| WO | WO 2016/126878 A2 | 8/2016 |
| WO | WO 2016/141121 A1 | 9/2016 |
| WO | WO 2016/154412 A2 | 9/2016 |

(56) References Cited

FOREIGN PATENT DOCUMENTS

| WO | WO 2016/183361 A1 | 11/2016 |
| --- | --- | --- |
| WO | WO 2016/191545 A1 | 12/2016 |
| WO | WO 2016/207859 A1 | 12/2016 |
| WO | WO 2017/048714 A1 | 3/2017 |
| WO | WO 2017/048850 A1 | 3/2017 |
| WO | WO 2017/049218 A2 | 3/2017 |
| WO | WO 2017/066706 A1 | 4/2017 |
| WO | WO 2017/085691 A1 | 5/2017 |
| WO | WO 2017/106754 A2 | 6/2017 |
| WO | WO 2017/132547 A1 | 8/2017 |
| WO | WO 2018/009461 A1 | 1/2018 |
| WO | WO 2018/170313 A1 | 3/2018 |
| WO | WO 2018/085854 A1 | 5/2018 |
| WO | WO 2018/102584 A1 | 6/2018 |
| WO | WO 2018/102585 A1 | 6/2018 |
| WO | WO 2018/129306 A1 | 7/2018 |
| WO | WO 2019/006401 A1 | 1/2019 |
| WO | WO 2019/060115 A1 | 3/2019 |
| WO | WO 2019/094607 A2 | 5/2019 |
| WO | WO 2019/157098 A1 | 8/2019 |
| WO | WO 2019/173684 A1 | 9/2019 |
| WO | WO 2019/210034 A1 | 10/2019 |

OTHER PUBLICATIONS

Xiang et al. 2000 (An autologous oral DNA vaccine protects against murine melanoma; PNAS 97(10):5492-5497) (Year: 2000).*

Wallecha et al. 2009 (Construction and Characterization of an Attenuated Listeria monocytogenes Strain for Clinical Use in Cancer Immunotherapy; Clinical and Vaccine Immunology 16(1): 96-103). (Year: 2009).*

Schnupf et al., "Listeriolysin 0 secreted by Listeria monocytogenes into the host cell cytosol is degraded by the N-end rule pathway," Infection and Immunity, 75(11):5135-5147, (2007).

WIPO Application No. PCT/US2016/020571, PCT International Preliminary Report on Patentability dated Sep. 5, 2017.

WIPO Application No. PCT/US2016/020571, PCT International Search Report dated Jun. 17, 2016.

WIPO Application No. PCT/US2016/020571, PCT Written Opinion of the International Searching Authority dated Jun. 17, 2016.

Shahabi, et al., "Live, attenuated strains of Listeria and *Salmonella* as vaccine vectors in cancer treatment," Bioengineered Bugs, 1:4, 235-239, (Jul./Aug. 2010).

Xiang, et al., "An autologous oral DNA vaccine protects against murine melanoma," PNAS, vol. 97, No. 10, 5492-5497, (May 9, 2000).

EP Application 1 675 9454 Supplementary European Search Report completed Sep. 21, 2018.

Wolf, et al., "Viral band bacterial minigene products are presented by MHC class I molecules with similar efficiencies," Molecular Immunology, 48, 463-471, (2011).

Duan, et al., "Progress of Listeria Monocytogenes as a Deliver Vehicle for Tumor accines," Chinese Journal of Zoonoses, 30 (7), 743-752, (2014) English Abstract.

Jin, Clonin and Expression of Key Enzymes in Isobutanol Biosynthetic Pathway, China Master Theses Full-text Database Basic Science, (1), (2014) English Abstract.

Yu, et al., "Attenuated Listeria Monocytogenes as tumor Vaccine Vector" Cellular & Molecular Immunology, 11 (2), 184-196, (2014).

* cited by examiner

*atggcgcgggatggtatactatacaagcgtatggttcaaaaagatactttgaattaagaagt
acaataaagttaacttcattagacaaaagaaaaacaaggaagaatagtacatagttataa
atacttggagagtgaggtgtaatatggggcagctgattttggggtttcatatatgtagtt
tcaagattagccattgttgcggcagtagtttacttcttatacttattgagaaaattgcaaa
taaatagaaaaaagccttgtcaacgaggcttttttatgcaaaaaatacgacgaatgaag
ccatgtgagacaatttggaatagcagacaacaaggaaggtagaacatgtttgaaaaattta
ctgattttcgattattattaacgcttgttaatttaaacatctcttattttgctaacatata
agtatacaaagggacataaaaggttaacagcgtttgttaaataggaagtatatgaaaatcc
tcttttgtgtttctaaatttattttaaggagtggaga*atgttgaaaaaaataattggtta
caaaatgcagtaatagcaatgctagtgttaattgtaggtctgtgcattaatatgggttctgg
aacaaaagtacaagctgagagtattcaacgaccaacgcctattaaccaagttttccagatc
ccggcctagcgaatgcagtgaaacaaaatttagggaagcaaagtgttacagaccttgtatca
caaaaggaactatctggagtacaaaatttcaatggagataatagcaacattcaatctcttgc
gggaatgcaattttcactaatttaaaagaacttcatctatcccataatcaaataagtgacc
ttagtcctttaaaggatctaactaagttagaagagctatctgtgaatagaaacagactgaaa
aatttaaacggaattccaagtgcttgtttatctcgcttgttttagataacaacgaactcag
agatactgactcgcttattcatttgaaaaatctagaaatcttatctattcgtaataataagt
taaaaagtattgtgatgcttggttttttatcaaaactagaggtattagatttgcatggtaat
gaaataacaaatacaggtggactaactagattgaagaaagttaactggatagatttaactgg
tcagaaatgtgtgaatgaaccagtaaaataccaaccagaattgtatataacaaatactgtca
aagacccagatggaagatggatatctccatattacatcagtaatggtgggagttatgtagat
ggttgtgtcctgtgggaattgccagtttatacagatgaagtaagctataagtttagcgaata
tataaacgttggggagactgaggctatatttgatggaacagttacacaacctatcaagaatt
aggacttgtgcacacctgtatactttgagctctcgtataatcacgagagctttttaaatatg
taagtcttaattatctcttgacaaaagaacgtttattcgtataaggttaccaagagatgaa
gaaactattttatttacaattcaccttgacaccaaaaactccatatgatatagtaaataagg
ttattaaacaagaaagaagaagcaacccgcttctcgcctcgttaacacgaacgttttcaggc
aaaaaattcaaactttcgtcgcgtagcttacgcgattttgaatgtgcgggattgctgaaaag
cagcccgttttttatggcctccgaacgaatgagttagcaggccgcagatttgaacagctat
tttctatcttgttgtaacaaaattaagtggaggtggctcaccattagcaaagacatgttggt
aaacgatgggattcgtgcacgtgaagtaagattgatcgaccaagacggtgaacaattaggcg
tgaagagtaaaatcgatgcgcttcaaattgctgaaaaggctaatcttgatctagtgcttgtt
gctccaacagcgaaaccgccagtagctcgta (SEQ ID NO: 74)

Figure 10

*GAATTC*atggcgcgggatggtatactatacaagcgtatggttcaaaaagatactttgaattaa
gaagtacaataaagttaacttcattagacaaaagaaaaaacaaggaagaatagtacatagtt
ataaatacttggagagtgaggtgtaatatgggggcagctgattttgggggtttcatatatgta
gtttcaagattagccattgttgcggcagtagtttacttcttatacttattgagaaaaattgca
aataaatagaaaaaagccttgtcaaacgaggctttttttatgcaaaaaatacgacgaatgaa
gccatgtgagacaatttggaatagcagacaacaaggaaggtagaacatgtttgaaaaattta
ctgattttcgattattattaacgcttgttaatttaaacatctcttattttgctaacatataa
gtatacaaagggacataaaaggttaacagcgtttgttaaataggaagtatatgaaaatcctc
ttttgtgttctaaatttatttttaaggagtggaga*GGATCC*ggacttgtgcacacctgtata
ctttgagctctcgtataatcacgagagcttttaaatatgtaagtcttaattatctcttgaca
aaagaacgtttattcgtataaggttaccaagagatgaagaaactattttatttacaattcac
cttgacaccaaaaactccatatgatatagtaaataaggttattaaacaagaaagaagaagcaa
cccgcttctcgcctcgttaacacgaacgttttcaggcaaaaaattcaaactttcgtcgcgtag
cttacgcgattttgaatgtgcgggattgctgaaaagcagcccgttttttatggcctccgaac
gaatgagttagcaggccgcagatttgaacagctattttctatcttgttgtaacaaaattaagt
ggaggtggctcaccattagcaaagacatgttggtaaacgatgggattcgtgcacgtgaagtaa
gattgatcgaccaagacggtgaacaattaggcgtgaagagtaaaatcgatgcgcttcaaattg
ctgaaaaggctaatcttgatctagtgcttgttgctccaacagcgaaaccgccagtagctcgta
*CTGCAG* (SEQ ID NO: 75)

Figure 11 gcgccaaatcattggttgattggtgaggatgtctgtgtgcgtgggtcgcgagatgggcgaataagaagcattaaagatcctgacaaatat
aatcaagcggctcatatgaaagattacgaatcgcttccactcacagaggaaggcgactggggcggagttcattataatagtggtatccc
gaataaagcagcctataatactatcactaaacttggaaaagaaaaaacagaacagctttattttcgcgccttaaagtactatttaacgaaaa
aatcccagtttaccgatgcgaaaaaagcgcttcaacaagcagcgaaagatttatatggtgaagatgcttctaaaaaagttgctgaagctt
gggaagcagttggggttaactgattaacaaatgttagagaaaaattaattctccaagtgatattcttaaaataattcatgaatattttttcttata
ttagctaattaagaagataactaactgctaatccaattttttaacggaacaaattagtgaaaatgaaggccgaattttccttgttctaaaaat
tgtattagcgtatcacgaggagggagtataag*tgggattaaacagatttatgcgtgcgatgatggtggttttcattactgccaattgcatt*
*acgattaaccccgacgtcgac*catacgacgttaattcttgcaatgttagctattggcgtgttctctttaggggcgtttatcaaaattatt*
*caattaagaaaaaataatta*aaaacacagaacgaaagaaaaagtgaggtgaatgatatgaaattcaaaaaggtggttctaggtatgtg
cttgatcgcaagtgttctagtctttccggtaacgataaaagcaaatgcctgttgtgatgaatacttacaaacacccgcagctccgcatgata
ttgacagcaaattaccacataaacttagttggtccgcggataacccgacaaatactgacgtaaatacgcactattggcttttaaacaagc
ggaaaaaatactagctaaagatgtaaatcatatgcgagctaatttaatgaatgaacttaaaaaattcgataaacaaatagctcaaggaata
tatgatgcggatcataaaaatccatattatgatactagtacattttatctcattttataatcctgatagagataatacttatttgccgggttttgc
taatgcgaaaataacaggagcaaagtatttcaatcaatcggtgactgattaccgagaagggaa (SEQ ID NO: 57)

Figure 13

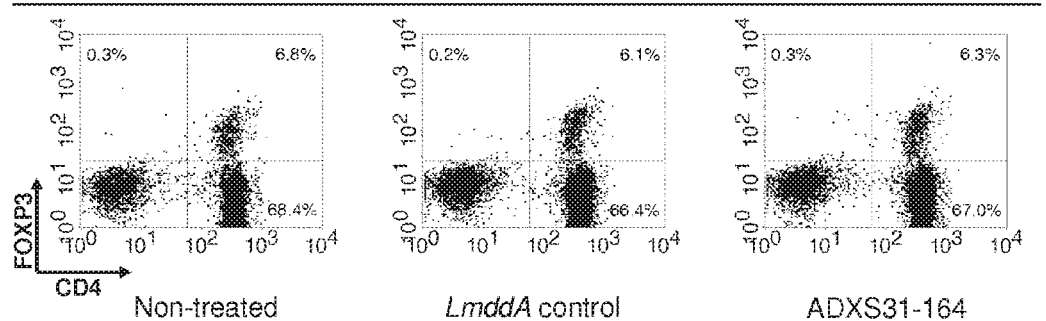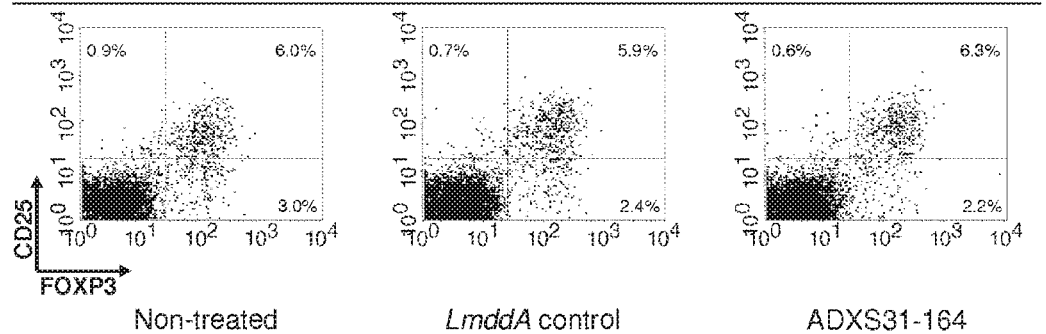
Figure 18

LISTERIA-BASED COMPOSITIONS COMPRISING A PEPTIDE MINIGENE EXPRESSION SYSTEM AND METHODS OF USE THEREOF

CROSS REFERENCE TO RELATED APPLICATIONS

This application is a US national stage of PCT/US2016/020571 filed Mar. 3, 2016, which claims priority from and the benefit of U.S. 62/127,614 filed Mar. 3, 2015, all of which are incorporated herein by reference.

REFERENCE TO SEQUENCE LISTING

This application includes an electronic sequence listing in a file named 502822_SEQLST.txt, created on Aug. 24, 2017 and containing 74,616 bytes, which is hereby incorporated by reference in its entirety for all purposes.

FIELD OF INTEREST

Disclosed are compositions, including *Listeria* delivery vectors comprising minigene expression constructs, and methods of using the same for inducing an immune response against an antigen-expressing tumor or cancer and for treating the same, and vaccinating against the same in subjects bearing the tumors or cancer.

BACKGROUND

*Listeria monocytogenes* is an intracellular pathogen that primarily infects antigen presenting cells and has adapted for life in the cytoplasm of these cells. Host cells, such as macrophages, actively phagocytose *L. monocytogenes* and the majority of the bacteria are degraded in the phagolysosome. Some of the bacteria escape into the host cytosol by perforating the phagosomal membrane through the action of a hemolysin, listeriolysin O (LLO). Once in the cytosol, *L. monocytogenes* can polymerize the host actin and pass directly from cell to cell further evading the host immune system and resulting in a negligible antibody response to *L. monocytogenes*.

Recombinant protein expression from *Listeria* has involved introducing DNA sequences encoding full-length proteins or large polypeptides containing the antigenic sequence(s) of interest, but this has not been possible in instances where the expression of multiple peptide determinants from heterologous sources was desired. In this instance, the peptides have been expressed as a single polypeptide construct containing the peptides of interest separated by amino acid linkers of varying lengths and these have required proteasomal activity for the production of MHC class I binding peptide determinants. This may lead to loss of antigen presentation.

Hence, there is a need for circumventing proteosomal activity and enhancing antigen presentation in order to augment immune responses. The present disclosure addresses this need by providing *Listeria* based compositions comprising a "minigene" expression system of nucleic acid sequences that encode minimal peptide determinants for presentation by MHC class I molecules. These minigenes can be expressed with the peptide immediately following a ubiquitin moiety (Ub-Peptide) and in doing so, this system circumvents the need for the antigen to enter the antigen-processing pathway, thereby allowing peptide antigens to be expressed directly into the cytosol of the cells infected with recombinant *Listeria*. Further, and as described in the detailed description disclosed herein, a minigene system of the disclosure provides the advantage that it allows multiple peptides to be loaded into cells using a single *Listeria* delivery vector.

SUMMARY

In one aspect, the present disclosure provides a recombinant *Listeria* strain comprising a minigene nucleic acid construct, said construct comprising an open reading frame encoding a chimeric protein, wherein said chimeric protein comprises s:
 a. a bacterial secretion signal sequence;
 b. a ubiquitin (Ub) protein;
 c. a peptide; and,
wherein said signal sequence, said ubiquitin and said peptide in a.-c. are respectively arranged in tandem from the amino-terminus to the carboxy-terminus.

In another aspect, the present disclosure provides for a method of eliciting an anti-tumor or anti-cancer response in a subject having a tumor or cancer, said method comprising the step of administering to said subject a recombinant *Listeria* comprising a minigene nucleic acid construct, said construct comprising an open reading frame encoding a chimeric protein, wherein said chimeric protein comprises:
 a. a bacterial secretion signal sequence;
 b. a ubiquitin (Ub) protein;
 c. a peptide; and,
wherein said signal sequence, said ubiquitin and said peptide in a.-c. are respectively arranged in tandem from the amino-terminus to the carboxy-terminus, thereby enhancing an anti-tumor response in said subject.

In one aspect, the disclosure provides a method of treating a tumor or cancer in a subject, said method comprising the step of administering to said subject a recombinant *Listeria* comprising a minigene nucleic acid construct, said construct comprising an open reading frame encoding a chimeric protein, wherein said chimeric protein comprises:
 a. a bacterial secretion signal sequence;
 b. a ubiquitin (Ub) protein;
 c. a peptide; and,
wherein said signal sequence, said ubiquitin and said peptide in a.-c. are respectively arranged in tandem from the amino-terminus to the carboxy-terminus, thereby enhancing an anti-tumor response in said subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The subject matter regarded as the disclosure is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIG. 6B Top panel: Listeria constructs containing PEST regions induce tumor regression. Bottom panel: Average tumor sizes at day 28 post-tumor challenge in 2 separate experiments.

(FIG. 8A) representative data from 1 experiment. (FIG. 8B) average and SE of data from all 3 experiments.

FIG. 10 shows the DNA sequence (SEQ ID NO: 74) present upstream and downstream of the inlC region on the genome of Listeria strain EGD. DNA-up (red), inlC gene (blue) and DNA-down (black).

FIG. 11 shows the sequence of DNA (SEQ ID NO: 75) that is cloned in the temperature sensitive plasmid, pKSV7 to create inl C deletion mutant. The restriction enzyme sites used for cloning of these regions are indicated in caps and underlined. GAATTC-EcoRI, GGATCC-BamHI and CTGCAg-PstI. The EcoRI-PstI insert is cloned in the vector, pKSV7.

FIG. 13 shows the DNA sequence (SEQ ID NO: 57) present upstream and downstream of the actA gene in the Listeria chromosome. The region in italics contains the residual actA sequence element that is present in the LmddΔactA strain. The underlined sequence gtcgac represent the restriction site of XhoI, which is the junction between the N-T and C-T region of actA.

(FIG. 15B) Expression and secretion of tLLO-ChHer2 was detected in Lm-LLO-ChHer2 (Lm-LLO-138) and LmddA-LLO-ChHer2 (ADXS31-164) by western blot analysis of the TCA precipitated cell culture supernatants blotted with anti-LLO antibody. A differential band of ~104 KD corresponds to tLLO-ChHer2. The endogenous LLO is detected as a 58 KD band. Listeria control lacked ChHer2 expression.

(FIG. 16A) Cytotoxic T cell responses elicited by Her2/neu Listeria-based vaccines in splenocytes from immunized mice were tested using NT-2 cells as stimulators and 3T3/neu cells as targets. Lm-control was based on the LmddA background that was identical in all ways but expressed an irrelevant antigen (HPV16-E7). (FIG. 16B) IFN-γ secreted by the splenocytes from immunized FVB/N mice into the cell culture medium, measured by ELISA, after 24 hours of in vitro stimulation with mitomycin C treated NT-2 cells. (FIG. 16C) IFN-γ secretion by splenocytes from HLA-A2 transgenic mice immunized with the chimeric vaccine, in response to in vitro incubation with peptides from different regions of the protein. A recombinant ChHer2 protein was used as positive control and an irrelevant peptide or no peptide groups constituted the negative controls as listed in the figure legend. IFN-γ ecretion was detected by an ELISA assay using cell culture supernatants harvested after 72 hours of co-incubation. Each data point was an average of triplicate data+/−standard error. *P value<0.001.

FIG. 18 shows FVB/N mice were inoculated s.c. with $1 \times 10^6$ NT-2 cells and immunized three times with each vaccine at one week intervals. Spleens were harvested 7 days after the second immunization. After isolation of the immune cells, they were stained for detection of Tregs by anti CD3, CD4, CD25 and FoxP3 antibodies. dot-plots of the Tregs from a representative experiment showing the frequency of $CD25^+/FoxP3^+$ T cells, expressed as percentages of the total $CD3^+$ or $CD3^+CD4^+$ T cells across the different treatment groups.

(FIG. 19A). dot-plots of the Tregs from a representative experiment. (FIG. 19B). Frequency of $CD25^+/FoxP3^+$ T cells, expressed as percentages of the total $CD3^+$ or $CD3^+CD4^+$ T cells (left panel) and intratumoral CD8/Tregs ratio (right panel) across the different treatment groups. Data is shown as mean±SEM obtained from 2 independent experiments.

(FIG. 20A) represents a construct producing the ovalbumin derived SIINFEKL peptide. (FIG. 20B) represents a comparable recombinant protein in which a GBM derived peptide has been introduced in place of SIINFEKL by PCR cloning. (FIG. 20C) represents a construct designed to express 4 separate peptide antigens from a strain of Listeria.

Figures 1A, 1B:
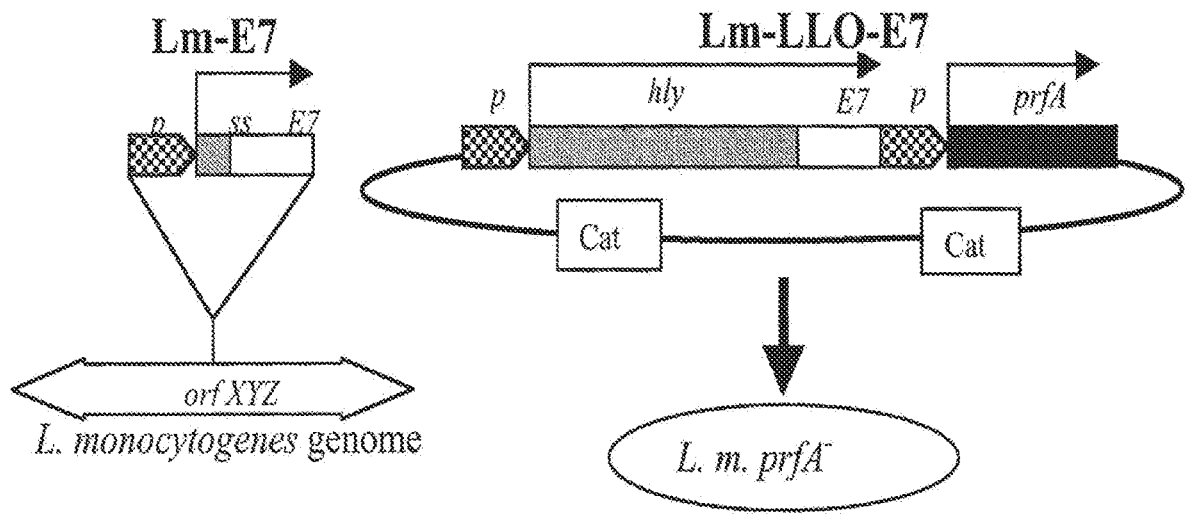
FIGS. 1A-B show that Lm-E7 and Lm-LLO-E7 use different expression systems to express and secrete E7. Lm-E7 was generated by introducing a gene cassette into the orfZ domain of the *L. monocytogenes* genome (FIG. 1A). The hly promoter drives expression of the hly signal sequence and the first five amino acids (AA) of LLO followed by HPV-16 E7 (FIG. 1B). Lm-LLO-E7 was generated by transforming the prfA-strain XFL-7 with the plasmid pGG-55. pGG-55 has the hly promoter driving expression of a non-hemolytic fusion of LLO-E7. pGG-55 also contains the prfA gene to select for retention of the plasmid by XFL-7 in vivo.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present disclosure may be practiced without these specific details. In other instances, well-known methods, procedures, and components have not been described in detail so as not to obscure the present invention.

In one embodiment, disclosed herein are compositions and methods for eliciting an anti-tumor or anti-cancer response.

In one aspect, the present disclosure provides a recombinant Listeria strain comprising a minigene nucleic acid construct comprising an open reading frame encoding a chimeric protein, wherein said chimeric protein comprises:
 a. a bacterial secretion signal sequence;
 b. a ubiquitin (Ub) protein;
 c. a peptide; and,
wherein said signal sequence, said ubiquitin and said peptide in a.-c. are respectively arranged in tandem from the amino-terminus to the carboxy-terminus.

In one embodiment, the Listeria further comprises two or more open reading frames linked by a Shine-Dalgarno ribosome binding site nucleic acid sequence.

In another embodiment, the recombinant Listeria further comprises one to four open reading frames linked by a Shine-Dalgarno ribosome binding site nucleic acid sequence between each open reading frame. In another embodiment, each open reading frame comprises a different peptide.

In another aspect, the present disclosure provides for a method of eliciting an anti-tumor or anti-cancer response in a subject having a tumor or cancer, said method comprising the step of administering to said subject a recombinant Listeria comprising a minigene nucleic acid construct comprising an open reading frame encoding a chimeric protein, wherein said chimeric protein comprises:
 a. a bacterial secretion signal sequence;
 b. a ubiquitin (Ub) protein;
 c. a peptide; and,
wherein said signal sequence, said ubiquitin and said peptide in a.-c. are respectively arranged in tandem from the amino-terminus to the carboxy-terminus, thereby enhancing an anti-tumor response in said subject.

In one aspect, the disclosure provides a method of treating a tumor or cancer in a subject, said method comprising the step of administering to said subject a recombinant Listeria comprising a minigene nucleic acid construct comprising an open reading frame encoding a chimeric protein, wherein said chimeric protein comprises:
 a. a bacterial secretion signal sequence;
 b. a ubiquitin (Ub) protein;
 c. a peptide; and,
wherein said signal sequence, said ubiquitin and said peptide in a.-c. are respectively arranged in tandem from the amino-terminus to the carboxy-terminus, thereby enhancing an anti-tumor response in said subject.

In one embodiment, the terms "nucleic acid molecule," "nucleic acid construct" and "minigene nucleic acid construct" are used interchangeably herein.

It will be appreciated by the skilled artisan that the term "nucleic acid" and grammatical equivalents thereof may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

In another embodiment, fusion peptides generated using the methods disclosed herein are further linked to a HIS tag or a SIINFECKL tag. These tags may be expressed and the antigenic epitopes presented allowing a clinician to follow the immunogenicity of the secreted peptide by following immune responses to these "tag" sequence peptides. Such immune response can be monitored using a number of reagents including but not limited to, monoclonal antibodies and DNA or RNA probes specific for these tags. It will be appreciated by a skilled artisan that the sequences for the tags may be incorporated into the nucleic acid sequences encoding the fusion peptide sequences. In another embodiment, vectors disclosed herein such as plasmid or phage vectors comprise the nucleic acid sequences encoding the fusion peptides or chimeric proteins disclosed herein.

It will be appreciated by the skilled artisan that the terms "cancer" and "tumor" used herein may have all the same meanings and qualities.

In another embodiment, disclosed herein are compositions and methods for inducing an immune response against a tumor antigen. In another embodiment, the tumor antigen is a heterologous antigen. In another embodiment, the tumor antigen is a self-antigen. In another embodiment, disclosed herein are compositions and methods for inducing an immune response against an infectious disease antigen. In another embodiment, the infectious disease antigen is a heterologous antigen. In another embodiment, the compositions and methods of this disclosure are used for vaccinating against a tumor or a cancer.

In yet another embodiment, the compositions and methods of the present disclosure prevent the occurrence of escape mutations following treatment. In another embodiment, disclosed herein are compositions and methods for providing progression free survival to a subject suffering from a tumor or cancer. In another embodiment, disclosed herein are compositions and methods for immunizing a subject against a cancer or tumor. In another embodiment, disclosed herein are compositions and methods for immunizing a subject against a cancer or tumor. In another embodiment, the cancer is metastasis.

Recombinant *Listeria* Strains

In one embodiment, disclosed herein is a recombinant attenuated *Listeria* strain comprising a nucleic acid construct encoding a chimeric protein. In another embodiment, the nucleic acid construct is a recombinant nucleic acid construct. In another embodiment, disclosed herein is a recombinant attenuated *Listeria* strain comprising a recombinant nucleic acid construct comprising an open reading frame encoding a bacterial secretion signal sequence (SS), a ubiquitin (Ub) protein, and a peptide sequence. In another embodiment, the nucleic acid construct encodes a chimeric protein comprising a bacterial secretion signal sequence, a ubiquitin protein, and a peptide sequence. In one embodiment, the chimeric protein is arranged in the following manner (SS-Ub-Peptide):

In one embodiment, the nucleic acid construct comprises a codon that corresponds to the carboxy-terminus of the peptide moiety is followed by two stop codons to ensure termination of protein synthesis.

In one embodiment, nucleic acids encoding the recombinant polypeptides disclosed herein also comprise a signal peptide or sequence. In one embodiment, the bacterial secretion signal sequence encoded by the nucleic acid constructs disclosed herein is a *Listeria* secretion signal sequence. In another embodiment, the fusion protein of methods and compositions of the present disclosure comprises an LLO signal sequence from Listeriolyson O (LLO). In one embodiment, a heterologous antigen may be expressed through the use of a signal sequence, such as a Listerial signal sequence, for example, the hemolysin (hly) signal sequence or the actA signal sequence. Alternatively, for example, foreign genes can be expressed downstream from a *L. monocytogenes* promoter without creating a fusion protein. In another embodiment, the signal peptide is bacterial (Listerial or non-Listerial). In one embodiment, the signal peptide is native to the bacterium. In another embodiment, the signal peptide is foreign to the bacterium. In another embodiment, the signal peptide is a signal peptide from *Listeria monocytogenes*, such as a secA1 signal peptide. In another embodiment, the signal peptide is an Usp45 signal peptide from *Lactococcus lactis*, or a Protective Antigen signal peptide from *Bacillus anthracis*. In another embodiment, the signal peptide is a secA2 signal peptide, such the p60 signal peptide from *Listeria monocytogenes*. In addition, the recombinant nucleic acid molecule optionally comprises a third polynucleotide sequence encoding p60, or a fragment thereof. In another embodiment, the signal peptide is a Tat signal peptide, such as a *B. subtilis* Tat signal peptide (e.g., PhoD). In one embodiment, the signal peptide is in the same translational reading frame encoding the recombinant polypeptide.

For all purposes herein, the terms "recombinant polypeptide," "fusion protein," "recombinant protein," and "chimeric protein" are used interchangeably herein.

In another embodiment, the secretion signal sequence is from a *Listeria* protein. In another embodiment, the secretion signal is an ActA$_{300}$ secretion signal. In another embodiment, the secretion signal is an ActA$_{100}$ secretion signal.

In one embodiment, the nucleic acid construct comprises an open reading frame encoding a ubiquitin protein. In one embodiment, the ubiquitin is a full-length protein. It will be appreciated by the skilled artisan that the Ubiquitin in the expressed construct disclosed herein (expressed from the nucleic acid construct disclosed herein) is cleaved at the carboxy-terminus from the rest of the recombinant chimeric protein expressed from the nucleic acid construct through the action of hydrolases upon entry to the host cell cytosol. This liberates the amino-terminus of the peptide moiety, producing a peptide (length depends on the specific peptide) in the host cell cytosol.

In one embodiment, the peptide encoded by the nucleic acid constructs disclosed herein is 8-10 amino acids (AA) in length. In another embodiment, the peptide is 10-20 AA long. In another embodiment, the peptide is a 21-30 AA long. In another embodiment, the peptide is 31-50 AA long. In another embodiment, the peptide is 51-100 AA long.

In one embodiment, the peptide is an antigenic peptide. In another embodiment, the peptide is derived from a tumor antigen. In another embodiment, the peptide is derived from an infectious disease antigen. In another embodiment, the peptide is derived from a self-antigen. In another embodiment, the peptide is derived from an angiogenic antigen.

In one embodiment, the antigen from which the peptide disclosed herein is derived from is derived from a fungal pathogen, bacteria, parasite, helminth, or viruses. In other embodiments, the antigen from which the peptide derived herein is selected from tetanus toxoid, hemagglutinin molecules from influenza virus, diphtheria toxoid, HIV gp120, HIV gag protein, IgA protease, insulin peptide B, *Spongospora subterranea* antigen, vibriose antigens, *Salmonella* antigens, pneumococcus antigens, respiratory syncytial virus antigens, *Haemophilus influenza* outer membrane proteins, *Helicobacter pylori* urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1 and E2 from type HPV-16, -18, -31, -33, -35 or -45 human papilloma viruses, the tumor antigens CEA, the ras protein, mutated or otherwise, the p53 protein, mutated or otherwise, Muc1, mesothelin, EGFRVIII or pSA.

In other embodiments, the peptide is derived from an antigen that is associated with one of the following diseases; cholera, diphtheria, Haemophilus, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and listeriosis.

In another embodiment, the antigen from which the peptide disclosed herein is derived is a tumor-associated antigen, which in one embodiment, is one of the following tumor antigens: a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, CEA (carcinoembryonic antigen) associated with colorectal cancer, gp100, a MART1 antigen associated with melanoma, or the PSA antigen associated with prostate cancer. In another embodiment, the antigen for the compositions and methods as disclosed herein are melanoma-associated antigens, which in one embodiment are TRP-2, MAGE-1, MAGE-3, gp-100, tyrosinase, HSP-70, beta-HCG, or a combination thereof. Other tumor-associated antigens known in the art are also contemplated in the present invention.

In one embodiment, the peptide is derived from a chimeric Her2 antigen described in U.S. patent application Ser. No. 12/945,386, which is hereby incorporated by reference herein in its entirety.

In another embodiment, the peptide is derived from an antigen selected from a HPV-E7 (from either an HPV16 or HPV18 strain), a HPV-E6 (from either an HPV16 or HPV18 strain), Her-2/neu, NY-ESO-1, telomerase (TERT, SCCE, CEA, LMP-1, p53, carboxic anhydrase IX (CAIX), PSMA, a prostate stem cell antigen (PSCA), a HMW-MAA, WT-1, HIV-1 Gag, Proteinase 3, Tyrosinase related protein 2, PSA (prostate-specific antigen), EGFR-III, survivin, baculoviral inhibitor of apoptosis repeat-containing 5 (BIRC5), LMP-1, p53, PSMA, PSCA, Muc 1, PSA (prostate-specific antigen), or a combination thereof.

In one embodiment, a polypeptide expressed by the *Listeria* of the present disclosure may be a neuropeptide growth factor antagonist, which in one embodiment is [D-Arg 1, D-Phe5, D-Trp7,9, Leu11] substance P, [Arg6, D-Trp7,9, NmePhe8] substance P(6-11). These and related embodiments are understood by one of skill in the art.

In another embodiment, the heterologous antigen is an infectious disease antigen. In one embodiment, the antigen is an auto antigen or a self-antigen.

In one embodiment, the peptide is capable of being loaded onto an MHC class I molecule. In another embodiment, the peptide is capable of being loaded onto MHC class II molecules. In another embodiment, the peptide is an MHC class I peptide. In another embodiment, the peptide is an MHC class II peptide. In another embodiment, the peptide can be recognized by T cell receptors on a CD8+ T cell, when bound to an MHC class I molecule on the surface of a host cell. In another embodiment, the peptide can be recognized by T cell receptors on a CD4+ T cell, when bound to an MHC class II molecule on the surface of a host cell. In another embodiment, the peptide can be recognized by an antibody or small molecule present on the surface of an effector CD4+ or CD8+ cell that is specific for binding the peptide, when bound to an MHC class I or MHC class II molecule on the surface of a host cell.

In one embodiment, the expression system disclosed herein comprises the use of the nucleic acid construct encoding the chimeric protein disclosed herein. In another embodiment, this expression system is designed to facilitate panels of recombinant proteins containing distinct peptide moieties at the carboxy terminus. This is accomplished, in one embodiment, by a PCR reaction utilizing a sequence encoding on the of the bacterial secretion signal sequence-ubiquitin-peptide (SS-Ub-Peptide) constructs as a template. In one embodiment, using a primer that extends into the carboxy-terminal region of the Ub sequence and introducing codons for the desired peptide sequence at the 3' end of the primer, a new SS-Ub-Peptide sequence can be generated in a single PCR reaction (see Examples herein). The 5' primer encoding the bacterial promoter and the first few nucleotides of the bacterial secretion signal sequence may be the same for all the constructs. A schematic representation of this construct is provided in FIG. 1 herein.

In one embodiment, the recombinant *Listeria* comprises a second nucleic acid molecule or construct comprising an open reading frame encoding a metabolic enzyme, wherein the metabolic enzyme complements a mutation, deletion or inactivation in an endogenous gene of the *Listeria*. In another embodiment, the metabolic enzyme complements an endogenous gene that is lacking in the chromosome of the recombinant *Listeria* strain. In another embodiment, the second nucleic acid molecule comprises an open reading frame encoding a second metabolic enzyme that complements a mutation in an endogenous gene of the *Listeria*. In another embodiment, the second nucleic acid molecule comprises an open reading frame encoding a second metabolic enzyme that complements an endogenous gene that is mutated in the chromosome of the recombinant *Listeria* strain.

For a full length protein or polypeptide, the term "fragment" refers to a protein or polypeptide that is shorter or comprises fewer amino acids than the full length protein or polypeptide.

In one embodiment, a fragment has 10-20 nucleic or amino acids, while in another embodiment, a fragment has more than 5 nucleic or amino acids, while in another embodiment, a fragment has 100-200 nucleic or amino acids, while in another embodiment, a fragment has 100-500 nucleic or amino acids, while in another embodiment, a fragment has 50-200 nucleic or amino acids, while in another embodiment, a fragment has 10-250 nucleic or amino acids.

In another embodiment, the nucleic constructs or nucleic acid molecules are expressed from at least one episomal or plasmid vector. In another embodiment, a plasmid vector is stably maintained in the recombinant *Listeria* strain in the absence of antibiotic selection. In another embodiment, the plasmid does not confer antibiotic resistance upon the recombinant *Listeria*. In one embodiment, the recombinant *Listeria* strain disclosed herein lacks antibiotic resistance genes. In another embodiment, the recombinant *Listeria* strain disclosed herein comprises a plasmid comprising a nucleic acid encoding an antibiotic resistance gene.

In one embodiment, the recombinant *Listeria* comprises an episomal vector that carries the nucleic acid construct disclosed herein. In another embodiment, the episomal vector is extrachromosomal in that it does not integrate into the genome of the *Listeria*. In another embodiment, the recombinant *Listeria* comprises a plasmid vector that carries the nucleic acid construct disclosed herein. In another embodiment, the plasmid vector contains integration sequences for integrating into the *Listeria* chromosome. In another embodiment, the terms "genome" and "chromosome" are used interchangeably herein.

In another embodiment, disclosed herein is an LLO protein for use in the compositions and methods disclosed herein. In another embodiment, a fragment of an LLO protein is used in the compositions and methods disclosed herein. In another embodiment, the fragment is a functional fragment. In another embodiment, the fragment is an immunogenic fragment.

The LLO protein utilized to construct vaccines of the present disclosure has, in another embodiment, the sequence:

```
(GenBank Accession No. P13128;;
                                         SEQ ID NO: 1
MKKIMLVFITLILVSLPIAQQTEAKDASAFNKENSISSMAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYPNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTDGKINTIDHSGGYVAQFNISWDEVNYDPEGNEIVQ

HKNWSENNKSKLAHFTSSIYLPGNARNINTVYAKECTGLAWEWWRTVIDD

RNLPLVKNRNISIWGTTLYPKYSNKVDNPIE
``` nucleic acid sequence is set forth in GenBank Accession No. X15127). In another embodiment, the LLO protein has a sequence set forth in GenBank Accession No. DQ054589.1, which refers to the hly gene from *Listeria* 10403S. The first 25 AA of the proprotein corresponding to this sequence are the signal sequence and are cleaved from LLO when it is secreted by the bacterium. Thus, in this embodiment, the full length active LLO protein is 504 residues long. In another embodiment, the above LLO fragment is used as the source of the LLO fragment incorporated in a vaccine of the present invention.

In another embodiment, the N-terminal fragment of an LLO protein utilized in compositions and methods of the present disclosure has the sequence:

```
                                         (SEQ ID NO: 2)
MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINTQNNADIQVVNAISSLTYPGALVKANSELVENQPDVLPVKR

DSLTLSIDLPGMTNQDNKIVVKNATKSNVNNAVNTLVERWNEKYAQAYSN

VSAKIDYDDEMAYSESQLIAKFGTAFKAVNNSLNVNFGAISEGKMQEEVI

SFKQIYYNVNVNEPTRPSRFFGKAVTKEQLQALGVNAENPPAYISSVAYG

RQVYLKLSTNSHSTKVKAAFDAAVSGKSVSGDVELTNIIKNSSFKAVIYG

GSAKDEVQIIDGNLGDLRDILKKGATFNRETPGVPIAYTTNFLKDNELAV

IKNNSEYIETTSKAYTDGKINTIDHSGGYVAQFNISWDEVNYD.
```

In another embodiment, the LLO fragment corresponds to about AA 20-442 of an LLO protein utilized herein.

In another embodiment, the LLO fragment has the sequence:

```
                                         (SEQ ID NO: 3)
MKKIMLVFITLILVSLPIAQQTEAKDASAFNKENSISSVAPPASPPASPK

TPIEKKHADEIDKYIQGLDYNKNNVLVYHGDAVTNVPPRKGYKDGNEYIV

VEKKKKSINQNNADIQVVNAISSLTYPGALVKANSELVENQPDVLPVKRD

SLTLSIDLPGMTNQDNKIVVKNATKSNVNNAVNTLVERWNEKYAQAYSNV

SAKIDYDDEMAYSESQLIAKFGTAFKAVNNSLNVNFGAISEGKMQEEVIS

FKQIYYNVNVNEPTRPSRFFGKAVTKEQLQALGVNAENPPAYISSVAYGR

QVYLKLSTNSHSTKVKAAFDAAVSGKSVSGDVELTNIIKNSSFKAVIYGG

SAKDEVQIIDGNLGDLRDILKKGATFNRETPGVPIAYTTNFLKDNELAVI

KNNSEYIETTSKAYTD.
```

In one embodiment, the LLO signal peptide or signal sequence comprises the following amino acids: MKKIMLVFITLILVSLPIAQQTEAK (SEQ 11) NO: 4).

As used herein, "truncated LLO", "tLLO", or "ΔLLO" refers to a fragment of LLO that comprises the PEST-like domain. In another embodiment, the term refers to an LLO fragment that comprises a PEST sequence. In another embodiment "ΔLLO" refers to 416AA LLO fragment as defined above.

In another embodiment, the terms truncated LLO, tLLO, or ΔLLO refer to an LLO fragment that does not contain the activation domain at the amino terminus and does not include cysteine 484. In another embodiment, the terms refer to an LLO fragment that is not hemolytic. In another embodiment, the LLO fragment is rendered non-hemolytic by deletion or mutation of the activation domain. In another embodiment, the LLO fragment is rendered non-hemolytic by deletion or mutation of cysteine 484. In another embodiment, the LLO fragment is rendered non-hemolytic by deletion or mutation at another location. In another embodiment, the LLO is rendered non-hemolytic by a deletion or mutation of the cholesterol binding domain (CBD) as detailed in U.S. Pat. No. 8,771,702, which is incorporated by reference herein.

In another embodiment, the LLO fragment consists of about the first 441 AA of the LLO protein. In another embodiment, the LLO fragment consists of about the first 420 AA of LLO. In another embodiment, the LLO fragment is a non-hemolytic form of the LLO protein.

In another embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1175. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300. In another embodiment, the LLO fragment consists of about residues 1-325. In another embodiment, the LLO fragment consists of about residues 1-350. In another embodiment, the LLO fragment consists of about residues 1-375. In another embodiment, the LLO fragment consists of about residues 1-400. In another embodiment, the LLO fragment consists of about residues 1-425.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein, then the residue numbers can be adjusted accordingly. Other LLO fragments are known in the art.

In another embodiment, the LLO fragment consists of about the first 441 AA of the LLO protein. In another embodiment, the LLO fragment consists of about the first 420 AA of LLO. In another embodiment, the LLO fragment is a non-hemolytic form of the LLO protein.

In another embodiment, the LLO fragment consists of about residues 1-25. In another embodiment, the LLO fragment consists of about residues 1-50. In another embodiment, the LLO fragment consists of about residues 1-75. In another embodiment, the LLO fragment consists of about residues 1-100. In another embodiment, the LLO fragment consists of about residues 1-125. In another embodiment, the LLO fragment consists of about residues 1-150. In another embodiment, the LLO fragment consists of about residues 1175. In another embodiment, the LLO fragment consists of about residues 1-200. In another embodiment, the LLO fragment consists of about residues 1-225. In another embodiment, the LLO fragment consists of about residues 1-250. In another embodiment, the LLO fragment consists of about residues 1-275. In another embodiment, the LLO fragment consists of about residues 1-300. In another embodiment, the LLO fragment consists of about residues 1-325. In another embodiment, the LLO fragment consists of about residues 1-350. In another embodiment, the LLO fragment consists of about residues 1-375. In another embodiment, the LLO fragment consists of about residues 1-400. In another embodiment, the LLO fragment consists of about residues 1-425.

In another embodiment, the LLO fragment contains residues of a homologous LLO protein that correspond to one of the above AA ranges. The residue numbers need not, in another embodiment, correspond exactly with the residue numbers enumerated above; e.g. if the homologous LLO protein has an insertion or deletion, relative to an LLO protein utilized herein, then the residue numbers can be adjusted accordingly Other LLO fragments are known in the art.

In another embodiment, a homologous LLO refers to identity to an LLO sequence (e.g. to one of SEQ ID No: 1-3) of greater than 70%. In another embodiment, a homologous LLO refers to identity to one of SEQ ID No: 1-3 of greater than 72%. In another embodiment, a homologous refers to identity to one of SEQ ID No: 1-3 of greater than 75%. In another embodiment, a homologous refers to identity to one of SEQ ID No: 1-3 of greater than 78%. In another embodiment, a homologous refers to identity to one of SEQ ID No: 1-3 of greater than 80%. In another embodiment, a homologous refers to identity to one of SEQ ID No: 1-34 of greater than 82%. In another embodiment, a homologous refers to identity to one of SEQ ID No: 1-3 of greater than 83%. In another embodiment, a homologous refers to identity to one of SEQ ID No: 1-3 of greater than 85%. In another embodiment, a homologous refers to identity to one of SEQ ID No: 1-3 of greater than 87%. In another embodiment, a homologous refers to identity to one of SEQ ID No: 1-3 of greater than 88%. In another embodiment, a homologous refers to identity to one of SEQ ID No: 1-3 of greater than 90%. In another embodiment, a homologous refers to identity to one of SEQ ID No: 1-3 of greater than 92%. In another embodiment, a homologous refers to identity to one of SEQ ID No: 1-3 of greater than 93%. In another embodiment, a homologous refers to identity to one of SEQ ID No: 1-3 of greater than 95%. In another embodiment, a homologous refers to identity to one of SEQ ID No: 1-3 of greater than 96%. In another embodiment, a homologous refers to identity to one of SEQ ID No: 1-3 of greater than 97%. In another embodiment, a homologous refers to identity to one of SEQ ID No: 1-3 of greater than 98%. In another embodiment, a homologous refers to identity to one of SEQ ID No: 1-3 of greater than 99%. In another embodiment, a homologous refers to identity to one of SEQ ID No: 1-3 of 100%.

In one embodiment, an ActA protein is encoded by a sequence set forth in SEQ ID NO: 5 MGLNRFMRA-MMVVFITANC ITINPDITAATDSEDSSLNTDEWEEEK-TEEQPSEVNTGPRYE TAREVS SRDIKELEKSNKVRN-TNKADLIAMLKEKAEKGPNINNNNS EQTENAAINE-EASGA DRPAIQVERRHPGLPSDSAAEIKKRRKAIAS-SDSELESLTYPDKPTKVNKKKVAKESVADA SESDLD-SSMQSADESSPQPLKANQQPFFPKVFKKIKDAGKW-VRDKIDENPEVKKAIVDKSA GLIDQLLTKKKSEEVN-ASDFPPPPTDEELRLALPETPMLLGFNAPATSEPSSF-EFPPPPTDEELRLALPETPMLLGFNAPATSEPSSFEFP-PPPTEDELEIIRETASSLDSSFTRGDLASLRNAINRHS QNFSDFPPIPTEEELNGRGGRPTSEEFSSLNSGDFTD-DENSETTEEEIDRLADLRDRGTGKHS RNAGFLPLNP-FASSPVPSLSPKVSKISDRALISDITKKTPFKNPSQPL-NVFNKKTTTKTVTKKPTPVKTAPKLAELPATKPQET-VLRENKTPFIEKQAETNKQSINMPSLPVIQKEATESD-KEEM KPQTEEKMVEESESANNANGKNRSAGIEEG-KLIAKSAEDEKAKEEPGNHTTLILAMLAIGV FSL-GAFIKIIQLRKNN (SEQ ID NO: 5). In another embodiment, an ActA protein comprises SEQ ID NO: 5. The first 29

AA of the proprotein corresponding to this sequence are the signal sequence and are cleaved from ActA protein when it is secreted by the bacterium. In one embodiment, an ActA polypeptide or peptide comprises the signal sequence, AA 1-29 of SEQ ID NO: 5 above. In another embodiment, an ActA polypeptide or peptide does not include the signal sequence, AA 1-29 of SEQ ID NO: 5 above.

In another embodiment, a recombinant nucleotide encoding a truncated ActA protein disclosed herein comprises the sequence set forth in SEQ ID NO: 6 Atgcgtgcgatgatggt-ggttttcattactgccaattgcattacgattaaccccgacataatatttgcagcgaca-gatagcgaagattctagtctaaa cacagatgaatgggaagaagaaaaaacaga-agagcaaccaagcgaggtaaatacgggaccaagatacgaaactgcacgt-gaagtaagttca cgtgatattaaagaactagaaaaatcgaataaagtgagaaat-acgaacaaagcagacctaatagcaatgttgaaagaaaaagcagaaaaaggtc caaatatcaataataacaacagtgaacaaactgagaatgcggctataaatgaa-gaggcttcaggagccgaccgaccagctatacaagtggagc gtcgtcatccag-gattgccatcggatagcgcagcggaaattaaaaaaagaaggaaagccatagcat-catcggatagtgagcttgaaagccttact tatccggataaaccaacaaaagtaa-ataagaaaaagtggcgaaagagtcagttgcggatgcttctgaaagtgacttagat-tctagcatgcagtca gcagatgagtcttcaccacaaccttaaaagcaaaccaac-aaccatttttccctaaagtatttaaaaaaataaaagatgcgggaaatgggtacgtg ataaaatcgacgaaaatcctgaagtaaagaaagcgattgttgataaaagtgca-gggttaattgaccaattattaaccaaaaagaaaagtgaagaggtaaatgcttc-ggacttcccgccaccacctacggatgaagagttaagacttgctttgccagaga-caccaatgcttcttggttttaatgctcctgctaca tcagaaccgagctcattcgaat-ttccaccaccacctacggatgaagagttaagacttgctttgccagagacgccaa-tgcttcttggttttaatgctcct gctacatcggaaccgagctcgttcgaatttccac-cgcctccaacagaagatgaactagaaatcatccgggaaacagcatcctcgcta-gattctagt tttacaagaggggatttagctagtttgagaaatgctattaatcgccat-agtcaaaatttctctgatttcccaccaatcccaacagaagaagagttgaacggg-agaggcggtagacca (SEQ ID NO: 6). In another embodiment, the recombinant nucleotide has the sequence set forth in SEQ ID NO: 6. In another embodiment, the recombinant nucleotide comprises any other sequence that encodes a fragment of an ActA protein.

In another embodiment, an ActA protein comprises the sequence set forth in SEQ ID NO: 7
M G L N R F M R A M M V V F I T A N C I T I N P D I I F A A T D S E D S S L N T D E W E E E K T E E Q P S E V N T G P R Y E T A R E V S S R D I E E L E K S N K V K N T N K A D L I A M L K A K A E K G P N N N N N N G E Q T G N V A I N E E A S G V D R P T L Q V E R R H P G L S S D S A A E I K K R R K A I A S S D S E L E S L T Y P D K P T K A N K R K V A K E S V V D A S E S D L D S S M Q S A D E S T P Q P L K A N Q K P F F P K V F K K I K D A G K W V R D K I D E N P E V K K A I V D K S A G L I D Q L L T K K K S E E V N A S D F P P P P T D E E L R L A L P E T P M L L G F N A P T P S E P S S F E F P P P P T D E E L R L A L P E T P M L L G F N A P A T S E P S S F E F P P P P T E D E L E I M R E T A P S L D S S F T S G D L A S L R S A I N R H S E N F S D F P P I P T E E E L N G R G G R P T S E E F S S L N S G D F T D D E N S E T T E E E I D R L A D L R D R G T G K H S R N A G F L P L N P F I S S P V P S L T P K V P K I S A P A L I S D I T K K A P F K N P S Q P L N V F N K K T T T K T V T K K P T P V K T A P K L A E L P A T K P Q E T V L R E N K T P F I E K Q A E T N K Q S I N M P S L P V I Q K E A T E S D K E E M K P Q T E E K M V E E S E S A N N A N G K N R S A G I E E G K L I A K S A E D E K A K E E P G N H T T L I L A M L A I G V F S L G A F I K I I Q L R K N N (SEQ ID NO: 7). The first 29 AA of the proprotein corresponding to this sequence are the signal sequence and are cleaved from ActA protein when it is secreted by the bacterium.

In one embodiment, an ActA polypeptide or peptide comprises the signal sequence, AA 1-29 of SEQ ID NO: 7. In another embodiment, an ActA polypeptide or peptide does not include the signal sequence, AA 1-29 of SEQ ID NO: 7. In one embodiment, a truncated ActA protein comprises an N-terminal fragment of an ActA protein. In another embodiment, a truncated ActA protein is an N-terminal fragment of an ActA protein.

In one embodiment, a truncated ActA protein comprises the sequence set forth in SEQ ID NO: 8 MRAMMVVFIT-ANCITINPDITAATDSEDSSLNTDEWEEEKTEEQPSE-VNTGPRYETAREVSSRDIKELEKSNKVRNTNKAD LI-AMLKEKAEKGPNINTNNNSEQTENAMNEEASGADR-PAIQ VERRHPGLPSDSAAEIKKRRKAIASSDSELESL-TYPDKPTKVNKKKVAKESVADASESDLD SSMQSAD-ESSPQPLKANQQPFFPKVFKKIKDAGKWVRDKIDEN-PEVKKAIVDKSAGLIDQL LTKKKSEEVNASDFPPPPT-DEELRLALPETPMLLGFNAPATSEPSSFEFPPPPTDE-ELRLALPE TPMLLGFNAPATSEPSSFEFPPPPTEDEL-EIIRETASSLDSSFTRGDLASLRNAINRHSQNFSD FPPIPTEEELNGRGGRP (SEQ ID NO: 8). In another embodiment, the ActA fragment comprises the sequence set forth in SEQ ID NO: 8.

In another embodiment, a truncated ActA protein comprises the sequence set forth in SEQ ID NO: 9:

(SEQ ID NO: 9)
MGLNRFMRAMMVVFITANCITINPDIIFAATDSEDSSLNTDEWEEEKTEE

QPSEVNTGPRYETAREVSSRDIKELEKSNKVRNTNKADLIAMLKEKAEK

G.

In another embodiment, the ActA fragment is any other ActA fragment known in the art.

In one embodiment, a truncated ActA protein comprises the sequence set forth in SEQ ID NO: 10

(SEQ ID NO: 10)
MRAMMVVFITANCITINPDITAATDSEDSSLNTDEWEEEKTEEQPSEVNT

GPRYETAREVSSRDIKELEKSNKVRNTNKADLIAMLKEKAEKGPNINNNN

SEQTENAMNEEASGADRPAIQVERRHPGLPSDSAAEIKKRRKAIASSDSE

LESLTYPDKPTKVNKKKVAKESVADASESDLDSSMQSADESSPQPLKANQ

QPFFPKVFKKIKDAGKWVRDKIDENPEVKKAIVDKSAGLIDQLLTKKKSE

EVNASDFPPPPTDEELRLALPETPMLLGFNAPATSEPSSFEFPPPPTDEE

LRLALPETPMLLGFNAPATSEPSSFEFPPPPTEDELEIIRETASSLDSSF

TRGDLASLRNAINRHSQNFSDFPPIPTEEELNGRGGRP.

In another embodiment, a truncated ActA protein comprises the sequence set forth in SEQ ID NO: 11:

(SEQ ID NO: 11)
MGLNRFMRAMMVVFITANCITINPDIIFAATDSEDSSLNTDEWEEEKTEE

QPSEVNTGPRYETAREVSSRDIKELEKSNKVRNTNKADLIAMLKEKAEK

G.

In another embodiment, a truncated ActA protein comprises the sequence set forth in SEQ ID NO: 12 A T D S E D S S L N T D E W E E E K T E E Q P S E V N T G P R Y E T A R E V S S R D I E E L E K S N K V K N T N K A D L I A M L K A K A E K G P N N N N N N G E Q T G N V A I N E E A S G (SEQlDNO:12). In another embodiment, a truncated ActA as set forth in SEQ ID NO: 12 is referred to as ActA/PEST1. In another embodiment, a truncated ActA comprises from the first 30 to amino acid 122 of the full length ActA sequence. In another embodiment, SEQ ID NO: 12 comprises from the first 30 to amino acid 122 of the full length ActA sequence. In another embodiment, a truncated ActA comprises from the first 30 to amino acid 122 of SEQ ID NO: 7. In another embodiment, SEQ ID NO: 12 comprises from the first 30 to amino acid 122 of SEQ ID NO: 7.

In another embodiment, a truncated ActA protein comprises the sequence set forth in SEQ ID NO: 13 M R A M M V V F I T A N C I T I N P D I I F A A T D S E D S S L N T D E W E E E K T E E Q P S E V N T G P R Y E T A R E V S S R D I E E L E K S N K V K N T N K A D L I A M L K A K A E K G P N N N N N N G E Q T G N V A I N E E A S G V D R P T L Q V (SEQ ID NO: 13). In another embodiment, a truncated ActA as set forth in SEQ ID NO: 12 is referred to as ActA/PEST1. In another embodiment, a truncated ActA comprises from the first 1 to amino acid 130 of the full length ActA sequence. In another embodiment, SEQ ID NO: 13 comprises from the first 1 to amino acid 130 of the full length ActA sequence. In another embodiment, a truncated ActA comprises from the first 1 to amino acid 130 of SEQ ID NO: 7. In another embodiment, SEQ ID NO: 13 comprises from the first 30 to amino acid 122 of SEQ ID NO: 7.

In another embodiment, a truncated ActA protein comprises the sequence set forth in SEQ ID NO: 14 A T D S E D S S L N T D E W E E E K T E E Q P S E V N T G P R Y E T A R E V S S R D I E E L E K S N K V K N T N K A D L I A M L K A K A E K G P N N N N N N G E Q T G N V A I N E E A S G V D R P T L Q V (SEQ ID NO: 14). In another embodiment, a truncated ActA as set forth in SEQ ID NO: 14 is referred to as ActA/PEST1. In another embodiment, a truncated ActA comprises from the first 30 to amino acid 122 of the full length ActA sequence. In another embodiment, SEQ ID NO: 14 comprises from the first 30 to amino acid 122 of the full length ActA sequence. In another embodiment, a truncated ActA comprises from the first 30 to amino acid 122 of SEQ ID NO: 7. In another embodiment, SEQ ID NO: 14 comprises from the first 30 to amino acid 122 of SEQ ID NO: 7.

In another embodiment, a truncated ActA protein comprises the sequence set forth in SEQ ID NO: 15 A T D S E D S S L N T D E W E E E K T E E Q P S E V N T G P R Y E T A R E V S S R D I E E L E K S N K V K N T N K A D L I A M L K A K A E K G P N N N N N N G E Q T G N V A I N E E A S G V D R P T L Q V E R R H P G L S S D S A A E I K K R R K A I A S S D S E L E S L T Y P D K P T K A N K R K V A K E S V V D A S E S D L D S S M Q S A D E S T P Q P L K A N Q K P F F P K V F K K I K D A G K W V R D K (SEQlDNO:15). In another embodiment, a truncated ActA as set forth in SEQ ID NO: 15 is referred to as ActA/PEST2. In another embodiment, a truncated ActA comprises from amino acid 30 to amino acid 229 of the full length ActA sequence. In another embodiment, SEQ ID NO: 15 comprises from about amino acid 30 to about amino acid 229 of the full length ActA sequence. In another embodiment, a truncated ActA comprises from about amino acid 30 to amino acid 229 of SEQ ID NO: 7.

In another embodiment, SEQ ID NO: 15 comprises from amino acid 30 to amino acid 229 of SEQ ID NO: 7.

In another embodiment, a truncated ActA protein comprises the sequence set forth in SEQ ID NO: 16 A T D S E D S S L N T D E W E E E K T E E Q P S E V N T G P R Y E T A R E V S S R D I E E L E K S N K V K N T N K A D L I A M L K A K A E K G P N N N N N N G E Q T G N V A I N E E A S G V D R P T L Q V E R R H P G L S S D S A A E I K K R R K A I A S S D S E L E S L T Y P D K P T K A N K R K V A K E S V V D A S E S D L D S S M Q S A D E S T P Q P L K A N Q K P F F P K V F K K I K D A G K W V R D K I D E N P E V K K A I V D K S A G L I D Q L L T K K K S E E V N A S D F P P P P T D E E L R L A L P E T P M L L G F N A P T P S E P S S F E F P P P P T D E E L R L A L P E T P M L L G F N A P A T S E P S S (SEQ ID NO: 16). In another embodiment, a truncated ActA as set forth in SEQ ID NO: 16 is referred to as ActA/PEST3. In another embodiment, this truncated ActA comprises from the first 30 to amino acid 332 of the full length ActA sequence. In another embodiment, SEQ ID NO: 16 comprises from the first 30 to amino acid 332 of the full length ActA sequence. In another embodiment, a truncated ActA comprises from about the first 30 to amino acid 332 of SEQ ID NO: 7. In another embodiment, SEQ ID NO: 16 comprises from the first 30 to amino acid 332 of SEQ ID NO: 7.

In another embodiment, a truncated ActA protein comprises the sequence set forth in SEQ ID NO: 17 A T D S E D S S L N T D E W E E E K T E E Q P S E V N T G P R Y E T A R E V S S R D I E E L E K S N K V K N T N K A D L I A M L K A K A E K G P N N N N N N G E Q T G N V A I N E E A S G V D R P T L Q V E R R H P G L S S D S A A E I K K R R K A I A S S D S E L E S L T Y P D K P T K A N K R K V A K E S V V D A S E S D L D S S M Q S A D E S T P Q P L K A N Q K P F F P K V F K K I K D A G K W V R D K I D E N P E V K K A I V D K S A G L I D Q L L T K K K S E E V N A S D F P P P P T D E E L R L A L P E T P M L L G F N A P T P S E P S S F E F P P P P T D E E L R L A L P E T P M L L G F N A P A T S E P S S F E F P P P P T E D E L E I M R E T A P S L D S S F T S G D L A S L R S A I N R H S E N F S D F P L I P T E E E L N G R G G R P T S E (SEQ ID NO: 17). In another embodiment, a truncated ActA as set forth in SEQ ID NO: 17 is referred to as ActA/PEST4. In another embodiment, this truncated ActA comprises from the first 30 to amino acid 399 of the full length ActA sequence. In another embodiment, SEQ ID NO: 25 comprises from the first 30 to amino acid 399 of the full length ActA sequence. In another embodiment, a truncated ActA comprises from the first 30 to amino acid 399 of SEQ ID NO: 7. In another embodiment, SEQ ID NO: 17 comprises from the first 30 to amino acid 399 of SEQ ID NO: 7.

In another embodiment, a truncated ActA sequence disclosed herein is further fused to an hly signal peptide at the N-terminus. In another embodiment, the truncated ActA fused to hly signal peptide comprises SEQ ID NO: 18
M K K I M L V F I T L I L V S L P I A Q Q T E A S R A T D S E D S S L N T D E W E E E K T E E Q P S E V N T G P R Y E T A R E V S S R D I E E L E K S N K V K N T N K A D L I A M L K A K A E K G P N N N N N N G E Q T G N V A I N E E A S G V D R P T L Q V E R R H P G L S S D S A A E I K K R R K A I A S S D S E L E S L T Y P D K P T K A N K R K V A K E S V V D A S E S D L D S S M Q S A D E S T P Q P L K A N Q K P F F P K V F K K I K D A G K W V R D K. In another embodiment, a truncated ActA as set forth in SEQ ID NO: 18 is referred to as "LA229".

In another embodiment, a truncated ActA fused to hly signal peptide is encoded by a sequence comprising SEQ ID NO: 19 Atgaaaaaaataatgctagtttttattacacttatattagttagtctaccaat-tgcgcaacaaactgaagcatctagagcgacagatagcgaagattccagtctaaa-cacagatgaatgggaagaagaaaaaacagaagagcagccaagcgagg taaa-tacgggaccaagatacgaaactgcacgtgaag taagttcacgtgatattgag-gaactagaaaaatcgaataaagtgaaaaatacgaacaaagcagacctaatag-caatgttgaaagcaaaagcagag aaaggtccgaataacaataataacaacggt-gagcaaacaggaaatgtggctataaatgaagaggcttcaggagtcgaccgac-caactctgcaag tggagcgtcgtcatccaggtctgtcatcggatagcgcagcg-gaaattaaaaaaagaagaaaagccatagcgtcgtcggatagtgagcttgaaag ccttacttatccagataaaccaacaaaagcaaataagagaaaagtggcg aaaga-gtcagttgtggatgcttctgaaagtgacttagattctagcatg cagtcagcagac-gagtctacaccacaaccttaaaagcaaatcaaaaaccattttccctaaagtatt-taaaaaaataaaagatgcggggaaatgg gtacgtgataaa (SEQ ID NO: 19). In another embodiment, SEQ ID NO: 19 comprises a sequence encoding a linker region (see bold, italic text) that is used to create a unique restriction enzyme site for XbaI so that different polypeptides, heterologous antigens, etc. can be cloned after the signal sequence. Hence, it will be appreciated by a skilled artisan that signal peptidases act on the sequences before the linker region to cleave signal peptide.

In another embodiment, the recombinant nucleotide encoding a truncated ActA protein comprises the sequence set forth in SEQ ID NO: 20

```
                                          (SEQ ID NO: 20)
atgcgtgcgatgatggtggttttcattactgccaattgcattacgattaa ccccgacataatatttgcagcgacagatagcgaagattctagtctaaaca cagatgaatgggaagaagaaaaaacagaagagcaaccaagcgaggtaaat acgggaccaagatacgaaactgcacgtgaagtaagttcacgtgatattaa agaactagaaaaatcgaataaagtgagaaatacgaacaaagcagacctaa tagcaatgttgaaagaaaaagcagaaaaaggtccaaatatcaataataac aacagtgaacaaactgagaatgcggctataaatgaagaggcttcaggagc cgaccgaccagctatacaagtggagcgtcgtcatccaggattgccatcgg atagcgcagcggaaattaaaaaaagaaggaaagccatagcatcatcggat agtgagcttgaaagccttacttatccggataaaccaacaaaagtaaataa gaaaaaagtggcgaaagagtcagttgcggatgcttctgaaagtgacttag attctagcatgcagtcagcagatgagtcttcaccacaaccttaaaagca aaccaacaaccattttccctaaagtatttaaaaaaataaaagatgcggg gaaatgggtacgtgataaaatcgacgaaatcctgaagtaaagaaagcga ttgttgataaaagtgcagggttaattgaccaattattaaccaaaagaaa agtgaagaggtaaatgcttcggacttcccgccaccacctacggatgaaga gttaagacttgctttgccagagacaccaatgcttcttggttttaatgctc ctgctacatcgaaccgagctcattcgaatttccaccaccacctacggat gaagagttaagacttgctttgccagagacgccaatgcttcttggttttaa tgctcctgctacatcggaaccgagctcgttcgaatttccaccgcctcaa cagaagatgaactagaaatcatccgggaaacagcatcctcgctagattct agttttacaagaggggatttagctagtttgagaaatgctattaatcgcca tagtcaaaatttctctgatttcccaccaatcccaacagaagaagagttga acgggagaggcggtagacca.
```

In another embodiment, the recombinant nucleotide has the sequence set forth in SEQ ID NO: 18. In another embodiment, the recombinant nucleotide comprises other sequences that encode a fragment of an ActA protein.

In another embodiment, the terms "truncated ActA," "N-terminal ActA fragment" or "ΔActA" are used interchangeably herein and refer to a fragment of ActA that comprises a PEST domain. In another embodiment, the terms refer to an ActA fragment that comprises a PEST sequence. In another embodiment, the terms refer to an immunogenic fragment of the ActA protein. In another embodiment, the terms refer to a truncated ActA fragment encoded by SEQ ID NO: 8-18 disclosed herein.

The N-terminal ActA protein fragment of methods and compositions of the present invention comprises, in one embodiment, a sequence selected from SEQ ID No: 8-18. In another embodiment, the ActA fragment comprises an ActA signal peptide. In another embodiment, the ActA fragment consists approximately of a sequence selected from SEQ ID NO: 8-18. In another embodiment, the ActA fragment consists essentially of a sequence selected from SEQ ID NO: 8-18. In another embodiment, the ActA fragment corresponds to a sequence selected from SEQ ID NO: 8-18. In another embodiment, the ActA fragment is homologous to a sequence selected from SEQ ID NO: 8-18.

In another embodiment, the PEST sequence is another PEST AA sequence derived from a prokaryotic organism. The PEST AA sequence may be other PEST sequences known in the art.

In another embodiment, the ActA fragment consists of about the first 100 AA of the ActA protein.

In another embodiment, the ActA fragment consists of about residues 1-25. In another embodiment, the ActA fragment consists of about residues 1-29. In another embodiment, the ActA fragment consists of about residues 1-50. In another embodiment, the ActA fragment consists of about residues 1-75. In another embodiment, the ActA fragment consists of about residues 1-100. In another embodiment, the ActA fragment consists of about residues 1-125. In another embodiment, the ActA fragment consists of about residues 1-150. In another embodiment, the ActA fragment consists of about residues 1-175. In another embodiment, the ActA fragment consists of about residues 1-200. In another embodiment, the ActA fragment consists of about residues 1-225. In another embodiment, the ActA fragment consists of about residues 1-250. In another embodiment, the ActA fragment consists of about residues 1-275. In another embodiment, the ActA fragment consists of about residues 1-300. In another embodiment, the ActA fragment consists of about residues 1-325. In another embodiment, the ActA fragment consists of about residues 1-338. In another embodiment, the ActA fragment consists of about residues 1-350. In another embodiment, the ActA fragment consists of about residues 1-375. In another embodiment, the ActA fragment consists of about residues 1-400. In another embodiment, the ActA fragment consists of about residues 1-450. In another embodiment, the ActA fragment consists of about residues 1-500. In another embodiment, the ActA fragment consists of about residues 1-550. In another embodiment, the ActA fragment consists of about residues 1-600. In another embodiment, the ActA fragment consists of about residues 1-639. In another embodiment, the ActA fragment consists of about residues 30-100. In another embodiment, the ActA fragment consists of about residues 30-125. In another embodiment, the ActA fragment consists of about residues 30-150. In another embodiment, the ActA fragment consists of about residues 30-175. In another embodiment, the ActA fragment consists of about residues 30-200. In another embodiment, the ActA fragment consists of about residues 30-225. In another embodiment, the ActA fragment consists of about residues 30-250. In another embodiment, the ActA fragment consists of about residues 30-275. In another embodiment, the ActA fragment consists of about residues 30-300. In another embodiment, the ActA fragment consists of about residues 30-325. In another embodiment, the ActA fragment consists of about residues 30-338. In another embodiment, the ActA fragment consists of about residues 30-350. In another embodiment, the ActA fragment consists of about residues 30-375. In another embodiment, the ActA fragment consists of about residues 30-400. In another embodiment, the ActA fragment consists of about residues 30-450. In another embodiment, the ActA fragment consists of about residues 30-500. In another embodiment, the ActA fragment consists of about residues 30-550. In another embodiment, the ActA fragment consists of about residues 1-600. In another embodiment, the ActA fragment consists of about residues 30-604.

In another embodiment, the ActA fragment contains residues of a homologous ActA protein that correspond to one of the above AA ranges. The residue numbers need not, in another embodiment, correspond exactly with the residue numbers enumerated above; e.g. if the homologous ActA protein has an insertion or deletion, relative to an ActA protein utilized herein, then the residue numbers can be adjusted accordingly. Other ActA fragments are known in the art.

In another embodiment, a homologous ActA refers to identity to an ActA sequence (e.g. to one of SEQ ID No: 5, 7-18) of greater than 70%. In another embodiment, a homologous ActA refers to identity to one of SEQ ID No: 5, 7-18 of greater than 72%. In another embodiment, a homologous refers to identity to one of SEQ ID No: 5, 7-18 of greater than 75%. In another embodiment, a homologous refers to identity to one of SEQ ID No: 5, 7-18 of greater than 78%. In another embodiment, a homologous refers to identity to one of SEQ ID No: 5, 7-18 of greater than 80%. In another embodiment, a homologous refers to identity to one of SEQ ID No: 5, 7-18 of greater than 82%. In another embodiment, a homologous refers to identity to one of SEQ ID No: 5, 7-18 of greater than 83%. In another embodiment, a homologous refers to identity to one of SEQ ID No: 5, 7-18 of greater than 85%. In another embodiment, a homologous refers to identity to one of SEQ ID No: 5, 7-18 of greater than 87%. In another embodiment, a homologous refers to identity to one of SEQ ID No: 5, 7-18 of greater than 88%. In another embodiment, a homologous refers to identity to one of SEQ ID No: 5, 7-18 greater than 90%. In another embodiment, a homologous refers to identity to one of SEQ ID No: 5, 7-18 of greater than 92%. In another embodiment, a homologous refers to identity to one of SEQ ID No: 5, 7-18 of greater than 93%. In another embodiment, a homologous refers to identity to one of SEQ ID No: 5, 7-18 of greater than 95%. In another embodiment, a homologous refers to identity to one of SEQ ID No: 5, 7-18 of greater than 96%. In another embodiment, a homologous refers to identity to one of SEQ ID No: 5, 7-18 of greater than 97%. In another embodiment, a homologous refers to identity to one of SEQ ID No: 5, 7-18 of greater than 98%. In another embodiment, a homologous refers to identity to one of SEQ ID No: 5, 7-18 of greater than 99%. In another embodiment, a homologous refers to identity to one of SEQ ID No: 5, 7-18 of 100%.

As used herein, the term "homology," when in reference to any nucleic acid sequence disclosed herein refers to a percentage of nucleotides in a candidate sequence that is identical with the nucleotides of a corresponding native nucleic acid sequence.

Homology may be determined by a computer algorithm for sequence alignment, by methods well described in the art. For example, computer algorithm analysis of nucleic acid sequence homology may include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from the sequences disclosed herein of greater than 68%. In another embodiment, "homology" refers to identity to a sequence selected from the sequences disclosed herein of greater than 70%. In another embodiment, "homology" refers to identity to a sequence selected from the sequences disclosed herein of greater than 72%. In another embodiment, the identity is greater than 75%. In another embodiment, the identity is greater than 78%. In another embodiment, the identity is greater than 80%. In another embodiment, the identity is greater than 82%. In another embodiment, the identity is greater than 83%. In another embodiment, the identity is greater than 85%. In another embodiment, the identity is greater than 87%. In another embodiment, the identity is greater than 88%. In another embodiment, the identity is greater than 90%. In another embodiment, the identity is greater than 92%. In another embodiment, the identity is greater than 93%. In another embodiment, the identity is greater than 95%. In another embodiment, the identity is greater than 96%. In another embodiment, the identity is greater than 97%. In another embodiment, the identity is greater than 98%. In another embodiment, the identity is greater than 99%. In another embodiment, the identity is 100%.

In another embodiment, the LLO protein, ActA protein, or fragment thereof of the present disclosure need not be that which is set forth exactly in the sequences set forth herein, but rather that other alterations, modifications, or changes can be made that retain the functional characteristics of an LLO or ActA protein as set forth elsewhere herein. In another embodiment, the present disclosure utilizes an analog of an LLO protein, ActA protein, or fragment thereof. Analogs differ, in another embodiment, from naturally occurring proteins or peptides by conservative AA sequence differences or by modifications which do not affect sequence, or by both.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). For example methods of hybridization may be carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 μm/mL denatured, sheared salmon sperm DNA.

In one embodiment, the recombinant *Listeria* disclosed herein is capable of escaping the phagolysosome.

In one embodiment, a nucleic acid sequence encoding a heterologous antigen or an antigenic portion thereof is integrated in frame in the *Listeria* chromosome. In another embodiment, the integrated nucleic acid sequence encoding a heterologous antigen is integrated in frame with ActA at the ActA locus. In another embodiment, the chromosomal nucleic acid encoding ActA is replaced by a nucleic acid molecule comprising a sequence encoding an antigen. In another embodiment, the antigen is any antigen disclosed herein and known in the art.

In one embodiment, the second nucleic acid molecule or construct disclosed herein comprises an open reading frame encoding a metabolic enzyme. In another embodiment, the metabolic enzyme complements an endogenous gene that is mutated in the chromosome of the recombinant *Listeria* strain. In another embodiment, the metabolic enzyme complements an endogenous gene that is lacking in the chromosome of the recombinant *Listeria* strain. In another embodiment, the metabolic enzyme encoded by the open reading frame is an alanine racemase enzyme (dal). In another embodiment, the metabolic enzyme encoded by the open reading frame is a D-amino acid transferase enzyme (dat). In another embodiment, the *Listeria* strains disclosed herein comprise a mutation in the endogenous dal/dat genes. In another embodiment, the *Listeria* lacks the dal/dat genes.

In another embodiment, a nucleic acid molecule of the methods and compositions of the present disclosure is operably linked to a promoter/regulatory sequence. In another embodiment, an open reading frame of methods and compositions of the present disclosure is operably linked to a promoter/regulatory sequence. In another embodiment, each of the open reading frames disclosed herein are operably linked to a promoter/regulatory sequence. In another embodiment, expression of each of the open reading frames disclosed herein is driven from a single promoter/regulatory sequence.

In one embodiment, the hly promoter and hly signal sequence are operably linked so as to drive expression of a chimeric protein disclosed herein. In another embodiment, an actA promoter and an actA signal sequence are operably linked so as to drive expression of a chimeric protein described herein.

"Metabolic enzyme" refers to an enzyme involved in synthesis of a nutrient required by the host bacteria. In another embodiment, the term refers to an enzyme required for synthesis of a nutrient required by the host bacteria. In another embodiment, the term refers to an enzyme involved in synthesis of a nutrient utilized by the host bacteria. In another embodiment, the term refers to an enzyme involved in synthesis of a nutrient required for sustained growth of the host bacteria. In another embodiment, the enzyme is required for synthesis of the nutrient.

In another embodiment, the recombinant *Listeria* is an attenuated auxotrophic strain.

In one embodiment the attenuated strain is Lm dal(−)dat (−) (Lmdd). In another embodiment, the attenuated strains is Lm dal(−)dat(−)AactA (LmddA). LmddA is based on a *Listeria* vaccine vector which is attenuated due to the deletion of virulence gene actA and retains the plasmid expression in vivo and in vitro by complementation of dal gene.

In another embodiment the attenuated strain is LmddA. In another embodiment, the attenuated strain is LmΔactA. In another embodiment, the attenuated strain is LmΔprfA. In another embodiment, the attenuated strain is LmΔplcB. In another embodiment, the attenuated strain is LmΔplcA. In another embodiment, the strain is the double mutant or triple mutant of any of the above-mentioned strains. In another embodiment, this strain exerts a strong adjuvant effect which is an inherent property of *Listeria*-based vaccines. In another embodiment, this strain is constructed from the EGD *Listeria* backbone. In another embodiment, the strain used in the disclosure is a *Listeria* strain that expresses a genomic hemolytic LLO.

In another embodiment, the *Listeria* strain is an auxotrophic mutant. In another embodiment, the *Listeria* strain is deficient in a gene encoding a vitamin synthesis gene. In another embodiment, the *Listeria* strain is deficient in a gene encoding pantothenic acid synthase.

In one embodiment, the *Listeria* strain is deficient in an amino acid (AA) metabolism enzyme. In one embodiment, the generation of auxotrophic strains of *Listeria* deficient in D-alanine, for example, may be accomplished in a number of ways that are well known to those of skill in the art, including deletion mutagenesis, insertion mutagenesis, and mutagenesis which results in the generation of frameshift mutations, mutations which cause premature termination of a protein, or mutation of regulatory sequences which affect gene expression. In another embodiment, mutagenesis can be accomplished using recombinant DNA techniques or using traditional mutagenesis technology using mutagenic chemicals or radiation and subsequent selection of mutants. In another embodiment, deletion mutants are preferred because of the accompanying low probability of reversion of the auxotrophic phenotype. In another embodiment, mutants of D-alanine which are generated according to the protocols presented herein may be tested for the ability to grow in the absence of D-alanine in a simple laboratory culture assay. In another embodiment, those mutants which are unable to grow in the absence of this compound are selected for further study.

In another embodiment, in addition to the aforementioned D-alanine associated genes, other genes involved in synthesis of a metabolic enzyme, as disclosed herein, may be used as targets for mutagenesis of *Listeria*.

In another embodiment, the metabolic enzyme complements an endogenous metabolic gene that is lacking in the remainder of the chromosome of the recombinant bacterial strain. In one embodiment, the endogenous metabolic gene is mutated in the chromosome. In another embodiment, the endogenous metabolic gene is deleted from the chromosome. In another embodiment, the metabolic enzyme is an amino acid metabolism enzyme. In another embodiment, the metabolic enzyme catalyzes a formation of an amino acid used for a cell wall synthesis in the recombinant *Listeria* strain. In another embodiment, the metabolic enzyme is an alanine racemase enzyme. In another embodiment, the metabolic enzyme is a D-amino acid transferase enzyme.

In one embodiment, the auxotrophic *Listeria* strain comprises an episomal expression vector comprising a metabolic enzyme that complements the auxotrophy of the auxotrophic *Listeria* strain. In another embodiment, the construct is contained in the *Listeria* strain in an episomal fashion. In another embodiment, the foreign antigen or peptide is expressed from a vector harbored by the recombinant *Listeria* strain. In another embodiment, the episomal expression vector lacks an antibiotic resistance marker. In another embodiment, the *Listeria* strain is deficient in a D-glutamic acid synthase gene. In another embodiment, the *Listeria* strain is deficient in the dat gene. In another embodiment, the *Listeria* strain is deficient in the dal gene. In another embodiment, the *Listeria* strain is deficient in the dga gene. In another embodiment, the *Listeria* strain is deficient in a gene involved in the synthesis of diaminopimelic acid.

CysK. In another embodiment, the gene is vitamin-B12 independent methionine synthase. In another embodiment, the gene is trpA. In another embodiment, the gene is trpB. In another embodiment, the gene is trpE. In another embodiment, the gene is asnB. In another embodiment, the gene is gltD. In another embodiment, the gene is gltB. In another embodiment, the gene is leuA. In another embodiment, the gene is argG. In another embodiment, the gene is thrC. In another embodiment, the Listeria strain is deficient in one or more of the genes described hereinabove.

In another embodiment, the Listeria strain is deficient in a synthase gene. In another embodiment, the gene is an AA synthesis gene. In another embodiment, the gene is folP. In another embodiment, the gene is dihydrouridine synthase family protein. In another embodiment, the gene is ispD. In another embodiment, the gene is ispF. In another embodiment, the gene is phosphoenolpyruvate synthase. In another embodiment, the gene is hisF. In another embodiment, the gene is hisH. In another embodiment, the gene is fliI. In another embodiment, the gene is ribosomal large subunit pseudouridine synthase. In another embodiment, the gene is ispD. In another embodiment, the gene is bifunctional GMP synthase/glutamine amidotransferase protein. In another embodiment, the gene is cobS. In another embodiment, the gene is cobB. In another embodiment, the gene is cbiD. In another embodiment, the gene is uroporphyrin-III C-methyltransferase/uroporphyrinogen-III synthase. In another embodiment, the gene is cobQ. In another embodiment, the gene is uppS. In another embodiment, the gene is truB. In another embodiment, the gene is dxs. In another embodiment, the gene is mvaS. In another embodiment, the gene is dapA. In another embodiment, the gene is ispG. In another embodiment, the gene is folC. In another embodiment, the gene is citrate synthase. In another embodiment, the gene is argJ. In another embodiment, the gene is 3-deoxy-7-phosphoheptulonate synthase. In another embodiment, the gene is indole-3-glycerol-phosphate synthase. In another embodiment, the gene is anthranilate synthase/glutamine amidotransferase component. In another embodiment, the gene is menB. In another embodiment, the gene is menaquinone-specific isochorismate synthase. In another embodiment, the gene is phosphoribosylformylglycinamidine synthase I or II. In another embodiment, the gene is phosphoribosylaminoimidazole-succinocarboxamide synthase. In another embodiment, the gene is carB. In another embodiment, the gene is carA. In another embodiment, the gene is thyA. In another embodiment, the gene is mgsA. In another embodiment, the gene is aroB. In another embodiment, the gene is hepB. In another embodiment, the gene is rluB. In another embodiment, the gene is ilvB. In another embodiment, the gene is ilvN. In another embodiment, the gene is alsS. In another embodiment, the gene is fabF. In another embodiment, the gene is fabH. In another embodiment, the gene is pseudouridine synthase. In another embodiment, the gene is pyrG. In another embodiment, the gene is truA. In another embodiment, the gene is pabB. In another embodiment, the gene is an atp synthase gene (e.g. atpC, atpD-2, aptG, atpA-2, etc).

In another embodiment, the gene is phoP. In another embodiment, the gene is aroA. In another embodiment, the gene is aroC. In another embodiment, the gene is aroD. In another embodiment, the gene is plcB.

In another embodiment, the Listeria strain is deficient in a peptide transporter. In another embodiment, the gene is ABC transporter/ATP-binding/permease protein. In another embodiment, the gene is oligopeptide ABC transporter/oligopeptide-binding protein. In another embodiment, the gene is oligopeptide ABC transporter/permease protein. In another embodiment, the gene is zinc ABC transporter/zinc-binding protein. In another embodiment, the gene is sugar ABC transporter. In another embodiment, the gene is phosphate transporter. In another embodiment, the gene is ZIP zinc transporter. In another embodiment, the gene is drug resistance transporter of the EmrB/QacA family. In another embodiment, the gene is sulfate transporter. In another embodiment, the gene is proton-dependent oligopeptide transporter. In another embodiment, the gene is magnesium transporter. In another embodiment, the gene is formate/nitrite transporter. In another embodiment, the gene is spermidine/putrescine ABC transporter. In another embodiment, the gene is Na/Pi-cotransporter. In another embodiment, the gene is sugar phosphate transporter. In another embodiment, the gene is glutamine ABC transporter. In another embodiment, the gene is major facilitator family transporter. In another embodiment, the gene is glycine betaine/L-proline ABC transporter. In another embodiment, the gene is molybdenum ABC transporter. In another embodiment, the gene is techoic acid ABC transporter. In another embodiment, the gene is cobalt ABC transporter. In another embodiment, the gene is ammonium transporter. In another embodiment, the gene is amino acid ABC transporter. In another embodiment, the gene is cell division ABC transporter. In another embodiment, the gene is manganese ABC transporter. In another embodiment, the gene is iron compound ABC transporter. In another embodiment, the gene is maltose/maltodextrin ABC transporter. In another embodiment, the gene is drug resistance transporter of the Bcr/CflA family. In another embodiment, the gene is a subunit of one of the above proteins.

In one embodiment, disclosed herein is a nucleic acid molecule that is used to transform the Listeria in order to arrive at a recombinant *Listeria*. In another embodiment, the nucleic acid disclosed herein used to transform *Listeria* lacks a virulence gene. In another embodiment, the nucleic acid molecule is integrated into the *Listeria* genome and carries a non-functional virulence gene. In another embodiment, the virulence gene is mutated in the recombinant *Listeria*. In yet another embodiment, the nucleic acid molecule is used to inactivate the endogenous gene present in the *Listeria* genome. In yet another embodiment, the virulence gene is an actA gene, an inlA gene, and inlB gene, an inlC gene, inlJ gene, a plbC gene, a bsh gene, or a prfA gene. It is to be understood by a skilled artisan, that the virulence gene can be any gene known in the art to be associated with virulence in the recombinant *Listeria*.

In yet another embodiment the *Listeria* strain is an inlA mutant, an inlB mutant, an inlC mutant, an inlJ mutant, prfA mutant, actA mutant, a dalldat mutant, a plcB deletion mutant, or a double mutant lacking both plcA and plcB. In another embodiment, the *Listeria* comprises a deletion or mutation of these genes individually or in combination. In another embodiment, the *Listeria* disclosed herein lack each one of genes. In another embodiment, the *Listeria* disclosed herein lack at least one and up to ten of any gene disclosed herein, including the actA, prfA, and dal/dat genes. In another embodiment, the prfA mutant is a D133V prfA mutant.

In one embodiment, the live attenuated *Listeria* is a recombinant *Listeria*. In another embodiment, the recombinant *Listeria* comprises a mutation or a deletion of a genomic internalin C (inlC) gene. In another embodiment, the recombinant *Listeria* comprises a mutation or a deletion of a genomic actA gene and a genomic internalin C gene. In one embodiment, translocation of *Listeria* to adjacent cells is inhibited by the deletion of the actA gene and/or the inlC gene, which are involved in the process, thereby resulting in unexpectedly high levels of attenuation with increased immunogenicity and utility as a vaccine backbone.

In one embodiment, the metabolic gene, the virulence gene, etc. is lacking in a chromosome of the *Listeria* strain. In another embodiment, the metabolic gene, virulence gene, etc. is lacking in the genome of the *Listeria* strain. In one embodiment, the virulence gene is mutated in the chromosome. In another embodiment, the virulence gene is deleted from the chromosome. In another embodiment, the virulence gene is inactivated in the chromosome.

In one embodiment, the recombinant *Listeria* strain disclosed herein is attenuated. In another embodiment, the recombinant *Listeria* lacks the actA virulence gene. In another embodiment, the recombinant *Listeria* lacks the prfA virulence gene. In another embodiment, the recombinant *Listeria* lacks the inlB gene. In another embodiment, the recombinant *Listeria* lacks both, the actA and inlB genes. In another embodiment, the recombinant *Listeria* strains disclosed herein comprise an inactivating mutation of the endogenous actA gene. In another embodiment, the recombinant *Listeria* strains disclosed herein comprise an inactivating mutation of the endogenous inlB gene. In another embodiment, the recombinant *Listeria* strains disclosed herein comprise an inactivating mutation of the endogenous inlC gene. In another embodiment, the recombinant *Listeria* strains disclosed herein comprise an inactivating mutation of the endogenous actA and inlB genes. In another embodiment, the recombinant *Listeria* strains disclosed herein comprise an inactivating mutation of the endogenous actA and inlC genes. In another embodiment, the recombinant *Listeria* strains disclosed herein comprise an inactivating mutation of the endogenous actA, inlB, and inlC genes. In another embodiment, the recombinant *Listeria* strains disclosed herein comprise an inactivating mutation of the endogenous actA, inlB, and inlC genes. In another embodiment, the recombinant *Listeria* strains disclosed herein comprise an inactivating mutation of the endogenous actA, inlB, and inlC genes. In another embodiment, the recombinant *Listeria* strains disclosed herein comprise an inactivating mutation in any single gene or combination of the following genes: actA, dal, dat, inlB, inlC, prfA, plcA, plcB. In one embodiment, the term "lacks" when in reference to a genomic virulence gene means that the virulence gene is either deleted (partial or whole deletion) or is otherwise not functionally expressed from the chromosome. Such a term may also encompass a partial deletion or a whole gene deletion of the virulence gene in the chromosome.

It will be appreciated by the skilled artisan that the term "mutation" and grammatical equivalents thereof, include any type of mutation or modification to the sequence (nucleic acid or amino acid sequence), and includes an amino acid deletion mutation, a substitution, a replacement, a truncation, an inactivation, a disruption, or a translocation. These types of mutations are readily known in the art.

In one embodiment, in order to select for auxotrophic bacteria comprising a plasmid encoding a metabolic enzyme or a complementing gene disclosed herein, transformed auxotrophic bacteria are grown on a media that will select for expression of the amino acid metabolism gene or the complementing gene. In another embodiment, a bacteria auxotrophic for D-glutamic acid synthesis is transformed with a plasmid comprising a gene for D-glutamic acid synthesis, and the auxotrophic bacteria will grow in the absence of D-glutamic acid, whereas auxotrophic bacteria that have not been transformed with the plasmid, or are not expressing the plasmid encoding a protein for D-glutamic acid synthesis, will not grow. In another embodiment, a bacterium auxotrophic for D-alanine synthesis will grow in the absence of D-alanine when transformed and expressing the plasmid of the present disclosure if the plasmid comprises an isolated nucleic acid encoding an amino acid metabolism enzyme for D-alanine synthesis. Such methods for making appropriate media comprising or lacking necessary growth factors, supplements, amino acids, vitamins, antibiotics, and the like are well known in the art, and are available commercially (Becton-Dickinson, Franklin Lakes, N.J.).

In another embodiment, once the auxotrophic bacteria comprising the plasmid of the present disclosure have been selected on appropriate media, the bacteria are propagated in the presence of a selective pressure. Such propagation comprises growing the bacteria in media without the auxotrophic factor. The presence of the plasmid expressing an amino acid metabolism enzyme in the auxotrophic bacteria ensures that the plasmid will replicate along with the bacteria, thus continually selecting for bacteria harboring the plasmid. The skilled artisan, when equipped with the present disclosure and methods herein will be readily able to scale-up the production of the *Listeria* vaccine vector by adjusting the volume of the media in which the auxotrophic bacteria comprising the plasmid are growing.

The skilled artisan will appreciate that, in another embodiment, other auxotroph strains and complementation systems are adopted for the use with this invention.

In one embodiment, the recombinant *Listeria* strain disclosed herein expresses the chimeric protein disclosed herein. In another embodiment, the recombinant *Listeria* strain comprises a plasmid that encodes the chimeric protein. In another embodiment, a recombinant nucleic acid disclosed herein is in a plasmid in the recombinant *Listeria* strain disclosed herein. In another embodiment, the plasmid is an episomal plasmid that does not integrate into the recombinant *Listeria* strain's chromosome. In another embodiment, the plasmid is a multicopy plasmid. In another embodiment, the plasmid is an integrative plasmid that integrates into the *Listeria* strain's chromosome.

In one embodiment, the recombinant *Listeria* strain as disclosed herein comprises a nucleic acid molecule encoding a tumor associated peptide.

In another embodiment, a recombinant *Listeria* strain of the methods and compositions as disclosed herein comprise a nucleic acid molecule operably integrated into the *Listeria* genome as an open reading frame with an endogenous ActA sequence. In another embodiment, a recombinant *Listeria* strain of the methods and compositions as disclosed herein comprise an episomal expression vector comprising a nucleic acid molecule encoding a chimeric protein comprising an peptide antigen fused on the Amino-terminus to an ubiquitin protein. In one embodiment, the expression and secretion of the peptide antigen is under the control of an actA promoter and ActA signal sequence and it is expressed as fusion to 1-233 amino acids of ActA (truncated ActA or tActA). In another embodiment, the expression and secretion of the peptide antigen is under the control of an actA promoter and ActA signal sequence and it is expressed as fusion to 1-100 amino acids of ActA (truncated ActA or tActA). In another embodiment, the expression and secretion of the peptide antigen is under the control of an actA promoter and ActA signal sequence and it is expressed as fusion to 1-300 amino acids of ActA (truncated ActA or tActA). In another embodiment, the truncated ActA consists of the first 390 amino acids of the wild type ActA protein as described in U.S. Pat. No. 7,655,238, which is incorporated by reference herein in its entirety. In another embodiment, the truncated ActA is an ActA-N100 or a modified version thereof (referred to as ActA-N100*) in which a PEST motif has been deleted and containing the nonconservative QDNKR substitution as described in US Patent Publication Serial No. 2014/0186387.

In another embodiment, a recombinant *Listeria* strain of the methods and compositions as disclosed herein comprise a nucleic acid molecule operably integrated into the *Listeria* genome as an open reading frame with an endogenous LLO sequence. In another embodiment, a recombinant *Listeria* strain of the methods and compositions as disclosed herein comprise an episomal expression vector comprising a nucleic acid molecule encoding a chimeric protein comprising an peptide antigen fused on the Amino-terminus to an ubiquitin protein. In one embodiment, the expression and secretion of the peptide antigen is under the control of an LLO promoter and LLO signal sequence and it is expressed as fusion to 1-50 amino acids of LLO (truncated LLO or tLLO). In another embodiment, the expression and secretion of the peptide antigen is under the control of an LLO promoter and LLO signal sequence and it is expressed as fusion to 1-100 amino acids of LLO (truncated LLO or tLLO). In another embodiment, the expression and secretion of the peptide antigen is under the control of an LLO promoter and LLO signal sequence and it is expressed as fusion to 1-300 amino acids of LLO (truncated LLO or tLLO). In another embodiment, the truncated LLO consists of the first 420 amino acids of the wild type LLO.

In one embodiment, no CTL activity is detected in naïve animals or mice injected with an irrelevant *Listeria* vaccine. While in another embodiment, the attenuated auxotrophic strain expressing a chimeric protein disclosed herein is able to stimulate the secretion of IFN-γ and elicit an anti-tumor immune response.

In another embodiment, *Listeria* strain exerts strong and antigen specific anti-tumor responses with ability to break tolerance toward a peptide antigen.

In one embodiment, the dal/dat/actA strain is highly attenuated and has a better safety profile than previous *Listeria* vaccine generation, as it is more rapidly cleared from the spleens of the immunized mice. In another embodiment, the *Listeria* strain causes a significant decrease in intra-tumoral T regulatory cells (Tregs). In another embodiment, the lower frequency of Tregs in tumors treated with LmddA vaccines result in an increased intratumoral CD8/Tregs ratio, suggesting that a more favorable tumor microenvironment can be obtained after immunization with LmddA vaccines.

In one embodiment, the term "peptide antigen" is used interchangeably with the following terms, "antigen," "antigen fragment," "antigenic peptide," or "antigen peptide." It will be understood by a skilled artisan that the term "peptide antigen" encompasses a heterologous antigen or fragment thereof capable of eliciting an immune response when presented in the context of a major histocompatibility complex (MHC) molecule to an antigen presenting cell (APC).

Protein and/or peptide homology for any amino acid sequence listed herein is determined, in one embodiment, by methods well described in the art, including immunoblot analysis, or via computer algorithm analysis of amino acid sequences, utilizing any of a number of software packages available, via established methods. Some of these packages may include the FASTA, BLAST, MPsrch or Scanps packages, and may employ the use of the Smith and Waterman algorithms, and/or global/local or BLOCKS alignments for analysis, for example.

In another embodiment, the construct or nucleic acid molecule disclosed herein is integrated into the *Listeria* chromosome using homologous recombination. Techniques for homologous recombination are well known in the art, and are described, for example, in Baloglu S, Boyle S M, et al. (Immune responses of mice to vaccinia virus recombinants expressing either *Listeria monocytogenes* partial listeriolysin or *Brucella abortus* ribosomal L7/L12 protein. Vet Microbiol 2005, 109(1-2): 11-7); and Jiang L L, Song H H, et al., (Characterization of a mutant *Listeria monocytogenes* strain expressing green fluorescent protein. Acta Biochim Biophys Sin (Shanghai) 2005, 37(1): 19-24). In another embodiment, homologous recombination is performed as described in U.S. Pat. No. 6,855,320. In this case, a recombinant Lm strain that expresses E7 was made by chromosomal integration of the E7 gene under the control of the hly promoter and with the inclusion of the hly signal sequence to ensure secretion of the gene product, yielding the recombinant referred to as Lm-AZ/E7. In another embodiment, a temperature sensitive plasmid is used to select the recombinants.

In another embodiment, the construct or nucleic acid molecule is integrated into the Listerial chromosome using transposon insertion. Techniques for transposon insertion are well known in the art, and are described, inter alia, by Sun et al. (Infection and Immunity 1990, 58: 3770-3778) in the construction of DP-L967. Transposon mutagenesis has the advantage, in another embodiment, that a stable genomic insertion mutant can be formed but the disadvantage that the position in the genome where the foreign gene has been inserted is unknown.

In another embodiment, the construct or nucleic acid molecule is integrated into the Listerial chromosome using phage integration sites (Lauer P, Chow M Y et al, Construction, characterization, and use of two *Listeria monocytogenes* site-specific phage integration vectors. J Bacteriol 2002; 184(15): 4177-86). In certain embodiments of this method, an integrase gene and attachment site of a bacteriophage (e.g. U153 or PSA listeriophage) is used to insert the heterologous gene into the corresponding attachment site, which may be any appropriate site in the genome (e.g. comK or the 3' end of the arg tRNA gene). In another embodiment, endogenous prophages are cured from the attachment site utilized prior to integration of the construct or heterologous gene. In another embodiment, this method results in single-copy integrants. In another embodiment, the present disclosure further comprises a phage based chromosomal integration system for clinical applications, where a host strain that is auxotrophic for essential enzymes, including, but not limited to, d-alanine racemase can be used, for example Lmdal(-)dat(-). In another embodiment, in order to avoid a "phage curing step," a phage integration system based on PSA is used. This requires, in another embodiment, continuous selection by antibiotics to maintain the integrated gene. Thus, in another embodiment, the current disclosure enables the establishment of a phage based chromosomal integration system that does not require selection with antibiotics. Instead, an auxotrophic host strain can be complemented.

In one embodiment of the methods and compositions as disclosed herein, the term "recombination site" or "site-specific recombination site" refers to a sequence of bases in a nucleic acid molecule that is recognized by a recombinase (along with associated proteins, in some cases) that mediates exchange or excision of the nucleic acid segments flanking the recombination sites. The recombinases and associated proteins are collectively referred to as "recombination proteins" see, e.g., Landy, A., (Current Opinion in Genetics & Development) 3:699-707; 1993).

It will be appreciated by the skilled artisan that the term "vector" may encompass plasmids. In another embodiment, the term refers to an integration vector capable of being transformed into the *Listeria* host and being incorporated in the *Listeria's* chromosome in a manner that allows expression of the genes comprised by said vector. In another embodiment, the term refers to a non-integration vector that does not integrate in the *Listeria's* chromosome but instead is present in the cytoplasm of said *Listeria*. In another embodiment, the term refers to a plasmid comprising an integration vector. In another embodiment, the integration vector is a site-specific integration vector.

The skilled artisan, when equipped with the present disclosure and the methods disclosed herein, will readily understand that different transcriptional promoters, terminators, carrier vectors or specific gene sequences (e.g. those in commercially available cloning vectors) can be used successfully in methods and compositions of the present invention. As is contemplated in the present invention, these functionalities are provided in, for example, the commercially available vectors known as the pUC series. In another embodiment, non-essential DNA sequences (e.g. antibiotic resistance genes) are removed. In another embodiment, a commercially available plasmid is used in the present invention. Such plasmids are available from a variety of sources, for example, Invitrogen (La Jolla, Calif.), Stratagene (La Jolla, Calif.), Clontech (Palo Alto, Calif.), or can be constructed using methods well known in the art.

Another embodiment is a plasmid such as pCR2.1 (Invitrogen, La Jolla, Calif.), which is a prokaryotic expression vector with a prokaryotic origin of replication and promoter/regulatory elements to facilitate expression in a prokaryotic organism. In another embodiment, extraneous nucleotide sequences are removed to decrease the size of the plasmid and increase the size of the cassette that can be placed therein.

Such methods are well known in the art, and are described in, for example, Sambrook et al. (1989, Molecular Cloning: A Laboratory Manual, Cold Spring Harbor Laboratory Press, New York) and Ausubei et al. (1997, Current Protocols in Molecular Biology, Green & Wiley, New York).

Antibiotic resistance genes are used in the conventional selection and cloning processes commonly employed in molecular biology and vaccine preparation. Antibiotic resistance genes contemplated in the present disclosure include, but are not limited to, gene products that confer resistance to ampicillin, penicillin, methicillin, streptomycin, erythromycin, kanamycin, tetracycline, cloramphenicol (CAT), neomycin, hygromycin, gentamicin and others well known in the art.

Plasmids and other expression vectors useful in the present disclosure are described elsewhere herein, and can include such features as a promoter/regulatory sequence, an origin of replication for gram negative and gram positive bacteria, an isolated nucleic acid encoding a fusion protein and an isolated nucleic acid encoding an amino acid metabolism gene. Further, an isolated nucleic acid encoding a fusion protein and an amino acid metabolism gene will have a promoter suitable for driving expression of such an isolated nucleic acid. Promoters useful for driving expression in a bacterial system are well known in the art, and include bacteriophage lambda, the bla promoter of the beta-lactamase gene of pBR322, and the CAT promoter of the chloramphenicol acetyl transferase gene of pBR325. Further examples of prokaryotic promoters include the major right and left promoters of 5 bacteriophage lambda (PL and PR), the trp, recA, lacZ, lad, and gal promoters of *E. coli*, the alpha-amylase (Ulmanen et al, 1985. J. Bacteriol. 162:176-182) and the S28-specific promoters of *B. subtilis* (Gilman et al, 1984 Gene 32:11-20), the promoters of the bacteriophages of *Bacillus* (Gryczan, 1982, In: The Molecular Biology of the Bacilli, Academic Press, Inc., New York), and Streptomyces promoters (Ward et al, 1986, Mol. Gen. Genet. 203:468-478). Additional prokaryotic promoters contemplated in the present disclosure are reviewed in, for example, Glick (1987, J. Ind. Microbiol. 1:277-282); Cenatiempo, (1986, Biochimie, 68:505-516); and Gottesman, (1984, Ann. Rev. Genet. 18:415-442). Further examples of promoter/regulatory elements contemplated in the present disclosure include, but are not limited to the Listerial prfA promoter, the Listerial hly promoter, the Listerial p60 promoter and the Listerial ActA promoter (GenBank Acc. No. NC_003210) or fragments thereof.

In another embodiment, a plasmid of methods and compositions of the comprise subsequences that are cleaved and the appropriate subsequences cloned using appropriate restriction enzymes. The fragments are then, in another embodiment, ligated to produce the desired DNA sequence. In another embodiment, DNA encoding the antigen is produced using DNA amplification methods, for example polymerase chain reaction (PCR), a technique that is well known in the art.

A "phage expression vector" or "phagemid" refers to any phage-based recombinant expression system for the purpose of expressing a nucleic acid sequence of the methods and compositions as disclosed herein in vitro or in vivo, constitutively or inducibly, in any cell, including prokaryotic, yeast, fungal, plant, insect or mammalian cell. A phage expression vector typically can both reproduce in a bacterial cell and, under proper conditions, produce phage particles. The term includes linear or circular expression systems and encompasses both phage-based expression vectors that remain episomal or integrate into the host cell genome.

In another embodiment, the present disclosure further comprises a phage based chromosomal integration system for clinical applications. A host strain that is auxotrophic for essential enzymes, including, but not limited to, d-alanine racemase will be used, for example Lmdal(−)dat(−). In another embodiment, in order to avoid a "phage curing step," a phage integration system based on PSA is used (Lauer, et al., 2002 J Bacteriol, 184:4177-4186). This requires, in another embodiment, continuous selection by antibiotics to maintain the integrated gene. Thus, in another embodiment, the current disclosure enables the establishment of a phage based chromosomal integration system that does not require selection with antibiotics. Instead, an auxotrophic host strain will be complemented.

The chimeric proteins of the present disclosure are synthesized, in another embodiment, using recombinant DNA methodology. This involves, in one embodiment, creating a DNA sequence that encodes the chimeric protein, placing the DNA in an expression cassette, such as the plasmid of the present invention, under the control of a particular promoter/regulatory element, and expressing the protein. DNA encoding the chimeric protein (e.g. SS-Ub-peptide) of the present disclosure is prepared, in another embodiment, by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al.

(1981, Tetra. Lett., 22: 15 1859-1862); and the solid support method of U.S. Pat. No. 4,458,066.

In another embodiment, DNA encoding the chimeric protein or the recombinant protein of the present disclosure is cloned using DNA amplification methods such as polymerase chain reaction (PCR). In another embodiment, chemical synthesis is used to produce a single stranded oligonucleotide. This single stranded oligonucleotide is converted, in various embodiments, into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences can be obtained by the ligation of shorter sequences. In another embodiment, subsequences are cloned and the appropriate subsequences cleaved using appropriate restriction enzymes. The fragments are then ligated to produce the desired DNA sequence.

In one embodiment, nucleic acid sequences encoding chimeric proteins disclosed herein are transformed into a variety of host cells, including *E. coli*, other bacterial hosts, such as *Listeria*, yeast, and various higher eukaryotic cells such as the COS, CHO and HeLa cells lines and myeloma cell lines. Nucleic acid sequences encoding a chimeric protein disclosed herein are operably linked to appropriate expression control sequences for each host. Promoter/regulatory sequences are described in detail elsewhere herein. In another embodiment, the plasmid encoding a chimeric protein disclosed herein further comprises additional promoter regulatory elements, as well as a ribosome binding site and a transcription termination signal. For eukaryotic cells, the control sequences will include a promoter and an enhancer derived from e.g. immunoglobulin genes, SV40, cytomegalovirus, etc., and a polyadenylation sequence. In another embodiment, the sequences include splice donor and acceptor sequences.

In one embodiment, a plasmid disclosed herein comprises at least one ribosome binding site and at least one transcription termination signals that allow encoding of at least one chimeric protein as disclosed herein, each comprising a different peptide antigen. In one embodiment, the plasmid disclosed herein comprises 1 to 4 ribosome binding ribosome binding sites and 1 to 4 transcription termination signals that allow encoding of 1 to 4 chimeric proteins as disclosed herein, each comprising a different peptide antigen. In one embodiment, the plasmid disclosed herein comprises 5 to 10 ribosome binding ribosome binding sites and 5 to 10 transcription termination signals that allow encoding of 5 to 10 chimeric proteins as disclosed herein, each comprising a different peptide antigen. In one embodiment, the plasmid disclosed herein comprises 11 to 20 ribosome binding ribosome binding sites and 11 to 20 transcription termination signals that allow encoding of 11 to 20 chimeric proteins as disclosed herein, each comprising a different peptide antigen. In one embodiment, the plasmid disclosed herein comprises 21 to 30 ribosome binding ribosome binding sites and 21 to 30 transcription termination signals that allow encoding of 21 to 30 chimeric proteins as disclosed herein, each comprising a different peptide antigen. In another embodiment, the ribosome binding sites are shine dalgarno ribosome binding sites.

In one embodiment, the term "operably linked" means that the transcriptional and translational regulatory nucleic acid, is positioned relative to any coding sequences in such a manner that transcription is initiated. Generally, this will mean that the promoter and transcriptional initiation or start sequences are positioned 5' to the coding region. In another embodiment, the term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In another embodiment, the term "operably linked" refers to the joining of several open reading frames in a transcription unit each encoding a protein or peptide so as to result in expression of a chimeric protein or polypeptide that functions as intended.

In one embodiment, an "open reading frame" or "ORF" is a portion of an organism's genome which contains a sequence of bases that could potentially encode a protein. In another embodiment, the start and stop ends of the ORF are not equivalent to the ends of the mRNA, but they are usually contained within the mRNA. In one embodiment, ORFs are located between the start-code sequence (initiation codon) and the stop-codon sequence (termination codon) of a gene. Thus, as an example, a nucleic acid molecule operably integrated into a genome as an open reading frame with an endogenous polypeptide is a nucleic acid molecule that has integrated into a genome in the same open reading frame as an endogenous polypeptide.

In one embodiment, the present disclosure provides a fusion polypeptide comprising a linker sequence. It will be understood by a skilled artisan that a "linker sequence" may encompass an amino acid sequence that joins two heterologous polypeptides, or fragments or domains thereof. In general, a linker is an amino acid sequence that covalently links the polypeptides to form a fusion polypeptide. A linker typically includes the amino acids translated from the remaining recombination signal after removal of a reporter gene from a display vector to create a fusion protein comprising an amino acid sequence encoded by an open reading frame and the display protein. As appreciated by one of skill in the art, the linker can comprise additional amino acids, such as glycine and other small neutral amino acids.

In one embodiment, the term "endogenous" describes an item that has developed or originated within the reference organism or arisen from causes within the reference organism. For example, endogenous refers to native.

Recombinant or chimeric proteins disclosed herein may be prepared by any suitable method, including, for example, cloning and restriction of appropriate sequences or direct chemical synthesis by methods discussed below. Alternatively, subsequences may be cloned and the appropriate subsequences cleaved using appropriate restriction enzymes. The fragments may then be ligated to produce the desired DNA sequence. In one embodiment, DNA encoding the antigen can be produced using DNA amplification methods, for example polymerase chain reaction (PCR). First, the segments of the native DNA on either side of the new terminus are amplified separately. The 5' end of the one amplified sequence encodes the peptide linker, while the 3' end of the other amplified sequence also encodes the peptide linker. Since the 5' end of the first fragment is complementary to the 3' end of the second fragment, the two fragments (after partial purification, e.g. on LMP agarose) can be used as an overlapping template in a third PCR reaction. The amplified sequence will contain codons, the segment on the carboxy side of the opening site (now forming the amino sequence), the linker, and the sequence on the amino side of the opening site (now forming the carboxyl sequence). The antigen is ligated into a plasmid.

"Stably maintained" refers to maintenance of a nucleic acid molecule or plasmid in the absence of selection (e.g. antibiotic selection) for 10 generations, without detectable loss. In another embodiment, the period is 15 generations. In another embodiment, the period is 20 generations. In another embodiment, the period is 25 generations. In another embodiment, the period is 30 generations. In another embodiment, the period is 40 generations. In another embodiment, the period is 50 generations. In another embodiment, the period is 60 generations. In another embodiment, the period is 80 generations. In another embodiment, the period is 100 generations. In another embodiment, the period is 150 generations. In another embodiment, the period is 200 generations. In another embodiment, the period is 300 generations. In another embodiment, the period is 500 generations. In another embodiment, the period is more than generations. In another embodiment, the nucleic acid molecule or plasmid is maintained stably in vitro (e.g. in culture). In another embodiment, the nucleic acid molecule or plasmid is maintained stably in vivo. In another embodiment, the nucleic acid molecule or plasmid is maintained stably both in vitro and in vitro.

A "functional fragment" is an immunogenic fragment and elicits an immune response when administered to a subject alone or in a therapeutic composition disclosed herein. For example, a functional fragment has biological activity as will be understood by a skilled artisan and as further disclosed herein. As used herein, the term "functional fragment" is used interchangeably with the term "immunogenic fragment"

It will be understood by a skilled artisan that the term "immunogenicity," "immunogenic" or grammatical equivalents thereof may refer to an innate ability of a protein, peptide, nucleic acid, antigen or organism to elicit an immune response in a human or non-human animal when the protein, peptide, nucleic acid, antigen or organism is administered to the animal. Thus, "enhancing the immunogenicity," may refer to increasing the ability of a protein, peptide, nucleic acid, antigen or organism to elicit an immune response in an animal when the protein, peptide, nucleic acid, antigen or organism is administered to an animal. The increased ability of a protein, peptide, nucleic acid, antigen or organism to elicit an immune response can be measured by, in one embodiment, a greater number of antibodies to a protein, peptide, nucleic acid, antigen or organism, a greater diversity of antibodies to an antigen or organism, a greater number of T-cells specific for a protein, peptide, nucleic acid, antigen or organism, a greater cytotoxic or helper T-cell response to a protein, peptide, nucleic acid, antigen or organism, and the like.

The recombinant *Listeria* strain of methods and compositions of the present disclosure is, in another embodiment, a recombinant *Listeria monocytogenes* strain. In another embodiment, the *Listeria* strain is a recombinant *Listeria seeligeri* strain. In another embodiment, the *Listeria* strain is a recombinant *Listeria grayi* strain. In another embodiment, the *Listeria* strain is a recombinant *Listeria ivanovii* strain. In another embodiment, the *Listeria* strain is a recombinant *Listeria murrayi* strain. In another embodiment, the *Listeria* strain is a recombinant *Listeria welshimeri* strain. In another embodiment, the *Listeria* strain is a recombinant strain of another *Listeria* species.

In one embodiment, attenuated *Listeria* strains, such as LM delta-actA mutant (Brundage et al, 1993, Proc. Natl. Acad. Sci., USA, 90:11890-11894), *L. monocytogenes* delta-plcA (Camilli et al, 1991, J. Exp. Med., 173:751-754), or delta-ActA, delta INL-b (Brockstedt et 5 al, 2004, PNAS, 101:13832-13837) are used in the present invention. In another embodiment, attenuated *Listeria* strains are constructed by introducing one or more attenuating mutations, as will be understood by one of average skill in the art when equipped with the disclosure herein. Examples of such strains include, but are not limited to *Listeria* strains auxotrophic for aromatic amino acids (Alexander et al, 1993, Infection and Immunity 10 61:2245-2248) and mutant for the formation of lipoteichoic acids (Abachin et al, 2002, Mol. Microbiol. 43:1-14) and those attenuated by a lack of a virulence gene (see examples herein).

In another embodiment, a recombinant *Listeria* strain of the present disclosure has been passaged through an animal host. In another embodiment, the passaging maximizes efficacy of the strain as a vaccine vector. In another embodiment, the passaging stabilizes the immunogenicity of the *Listeria* strain. In another embodiment, the passaging stabilizes the virulence of the *Listeria* strain. In another embodiment, the passaging increases the immunogenicity of the *Listeria* strain. In another embodiment, the passaging increases the virulence of the *Listeria* strain. In another embodiment, the passaging removes unstable sub-strains of the *Listeria* strain. In another embodiment, the passaging reduces the prevalence of unstable sub-strains of the *Listeria* strain. In another embodiment, the passaging is performed as described herein. In another embodiment, the passaging is performed by other methods known in the art.

In one embodiment, a *Listeria* strain contains a genomic insertion of a minigene nucleic acid construct disclosed herein. In another embodiment, a *Listeria* strain carries a plasmid comprising a minigene nucleic acid construct disclosed herein.

In another embodiment, a recombinant nucleic acid of the present disclosure is operably linked to a promoter/regulatory sequence that drives expression of the encoded peptide in the *Listeria* strain. Promoter/regulatory sequences useful for driving constitutive expression of a gene are well known in the art and include, but are not limited to, for example, the $P_{hlyA}$, $P_{ActA}$, and p60 promoters of *Listeria*, the *Streptococcus* bac promoter, the *Streptomyces griseus* sgiA promoter, and the *B. thuringiensis* phaZ promoter.

In another embodiment, inducible and tissue specific expression of the nucleic acid encoding a peptide of the present disclosure is accomplished by placing the nucleic acid encoding the peptide under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In another embodiment, a promoter that is induced in response to inducing agents such as metals, glucocorticoids, and the like, is utilized. Thus, it will be appreciated that the disclosure includes the use of any promoter/regulatory sequence, which is either known or unknown, and which is capable of driving expression of the desired protein operably linked thereto.

It will be appreciated by a skilled artisan that the term "heterologous" encompasses a nucleic acid, amino acid, peptide, polypeptide, peptide or protein derived from a different species than the reference species. Thus, for example, a *Listeria* strain expressing a heterologous polypeptide, in one embodiment, would express a polypeptide that is not native or endogenous to the *Listeria* strain, or in another embodiment, a polypeptide that is not normally expressed by the *Listeria* strain, or in another embodiment, a polypeptide from a source other than the *Listeria* strain. In another embodiment, heterologous may be used to describe something derived from a different organism within the same species.

It will be appreciated by the skilled artisan that the term "episomal expression vector" encompasses a nucleic acid vector which may be linear or circular, and which is usually double-stranded in form and is extrachromosomal in that it is present in the cytoplasm of a host bacteria or cell as opposed to being integrated into the bacteria's or cell's genome. In one embodiment, an episomal expression vector comprises a gene of interest. In another embodiment, episomal vectors persist in multiple copies in the bacterial cytoplasm, resulting in amplification of the gene of interest, which in one embodiment is a nucleic acid molecule or construct disclosed herein. In another embodiment, viral trans-acting factors are supplied when necessary. An episomal expression vector may be referred to as a plasmid herein. An "integrative plasmid" comprises sequences that target its insertion or the insertion of the gene of interest carried within into a host genome. In another embodiment, an inserted gene of interest is not interrupted or subjected to regulatory constraints which often occur from integration into cellular DNA. In another embodiment, the presence of the inserted heterologous gene does not lead to rearrangement or interruption of the cell's own important regions. In another embodiment, in stable transfection procedures, the use of episomal vectors often results in higher transfection efficiency than the use of chromosome-integrating plasmids (Belt, P. B. G. M., et al (1991) Efficient cDNA cloning by direct phenotypic correction of a mutant human cell line (HPRT2) using an Epstein-Barr virus-derived cDNA expression vector. Nucleic Acids Res. 19, 4861-4866; Mazda, O., et al. (1997) Extremely efficient gene transfection into lympho-hematopoietic cell lines by Epstein-Barr virus-based vectors. J. Immunol. Methods 204, 143-151). In one embodiment, the episomal expression vectors of the methods and compositions as disclosed herein may be delivered to cells in vivo, ex vivo, or in vitro by any of a variety of the methods employed to deliver DNA molecules to cells. The vectors may also be delivered alone or in the form of a pharmaceutical composition that enhances delivery to cells of a subject.

It will be appreciated by a skilled artisan that the term "fused" may encompass operable linkage by covalent bonding. In one embodiment, the term encompasses recombinant fusion (of nucleic acid sequences or open reading frames thereof). In another embodiment, the term encompasses chemical conjugation.

It is to be understood that the term "Transforming" may encompass engineering a bacterial cell to take up a plasmid or other heterologous DNA molecule. "Transforming" may also refer to engineering a bacterial cell to express a gene of a plasmid or other heterologous DNA molecule.

Methods for transforming bacteria are well known in the art, and include calcium-chloride competent cell-based methods, electroporation methods, bacteriophage-mediated transduction, chemical, and physical transformation techniques (de Boer et al, 1989, Cell 56:641-649; Miller et al, 1995, FASEB J., 9:190-199; Sambrook et al. 1989, Molecular Cloning: A Laboratory Manual, Cold Spring Harbor Laboratory, New York; Ausubel et al., 1997, Current Protocols in Molecular Biology, John Wiley & Sons, New York; Gerhardt et al., eds., 1994, Methods for General and Molecular Bacteriology, American Society for Microbiology, Washington, D.C.; Miller, 1992, A Short Course in Bacterial Genetics, Cold Spring Harbor Laboratory Press, Cold Spring Harbor, N.Y.) In another embodiment, the Listeria vaccine strain of the present disclosure is transformed by electroporation.

In another embodiment, conjugation is used to introduce genetic material and/or plasmids into bacteria. Methods for conjugation are well known in the art, and are described, for example, in Nikodinovic J. et al (A second generation snp-derived Escherichia coli-Streptomyces shuttle expression vector that is generally transferable by conjugation. Plasmid. 2006 November; 56(3):223-7) and Auchtung J M et al (Regulation of a Bacillus subtilis mobile genetic element by intercellular signaling and the global DNA damage response. Proc Natl Acad Sci USA. 2005 Aug. 30; 102(35): 12554-9).

It will be appreciated by a skilled artisan that the term "attenuation," may encompass a diminution in the ability of the bacterium to cause disease in an animal. In other words, the pathogenic characteristics of the attenuated Listeria strain have been lessened compared with wild-type Listeria, although the attenuated Listeria is capable of growth and maintenance in culture. Using as an example the intravenous inoculation of Balb/c mice with an attenuated Listeria, the lethal dose at which 50% of inoculated animals survive ($LD_{50}$) is preferably increased above the $LD_{50}$ of wild-type Listeria by at least about 10-fold, more preferably by at least about 100-fold, more preferably at least about 1,000 fold, even more preferably at least about 10,000 fold, and most preferably at least about 100,000-fold. An attenuated strain of Listeria is thus one which does not kill an animal to which it is administered, or is one which kills the animal only when the number of bacteria administered is vastly greater than the number of wild type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. The attenuated strains of the present disclosure are therefore environmentally safe in that they are incapable of uncontrolled replication.

Compositions

In another embodiment, disclosed herein is a pharmaceutical composition comprising a recombinant Listeria comprising a minigene nucleic acid construct encoding achimeric protein disclosed hereinand wherein administering the pharmaceutical composition to a subject having a disease, including a cancer, treats, ameliorates, said disease or said cancer. In another embodiment, disclosed herein is a pharmaceutical composition comprising the minigene nucleic acid construct encoding the chimeric protein disclosed herein. In another embodiment, the pharmaceutical composition is administered with an adjuvant.

In one embodiment, compositions of the present disclosure are immunogenic compositions. In one embodiment, compositions of the present disclosure induce a strong innate stimulation of interferon-gamma, which in one embodiment, has anti-angiogenic properties. In one embodiment, a Listeria of the present disclosure induces a strong innate stimulation of interferon-gamma, which in one embodiment, has anti-angiogenic properties (Dominiecki et al., Cancer Immunol Immunother. 2005 May; 54(5):477-88. Epub 2004 Oct. 6, incorporated herein by reference in its entirety; Beatty and Paterson, J. Immunol. 2001 Feb. 15; 166(4):2276-82, incorporated herein by reference in its entirety). In one embodiment, anti-angiogenic properties of Listeria are mediated by $CD4^+$ T cells (Beatty and Paterson, 2001). In another embodiment, anti-angiogenic properties of *Listeria* are mediated by CD8+ T cells. In another embodiment, IFN-gamma secretion as a result of *Listeria* vaccination is mediated by NK cells, NKT cells, Th 1 CD4+ T cells, TC1 CD8+ T cells, or a combination thereof.

In another embodiment, administration of compositions of the present disclosure induces production of one or more anti-angiogenic proteins or factors. In one embodiment, the anti-angiogenic protein is IFN-gamma. In another embodiment, the anti-angiogenic protein is pigment epithelium-derived factor (PEDF); angiostatin; endostatin; fms-like tyrosine kinase (sFlt)-1; or soluble endoglin (sEng). In one embodiment, a *Listeria* of the present disclosure is involved in the release of anti-angiogenic factors, and, therefore, in one embodiment, has a therapeutic role in addition to its role as a vector for introducing an antigen to a subject. In one embodiment, administration of the compositions of the present disclosure stimulates a Stimulator of Interferon Genes (STING) pathway in the host.

The immune response induced by methods and compositions as disclosed herein is, in another embodiment, a T cell response. In another embodiment, the immune response comprises a T cell response. In another embodiment, the response is a CD8+ T cell response. In another embodiment, the response comprises a CD8+ T cell response.

In another embodiment, the immune response elicited by methods and compositions of the present disclosure comprises a CD8+ T cell-mediated response. In another embodiment, the immune response consists primarily of a CD8+ T cell-mediated response. In another embodiment, the only detectable component of the immune response is a CD8+ T cell-mediated response.

In another embodiment, the immune response elicited by methods and compositions disclosed herein comprises a CD4+ T cell-mediated response. In another embodiment, the immune response consists primarily of a CD4+ T cell-mediated response. In another embodiment, the only detectable component of the immune response is a CD4+ T cell-mediated response. In another embodiment, the CD4+ T cell-mediated response is accompanied by a measurable antibody response against the antigen. In another embodiment, the CD4+ T cell-mediated response is not accompanied by a measurable antibody response against the antigen.

In another embodiment, the present disclosure provides a method of inducing a CD8+ T cell-mediated immune response in a subject against a subdominant CD8+ T cell epitope of an antigen.

In one embodiment, disclosed herein is a method of increasing intratumoral ratio of CD8+/T regulatory cells, wherein and in another embodiment, the method comprises the step of administering to the subject a composition comprising the chimeric protein, recombinant *Listeria*, or recombinant vector of the present invention.

In another embodiment, disclosed herein is a method of increasing intratumoral ratio of CD8+/T regulatory cells, wherein and in another embodiment, the method comprises the step of administering to the subject a composition comprising the chimeric protein, recombinant *Listeria*, or recombinant vector of the present invention.

In another embodiment, the immune response elicited by the methods and compositions disclosed herein comprises an immune response to at least one subdominant epitope of the native antigen. In another embodiment, the immune response does not comprise an immune response to a subdominant epitope. In another embodiment, the immune response consists primarily of an immune response to at least one subdominant epitope. In another embodiment, the only measurable component of the immune response is an immune response to at least one subdominant epitope.

In another embodiment, administration of compositions of the present disclosure increase the number of antigen-specific T cells. In another embodiment, administration of compositions activates co-stimulatory receptors on T cells. In another embodiment, administration of compositions induces proliferation of memory and/or effector T cells. In another embodiment, administration of compositions increases proliferation of T cells.

Compositions of this disclosure may be used in methods of this disclosure in order to elicit an enhanced anti-tumor T cell response in a subject, in order to inhibit tumor-mediated immunosuppression in a subject, or for increasing the ratio or T effector cells to regulatory T cells ($T_{regs}$) in the spleen and tumor of a subject, or any combination thereof.

In another embodiment, a composition comprising a *Listeria* strain of the present invention, further comprises an adjuvant. In one embodiment, a composition of the present disclosure further comprises an adjuvant. The adjuvant utilized in methods and compositions of the present disclosure is, in another embodiment, a granulocyte/macrophage colony-stimulating factor (GM-CSF) protein. In another embodiment, the adjuvant comprises a GM-CSF protein. In another embodiment, the adjuvant is a nucleotide molecule encoding GM-CSF. In another embodiment, the adjuvant comprises a nucleotide molecule encoding GM-CSF. In another embodiment, the adjuvant is saponin QS21. In another embodiment, the adjuvant comprises saponin QS21. In another embodiment, the adjuvant is monophosphoryl lipid A. In another embodiment, the adjuvant comprises monophosphoryl lipid A. In another embodiment, the adjuvant is SBAS2. In another embodiment, the adjuvant comprises SBAS2. In another embodiment, the adjuvant is an unmethylated CpG-containing oligonucleotide. In another embodiment, the adjuvant comprises an unmethylated CpG-containing oligonucleotide. In another embodiment, the adjuvant is an immune-stimulating cytokine. In another embodiment, the adjuvant comprises an immune-stimulating cytokine. In another embodiment, the adjuvant is a nucleotide molecule encoding an immune-stimulating cytokine. In another embodiment, the adjuvant comprises a nucleotide molecule encoding an immune-stimulating cytokine. In another embodiment, the adjuvant is or comprises a quill glycoside. In another embodiment, the adjuvant is or comprises a bacterial mitogen. In another embodiment, the adjuvant is or comprises a bacterial toxin. Other adjuvants are known in the art.

In one embodiment, the present disclosure provides a recombinant *Listeria* strain expressing the peptide antigen. In another embodiment, the present disclosure provides vaccines and immunogenic compositions comprising the recombinant *Listeria* disclosed herein. In another embodiment, the present disclosure provides pharmaceutical compositions comprising the recombinant *Listeria* disclosed herein.

In one embodiment, an immunogenic composition of this disclosure comprises a recombinant *Listeria* strain comprising a nucleic acid molecule encoding the chimeric protein disclosed herein.

In some embodiments, an additional polypeptide or an additional adjuvant polypeptide augments antigen presentation and immunity in a similar fashion to LLO.

In one embodiment, the pharmaceutical compositions disclosed herein are co-administered with an additional therapy. In another embodiment, the additional therapy is surgery, chemotherapy, radiotherapy, an immunotherapy or a combination thereof. In another embodiment, the additional therapy precedes administration of the pharmaceutical composition comprising the recombinant *Listeria*. In another embodiment, the additional therapy follows administration of the pharmaceutical composition comprising the recombinant *Listeria*. In another embodiment, the additional therapy is an antibody therapy. In another embodiment, the antibody therapy is an anti-PD1, anti-CTLA4. In another embodiment, the pharmaceutical composition comprising the recombinant *Listeria* is administered in increasing doses in order to increase the T-effector cell to regulatory T cell ration and generate a more potent anti-tumor immune response. It will be appreciated by a skilled artisan that the anti-tumor immune response can be further strengthened by providing the subject having a tumor with cytokines including, but not limited to IFN-γ, TNF-α, and other cytokines known in the art to enhance cellular immune response, some of which can be found in U.S. Pat. No. 6,991,785, incorporated by reference herein.

In one embodiment, disclosed herein is a vaccine comprising a recombinant *Listeria* of the present invention. In another embodiment, disclosed herein is a vaccine comprising a recombinant attenuated *Listeria* expressing a minigene construct of the present invention.

In another embodiment, disclosed herein is a pharmaceutical composition comprising a recombinant *Listeria* of the present invention. In another embodiment, disclosed herein is a pharmaceutical composition comprising a recombinant attenuated *Listeria* expressing a minigene construct of the present invention.

In another embodiment, disclosed herein is an immunogenic composition comprising a recombinant polypeptide or a nucleic acid construct encoding the same or a recombinant *Listeria* encoding the nucleic acid construct of the present invention.

In another embodiment, disclosed herein is a pharmaceutical composition comprising a nucleotide molecule or recombinant polypeptide of the present invention.

In another embodiment, disclosed herein is a vector comprising a nucleotide molecule or recombinant polypeptide of the present invention.

In another embodiment, disclosed herein is a recombinant form of *Listeria* comprising a nucleotide molecule of the present invention.

In another embodiment, disclosed herein is a vaccine comprising a recombinant form of *Listeria* of the present invention. In another embodiment, disclosed herein is a pharmaceutical composition comprising a recombinant form of *Listeria* of the present invention.

In another embodiment, disclosed herein is a culture of a recombinant form of *Listeria* of the present invention.

In another embodiment, the *Listeria* of methods and compositions of the present disclosure is *Listeria monocytogenes*. In another embodiment, the *Listeria* is *Listeria ivanovii*. In another embodiment, the *Listeria* is *Listeria welshimeri*. In another embodiment, the *Listeria* is *Listeria seeligeri*. Antigens The terms "antigen," "antigenic polypeptide," "antigen fragment," are used interchangeably herein and, as will be appreciated by a skilled artisan, may encompass polypeptides, or peptides (including recombinant peptides) that are loaded onto and presented on MHC class I and/or class II molecules on a host's cell's surface and can be recognized or detected by an immune cell of the host, thereby leading to the mounting of an immune response against the polypeptide, peptide or cell presenting the same. Similarly, the immune response may also extend to other cells within the host, including diseased cells such as tumor or cancer cells that express the same polypeptides or peptides.

It will also be appreciated by a skilled artisan that the terms "antigenic portion thereof", "a fragment thereof" and "immunogenic portion thereof" in regard to a protein, peptide or polypeptide are used interchangeably herein and may encompass a protein, polypeptide, peptide, including recombinant forms thereof comprising a domain or segment that leads to the mounting of an immune response when present in, or, in some embodiments, detected by, a host, either alone, or in the context of a fusion protein, as described herein.

It will be appreciated by a skilled artisan that the term "heterologous" encompasses a nucleic acid, amino acid, peptide, polypeptide, or protein derived from a different species than the reference species. Thus, for example, a *Listeria* strain expressing a heterologous polypeptide, in one embodiment, would express a polypeptide that is not native or endogenous to the *Listeria* strain, or in another embodiment, a polypeptide that is not normally expressed by the *Listeria* strain, or in another embodiment, a polypeptide from a source other than the *Listeria* strain. In another embodiment, heterologous may be used to describe something derived from a different organism within the same species. In another embodiment, the heterologous antigen is expressed by a recombinant strain of *Listeria*, and is processed and presented to cytotoxic T-cells upon infection of mammalian cells by the recombinant strain. In another embodiment, the heterologous antigen expressed by *Listeria* species need not precisely match the corresponding unmodified antigen or protein in the tumor cell or infectious agent so long as it results in a T-cell response that recognizes the unmodified antigen or protein which is naturally expressed in the mammal. In one embodiment, the term "antigenic polypeptide", "protein antigen", "antigen", are used interchangeably herein.

In one embodiment, an antigen may be foreign, that is, heterologous to the host and is referred to as a "heretologous antigen" herein. In another embodiment, the antigen is a self-antigen, which is an antigen that is present in the host but the host does not elicit an immune response against it because of immunologic tolerance. It will be appreciated by a skilled artisan that a heterologous antigen as well as a self-antigen may encompass a tumor antigen, a tumor-associated antigen or an angiogenic antigen. In addition, a heterologous antigen may encompass an infectious disease antigen. In another embodiment, the antigen is an angiogenic antigen.

In one embodiment, a peptide disclosed herein is derived from a tumor-associated antigen. In one embodiment, the tumor-associated antigen is selected from HPV-E7, HPV-E6, Her-2, NY-ESO-1, a high molecular weight melanoma-associated (HMW-MAA) antigen or fragment thereof, hepsin, survivin, PSG4, a VEGFR-2 fragment, survivin, a B-cell receptor antigen, Tyrosinase related protein 2, or a PSA (prostate-specific antigen) or a combination thereof. In another embodiment, the antigen is an infectious disease antigen such as is HIV-1 Gag, a MAGE (Melanoma-Associated Antigen E) protein, e.g. MAGE 1, MAGE 2, MAGE 3, MAGE 4, a tyrosinase; a mutant ras protein; a mutant p53 protein; p97 melanoma antigen, a ras peptide or p53 peptide associated with advanced cancers; the HPV 16/18 antigens associated with cervical cancers, KLH antigen associated with breast carcinoma, carcinoembryonic antigen (CEA), gp100, a MART1 antigen associated with melanoma, interleukin-13 receptor alpha (IR13-R alpha), a telomerase (TERT), stratum corneum chymotryptic enzyme (SCCE)

antigen, CEA, LMP-1, p53, proteinase 3, synovial sarcoma, carbonic anhydrase IX (CAIX), survivin, GP100, testisin peptide, PSMA, prostate stem cell antigen (PSCA), or wilm's tumor (WT-1) antigen. It is to be understood that fragments of any antigen disclosed herein or disclosed in the art are also encompassed by the present invention.

In one embodiment, the disease disclosed herein is an infectious disease. In one embodiment, the infectious disease is one caused by, but not limited to, any one of the following pathogens: leishmania, Entamoeba histolytica (which causes amebiasis), trichuris, BCG/Tuberculosis, Malaria, Plasmodium falciparum, Plasmodium malariae, Plasmodium vivax, Rotavirus, Cholera, Diptheria-Tetanus, Pertussis, Haemophilus influenzae, Hepatitis B, Human papilloma virus, Influenza seasonal), Influenza A (H1N1) Pandemic, Measles and Rubella, Mumps, Meningococcus A+C, Oral Polio Vaccines, mono, bi and trivalent, Pneumococcal, Rabies, Tetanus Toxoid, Yellow Fever, Bacillus anthracis (anthrax), Clostridium botulinum toxin (botulism), Yersinia pestis (plague), Variola major (smallpox) and other related pox viruses, Francisella tularensis (tularemia), Viral hemorrhagic fevers, Arenaviruses (LCM, Junin virus, Machupo virus, Guanarito virus, Lassa Fever), Bunyaviruses (Hantaviruses, Rift Valley Fever), Flaviruses (Dengue), Filoviruses (Ebola, Marburg), Burkholderia pseudomallei, Coxiella burnetii (Q fever), Brucella species (brucellosis), Burkholderia mallei (glanders), Chlamydia psittaci (Psittacosis), Ricin toxin (from Ricinus communis), Epsilon toxin of Clostridium perfringens, Staphylococcus enterotoxin B, Typhus fever (Rickettsia prowazekii), other Rickettsias, Food- and Waterborne Pathogens, Bacteria (Diarrheagenic E. coli, Pathogenic Vibrios, Shigella species, Salmonella BCG/, Campylobacter jejuni, Yersinia enterocolitica), Viruses (Caliciviruses, Hepatitis A, West Nile Virus, LaCrosse, Calif. encephalitis, VEE, EEE, WEE, Japanese Encephalitis Virus, Kyasanur Forest Virus, Nipah virus, hantaviruses, Tickborne hemorrhagic fever viruses, Chikungunya virus, Crimean-Congo Hemorrhagic fever virus, Tickborne encephalitis viruses, Hepatitis B virus, Hepatitis C virus, Herpes Simplex virus (HSV), Human immunodeficiency virus (HIV), Human papillomavirus (HPV)), Protozoa (Cryptosporidium parvum, Cyclospora cayatanensis, Giardia lamblia, Entamoeba histolytica, Toxoplasma), Fungi (Microsporidia), Yellow fever, Tuberculosis, including drug-resistant TB, Rabies, Prions, Severe acute respiratory syndrome associated coronavirus (SARS-CoV), Coccidioides posadasii, Coccidioides immitis, Bacterial vaginosis, Chlamydia trachomatis, Cytomegalovirus, Granuloma inguinale, Hemophilus ducreyi, Neisseria gonorrhea, Treponema pallidum, Trichomonas vaginalis, or any other infectious disease known in the art that is not listed herein.

In one embodiment, pathogenic protozoans and helminths infections include: amebiasis; malaria; leishmaniasis; trypanosomiasis; toxoplasmosis; Pneumocystis carinii; babesiosis; giardiasis; trichinosis; filariasis; schistosomiasis; nematodes; trematodes or flukes; and cestode (tapeworm) infections.

In one embodiment an HPV antigen such as an E6 or E7 antigen disclosed herein is selected from an HPV 6 strain, and HPV 11 strain, HPV 16 strain, an HPV-18 strain, an HPV-31 strain, an HPV-35 strain, an HPV-39 strain, an HPV-45 strain, an HPV-51 strain an HPV-52 strain, an HPV-58 strain or an HPV-59 strain. In another embodiment, the HPV antigen is selected from a high-risk HPV strain. In another embodiment, the HPV strain is a mucosal HPV type. In another embodiment, HPV antigens can be selected from all HPV strains, including non oncogenic HPVs such as type 6, 11, etc. that cause warts and dysplasia.

In one embodiment, an HPV-16 E6 and E7 is utilized instead of or in combination with an HPV-18 E6 and E7. In such an embodiment, the recombinant Listeria may express the HPV-16 E6 and E7 from the chromosome and the HPV-18 E6 and E7 from a plasmid, or vice versa. In another embodiment, the HPV-16 E6 and E7 antigens and the HPV-18 E6 and E7 antigens are expressed from a plasmid present in a recombinant Listeria disclosed herein. In another embodiment, the HPV-16 E6 and E7 antigens and the HPV-18 E6 and E7 antigens are expressed from the chromosome of a recombinant Listeria disclosed herein. In another embodiment, the HPV-16 E6 and E7 antigens and the HPV-18 E6 and E7 antigens are expressed in any combination of the above embodiments, including where each E6 and E7 antigen from each HPV strain is expressed from either the plasmid or the chromosome.

In one embodiment, the antigen is a chimeric Her2 antigen described in U.S. patent application Ser. No. 12/945, 386, which is hereby incorporated by reference herein in its entirety.

In other embodiments, the antigen is associated with one of the following diseases; cholera, diphtheria, Haemophilus, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and listeriosis.

In another embodiment, the condition disclosed herein is a dysplasia. In another embodiment, the disease is a neoplasia. In another embodiment, the disease is anal intraepithelial neoplasia (AIN). In another embodiment, the disease is vaginal intraepithelial neoplasia (VIN). In another embodiment, the disease is a cervical intraepithelial neoplasia (CIN).

In another embodiment, a condition disclosed herein is a pre-malignant condition or a condition that proceeds to develop into a disease, chronic or acute, if left untreated.

In another embodiment, a tumor-associated antigen disclosed herein is an angiogenic antigen which is expressed on both activated pericytes and pericytes in tumor angiogeneic vasculature, which is associated with neovascularization in vivo. Angiogenic antigens are known in the art see for example WO2010/102140, which is incorporated by reference herein. For example, an angiogenic factor may be selected from; Angiopoietin-1 (Ang 1), Angiopoietin 3, Angiopoietin 4, Angiopoietin 6; Del-1; Fibroblast growth factors: acidic (aFGF) and basic (bFGF); Follistatin; Granulocyte colony-stimulating factor (G-CSF); Hepatocyte growth factor (HGF)/scatter factor (SF); Interleukin-8 (IL-8); Leptin; Midkine; Placental growth factor; Platelet-derived endothelial cell growth factor (PD-ECGF); Platelet-derived growth factor-BB (PDGF-BB); Pleiotrophin (PTN); Progranulin; Proliferin; survivin; Transforming growth factor-alpha (TGF-alpha); Transforming growth factor-beta (TGF-beta); Tumor necrosis factor-alpha (TNF-alpha); Vascular endothelial growth factor (VEGF)/vascular permeability factor (VPF). In another embodiment, an angiogenic factor is an angiogenic protein. In one embodiment, a growth factor is an angiogenic protein. In one embodiment, an angiogenic protein for use in the compositions and methods of the present invention is Fibroblast growth factors (FGF); VEGF; VEGFR and Neuropilin 1 (NRP-1); Tie2; Platelet-derived growth factor (PDGF; BB-homodimer) and PDGFR; Transforming growth factor-beta (TGF-β), endoglin and TGF-β receptors; monocyte chemotactic protein-1 (MCP-1); Integrins αVβ3, αVβ5 and α5β1; VE-cadherin and CD31; ephrin; plasminogen activators; plasminogen activator inhibitor-1; Nitric oxide synthase (NOS) and COX-2; AC133; or Id1/Id3, a TGFbeta co-receptor or endoglin (which is also known as CD105; EDG; HHT1; ORW; or ORW1).

In one embodiment, neoepitopes are generated and obtained as disclosed in any one of the following US applications (U.S. Ser. No. 62/166,591; U.S. Ser. No. 62/174,692; U.S. Ser. No. 62/218,936; U.S. Ser. No. 62/184,125, which are all incorporated by reference herein in their entirety.

In one embodiment, disclosed herein is a method of preventing persistence of a *Listeria* strain on a tissue within a subject following administration of a *Listeria*-based immunotherapy regimen, the method comprising the step of administering an effective amount of a regimen of antibiotics following administration of said recombinant *Listeria*-based immunotherapy, thereby preventing said persistence of said *Listeria* strain within said subject.

In another embodiment, the *Listeria* strain comprises a nucleic acid molecule comprising an open reading frame encoding one or more peptides encoding one or more neoepitopes, wherein said one or more peptides are fused to an immunogenic protein or peptide. In another embodiment an immunogenic protein or peptide comprises a truncated LLO (tLLO), truncated ActA (tActA), or PEST amino acid sequence peptide.

In one embodiment, disclosed herein is a recombinant attenuated *Listeria* strain, wherein the *Listeria* strain comprises a nucleic acid sequence comprising one or more open reading frames encoding one or more peptides comprising one or more personalized neo-epitopes, wherein the neo-epitope(s) comprises immunogenic epitopes present in a disease or condition-bearing tissue or cell of a subject having the disease or condition. In another embodiment, one or more neoepitopes are present in a disease or condition-bearing tissue or cell of a subject having the disease or condition.

In another embodiment, administrating the *Listeria* strain to a subject having said disease or condition generates an immune response targeted to the subject's disease or condition.

In another embodiment, the strain is a personalized immunotherapy vector for said subject targeted to said subject's disease or condition.

In another embodiment, the peptides comprise at least two different neo-epitopes amino acid sequences.

In another embodiment, the peptides comprise one or more neo-epitopes repeats of the same amino acid sequence.

In another embodiment, the *Listeria* strain comprises one neo-epitope. In another embodiment, the *Listeria* strain comprises the neo-epitopes in the range of about 1-100. Alternatively, the *Listeria* strain comprises the neo-epitopes in the range of about 1-5, 5-10, 10-15, 15-20, 10-20, 20-30, 30-40, 40-50, 50-60, 60-70, 70-80, 80-90, 90-100, 5-15, 5-20, 5-25, 15-20, 15-25, 15-30, 15-35, 20-25, 20-35, 20-45, 30-45, 30-55, 40-55, 40-65, 50-65, 50-75, 60-75, 60-85, 70-85, 70-95, 80-95, 80-105 or 95-105. Alternatively, the *Listeria* strain comprises the neo-epitopes in the range of about 50-100. Alternatively, the *Listeria* strain comprises up to about 100 the neo-epitopes.

In another embodiment, the *Listeria* strain comprises above about 100 the neo-epitopes. In another embodiment, the *Listeria* strain comprises up to about 10 the neo-epitopes. In another embodiment, the *Listeria* strain comprises up to about 20 the neo-epitopes. In another embodiment, the *Listeria* strain comprises up to about 50 the neo-epitopes. Alternatively, the *Listeria* strain comprises about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 the neo-epitopes.

In one embodiment described herein, incorporation of amino acids in the range of about 5-30 amino acids flanking on each side of the detected mutation are generated. Additionally or alternatively, varying sizes of neo-epitope inserts are inserted in the range of about 8-27 amino acid sequence long. Additionally or alternatively, varying sizes of neo-epitope inserts are inserted in the range of about 5-50 amino acid sequence long.

In another embodiment, the neo-epitope sequences are tumor specific, metastases specific, bacterial infection specific, viral infection specific, and any combination thereof. Additionally or alternatively, the neo-epitope sequences are inflammation specific, immune regulation molecule epitope specific, T-cell specific, an autoimmune disease specific, Graft-versus-host disease (GvHD) specific, and any combination thereof.

In another embodiment, one or more neo-epitopes comprise linear neo-epitopes. Additionally or alternatively, one or more neo-epitopes comprise a solvent-exposed epitope.

In another embodiment, one or more neo-epitopes comprise a T-cell epitope.

Therapeutic Methods and Compositions of Use Thereof

In another embodiment, the present disclosure provides an immunogenic composition as described above, for treating a disease or condition, including a tumor or cancer. For example, an immunogenic composition used in a method of this disclosure comprises a *Listeria* strain expressing a minigene nucleic acid construct as described herein.

In one embodiment, the condition disclosed herein is a dysplasia. In another embodiment, the disease is a neoplasia.

In another embodiment, the disease is anal intraepithelial neoplasia (AIN). In another embodiment, the disease is vaginal intraepithelial neoplasia (VIN). In another embodiment, the disease is a cervical intraepithelial neoplasia (CIN).

In another embodiment, a condition disclosed herein is a pre-malignant condition or a condition that proceeds to develop into a disease, chronic or acute, if left untreated.

In one embodiment, the cancer disclosed herein is a breast cancer, a central nervous system (CNS) cancer, a head and neck cancer, an osteosarcoma (OSA), a canine osteosarcoma (OSA), a colorectal cancer, a renal cell carcinoma, a pancreatic ductal adenocarcinoma, Ewing's sarcoma (ES), a pancreatic cancer, an ovarian cancer, a gastric cancer, a carcinomatous lesion of the pancreas, a pulmonary adenocarcinoma, a colorectal adenocarcinoma, a pulmonary squamous adenocarcinoma, a gastric adenocarcinoma, an ovarian surface epithelial neoplasm (e.g. a benign, proliferative or malignant variety thereof, an oral squamous cell carcinoma, a non-small-cell lung carcinoma, a CNS carcinoma, an endometrial carcinoma, a bladder cancer, a mesothelioma, a malignant mesothelioma (MM, a prostate carcinoma, a melanoma or any other cancer known in the art. In another embodiment, the cancer is lymphoma, leukemia, or myeloma. In another embodiment, the lymphoma is a Hodgkin's Lymphoma. In another embodiment, the lymphoma is non-Hodgkin's Lymphoma. In another embodiment, the cancer is a multiple melanoma.

In yet another embodiment, the cancer is acute lymphocytic leukemia (ALL). In another embodiment, the cancer is acute myeloid leukemia (AML). In another embodiment, the cancer is chronic lymphocytic leukemia (CLL). In another embodiment, the cancer is hairy cell leukemia (HCL). In another embodiment, the cancer is T-cell prolymphocytic leukemia (T-PLL). In another embodiment, the cancer is large granular lymphocytic leukemia. In another embodiment, the cancer is Adult T-cell leukemia. In another embodiment, the cancer is chronic myeloid leukemia (CML). In another embodiment, the cancer is chronic myelomonocytic leukemia (CMML). In another embodiment, the cancer is a lymphoma. In another embodiment, the cancer is cutaneous lymphoma. In another embodiment, the cancer is Hodgkin Disease. In another embodiment, the cancer is Non-Hodgkin Lymphoma (NHL). In another embodiment, the cancer is a low-grade NHL. In another embodiment, the cancer is diffuse large B cell lymphoma. In another embodiment, the cancer is low-grade NHL. In another embodiment, the cancer is precursor T cell lymphoma. In another embodiment, the cancer is peripheral T cell lymphoma. In another embodiment, the cancer is peripheral mantle cell lymphoma. In another embodiment, the cancer is multiple myeloma. In another embodiment, the cancer is follicular lymphoma. In another embodiment, the cancer is an immunoproliferative disease. In another embodiment, the cancer is B cell chronic lymphocytic leukemia. In another embodiment, the cancer is Burkitt lymphoma. In another embodiment, the cancer is MALT lymphoma. In another embodiment, the cancer is mycosis fungoides. In another embodiment, the cancer is nodular sclerosis. In another embodiment, the cancer is a low-grade lymphoma. In another embodiment, the cancer is residual disease from one of the above types of lymphoma or leukemia. In another embodiment, the cancer is any other type of lymphoma or leukemia known in the art. In another embodiment, the cancer is any other known type of lymphoma that expresses survivin. In another embodiment, the cancer is Myelodysplastic Syndrome. In another embodiment, the cancer is any survivin-expressing blood cancer. In another embodiment, said cancer or solid tumor is a result of relapse or metastatic disease. In another embodiment, the cancer is refractory. In another embodiment, the cancer is advanced. In another embodiment, the cancer is a metastasis.

In another embodiment, the tumor is an osteosarcoma tumor, a breast tumor, a head and neck tumor or any other tumor that can progress to any cancer disclosed herein and known in the art.

In another embodiment, cells of the tumor that is targeted by methods and compositions of the present disclosure express an antigen associated with a peptide expressed by the recombinant *Listeria* strain disclosed herein. In another embodiment, the peptide antigen is associated with an angiogenic tumor antigen (for example HMW-MAA). Following the administration of the immunogenic compositions disclosed herein, the methods disclosed herein induce the expansion of T effector cells in peripheral lymphoid organs leading to an enhanced presence of T effector cells at the tumor site. In another embodiment, the methods disclosed herein induce the expansion of T effector cells in peripheral lymphoid organs leading to an enhanced presence of T effector cells at the periphery. Such expansion of T effector cells leads to an increased ratio of T effector cells to regulatory T cells in the periphery and at the tumor site without affecting the number of Tregs. It will be appreciated by the skilled artisan that peripheral lymphoid organs include, but are not limited to, the spleen, peyer's patches, the lymph nodes, the adenoids, etc. In one embodiment, the increased ratio of T effector cells to regulatory T cells occurs in the periphery without affecting the number of Tregs. In another embodiment, the increased ratio of T effector cells to regulatory T cells occurs in the periphery, the lymphoid organs and at the tumor site without affecting the number of Tregs at these sites. In another embodiment, the increased ratio of T effector cells decreases the frequency of Tregs, but not the total number of Tregs at these sites.

In another embodiment, disclosed herein is a method of preventing a cancer in a subject, the method comprising the step of administering a recombinant *Listeria* comprising a minigene nucleic acid construct encoding a chimeric protein, wherein said chimeric protein comprises a tumor antigen-associated peptide. In another embodiment, disclosed herein is a method of preventing a tumor growth in a subject, the method comprising the step of administering a composition comprising recombinant *Listeria* comprising a minigene nucleic acid construct encoding a chimeric protein, wherein said chimeric protein comprises a tumor antigen-associated peptide.

In one embodiment, disclosed herein is a method of treating a cancer in a subject, the method comprising the step of administering a composition comprising a recombinant *Listeria* comprising a minigene nucleic acid construct encoding a chimeric protein, wherein said chimeric protein comprises a tumor antigen-associated peptide. In one embodiment, disclosed herein is a method of treating a tumor growth in a subject, the method comprising the step of administering a recombinant *Listeria* comprising a minigene nucleic acid construct encoding a chimeric protein, wherein said chimeric protein comprises a tumor antigen-associated peptide.

In one embodiment, disclosed herein is a method of prolonging the survival of a subject having a cancer, the method comprising the step of administering a composition comprising a recombinant *Listeria* comprising a minigene nucleic acid construct encoding a chimeric protein, wherein said chimeric protein comprises a tumor antigen-associated peptide. In one embodiment, disclosed herein is a method of prolonging the survival of a subject having a tumor growth, the method comprising the step of administering a composition comprising a recombinant *Listeria* comprising a minigene nucleic acid construct encoding a chimeric protein, wherein said chimeric protein comprises a tumor antigen-associated peptide.

In one embodiment, disclosed herein is a method of inhibiting, impeding, or delaying metastatic disease in a subject having a disease, the method comprising the step of administering a composition comprising a recombinant *Listeria* comprising a minigene nucleic acid construct encoding a chimeric protein, wherein said chimeric protein comprises a peptide associated with said disease.In one embodiment, the present disclosure provides a method of inducing an anti-tumor or anti-cancer immune response in a subject, the method comprising administering to the subject a composition of the present invention.

In another embodiment, disclosed herein is a method of inducing regression of a tumor or cancer in a subject, the method comprising the step of administering to the subject a composition comprising a recombinant *Listeria* strain disclosed herein.

In one embodiment, disclosed herein is a method of decreasing the frequency of intra-tumoral T regulatory cells, the method comprising the step of administering to the subject a composition comprising a recombinant *Listeria* strain disclosed herein.

In one embodiment, disclosed herein is a method of decreasing the frequency of intra-tumoral myeloid derived suppressor cells, the method comprises the step of administering to the subject a composition comprising a recombinant *Listeria* strain disclosed herein.

In another embodiment, disclosed herein is a method of decreasing the frequency of myeloid derived suppressor cells (MDSCs), the method comprises the step of administering to the subject a composition comprising a recombinant *Listeria* vaccine strain disclosed herein.

In another embodiment, disclosed herein is a method of treating a metastatic tumor or cancer in a subject, the method comprising the step of administering to the subject a composition comprising a recombinant *Listeria* strain disclosed herein.

In one embodiment, methods of this disclosure break tolerance in a subject to a tumor or cancer in said subject, the method comprising the step of administering to the subject a composition comprising a recombinant *Listeria* strain disclosed herein.

In another embodiment, the present disclosure provides a method of impeding a growth of a tumor or cancer in a subject, the method comprises administering to the subject a subject a composition comprising the recombinant *Listeria* strain disclosed herein, thereby impeding a growth of a tumor or cancer in a subject.

In another embodiment, the present disclosure provides a method of reducing an incidence of cancer, comprising the step of administering a composition comprising a recombinant *Listeria* of the present invention. In another embodiment, the present disclosure provides a method of ameliorating cancer, comprising the step of administering a composition comprising a recombinant *Listeria* of the present invention.

In one embodiment, any composition disclosed herein comprising a *Listeria* strain described herein may be used in the methods of this invention.

In one embodiment, disclosed herein is a method of administering a composition of the present invention. In another embodiment, disclosed herein is a method of administering a vaccine comprising the recombinant *Listeria* of the present invention. In another embodiment, disclosed herein is a method of administering a recombinant polypeptide of the present invention. In another embodiment, disclosed herein is a method of administering a nucleic acid construct encoding a recombinant polypeptide of the present invention. In another embodiment, the administering is performed with a different attenuated bacterial vector. In another embodiment, the administering is performed with a different attenuated *Listeria* monocytogenes vector. In another embodiment, the administering is performed with a DNA vaccine (e.g. a naked DNA vaccine). In another embodiment, administration of a recombinant polypeptide of the present disclosure is performed by producing the protein recombinantly, then administering the recombinant protein to a subject.

In one embodiment, the present disclosure provides a method for "epitope spreading" of a tumor. In another embodiment, the immunization using the compositions and methods disclosed herein induce epitope spreading onto other tumors bearing antigens other than the antigen carried in the vaccine of the present invention. This results in an extension of the anti-tumor response onto the other tumors.

In another embodiment, the dominant epitope or subdominant epitope is dominant or subdominant, respectively, in the subject being treated. In another embodiment, the dominant epitope or subdominant epitope is dominant or subdominant in a population being treated.

In one embodiment, disclosed herein is a method of treating, suppressing, or inhibiting a cancer or a tumor growth in a subject by epitope spreading wherein and in another embodiment, said cancer is associated with expression of an antigen or fragment thereof comprised in the composition of the present invention. In another embodiment, the method comprises administering to said subject a composition comprising the recombinant polypeptide, recombinant *Listeria*, or recombinant vector of the present invention. In yet another embodiment, the subject mounts an immune response against the antigen-expressing cancer or the antigen-expressing tumor, thereby treating, suppressing, or inhibiting a cancer or a tumor growth in a subject.

In one embodiment, the term "Dominant CD8$^+$ T cell epitope" or "Dominant epitope" refers to an epitope that is recognized by over 30% of the antigen-specific CD8$^+$ T cells that are elicited by vaccination, infection, or a malignant growth with a protein or a pathogen or cancer cell containing the protein. In another embodiment, the term refers to an epitope recognized by over 35% of the antigen-specific CD8$^+$ T cells that are elicited thereby. In another embodiment, the term refers to an epitope recognized by over 40% of the antigen-specific CD8$^+$ T cells. In another embodiment, the term refers to an epitope recognized by over 45% of the antigen-specific CD8$^+$ T cells. In another embodiment, the term refers to an epitope recognized by over 50% of the antigen-specific CD8$^+$ T cells. In another embodiment, the term refers to an epitope recognized by over 55% of the antigen-specific CD8$^+$ T cells. In another embodiment, the term refers to an epitope recognized by over 60% of the antigen-specific CD8$^+$ T cells. In another embodiment, the term refers to an epitope recognized by over 65% of the antigen-specific CD8$^+$ T cells. In another embodiment, the term refers to an epitope recognized by over 70% of the antigen-specific CD8$^+$ T cells. In another embodiment, the term refers to an epitope recognized by over 75% of the antigen-specific CD8$^+$ T cells. In another embodiment, the term refers to an epitope recognized by over 80% of the antigen-specific CD8+ T cells. In another embodiment, the term refers to an epitope recognized by over 85% of the antigen-specific CD8+ T cells. In another embodiment, the term refers to an epitope recognized by over 90% of the antigen-specific CD8+ T cells. In another embodiment, the term refers to an epitope recognized by over 95% of the antigen-specific CD8+ T cells. In another embodiment, the term refers to an epitope recognized by over 96% of the antigen-specific CD8+ T cells. In another embodiment, the term refers to an epitope recognized by over 97% of the antigen-specific CD8+ T cells. In another embodiment, the term refers to an epitope recognized by over 98% of the antigen-specific CD8+ T cells.

In one embodiment, the term "Subdominant CD8+ T cell epitope" or "subdominant epitope" refers to an epitope recognized by fewer than 30% of the antigen-specific CD8+ T cells that are elicited by vaccination, infection, or a malignant growth with a protein or a pathogen or cancer cell containing the protein. In another embodiment, the term refers to an epitope recognized by fewer than 28% of the antigen-specific CD8+ T cells. In another embodiment, the term refers to an epitope recognized by over 26% of the antigen-specific CD8+ T cells. In another embodiment, the term refers to an epitope recognized by fewer than 24% of the antigen-specific CD8+ T cells. In another embodiment, the term refers to an epitope recognized by over 22% of the antigen-specific CD8+ T cells. In another embodiment, the term refers to an epitope recognized by fewer than 20% of the antigen-specific CD8+ T cells. In another embodiment, the term refers to an epitope recognized by over 18% of the antigen-specific CD8+ T cells. In another embodiment, the term refers to an epitope recognized by fewer than 16% of the antigen-specific CD8+ T cells. In another embodiment, the term refers to an epitope recognized by over 14% of the antigen-specific CD8+ T cells. In another embodiment, the term refers to an epitope recognized by over 12% of the antigen-specific CD8+ T cells. In another embodiment, the term refers to an epitope recognized by fewer than 10% of the antigen-specific CD8+ T cells. In another embodiment, the term refers to an epitope recognized by over 8% of the antigen-specific CD8+ T cells. In another embodiment, the term refers to an epitope recognized by fewer than 6% of the antigen-specific CD8+ T cells. In another embodiment, the term refers to an epitope recognized by fewer than 5% of the antigen-specific CD8+ T cells. In another embodiment, the term refers to an epitope recognized by over 4% of the antigen-specific CD8+ T cells. In another embodiment, the term refers to an epitope recognized by fewer than 3% of the antigen-specific CD8+ T cells. In another embodiment, the term refers to an epitope recognized by fewer than 2% of the antigen-specific CD8+ T cells. In another embodiment, the term refers to an epitope recognized by fewer than 1% of the antigen-specific CD8+ T cells. In another embodiment, the term refers to an epitope recognized by fewer than 0.5% of the antigen-specific CD8+ T cells.

The antigen comprising the peptide in methods and compositions of the present disclosure is, in one embodiment, expressed at a detectable level on a non-tumor cell of the subject. In another embodiment, the antigen is expressed at a detectable level on at least a certain percentage (e.g. 0.01%, 0.03%, 0.1%, 0.3%, 1%, 2%, 3%, or 5%) of non-tumor cells of the subject. In one embodiment, "non-tumor cell" refers to a cell outside the body of the tumor. In another embodiment, "non-tumor cell" refers to a non-malignant cell. In another embodiment, "non-tumor cell" refers to a non-transformed cell. In another embodiment, the non-tumor cell is a somatic cell. In another embodiment, the non-tumor cell is a germ cell.

"Detectable level" refers to a level that is detectable when using a standard assay. In one embodiment, the assay is an immunological assay. In one embodiment, the assay is enzyme-linked immunoassay (ELISA). In another embodiment, the assay is Western blot. In another embodiment, the assay is FACS. In another embodiment, the assay is a gene-expression assay. It is to be understood by a skilled artisan that other assays available in the art can be used in the methods disclosed herein. In another embodiment, a detectable level is determined relative to the background level of a particular assay. Methods for performing each of these techniques are well known to those skilled in the art.

In one embodiment, vaccination with recombinant antigen-expressing LM induces epitope spreading.

In one embodiment, the present disclosure provides a method for "epitope spreading" of an anti-tumor response. In another embodiment, the immunization using the compositions and methods disclosed herein induce epitope spreading onto other tumors.

In another embodiment, the dominant epitope or subdominant epitope is dominant or subdominant, respectively, in the subject being treated. In another embodiment, the dominant epitope or subdominant epitope is dominant or subdominant in a population being treated.

In one embodiment, disclosed herein is a method of treating, suppressing, or inhibiting a cancer or a tumor growth in a subject by epitope spreading wherein and in another embodiment, said cancer is associated with expression of an antigen or fragment thereof comprised in the composition of the present invention. In another embodiment, the method comprises administering to said subject a composition comprising the recombinant polypeptide, recombinant *Listeria*, or recombinant vector of the present invention. In yet another embodiment, the subject mounts an immune response against the antigen-expressing cancer or the antigen-expressing tumor, thereby treating, suppressing, or inhibiting a cancer or a tumor growth in a subject.

In another embodiment, the present disclosure provides a method for inducing formation of cytotoxic T cells in a host having cancer, comprising administering to the host a composition of the present invention, thereby inducing formation of cytotoxic T cells in a host having cancer.

In one embodiment, the composition is administered to the cells of the subject ex vivo; in another embodiment, the composition is administered to the cells of a donor ex vivo; in another embodiment, the composition is administered to the cells of a donor in vivo, and then is transferred to the subject.

In another embodiment of the methods of the present invention, the subject mounts an immune response against the antigen-expressing tumor or target antigen, thereby mediating the anti-tumor effects.

In one embodiment, repeat administrations (booster doses) of compositions of this disclosure may be undertaken immediately following the first course of treatment or after an interval of days, weeks or months to achieve tumor regression. In another embodiment, repeat doses may be undertaken immediately following the first course of treatment or after an interval of days, weeks or months to achieve suppression of tumor growth. Assessment may be determined by any of the techniques known in the art, including diagnostic methods such as imaging techniques, analysis of serum tumor markers, biopsy, or the presence, absence or amelioration of tumor associated symptoms.

In one embodiment, disclosed herein is a method of increasing a ratio of T effector cells to regulatory T cells (Tregs) in the spleen and tumor microenvironments of a subject, comprising administering the immunogenic composition disclosed herein. In another embodiment, increasing a ratio of T effector cells to regulatory T cells (Tregs) in the spleen and tumor microenvironments in a subject allows for a more profound anti-tumor response in the subject. In another embodiment, a regulatory T cells is a CD4+FoxP3+ T cell.

In another embodiment, the T effector cells comprise CD4+FoxP3− T cells. In another embodiment, the T effector cells are CD4+FoxP3− T cells. In another embodiment, the T effector cells comprise CD4+FoxP3− T cells and CD8+ T cells. In another embodiment, the T effector cells are CD4+FoxP3− T cells and CD8+ T cells.

In one embodiment, the present disclosure provides methods of treating, protecting against, and inducing an immune response against a tumor or a cancer, comprising the step of administering to a subject the immunogenic composition disclosed herein.

In one embodiment, the present disclosure provides a method of preventing or treating a tumor or cancer in a human subject, comprising the step of administering to the subject the immunogenic composition disclosed herein. In another embodiment, the immune response is a T-cell response. In another embodiment, the T-cell response is a CD4+FoxP3− T cell response. In another embodiment, the T-cell response is a CD8+ T cell response. In another embodiment, the T-cell response is a CD4+FoxP3− and CD8+ T cell response.

In another embodiment, the present disclosure provides a method of protecting a subject against a tumor or cancer, comprising the step of administering to the subject an immunogenic composition disclosed herein. In another embodiment, the present disclosure provides a method of inducing regression of a tumor in a subject, comprising the step of administering to the subject an immunogenic composition disclosed herein. In another embodiment, the present disclosure provides a method of reducing the incidence or relapse of a tumor or cancer, comprising the step of administering to the subject an immunogenic composition disclosed herein. In another embodiment, the present disclosure provides a method of suppressing the formation of a tumor in a subject, comprising the step of administering to the subject an immunogenic composition disclosed herein. In another embodiment, the present disclosure provides a method of inducing a remission of a cancer in a subject, comprising the step of administering to the subject an immunogenic composition disclosed herein.

In one embodiment, a minigene nucleic acid construct comprising an open reading frame encoding a chimeric peptide as disclosed herein, is integrated into a *Listeria* genome. In another embodiment, the minigene construct is in a plasmid in a recombinant *Listeria* vaccine strain. In another embodiment, the minigene construct is in an extrachromosomal plasmid in said *Listeria*. In another embodiment, the construct is expressed from an extrachromosomal plasmid in said *Listeria*.

In another embodiment, a method of treating reduces lymph node size. Reduction of lymph node size may be partial or by 100%. In another embodiment, methods of this disclosure reduce lymph node size by 90%. In another embodiment, methods of this disclosure reduce lymph node size by 80%. In another embodiment, methods reduce lymph node size by 70%. In another embodiment, methods reduce lymph node size by 60%. In another embodiment, methods reduce lymph node size by 50%.

In another embodiment, a method of treating increases the time to disease progression. In one embodiment the time to disease progression was increased by at least 2 moths as compared to untreated subject. In one embodiment the time to disease progression was increased by at least 4 moths as compared to untreated subject. In one embodiment the time to disease progression was increased by at least 6 moths as compared to untreated subject. In one embodiment the time to disease progression was increased by at least 1 year as compared to untreated subject. In one embodiment the time to disease progression was increased by at least 2 years as compared to untreated subject. In one embodiment the time to disease progression was increased by at least 3 years as compared to untreated subject. In one embodiment the time to disease progression was increased by at least 4 years as compared to untreated subject. In one embodiment the time to disease progression was increased by at least 5 years as compared to untreated subject.

In one embodiment, the method comprises the step of co-administering the recombinant *Listeria* with an additional therapy. In another embodiment, the additional therapy is surgery, chemotherapy, an immunotherapy, a radiation therapy, antibody based immuno therapy, or a combination thereof. In another embodiment, the additional therapy precedes administration of the recombinant *Listeria*. In another embodiment, the additional therapy follows administration of the recombinant *Listeria*. In another embodiment, the additional therapy is an antibody therapy. In another embodiment, the recombinant *Listeria* is administered in increasing doses in order to increase the T-effector cell to regulatory T cell ration and generate a more potent anti-tumor immune response. It will be appreciated by a skilled artisan that the anti-tumor immune response can be further strengthened by providing the subject having a tumor with cytokines including, but not limited to IFN-γ, TNF-α, and other cytokines known in the art to enhance cellular immune response, some of which can be found in U.S. Pat. No. 6,991,785, incorporated by reference herein.

In one embodiment, the methods disclosed herein further comprise the step of co-administering an immunogenic composition disclosed herein with an antibody or functional fragment thereof that enhances an anti-tumor immune response in said subject.

In another embodiment, disclosed herein is a method of increasing survival of a subject suffering from cancer or having a tumor, the method comprising the step of administering to the subject an immunogenic composition comprising a recombinant *Listeria* vaccine strain, disclosed herein.

In another embodiment, disclosed herein is a method of increasing antigen-specific T cells in a subject suffering from cancer or having a tumor, the method comprising the step of administering to the subject an immunogenic composition comprising a recombinant *Listeria* vaccine, disclosed herein.

In one embodiment, a treatment protocol of the present disclosure is therapeutic. In another embodiment, the protocol is prophylactic. In another embodiment, the compositions of the present disclosure are used to protect people at risk for cancer such as breast cancer or other types of tumors because of familial genetics or other circumstances that predispose them to these types of ailments as will be understood by a skilled artisan. In another embodiment, the compositions are used as a cancer immunotherapy after debulking of tumor growth by surgery, conventional chemotherapy or radiation treatment. Following such treatments, the compositions of the present disclosure are administered so that the cytotoxic T-cell (CTL) response to the tumor antigen of the vaccine destroys remaining metastases and prolongs remission from the cancer. In another embodiment, compositions are used as a cancer immunotherapy in combination with surgery, conventional chemotherapy or radiation treatment. In another embodiment, compositions of the present disclosure are used to effect the growth of previously established tumors and to kill existing tumor cells.

Various embodiments of dosage ranges are contemplated by this invention. In one embodiment, in the case of vaccine vectors, the dosage is in the range of 0.4 $LD_{50}$/dose. In another embodiment, the dosage is from about 0.4-4.9 $LD_{50}$/dose. In another embodiment the dosage is from about 0.5-0.59 $LD_{50}$/dose. In another embodiment the dosage is from about 0.6-0.69 $LD_{50}$/dose. In another embodiment the dosage is from about 0.7-0.79 $LD_{50}$/dose. In another embodiment the dosage is about 0.8 $LD_{50}$/dose. In another embodiment, the dosage is 0.4 $LD_{50}$/dose to 0.8 of the $LD_{50}$/dose.

In another embodiment, the dosage is $10^7$ bacteria/dose. In another embodiment, the dosage is $1.5 \times 10^7$ bacteria/dose. In another embodiment, the dosage is $2 \times 10^7$ bacteria/dose. In another embodiment, the dosage is $3 \times 10^7$ bacteria/dose. In another embodiment, the dosage is $4 \times 10^7$ bacteria/dose. In another embodiment, the dosage is $6 \times 10^7$ bacteria/dose. In another embodiment, the dosage is $8 \times 10^7$ bacteria/dose. In another embodiment, the dosage is $1 \times 10^8$ bacteria/dose. In another embodiment, the dosage is $1.5 \times 10^8$ bacteria/dose. In another embodiment, the dosage is $2 \times 10^8$ bacteria/dose. In another embodiment, the dosage is $3 \times 10^8$ bacteria/dose. In another embodiment, the dosage is $4 \times 10^8$ bacteria/dose. In another embodiment, the dosage is $6 \times 10^8$ bacteria/dose. In another embodiment, the dosage is $8 \times 10^8$ bacteria/dose. In another embodiment, the dosage is $1 \times 10^9$ bacteria/dose. In another embodiment, the dosage is $1.5 \times 10^9$ bacteria/dose. In another embodiment, the dosage is $2 \times 10^9$ bacteria/dose. In another embodiment, the dosage is $3 \times 10^9$ bacteria/dose. In another embodiment, the dosage is $5 \times 10^9$ bacteria/dose. In another embodiment, the dosage is $6 \times 10^9$ bacteria/dose. In another embodiment, the dosage is $8 \times 10^9$ bacteria/dose. In another embodiment, the dosage is $1 \times 10^{10}$ bacteria/dose. In another embodiment, the dosage is $1.5 \times 10^{10}$ bacteria/dose. In another embodiment, the dosage is $2 \times 10^{10}$ bacteria/dose. In another embodiment, the dosage is $3 \times 10^{10}$ bacteria/dose. In another embodiment, the dosage is $5 \times 10^{10}$ bacteria/dose. In another embodiment, the dosage is $6 \times 10^{10}$ bacteria/dose. In another embodiment, the dosage is $8 \times 10^{10}$ bacteria/dose. In another embodiment, the dosage is $8 \times 10^9$ bacteria/dose. In another embodiment, the dosage is $1 \times 10^{11}$ bacteria/dose. In another embodiment, the dosage is $1.5 \times 10^{11}$ bacteria/dose. In another embodiment, the dosage is $2 \times 10^{11}$ bacteria/dose. In another embodiment, the dosage is $3 \times 10^{11}$ bacteria/dose. In another embodiment, the dosage is $5 \times 10^{11}$ bacteria/dose. In another embodiment, the dosage is $6 \times 10^{11}$ bacteria/dose. In another embodiment, the dosage is $8 \times 10^{11}$ bacteria/dose.

Various administration regimens are also contemplated by this invention. In one embodiment, the pharmaceutical composition comprising the bacteria as described in this disclosure is administered once. In another embodiment, the composition is administered more than once. In another embodiment, the composition is administered twice with a one week interval between administrations. In another embodiment, the composition is administered twice with a two weeks interval between administrations. In another embodiment, the composition is administered twice with a three weeks interval between administrations. In another embodiment, the composition is administered three times with a one week interval between administrations. In another embodiment, the composition is administered three times with a two weeks interval between administrations. In another embodiment, the composition is administered three times with a three weeks interval between administrations. In another embodiment, any of the above regimens are followed up with further administrations. In some embodiments, further administrations are prophylactic. In another embodiments further booster administrations are done when the subject experiences cancer relapse. In another embodiments further booster administrations are done when the subject experiences cancer remission. In some embodiments, the booster regimen comprises monthly administration of the composition. In another embodiment, the booster regimen comprises bi-monthly administration of the composition. In yet another embodiment, the booster regimen comprises administration of the composition with an interval of two or more months. In other embodiment, the booster regimen comprises one additional administration. In another embodiment, booster regimen comprises more than one additional administration. In yet another embodiment, the booster regimen comprises two additional administrations. In yet another embodiment, the booster regimen comprises three additional administrations. In another embodiment, the follow up administration regimen comprises more than three additional administrations.

In another embodiment, a method of the present disclosure further comprises boosting the subject with an immunogenic composition comprising an attenuated *Listeria* strain disclosed herein. In another embodiment, a method of the present disclosure comprises the step of administering a booster dose of the immunogenic composition comprising an attenuated *Listeria* strain disclosed herein. In another embodiment, the methods of the present disclosure further comprise the step of administering to the subject a booster immunogenic composition. In one embodiment, the booster dose follows a single priming dose of said immunogenic composition. In another embodiment, a single booster dose is administered after the priming dose. In another embodiment, two booster doses are administered after the priming dose. In another embodiment, three booster doses are administered after the priming dose. In one embodiment, the period between a prime and a boost dose of an immunogenic composition comprising the attenuated *Listeria* disclosed herein is experimentally determined by the skilled artisan.

In another embodiment, the booster dose is an alternate form of an immunogenic composition comprising a *Listeria* disclosed herein. In another embodiment, the booster dose comprises the immunogenic composition disclosed herein and an adjuvant. Heterologous "prime boost" strategies have been effective for enhancing immune responses and protection against numerous pathogens. Schneider et al., Immunol. Rev. 170:29-38 (1999); Robinson, H. L., Nat. Rev. Immunol. 2:239-50 (2002); Gonzalo, R. M. et al., Strain 20:1226-31 (2002); Tanghe, A., Infect. Immun. 69:3041-7 (2001). Providing antigen in different forms in the prime and the boost injections appears to maximize the immune response to the antigen. DNA strain priming followed by boosting with protein in adjuvant or by viral vector delivery of DNA encoding antigen appears to be the most effective way of improving antigen specific antibody and CD4+ T-cell responses or CD8+ T-cell responses respectively. Shiver J. W. et al., Nature 415: 331-5 (2002); Gilbert, S. C. et al., Strain 20:1039-45 (2002); Billaut-Mulot, O. et al., Strain 19:95-102 (2000); Sin, J. I. et al., DNA Cell Biol. 18:771-9 (1999). Recent data from monkey vaccination studies suggests that adding CRL1005 poloxamer (12 kDa, 5% POE), to DNA encoding the HIV gag antigen enhances T-cell responses when monkeys are vaccinated with an HIV gag DNA prime followed by a boost with an adenoviral vector expressing HIV gag (Ad5-gag). The cellular immune responses for a DNA/poloxamer prime followed by an Ad5-gag boost were greater than the responses induced with a DNA (without poloxamer) prime followed by Ad5-gag boost or for Ad5-gag only. Shiver, J. W. et al. Nature 415:331-5 (2002). U.S. Patent Appl. Publication No. US 2002/0165172 A1 describes simultaneous administration of a vector construct encoding an immunogenic portion of an antigen and a protein comprising the immunogenic portion of an antigen such that an immune response is generated. The document is limited to hepatitis B antigens and HIV antigens. Moreover, U.S. Pat. No. 6,500,432 is directed to methods of enhancing an immune response of nucleic acid vaccination by simultaneous administration of a polynucleotide and polypeptide of interest. According to the patent, simultaneous administration means administration of the polynucleotide and the polypeptide during the same immune response, preferably within 0-10 or 3-7 days of each other. The antigens contemplated include, among others, those of Hepatitis (all forms), HSV, HIV, CMV, EBV, RSV, VZV, HPV, polio, influenza, parasites (e.g., from the genus *Plasmodium*), and pathogenic bacteria (including but not limited to *M. tuberculosis, M. leprae, Chlamydia, Shigella, B. burgdorferi*, enterotoxigenic *E. coli, S. typhosa, H. pylori, V. cholerae, B. pertussis*, etc.). All of the above references are herein incorporated by reference in their entireties.

In one embodiment, a vaccine or immunogenic composition of the present disclosure is administered alone to a subject. In another embodiment, the vaccine or immunogenic composition is administered together with another cancer therapy such as, but not limited to, radiotherapy, chemotherapy or a checkpoint inhibitor such as an anti-PD-1 antibody, an IDO pathway inhibitor, etc., or any combination thereof.

In one embodiment, a treatment protocol of the present disclosure is therapeutic. In another embodiment, the protocol is prophylactic. In another embodiment, the compositions of the present disclosure are used to protect people at risk for cancer such as breast cancer or other types of tumors because of familial genetics or other circumstances that predispose them to these types of ailments as will be understood by a skilled artisan. In another embodiment, the vaccines or immunogenic composition are used as a cancer immunotherapy after debulking of tumor growth by surgery, conventional chemotherapy or radiation treatment. Following such treatments, the vaccines of the present disclosure are administered so that the CTL response to the tumor antigen of the vaccine destroys remaining metastases and prolongs remission from a cancer. In another embodiment, vaccines of the present disclosure are used to effect the growth of previously established tumors and to kill existing tumor cells.

As used herein, the singular form "a," "an" and "the" include plural references unless the context clearly dictates otherwise. For example, the term "a compound" or "at least one compound" may include a plurality of compounds, including mixtures thereof.

Throughout this application, various embodiments of this disclosure may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

It will be understood by a skilled artisan that the term "method" encompasses manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

In the following examples, numerous specific details are set forth in order to provide a thorough understanding of the invention. However, it will be understood by those skilled in the art that the present disclosure may be practiced without these specific details. In other instances, well-known methods, procedures, and components have not been described in detail so as not to obscure the present invention.
Pharmaceutical Formulations and Administration The pharmaceutical compositions containing vaccines, immunogenic compositions, or recombinant *Listeria* of the present disclosure are, in another embodiment, administered to a subject by any method known to a person skilled in the art, such as parenterally, paracancerally, transmucosally, transdermally, intramuscularly, intravenously, intra-dermally, subcutaneously, orally, intra-peritoneally, intra-ventricularly, intra-cranially, intra-vaginally or intra-tumorally.

In one embodiment, disclosed herein is a method of treating, suppressing, or inhibiting at least one cancer in a subject comprising administering a recombinant *Listeria* strain to said subject.

In one embodiment, cancer or tumors may be prevented in specific populations known to be susceptible to a particular cancer or tumor by administering the immunogenic compositions disclosed herein. In one embodiment, such susceptibilty may be due to environmental factors, such as smoking, which in one embodiment, may cause a population to be subject to lung cancer, while in another embodiment, such susceptbility may be due to genetic factors, for example a population with BRCA1/2 mutations may be susceptible, in one embodiment, to breast cancer, and in another embodiment, to ovarian cancer. In another embodiment, one or more mutations on chromosome 8q24, chromosome 17q12, and chromosome 17q24.3 may increase susceptibility to prostate cancer, as is known in the art. Other genetic and environmental factors contributing to cancer susceptibility are known in the art.

In another embodiment of the methods and compositions disclosed herein, the vaccines or compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present disclosure comprise, in addition to the active compound and the inert carrier or diluent, a hard gelating capsule.

In another embodiment, the vaccines or compositions are administered by intravenous, intra-arterial, or intra-muscular injection of a liquid preparation. Suitable liquid formulations include solutions, suspensions, dispersions, emulsions, oils and the like. In one embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intramuscularly and are thus formulated in a form suitable for intra-muscular administration.

The terms "immunogenic composition," "composition" and "pharmaceutical composition" may be used interchangeably. For example, in one embodiment, a composition of this disclosure may encompass the recombinant *Listeria* described herein, and an adjuvant. In another embodiment, an immunogenic composition comprises a recombinant *Listeria* disclosed herein. In another embodiment, an immunogenic composition comprises an adjuvant known in the art or as disclosed herein. It is also to be understood that administration of such compositions enhance an immune response, or increase a T effector cell to regulatory T cell ratio or elicit an anti-tumor immune response, as further disclosed herein.

The term "pharmaceutical composition" encompasses a therapeutically effective amount of the active ingredient or ingredients including the *Listeria* strain together with a pharmaceutically acceptable carrier or diluent.

It will be understood by the skilled artisan that the term "administering" encompasses bringing a subject in contact with a composition of the present invention. In one embodiment, administration can be accomplished in vitro, i.e. in a test tube, or in vivo, i.e. in cells or tissues of living organisms, for example humans. In one embodiment, the present disclosure encompasses administering the *Listeria* strains and compositions thereof of the present disclosure to a subject.

In one embodiment, the term "treating" refers to curing a disease. In another embodiment, "treating" refers to preventing a disease. In another embodiment, "treating" refers to reducing the incidence of a disease. In another embodiment, "treating" refers to ameliorating symptoms of a disease. In another embodiment, "treating" refers to increasing performance free survival or overall survival of a patient. In another embodiment, "treating" refers to stabilizing the progression of a disease. In another embodiment, "treating" refers to inducing remission. In another embodiment, "treating" refers to slowing the progression of a disease. In another embodiment, "treating" when in reference to a tumor or cancer, refers to inducing the regression of the tumor or cancer. The terms "reducing," "suppressing," and "inhibiting" refer to lessening or decreasing.

In one embodiment, the term "treating" refers to both therapeutic treatment and prophylactic or preventative measures, wherein the object is to prevent or lessen the targeted pathologic condition or disorder as described herein. Thus, in one embodiment, treating may include directly affecting or curing, suppressing, inhibiting, preventing, reducing the severity of, delaying the onset of, reducing symptoms associated with the disease, disorder or condition, or a combination thereof. Thus, in one embodiment, "treating" refers inter alia to delaying progression, expediting remission, inducing remission, augmenting remission, speeding recovery, increasing efficacy of or decreasing resistance to alternative therapeutics, or a combination thereof. In one embodiment, "preventing" or "impeding" refers, inter alia, to delaying the onset of symptoms, preventing relapse to a disease, decreasing the number or frequency of relapse episodes, increasing latency between symptomatic episodes, or a combination thereof. In one embodiment, "suppressing" or "inhibiting", refers inter alia to reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof.

In one embodiment, symptoms are primary, while in another embodiment, symptoms are secondary. In one embodiment, "primary" refers to a symptom that is a direct result of a particular disease or disorder, while in one embodiment, "secondary" refers to a symptom that is derived from or consequent to a primary cause. In one embodiment, the compounds for use in the present disclosure treat primary or secondary symptoms or secondary complications. In another embodiment, "symptoms" may be any manifestation of a disease or pathological condition.

The term "about" as used herein means in quantitative terms plus or minus 5%, or in another embodiment plus or minus 10%, or in another embodiment plus or minus 15%, or in another embodiment plus or minus 20%.

It is to be understood by the skilled artisan that the term "subject" can encompass a mammal including an adult human or a human child, teenager or adolescent in need of therapy for, or susceptible to, a condition or its sequelae, and also may include non-human mammals such as dogs, cats, pigs, cows, sheep, goats, horses, rats, and mice. It will also be appreciated that the term may encompass livestock. The term "subject" does not exclude an individual that is normal in all respects.

It will be appreciated by the skilled artisan that the term "mammal" for purposes of treatment refers to any animal classified as a mammal, including, but not limited to, humans, domestic and farm animals, and zoo, sports, or pet animals, such as canines, including dogs, and horses, cats, cattle, pigs, sheep, etc.

A "therapeutically effective amount", in reference to the treatment of tumor, refers to an amount capable of invoking one or more of the following effects: (1) inhibition, to some extent, of tumor growth, including, slowing down and complete growth arrest; (2) reduction in the number of tumor cells; (3) reduction in tumor size; (4) inhibition (i.e., reduction, slowing down or complete stopping) of tumor cell infiltration into peripheral organs; (5) inhibition (i.e., reduction, slowing down or complete stopping) of metastasis; (6) enhancement of anti-tumor immune response, which may, but does not have to, result in the regression or rejection of the tumor; and/or (7) relief, to some extent, of one or more symptoms associated with the disorder. A "therapeutically effective amount" of a vaccine disclosed herein for purposes of treatment of tumor may be determined empirically and in a routine manner.

In the following examples, numerous specific details are set forth in order to provide a thorough understanding of the invention. However, it will be understood by those skilled in the art that the present disclosure may be practiced without these specific details. In other instances, well-known methods, procedures, and components have not been described in detail so as not to obscure the present invention. Thus these examples should in no way be construed, as limiting the broad scope of the invention.

EXAMPLES

Materials and Experimental Methods (Examples 1-2)

Example 1: LLO-Antigen Fusions Induce Anti-Tumor Immunity

Cell Lines

The C57BL/6 syngeneic TC-1 tumor was immortalized with HPV-16 E6 and E7 and transformed with the c-Ha-ras oncogene. TC-1, provided by T. C. Wu (Johns Hopkins University School of Medicine, Baltimore, M.D.) is a highly tumorigenic lung epithelial cell expressing low levels of with HPV-16 E6 and E7 and transformed with the c-Ha-ras oncogene. TC-1 was grown in RPMI 1640, 10% FCS, 2 mM L-glutamine, 100 U/ml penicillin, 100 µg/ml streptomycin, 100 µM nonessential amino acids, 1 mM sodium pyruvate, 50 micromolar (mcM) 2-ME, 400 microgram (mcg)/ml G418, and 10% National Collection Type Culture-109 medium at 37° with 10% $CO_2$. C3 is a mouse embryo cell from C57BL/6 mice immortalized with the complete genome of HPV 16 and transformed with pEJ-ras. EL-4/E7 is the thymoma EL-4 retrovirally transduced with E7.

L. monocytogenes Strains and Propagation

Figure 2:
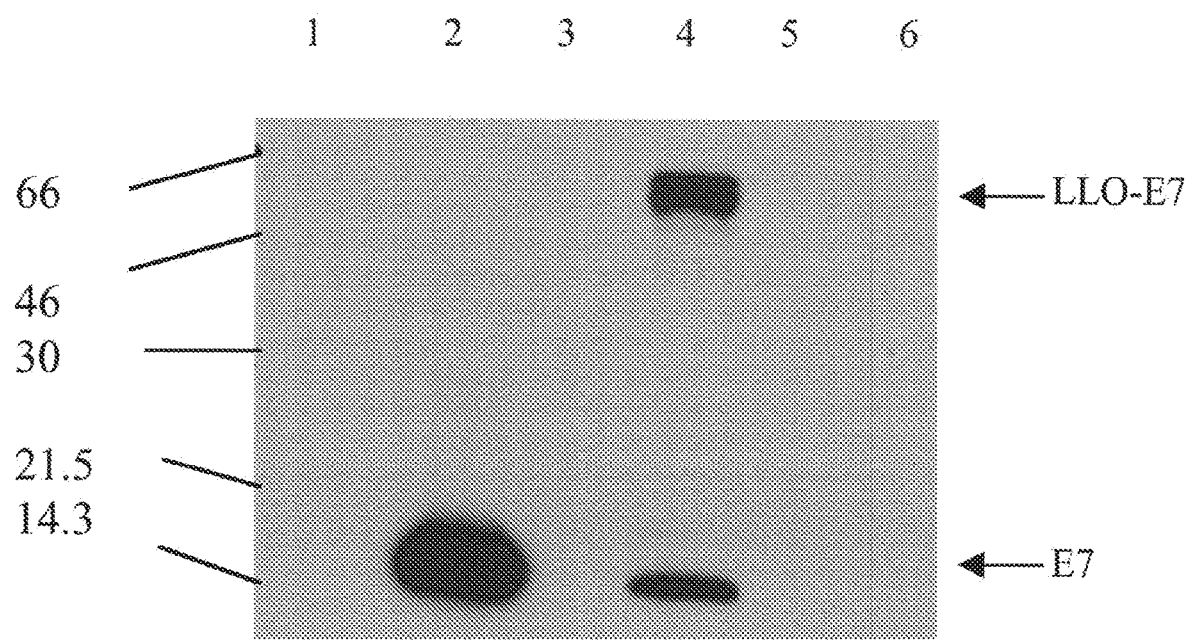
FIG. 2 shows that Lm-E7 and Lm-LLO-E7 secrete E7. Lm-Gag (lane 1), Lm-E7 (lane 2), Lm-LLO-NP (lane 3), Lm-LLO-E7 (lane 4), XFL-7 (lane 5), and 10403S (lane 6) were grown overnight at 37° C. in Luria-Bertoni broth. Equivalent numbers of bacteria, as determined by OD at 600 nm absorbance, were pelleted and 18 ml of each supernatant was TCA precipitated. E7 expression was analyzed by Western blot. The blot was probed with an anti-E7 mAb, followed by HRP-conjugated anti-mouse (Amersham), and then developed using ECL detection reagents.

Listeria strains used were Lm-LLO-E7 (hly-E7 fusion gene in an episomal expression system; FIG. 1A), Lm-E7 (single-copy E7 gene cassette integrated into Listeria genome), Lm-LLO-NP ("DP-L2028"; hly-NP fusion gene in an episomal expression system), and Lm-Gag ("ZY-18"; single-copy HIV-1 Gag gene cassette integrated into the chromosome). E7 was amplified by PCR using the primers 5'-GG<u>CTCGAG</u>CATGGAGATACACC-3' (SEQ ID No: 21; XhoI site is underlined) and 5'-GGGG<u>ACTAGT</u>T-TATGGTTTCTGAGAACA-3' (SEQ ID No: 21; SpeI site is underlined) and ligated into pCR2.1 (Invitrogen, San Diego, Calif.). E7 was excised from pCR2.1 by XhoI/SpeI digestion and ligated into pGG-55. The hly-E7 fusion gene and the pluripotential transcription factor prfA were cloned into pAM401, a multicopy shuttle plasmid (Wirth R et al, J Bacteriol, 165: 831, 1986), generating pGG-55. The hly promoter drives the expression of the first 441 AA of the hly gene product, (lacking the hemolytic C-terminus, referred to below as "ΔLLO"), which is joined by the XhoI site to the E7 gene, yielding a hly-E7 fusion gene that is transcribed and secreted as LLO-E7. Transformation of a prfA negative strain of Listeria, XFL-7 (provided by Dr. Hao Shen, University of Pennsylvania), with pGG-55 selected for the retention of the plasmid in vivo (FIGS. 1A-B). The hly promoter and gene fragment were generated using primers 5'-GGGG<u>GCTAGC</u>CCTCCTTTGATTAGTATATTC-3' (SEQ ID No: 23; NheI site is underlined) and 5'-CTCC<u>CTCGAG</u>ATCATAATTTACTTCATC-3' (SEQ ID No: 24; XhoI site is underlined). The prfA gene was PCR amplified using primers 5'-GACTACAAGGACGATGACCGA-CAAGTGATAA<u>CCCGGG</u>ATCTAAATAAATCCGTTT-3' (SEQ ID No: 25; XbaI site is underlined) and 5'-CCC GT<u>CGAC</u>CAGCTCTTCTTGGTGAAG-3' (SEQ ID No: 26; SalI site is underlined). Lm-E7 was generated by introducing an expression cassette containing the hly promoter and signal sequence driving the expression and secretion of E7 into the orfZ domain of the LM genome. E7 was amplified by PCR using the primers 5'-GC<u>GGATCC</u>CATGGAGATACACCTAC-3' (SEQ ID No: 27; BamHI site is underlined) and 5'-GC<u>TCTAGA</u>T-TATGGTTTCTGAG-3' (SEQ ID No: 28; XbaI site is underlined). E7 was then ligated into the pZY-21 shuttle vector. LM strain 10403S was transformed with the resulting plasmid, pZY-21-E7, which includes an expression cassette inserted in the middle of a 1.6-kb sequence that corresponds to the ora, Y, Z domain of the LM genome. The homology domain allows for insertion of the E7 gene cassette into the orfZ domain by homologous recombination. Clones were screened for integration of the E7 gene cassette into the orfZ domain. Bacteria were grown in brain heart infusion medium with (Lm-LLO-E7 and Lm-LLO-NP) or without (Lm-E7 and ZY-18) chloramphenicol (20 µg/ml). Bacteria were frozen in aliquots at −80° C. Expression was verified by Western blotting (FIG. 2).

Western Blotting

Listeria strains were grown in Luria-Bertoni medium at 37° C. and were harvested at the same optical density measured at 600 nm. The supernatants were TCA precipitated and resuspended in 1× sample buffer supplemented with 0.1 N NaOH. Identical amounts of each cell pellet or each TCA-precipitated supernatant were loaded on 4-20% Tris-glycine SDS-PAGE gels (NOVEX, San Diego, Calif.). The gels were transferred to polyvinylidene difluoride and probed with an anti-E7 monoclonal antibody (mAb) (Zymed Laboratories, South San Francisco, Calif.), then incubated with HRP-conjugated anti-mouse secondary Ab (Amersham Pharmacia Biotech, Little Chalfont, U.K.), developed with Amersham ECL detection reagents, and exposed to Hyperfilm (Amersham Pharmacia Biotech).

Measurement of Tumor Growth

Tumors were measured every other day with calipers spanning the shortest and longest surface diameters. The mean of these two measurements was plotted as the mean tumor diameter in millimeters against various time points. Mice were sacrificed when the tumor diameter reached 20 mm. Tumor measurements for each time point are shown only for surviving mice.

Effects of Listeria Recombinants on Established Tumor Growth

Six- to 8-wk-old C57BL/6 mice (Charles River) received $2 \times 10^5$ TC-1 cells s.c. on the left flank. One week following tumor inoculation, the tumors had reached a palpable size of 4-5 mm in diameter. Groups of eight mice were then treated with 0.1 $LD_{50}$ i.p. Lm-LLO-E7 ($10^7$ CFU), Lm-E7 ($10^6$ CFU), Lm-LLO-NP ($10^7$ CFU), or Lm-Gag ($5 \times 10^5$ CFU) on days 7 and 14.

$^{51}$Cr Release Assay

C57BL/6 mice, 6-8 wk old, were immunized i.p. with 0.1 $LD_{50}$ Lm-LLO-E7, Lm-E7, Lm-LLO-NP, or Lm-Gag. Ten days post-immunization, spleens were harvested. Splenocytes were established in culture with irradiated TC-1 cells (100:1, splenocytes:TC-1) as feeder cells; stimulated in vitro for 5 days, then used in a standard $^{51}$Cr release assay, using the following targets: EL-4, EL-4/E7, or EL-4 pulsed with E7 H-2b peptide (RAHYNIVTF) (SEQ ID NO: 29). E:T cell ratios, performed in triplicate, were 80:1, 40:1, 20:1, 10:1, 5:1, and 2.5:1. Following a 4-h incubation at 37° C., cells were pelleted, and 50 μl supernatant was removed from each well. Samples were assayed with a Wallac 1450 scintillation counter (Gaithersburg, Md.). The percent specific lysis was determined as [(experimental counts per minute (cpm)−spontaneous cpm)/(total cpm−spontaneous cpm)]×100.

TC-1-Specific Proliferation

C57BL/6 mice were immunized with 0.1 $LD_{50}$ and boosted by i.p. injection 20 days later with 1 $LD_{50}$ Lm-LLO-E7, Lm-E7, Lm-LLO-NP, or Lm-Gag. Six days after boosting, spleens were harvested from immunized and naive mice. Splenocytes were established in culture at $5\times10^5$/well in flat-bottom 96-well plates with $2.5\times10^4$, $1.25\times10^4$, $6\times10^3$, or $3\times10^3$ irradiated TC-1 cells/well as a source of E7 Ag, or without TC-1 cells or with 10 μg/ml Con A. Cells were pulsed 45 h later with 0.5 μCi [$^3$H]thymidine/well. Plates were harvested 18 h later using a Tomtec harvester 96 (Orange, Conn.), and proliferation was assessed with a Wallac 1450 scintillation counter. The change in cpm was calculated as experimental cpm−no Ag cpm.

Flow Cytometric Analysis

C57BL/6 mice were immunized intravenously (i.v.) with 0.1 $LD_{50}$ Lm-LLO-E7 or Lm-E7 and boosted 30 days later. Three-color flow cytometry for CD8 (53-6.7, PE conjugated), CD62 ligand (CD62L; MEL-14, APC conjugated), and E7 H-2Db tetramer was performed using a FACSCalibur® flow cytometer with CellQuest® software (Becton Dickinson, Mountain View, Calif.). Splenocytes harvested 5 days after the boost were stained at room temperature (rt) with H-2Db tetramers loaded with the E7 peptide (RAHYNIVTF) (SEQ ID NO: 29) or a control (HIV-Gag) peptide. Tetramers were used at a 1/200 dilution and were provided by Dr. Larry R. Pease (Mayo Clinic, Rochester, Minn.) and by the NIAID Tetramer Core Facility and the NIH AIDS Research and Reference Reagent Program. Tetramert$^+$, CD8$^+$, CD62L$^{low}$ cells were analyzed.

B16F0-Ova Experiment

24 C57BL/6 mice were inoculated with $5\times10^5$ B 16F0-Ova cells. On days 3, 10 and 17, groups of 8 mice were immunized with 0.1 $LD_{50}$ Lm-OVA ($10^6$ cfu), Lm-LLO-OVA ($10^8$ cfu) and eight animals were left untreated.

Statistics

For comparisons of tumor diameters, mean and SD of tumor size for each group were determined, and statistical significance was determined by Student's t test. p≤0.05 was considered significant.

Results

Figure 3:
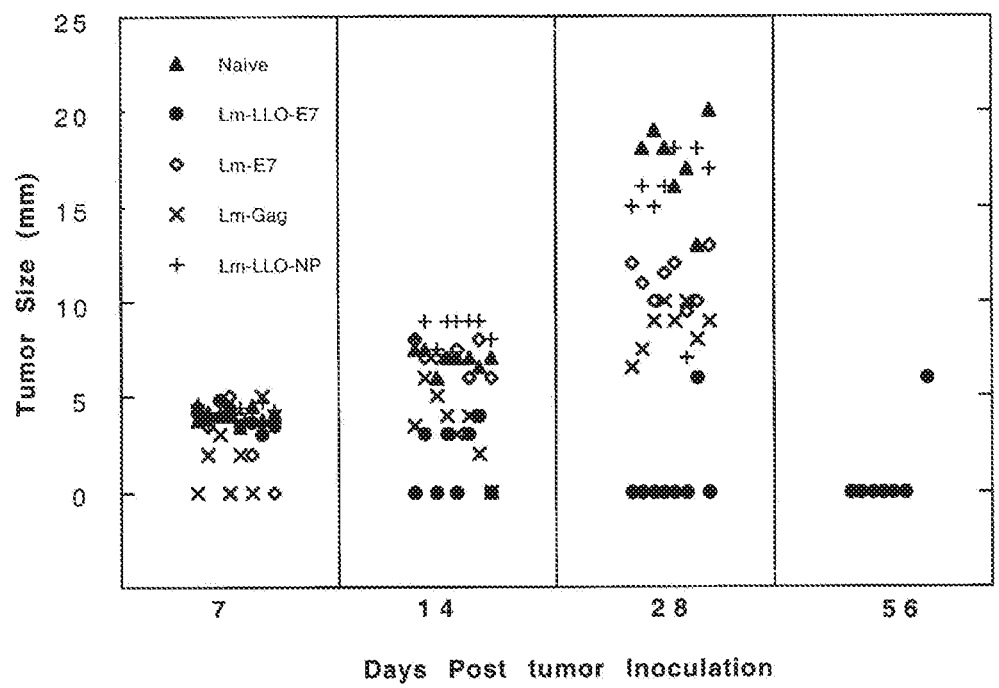
FIG. 3 shows that tumor immunotherapeutic efficacy of LLO-E7 fusions. Tumor size in millimeters in mice is shown at 7, 14, 21, 28 and 56 days post tumor-inoculation. Naive mice: open-circles; Lm-LLO-E7: filled circles; Lm-E7: squares; Lm-Gag: open diamonds; and Lm-LLO-NP: filled triangles.

Lm-E7 and Lm-LLO-E7 were compared for their abilities to impact on TC-1 growth. Subcutaneous tumors were established on the left flank of C57BL/6 mice. Seven days later tumors had reached a palpable size (4-5 mm). Mice were vaccinated on days 7 and 14 with 0.1 $LD_{50}$ Lm-E7, Lm-LLO-E7, or, as controls, Lm-Gag and Lm-LLO-NP. Lm-LLO-E7 induced complete regression of 75% of established TC-1 tumors, while tumor growth was controlled in the other 2 mice in the group (FIG. 3). By contrast, immunization with Lm-E7 and Lm-Gag did not induce tumor regression. This experiment was repeated multiple times, always with very similar results. In addition, similar results were achieved for Lm-LLO-E7 under different immunization protocols. In another experiment, a single immunization was able to cure mice of established 5 mm TC-1 tumors.

In other experiments, similar results were obtained with 2 other E7-expressing tumor cell lines: C3 and EL-4/E7. To confirm the efficacy of vaccination with Lm-LLO-E7, animals that had eliminated their tumors were re-challenged with TC-1 or EL-4/E7 tumor cells on day 60 or day 40, respectively. Animals immunized with Lm-LLO-E7 remained tumor free until termination of the experiment (day 124 in the case of TC-1 and day 54 for EL-4/E7).

Thus, expression of an antigen as a fusion protein with ΔLLO enhances the immunogenicity of the antigen.

Example 2: Lm-LLO-E7 Treatment Elicits TC-1 Specific Splenocyte Proliferation

Figure 4:
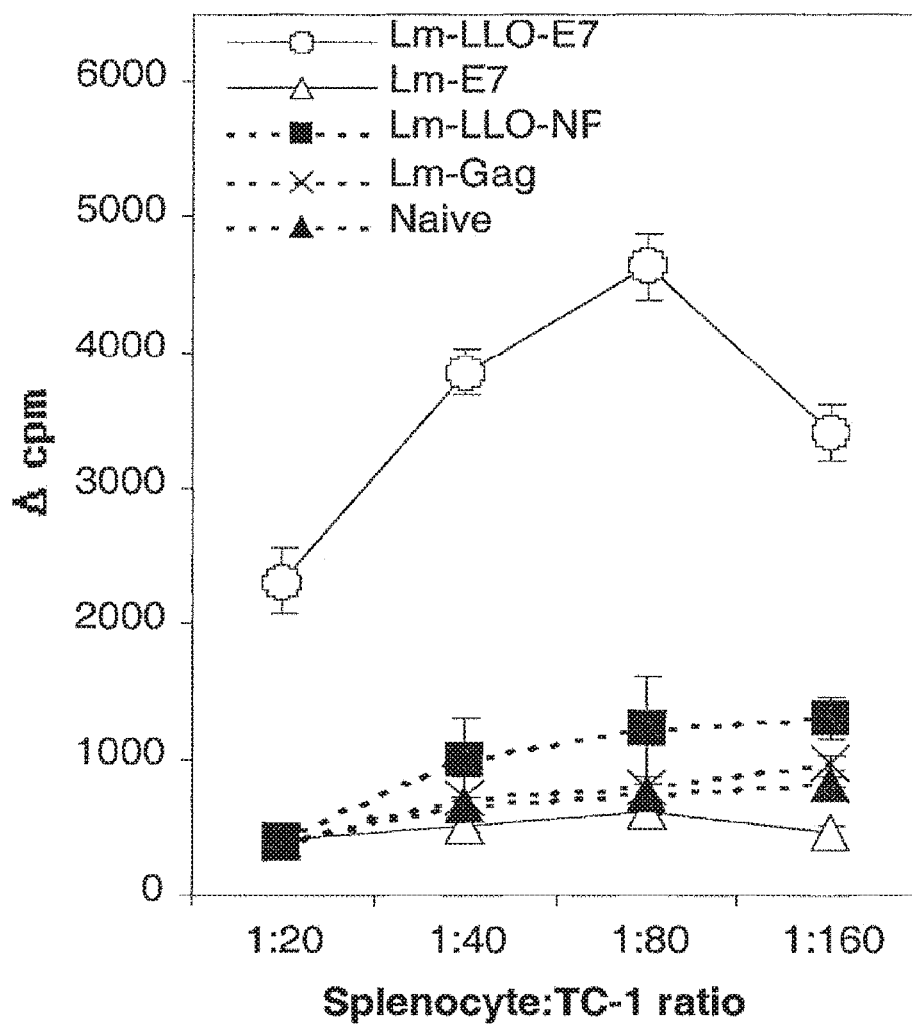
FIG. 4 shows that splenocytes from Lm-LLO-E7-immunized mice proliferate when exposed to TC-1 cells. C57BL/6 mice were immunized and boosted with Lm-LLO-E7, Lm-E7, or control rLm strains. Splenocytes were harvested 6 days after the boost and plated with irradiated TC-1 cells at the ratios shown. The cells were pulsed with $^3$H thymidine and harvested. Cpm is defined as (experimental cpm)–(no-TC-1 control).

To measure induction of T cells by Lm-E7 with Lm-LLO-E7, E7-specific proliferative responses, a measure of antigen-specific immunocompetence, were measured in immunized mice. Splenocytes from Lm-LLO-E7-immunized mice proliferated when exposed to irradiated TC-1 cells as a source of E7, at splenocyte: TC-1 ratios of 20:1, 40:1, 80:1, and 160:1 (FIG. 4). Conversely, splenocytes from Lm-E7 and rLm control-immunized mice exhibited only background levels of proliferation.

Example 3: ActA-E7 and PEST-E7 Fusions Confer Anti-Tumor Immunity

Materials and Experimental Methods

Construction of Lm-ActA-E7

Lm-ActA-E7 is a recombinant strain of LM, comprising a plasmid that expresses the E7 protein fused to a truncated version of the actA protein. Lm-actA-E7 was generated by introducing a plasmid vector pDD-1, constructed by modifying pDP-2028, into Listeria. pDD-1 comprises an expression cassette expressing a copy of the 310 bp hly promoter and the hly signal sequence (ss), which drives the expression and secretion of ActA-E7; 1170 bp of the actA gene that comprises four PEST sequences (the truncated ActA polypeptide consists of the first 390 AA of the molecule; the 300 bp HPV E7 gene; the 1019 bp prfA gene (controls expression of the virulence genes); and the CAT gene (chloramphenicol resistance gene) for selection of transformed bacteria clones (Sewell et al. (2004), Arch. Otolaryngol. Head Neck Surg., 130: 92-97).

The hly promoter (pHly) and gene fragment were PCR amplified from pGG55 (Example 1) using primer 5'-GGGG TCTAGACCTCCTTTGATTAGTATATTC-3' (Xba I site is underlined; SEQ ID NO: 30) and primer 5'-ATCTTCGC-TATCTGTCGCCGCGGCGCGTGCTTCAGTTTGTTG-CGC-3' (Not I site is underlined. The first 18 nucleotides are the ActA gene overlap; SEQ ID NO: 31). The actA gene was PCR amplified from the LM 10403s wildtype genome using primer 5'-GCGCAACAAACTGAAGCAGCGGCCGCGG-CGACAGATAGCGAAGAT-3' (NotI site is underlined; SEQ ID NO: 32) and primer 5'-TGTAGGTGTATCTCCATG CTCGAGAGCTAGGCGATCAATTTC-3' (XhoI site is underlined; SEQ ID NO: 33). The E7 gene was PCR amplified from pGG55 (pLLO-E7) using primer 5'-GGAAT-TGATCGCCTAGCTCTCGAGCATGGAGATACACCT-ACA-3' (XhoI site is underlined; SEQ ID NO: 34) and primer 5'-AAACGGATTTATTTAGATCCCGGGTTATG-GTTTCTGAGAACA-3' (XmaI site is underlined; SEQ ID NO: 35). The prfA gene was PCR amplified from the LM 10403s wild-type genome using primer 5'-TGTTCT-CAGAAACCATAACCCGGGATCTAAATAAATCCG-TTT-3' (XmaI site is underlined; SEQ ID NO: 36) and primer 5'-GGGGGTCGACCAGCTCTTCTTGGTGAAG-3' (SalI site is underlined; SEQ ID NO: 37). The hly promoter-actA gene fusion (pHly-actA) was PCR generated and amplified from purified pHly DNA and purified actA DNA using the upstream pHly primer (SEQ ID NO: 30) and downstream actA primer (SEQ ID NO: 33).

The E7 gene fused to the prfA gene (E7-prfA) was PCR generated and amplified from purified E7 DNA and purified prfA DNA using the upstream E7 primer (SEQ ID NO: 34) and downstream prfA gene primer (SEQ ID NO: 37).

The pHly-actA fusion product fused to the E7-prfA fusion product was PCR generated and amplified from purified fused pHly-actA DNA product and purified fused E7-prfA DNA product using the upstream pHly primer (SEQ ID NO: 30) and downstream prfA gene primer (SEQ ID NO: 37) and ligated into pCRII (Invitrogen, La Jolla, Calif.). Competent *E. coli* (TOP10'F, Invitrogen, La Jolla, Calif.) were transformed with pCRII-ActAE7. After lysis and isolation, the plasmid was screened by restriction analysis using B amHI (expected fragment sizes 770 bp and 6400 bp (or when the insert was reversed into the vector: 2500 bp and 4100 bp)) and BstXI (expected fragment sizes 2800 bp and 3900 bp) and also screened with PCR analysis using the upstream pHly primer (SEQ ID NO: 30) and the downstream prfA gene primer (SEQ ID NO: 37).

The pHly-actA-E7-prfA DNA insert was excised from pCRII by double digestion with Xba I and Sal I and ligated into pDP-2028 also digested with Xba I and Sal I. After transforming TOP10'F competent *E. coli* (Invitrogen, La Jolla, Calif.) with expression system pActAE7, chloramphenicol resistant clones were screened by PCR analysis using the upstream pHly primer (SEQ ID NO: 30) and the downstream PrfA gene primer (SEQ ID NO: 37). A clone comprising pActAE7 was grown in brain heart infusion medium (with chloramphenicol (20 mcg (microgram)/ml (milliliter), Difco, Detroit, Mich.) and pActAE7 was isolated from the bacteria cell using a midiprep DNA purification system kit (Promega, Madison, Wis.). A prfA-negative strain of penicillin-treated *Listeria* (strain XFL-7) was transformed with expression system pActAE7, as described in Ikonomidis et al. (1994, J. Exp. Med. 180: 2209-2218) and clones were selected for the retention of the plasmid in vivo. Clones were grown in brain heart infusion with chloramphenicol (20 mcg/ml) at 37° C. Bacteria were frozen in aliquots at −80° C.

Immunoblot Verification of Antigen Expression

Figure 5A:
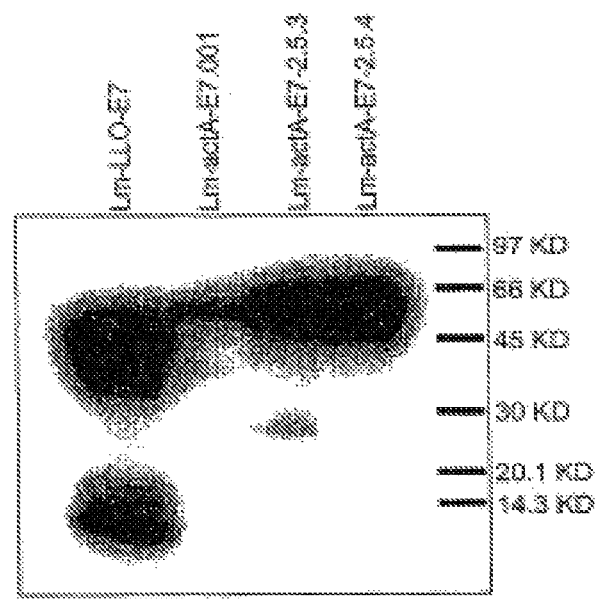
FIG. 5A shows (A) Western blot demonstrating that Lm-ActA-E7 secretes E7. Lane 1: Lm-LLO-E7; lane 2: Lm-ActA-E7.001; lane 3; Lm-ActA-E7-2.5.3; lane 4: Lm-ActA-E7-2.5.4.

To verify that Lm-ActA-E7 secretes ActA-E7, (about 64 kD), *Listeria* strains were grown in Luria-Bertoni (LB) medium at 37° C. Protein was precipitated from the culture supernatant with trichloroacetic acid (TCA) and resuspended in 1× sample buffer with 0.1N sodium hydroxide. Identical amounts of each TCA precipitated supernatant were loaded on 4% to 20% Tris-glycine sodium dodecyl sulfate-polyacrylamide gels (NOVEX, San Diego, Calif.). Gels were transferred to polyvinylidene difluoride membranes and probed with 1:2500 anti-E7 monoclonal antibody (Zymed Laboratories, South San Francisco, Calif.), then with 1:5000 horseradish peroxidase-conjugated anti-mouse IgG (Amersham Pharmacia Biotech, Little Chalfont, England). Blots were developed with Amersham enhanced chemiluminescence detection reagents and exposed to autoradiography film (Amersham) (FIG. 5A).

Figure 6A:
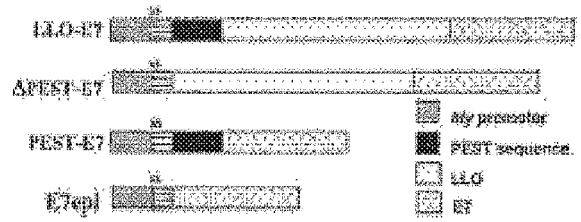
FIG. 6A shows schematic representation of the plasmid inserts used to create 4 LM vaccines. Lm-LLO-E7 insert contains all of the Listeria genes used. It contains the hly promoter, the first 1.3 kb of the hly gene (which encodes the protein LLO), and the HPV-16 E7 gene. The first 1.3 kb of hly includes the signal sequence (ss) and the PEST region. Lm-PEST-E7 includes the hly promoter, the signal sequence, and PEST and E7 sequences but excludes the remainder of the truncated LLO gene. Lm-ΔPEST-E7 excludes the PEST region, but contains the hly promoter, the signal sequence, E7, and the remainder of the truncated LLO. Lm-E7epi has only the hly promoter, the signal sequence, and E7.

Construction of Lm-PEST-E7, Lm-APEST-E7, and Lm-E7epi (FIG. 6A)

Lm-PEST-E7 is identical to Lm-LLO-E7, except that it contains only the promoter and PEST sequence of the hly gene, specifically the first 50 AA of LLO. To construct Lm-PEST-E7, the hly promoter and PEST regions were fused to the full-length E7 gene using the SOE (gene splicing by overlap extension) PCR technique. The E7 gene and the hly-PEST gene fragment were amplified from the plasmid pGG-55, which contains the first 441 AA of LLO, and spliced together by conventional PCR techniques. To create a final plasmid, pVS16.5, the hly-PEST-E7 fragment and the prfA gene were subcloned into the plasmid pAM401, which includes a chloramphenicol resistance gene for selection in vitro, and the resultant plasmid was used to transform XFL-7.

Lm-ΔPEST-E7 is a recombinant *Listeria* strain that is identical to Lm-LLO-E7 except that it lacks the PEST sequence. It was made essentially as described for Lm-PEST-E7, except that the episomal expression system was constructed using primers designed to remove the PEST-containing region (bp 333-387) from the hly-E7 fusion gene. Lm-E7epi is a recombinant strain that secretes E7 without the PEST region or LLO. The plasmid used to transform this strain contains a gene fragment of the hly promoter and signal sequence fused to the E7 gene. This construct differs from the original Lm-E7, which expressed a single copy of the E7 gene integrated into the chromosome. Lm-E7epi is completely isogenic to Lm-LLO-E7, Lm-PEST-E7, and Lm-ΔPEST-E7 except for the form of the E7 antigen expressed.

Results

Figure 5B:
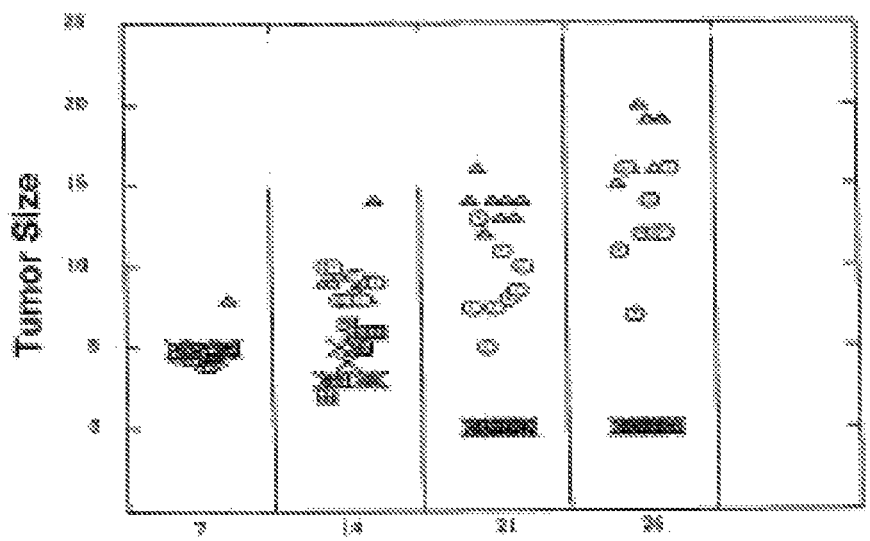
FIG. 5B shows Tumor size in mice administered Lm-ActA-E7 (rectangles), Lm-E7 (ovals), Lm-LLO-E7 (X), and naive mice (non-vaccinated; solid triangles).

To compare the anti-tumor immunity induced by Lm-ActA-E7 versus Lm-LLO-E7, $2 \times 10^5$ TC-1 tumor cells were implanted subcutaneously in mice and allowed to grow to a palpable size (approximately 5 millimeters [mm]). Mice were immunized i.p. with one $LD_{50}$ of either Lm-ActA-E7 ($5 \times 10^8$ CFU), (crosses) Lm-LLO-E7 ($10^8$ CFU) (squares) or Lm-E7 ($10^6$ CFU) (circles) on days 7 and 14. By day 26, all of the animals in the Lm-LLO-E7 and Lm-ActA-E7 were tumor free and remained so, whereas all of the naive animals (triangles) and the animals immunized with Lm-E7 grew large tumors (FIG. 5B). Thus, vaccination with ActA-E7 fusions causes tumor regression.

Figure 6B:
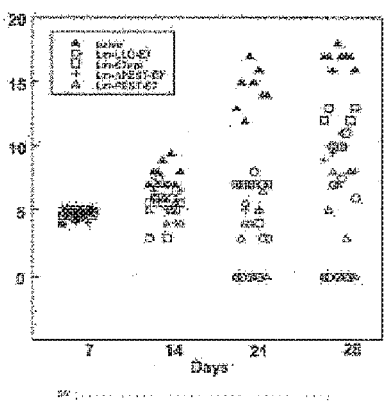
Figure 6C:
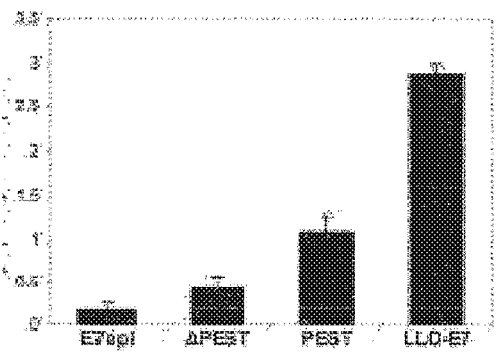
FIG. 6C shows Listeria constructs containing PEST regions induce a higher percentage of E7-specific lymphocytes in the spleen. Average and SE of data from 3 experiments are depicted.

In addition, Lm-LLO-E7, Lm-PEST-E7, Lm-ΔPEST-E7, and Lm-E7epi were compared for their ability to cause regression of E7-expressing tumors. S.c. TC-1 tumors were established on the left flank of 40 C57BL/6 mice. After tumors had reached 4-5 mm, mice were divided into 5 groups of 8 mice. Each groups was treated with 1 of 4 recombinant LM vaccines, and 1 group was left untreated. Lm-LLO-E7 and Lm-PEST-E7 induced regression of established tumors in 5/8 and 3/8 cases, respectively. There was no statistical difference between the average tumor size of mice treated with Lm-PEST-E7 or Lm-LLO-E7 at any time point. However, the vaccines that expressed E7 without the PEST sequences, Lm-ΔPEST-E7 and Lm-E7epi, failed to cause tumor regression in all mice except one (FIG. 6B, top panel). This was representative of 2 experiments, wherein a statistically significant difference in mean tumor sizes at day 28 was observed between tumors treated with Lm-LLO-E7 or Lm-PEST-E7 and those treated with Lm-E7epi or Lm-ΔPEST-E7; $P<0.001$, Student's t test; FIG. 6B, bottom panel). In addition, increased percentages of tetramer-positive splenocytes were seen reproducibly over 3 experiments in the spleens of mice vaccinated with PEST-containing vaccines (FIG. 6C). Thus, vaccination with PEST-E7 fusions causes tumor regression.

Example 4: Fusion of E7 to LLO, ActA, or a Pest-Like Sequence Enhances E7-Specific Immunity and Generates Tumor-Infiltrating E7-Specific CD8$^+$ Cells Materials and Experimental Methods 500 mcl (microliter) of MATRIGEL®, comprising 100 mcl of $2 \times 10^5$ TC-1 tumor cells in phosphate buffered saline (PBS) plus 400 mcl of MATRIGEL® (BD Biosciences, Franklin Lakes, N.J.) were implanted subcutaneously on the left flank of 12 C57BL/6 mice (n=3). Mice were immunized intraperitoneally on day 7, 14 and 21, and spleens and tumors were harvested on day 28. Tumor MATRIGELs were removed from the mice and incubated at 4° C. overnight in tubes containing 2 milliliters (ml) of RP 10 medium on ice. Tumors were minced with forceps, cut into 2 mm blocks, and incubated at 37° C. for 1 hour with 3 ml of enzyme mixture (0.2 mg/ml collagenase-P, 1 mg/ml DNAse-1 in PBS). The tissue suspension was filtered through nylon mesh and washed with 5% fetal bovine serum+0.05% of $NaN_3$ in PBS for tetramer and IFN-gamma staining.

Splenocytes and tumor cells were incubated with 1 micromole (mcm) E7 peptide for 5 hours in the presence of brefeldin A at $10^7$ cells/ml. Cells were washed twice and incubated in 50 mcl of anti-mouse Fc receptor supernatant (2.4 G2) for 1 hour or overnight at 4° C. Cells were stained for surface molecules CD8 and CD62L, permeabilized, fixed using the permeabilization kit Golgi-stop® or Golgi-Plug® (Pharmingen, San Diego, Calif.), and stained for IFN-gamma. 500,000 events were acquired using two-laser flow cytometer FACSCalibur and analyzed using Cellquest Software (Becton Dickinson, Franklin Lakes, N.J.). Percentages of IFN-gamma secreting cells within the activated ($CD62L^{low}$) $CD8^+$ T cells were calculated.

For tetramer staining, $H-2D^b$ tetramer was loaded with phycoerythrin (PE)-conjugated E7 peptide (RAHYNIVTF, SEQ ID NO: 27), stained at rt for 1 hour, and stained with anti-allophycocyanin (APC) conjugated MEL-14 (CD62L) and FITC-conjugated $CD8^+$ at 4° C. for 30 min. Cells were analyzed comparing tetramer$^+$$CD8^+$ $CD62L^{low}$ cells in the spleen and in the tumor.

Results

Figure 7A:
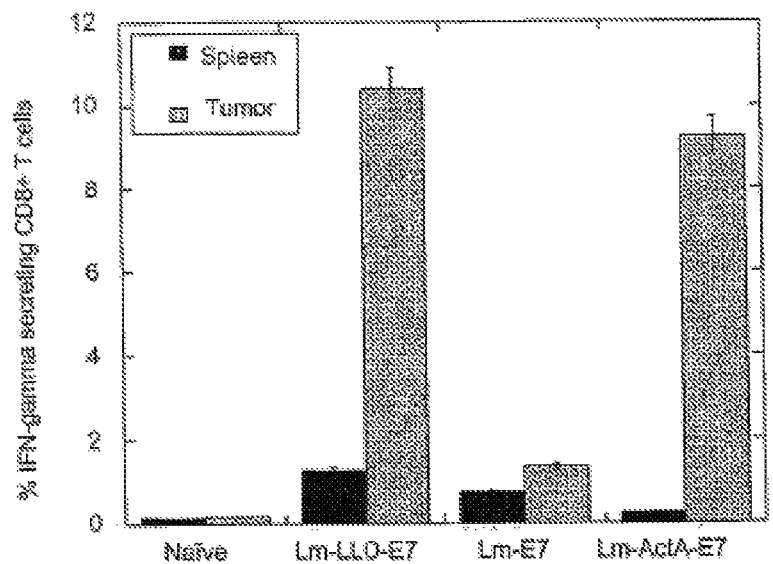
FIG. 7A shows Induction of E7-specific IFN-gamma-secreting CD8$^+$ T cells in the spleens and the numbers penetrating the tumors, in mice administered TC-1 tumor cells and subsequently administered Lm-E7, Lm-LLO-E7, Lm-ActA-E7, or no vaccine (naive).
Figure 7B:
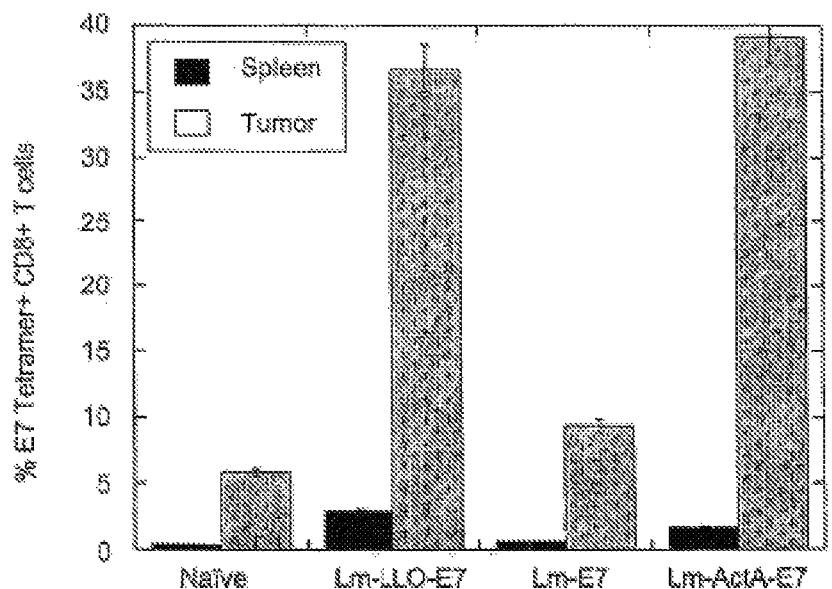
FIG. 7B shows induction and penetration of E7 specific CD8$^+$ cells in the spleens and tumors of the mice described for (A).

To analyze the ability of Lm-ActA-E7 to enhance antigen specific immunity, mice were implanted with TC-1 tumor cells and immunized with either Lm-LLO-E7 ($1\times10^7$ CFU), Lm-E7 ($1\times10^6$ CFU), or Lm-ActA-E7 ($2\times10^8$ CFU), or were untreated (naïve). Tumors of mice from the Lm-LLO-E7 and Lm-ActA-E7 groups contained a higher percentage of IFN-gamma-secreting $CD8^+$ T cells (FIG. 7A) and tetramer-specific $CD8^+$ cells (FIG. 7B) than in Lm-E7 or naive mice.

Figure 8A:
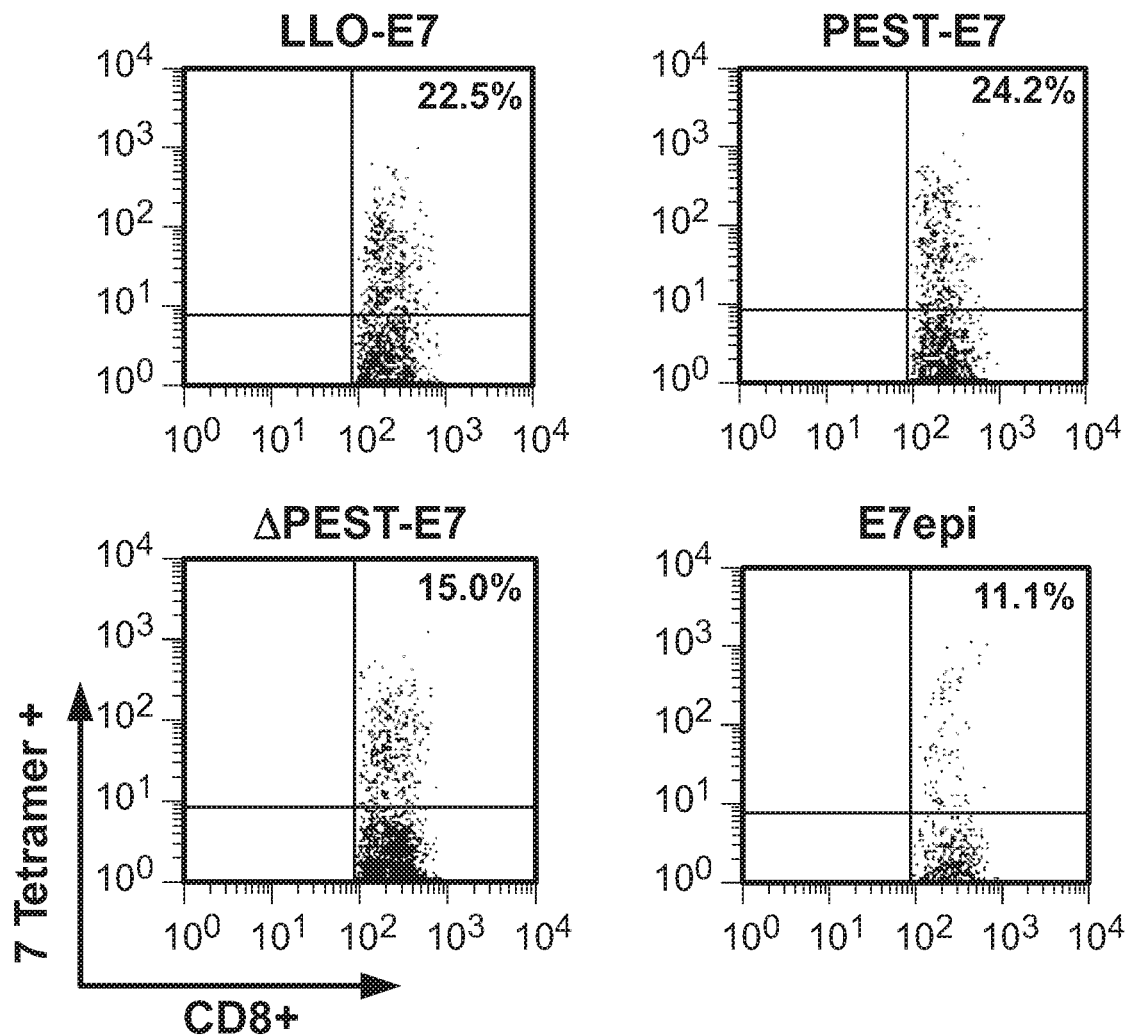
FIGS. 8A-B show Listeria constructs containing PEST regions induce a higher percentage of E7-specific lymphocytes within the tumor.
Figure 8B:
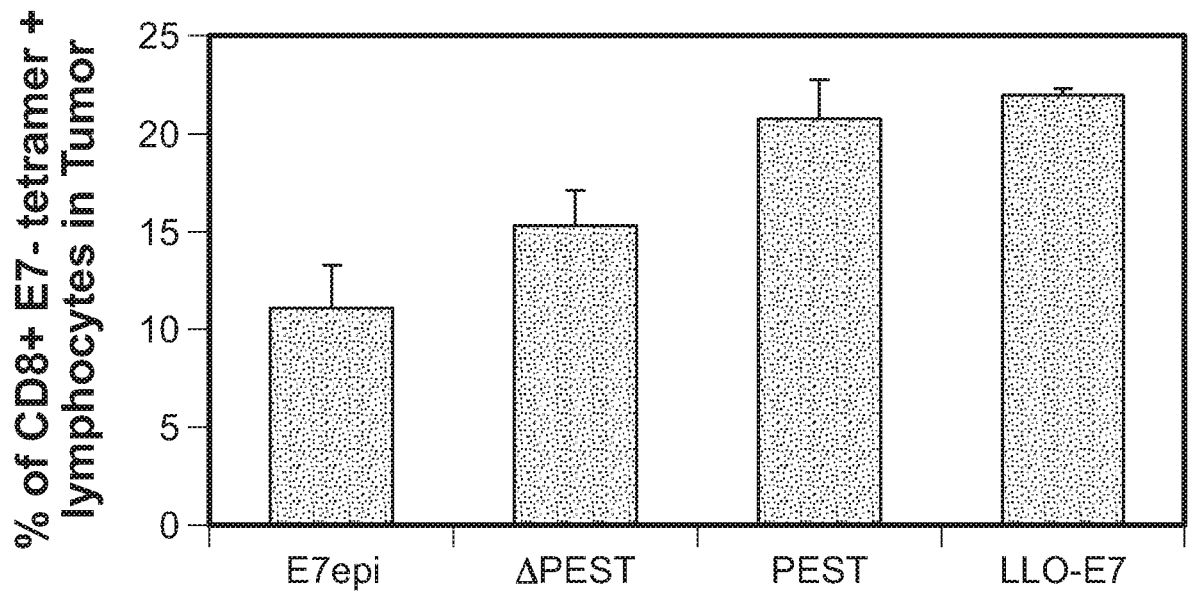

In another experiment, tumor-bearing mice were administered Lm-LLO-E7, Lm-PEST-E7, Lm-ΔPEST-E7, or Lm-E7epi, and levels of E7-specific lymphocytes within the tumor were measured. Mice were treated on days 7 and 14 with 0.1 $LD_{50}$ of the 4 vaccines. Tumors were harvested on day 21 and stained with antibodies to CD62L, CD8, and with the E7/Db tetramer. An increased percentage of tetramer-positive lymphocytes within the tumor were seen in mice vaccinated with Lm-LLO-E7 and Lm-PEST-E7 (FIG. 8A). This result was reproducible over three experiments (FIG. 8B).

Thus, Lm-LLO-E7, Lm-ActA-E7, and Lm-PEST-E7 are each efficacious at induction of tumor-infiltrating $CD8^+$ T cells and tumor regression.

Materials and Experimental Methods (Examples 5-10)

Bacterial Strains, Transformation and Selection

*E. coli* strain MB2159 was used for transformations, using standard protocols. Bacterial cells were prepared for electroporation by washing with $H_2O$.

*E. coli* strain MB2159 (Strych U et al, FEMS Microbiol Lett. 2001 Mar. 15; 196(2):93-8) is an alr (−)/dadX (−) deficient mutant that is not able to synthesize D-alanine racemase. *Listeria* strain Lm dal(−)/dat(−) (Lmdd) similarly is not able to synthesize D-alanine racemase due to partial deletions of the dal and the dat genes.

Plasmid Constructions

Using the published sequence of the plcA gene (Mengaud et al., Infect. Immun. 1989 57, 3695-3701), PCR was used to amplify the gene from chromosomal DNA. The amplified product was then ligated into pAM401 using SalI- and XbaI-generated DNA ends to generate pDP1462.

Plasmid pDP1500, containing prfA alone, was constructed by deleting the plcA gene, bases 429 to 1349 (Mengaud et al., supra), from pDP1462 after restriction with XbaI and PstI, treatment of the DNA ends with T4 DNA polymerase to make them blunt, and intramolecular ligation.

Plasmid pDP1499, containing the plcA promoter and a portion of the 3' end of plcA, was constructed by deleting a plcA internal fragment, bases 428 to 882 (Mengaud et al., Infect. Immun. 1989 57, 3695-3701), from pDP1339 after restriction with PstI and NsiI and intramolecular ligation.

pDP1526 (pKSV7::ΔplcA) was constructed by a single three-part ligation of pKSV7 restricted with BAMHI and XbaI, the 468 bp XbaI and NsiI-generated fragment from pAM401::plcA containing the 5' end of plcA (bases 882 to 1351; Mengaud et al., supra) and, the 501 bp PstI- and BamHI-generated fragment from pAM401::plcA prfA containing the 3' end of plcA (bases 77 to 429; Mengaud et al., supra).

The prfA promoter, bases 1-429 (Mengaud et al., supra), was isolated by EcoRI and PstI double digestion of pDP1462 and the fragment was subsequently ligated into EcoRI- and PstI-restricted pKSV7 to generate pDP1498. Two random HindIII-generated 10403S chromosomal DNA fragments, approximately 3 kb in length, were ligated into HindIII-restricted pKSV7, to generate the random integration control plasmids pDP1519 and pDP1521.

Construction of *L. monocytogenes* Mutant Strains

*L. monocytogenes* strain DP-L1387 was isolated as a mutant with reduced lecithinase (PC-PLC) from a Tn917-LTV3 bank of SLCC 5764, constructed as previously described (Camilli et al., J. Bacteriol. 1990, 172, 3738-3744). The site of Tn917-LTV3 insertion was determined by sequencing one transposon-chromosomal DNA junction as previously described (Sun et al., Infect. Immun. 1990 58, 3770-3778). *L. monocytogenes* was transformed with plasmid DNA as previously described (Camilli et al., supra). Selective pressure for maintenance of pAM401, pKSV7, and their derivatives in *L. monocytogenes* was exerted in the presence of 10 µg of chloramphenicol per ml of media. In addition, maintenance of pKSV7 derivatives required growth at 30° C., a permissive temperature for plasmid replication in Gram-positive bacteria.

Integration of pKSV7 derivatives into the *L. monocytogenes* chromosome occurred by homologous recombination between *L. monocytogenes* DNA sequences on the plasmids and their corresponding chromosomal alleles. Integration mutants were enriched by growth for approximately 30 generations at 40° C., a non-permissive temperature for pKSV7 replication, in Brain Heart Infusion (BHI) broth containing 10 µg chloramphenicol per ml of media. Each integration strain was subsequently colony purified on BHI agar containing 10 µg chloramphenicol per ml of media and incubated at 40° C. Southern blot analyses of chromosomal DNA isolated from each integration strain confirmed the presence of the integrated plasmid.

Construction of DP-L1552 is achieved by integration of the pKSV7 derivative, pDP1526, to generate a merodiploid intermediate as described above. Spontaneous excision of the integrated plasmid, through intramolecular homologous recombination, occurred at a low frequency. Bacteria in which the plasmid had excised from the chromosome were enriched by growth at 30° C. in BHI broth for approximately 50 generations. The nature of the selective pressure during this step was not known but may be due to a slight growth defect of strains containing integrated temperature-sensitive plasmids. Approximately 50% of excision events, i.e., those resulting from homologous recombination between sequences 3' of the deletion, resulted in allelic exchange of ΔplcA for the wild-type allele on the chromosome.

The excised plasmids were cured by growing the bacteria at 40° C. in BHI for approximately 30 generations. Bacteria cured of the plasmid retaining the ΔplcA allele on the chromosome were identified by their failure to produce a zone of turbidity surrounding colonies after growth on BHI agar plates containing a 5 ml overlay of BHI agar/2.5% egg yolk/2.5% phosphate-buffered saline (PBS) (BHI/egg yolk agar). The turbid zones resulted from PI-PLC hydrolysis of PI in the egg yolk, giving an insoluble diacylglycerol precipitate. The correct plcA deletion on the *L. monocytogenes* chromosome was confirmed by amplifying the deleted allele using PCR and sequencing across the deletion.

Thus, PI-PLC negative mutants (plcA deletion mutants) may be used according to the present disclosure to generate attenuated *L. monocytogenes* vaccines. Other mutants were made using the same method, namely, an actA deletion mutant, a plcB deletion mutant, and a double mutant lacking both plcA and plcB, all of which may also be used according to the present disclosure to generate attenuated *L. monocytogenes* vaccines. Given the present disclosure, one skilled in the art would be able to create other attenuated mutants in addition to those mentioned above.

Construction of Lmdd

The dal gene was initially inactivated by means of a double-allelic exchange between the chromosomal gene and the temperature-sensitive shuttle plasmid pKSV7 (Smith K et al, Biochimie. 1992 July-August; 74(7-8):705-11) carrying an erythromycin resistance gene between a 450-bp fragment from the 5' end of the original 850-bp dal gene PCR product and a 450-bp fragment from the 3' end of the dal gene PCR product. Subsequently, a dal deletion mutant covering 82% of the gene was constructed by a similar exchange reaction with pKSV7 carrying homology regions from the 5' and 3' ends of the intact gene (including sequences upstream and downstream of the gene) surrounding the desired deletion. PCR analysis was used to confirm the structure of this chromosomal deletion.

The chromosomal dat gene was inactivated by a similar allelic exchange reaction. pKSV7 was modified to carry 450-bp fragments derived by PCR from both the 5' and 3' ends of the intact dat gene (including sequences upstream and downstream of the gene). These two fragments were ligated by appropriate PCR. Exchange of this construct into the chromosome resulted in the deletion of 30% of the central bases of the dat gene, which was confirmed by PCR analysis.

Bacterial Culture and In Vivo Passaging of *Listeria*

*E. coli* were cultured following standard methods. *Listeria* were grown at 37° C., 250 rpm shaking in LB media (Difco, Detroit, Mich.).+50 μg/ml streptomycin, and harvested during exponential growth phase. For Lm-LLOE7, 37 μg/ml chloramphenicol was added to the media. For growth kinetics determinations, bacteria were grown for 16 hours in 10 ml of LB+ antibiotics. The $OD_{600nm}$ was measured and culture densities were normalized between the strains. The culture was diluted 1:50 into LB+ suitable antibiotics and D-alanine if applicable.

Passaging of LM in Mice $1\times10^8$ CFU were injected intraperitoneally (i.p.) into C57BL/6 mice. On day three, spleens were isolated and homogenized in PBS. An aliquot of the spleen suspension was plated on LB plates with antibiotics as applicable. Several colonies were expanded and mixed to establish an injection stock.

Construction of Antibiotic Resistance Factor Free Plasmid pTV3

Construction of p60-Dal Cassette.

The first step in the construction of the antibiotic resistance gene-free vector was construction of a fusion of a truncated p60 promoter to the dal gene. The LM alanine racemase (dal) gene (forward primer: 5'-CCA TGG TGA CAG GCT GGC ATC-3'; SEQ ID NO: 38) (reverse primer: 5'-GCT AGC CTA ATG GAT GTA TTT TCT AGG-3'; SEQ ID NO: 39) and a minimal p60 promoter sequence (forward primer: 5'-TTA ATT AAC AAA TAG TTG GTA TAG TCC-3'; SEQ ID No: 40) (reverse primer: 5'-GAC GAT GCC AGC CTG TCA CCA TGG AAA ACT CCT CTC-3'; SEQ ID No: 41) were isolated by PCR amplification from the genome of LM strain 10403S. The primers introduced a PacI site upstream of the p60 sequence, an NheI site downstream of the dal sequence (restriction sites in bold type), and an overlapping dal sequence (the first 18 bp) downstream of the p60 promoter for subsequent fusion of p60 and dal by splice overlap extension (SOE)-PCR. The sequence of the truncated p60 promoter was: CAAATAGTTGGTATAGTCCTCTTTAGCCTTTGGAGT-ATTATCTCATCATTTGTTTTTTAGGTGAAAACTGG G-TAAACTTAGTATTATCAATATAAAATTAATTCTCAA-ATACTTAA TTACGTACTGGGATTTTCTGAAAAAAG-AGAGGAGTTTTCC (SEQ ID NO: 42) (Kohler et al, J Bacteriol 173: 4668-74, 1991). Using SOE-PCR, the p60 and dal PCR products were fused and cloned into cloning vector pCR2.1 (Invitrogen, La Jolla, Calif.).

Removal of Antibiotic Resistance Genes from pGG55.

The subsequent cloning strategy for removing the Chloramphenicol acetyltransferase (CAT) genes from pGG55 and introducing the p60-dal cassette also intermittently resulted in the removal of the gram-positive replication region (oriRep; Brantl et al, Nucleic Acid Res 18: 4783-4790, 1990). In order to re-introduce the gram-positive oriRep, the oriRep was PCR-amplified from pGG55, using a 5'-primer that added a NarI/EheI site upstream of the sequence (GGCGCCACTAACTCAACGCTAGTAG, SEQ ID NO: 43) and a 3'-primer that added a NheI site downstream of the sequence (GCTAGCCAGC-AAAGAAAAACAAACACG, SEQ ID NO: 44). The PCR product was cloned into cloning vector pCR2.1 and sequence verified.

In order to incorporate the p60-dal sequence into the pGG55 vector, the p60-dal expression cassette was excised from pCR-p60dal by PacI/NheI double digestion. The replication region for gram-positive bacteria in pGG55 was amplified from pCR-oriRep by PCR (primer 1, 5'-GTC GAC GGT CAC CGG CGC CAC TAA CTC AAC GCT AGT AG-3'; SEQ ID No: 45); (primer 2, 5'-TTA ATT AAG CTA GCC AGC AAA GAA AAA CAA ACA CG-3'; SEQ ID No: 46) to introduce additional restriction sites for EheI and NheI. The PCR product was ligated into pCR2.1-TOPO (Invitrogen, Carlsbad, Calif.), and the sequence was verified.

The replication region was excised by EheI/NheI digestion, and vector pGG55 was double digested with EheI and NheI, removing both CAT genes from the plasmid simultaneously. The two inserts, p60-dal and oriRep, and the pGG55 fragment were ligated together, yielding pTV3 (FIG. 9). pTV3 also contains a prfA (pathogenicity regulating factor A) gene. This gene is not necessary for the function of pTV3, but can be used in situations wherein an additional selected marker is required or desired.

Preparation of DNA for Real-Time PCR

Total *Listeria* DNA was prepared using the Masterpure® Total DNA kit (Epicentre, Madison, Wis.). *Listeria* were cultured for 24 hours at 37° C. and shaken at 250 rpm in 25 ml of Luria-Bertoni broth (LB). Bacterial cells were pelleted by centrifugation, resuspended in PBS supplemented with 5 mg/ml of lysozyme and incubated for 20 minutes at 37° C., after which DNA was isolated.

In order to obtain standard target DNA for real-time PCR, the LLO-E7 gene was PCR amplified from pGG55 (5'-ATGAAAAAAATAATGCTAGTTTTTATTAC-3' (SEQ ID NO: 47); 5'-GCGGCCGCTTAATGATGATGATGAT-GATGTGGTTTCTG AGAACAGATG-3' (SEQ ID NO: 48)) and cloned into vector pETblueI (Novagen, San Diego, Calif.). Similarly, the plcA amplicon was cloned into pCR2.1. *E. coli* were transformed with pET-LLOE7 and pCR-plcA, respectively, and purified plasmid DNA was prepared for use in real-time PCR.

Real-Time PCR

Taqman primer-probe sets (Applied Biosystems, Foster City, Calif.) were designed using the ABI PrimerExpress software (Applied Biosystems) with E7 as a plasmid target, using the following primers: 5'-GCAAGTGTGACTC-TACGCTTCG-3' (SEQ ID NO: 49); 5'-TGCCCAT-TAACAGGTCTTCCA-3' (SEQ ID NO: 50); 5'-FAM-TGCGTA CAAAGCACACACGTAGACATTCGTAC-TAMRA-3' (SEQ ID NO: 51) and the one-copy gene plcA (TGACATCGTTTGTGTTTGAGCTAG-3' (SEQ ID NO: 52), 5'-GCAGCGCTCTCTATACCAGGTAC-3' (SEQ ID NO: 53); 5'-TET-TTAATGTCCATGTTA TGTCTCCGT-TATAGCTCATCGTA-TAMRA-3'; SEQ ID NO: 54) as a *Listeria* genome target.

0.4 μM primer and 0.05 mM probe were mixed with PuRE Taq RTG PCR beads (Amersham, Piscataway, N.J.) as recommended by the manufacturer. Standard curves were prepared for each target with purified plasmid DNA, pET-LLOE7 and pCR-plcA (internal standard) and used to calculate gene copy numbers in unknown samples. Mean ratios of E7 copies/plcA copies were calculated based on the standard curves and calibrated by dividing the results for Lmdd-TV3 and Lm-LLOE7 with the results from Lm-E7, a *Listeria* strain with a single copy of the E7 gene integrated into the genome. All samples were run in triplicate in each qPCR assay which was repeated three times. Variation between samples was analyzed by Two-Way ANOVA using the KyPlot software. Results were deemed statistically significant if $p<0.05$.

Growth Measurements

Bacteria were grown at 37° C., 250 rpm shaking in Luria Bertani (LB) Medium+/−100 micrograms (μg)/ml D-alanine and/or 37 μg/ml chloramphenicol. The starting inoculum was adjusted based on $OD_{600}$ nm measurements to be the same for all strains.

Hemolytic Lysis Assay $4 \times 10^9$ CFU of *Listeria* were thawed, pelleted by centrifugation (1 minute, 14000 rpm) and resuspended in 100 μl PBS, pH 5.5 with 1 M cysteine. Bacteria were serially diluted 1:2 and incubated for 45 minutes at 37° C. in order to activate secreted LLO. Defibrinated total sheep blood (Cedarlane, Hornby, Ontario, Canada) was washed twice with 5 volumes of PBS and three to four times with 6 volumes of PBS-Cysteine until the supernatant remained clear, pelleting cells at 3000×g for 8 minutes between wash steps, then resuspended to a final concentration of 10% (v/v) in PBS-Cysteine. 100 μl of 10% washed blood cells were mixed with 100 μl of *Listeria* suspension and incubated for additional 45 minutes at 37° C. Un-lysed blood cells were then pelleted by centrifugation (10 minutes, 1000×g). 100 μl of supernatant was transferred into a new plate and the $OD_{530nm}$ was determined and plotted against the sample dilution.

Therapeutic Efficacy of Lmdd-Tv3

$10^5$ TC-1 (ATCC, Manassas, Va.) were implanted subcutaneously in C57BL/6 mice (n=8) and allowed to grow for about 7 days, after which tumors were palpable. TC-1 is a C57BL/6 epithelial cell line that was immortalized with HPV E6 and E7 and transformed with activated ras, which forms tumors upon subcutaneous implantation. Mice were immunized with 0.1 $LD_{50}$ of the appropriate *Listeria* strain on days 7 and 14 following implantation of tumor cells. A non-immunized control group (naïve) was also included. Tumor growth was measured with electronic calipers.

Generation of an ActA Deletion Mutant

Figure 12:
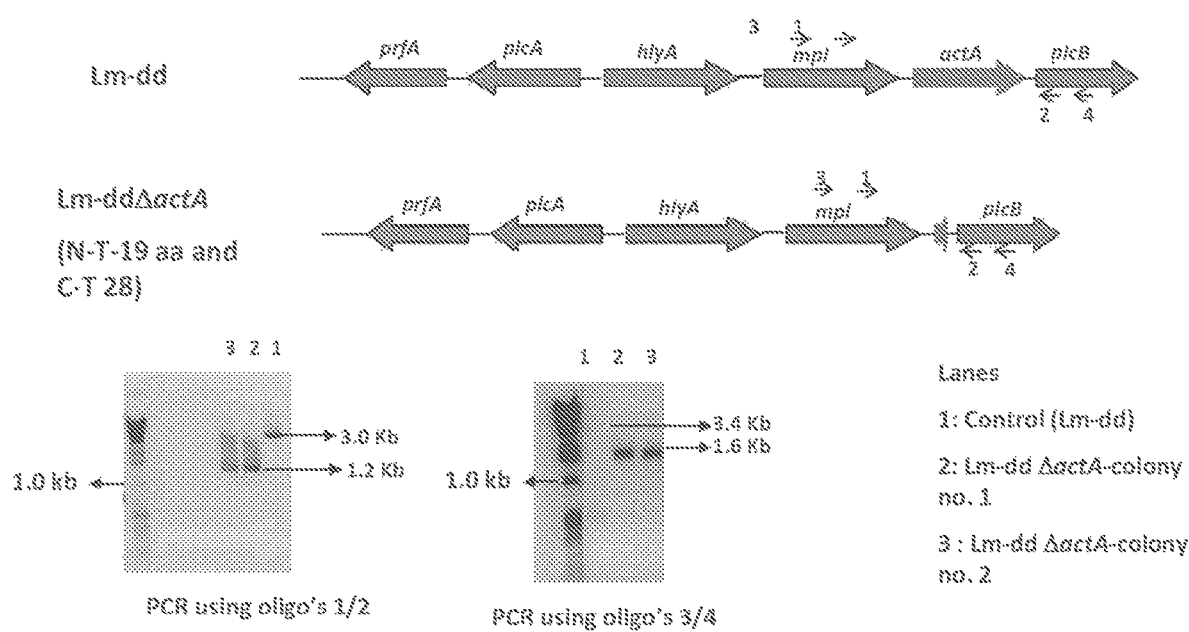
FIG. 12 shows a Schematic representation of the Lm-dd and Lm-dd actA strains. The gel showing the size of PCR products using oligo's 1/2 and oligo's 3/4 obtained using e chromosomal DNA of the strains, Lm-dd and Lm-ddΔactA as template.

The strain Lm dal dat (Lmdd) was attenuated by the irreversible deletion of the virulence factor, ActA. An in frame deletion of actA in the Lmdaldat (Lmdd) background was constructed to avoid any polar effects on the expression of downstream genes. The Lm dal dat ΔactA contains the first 19 amino acids at the N-terminal and 28 amino acid residues of the C-terminal with a deletion of 591 amino acids of ActA. The deletion of the gene into the chromosomal spot was verified using primers that anneal external to the actA deletion region. These are primers 3 (Adv 305-tgggatggc-caagaaattc) (SEQ ID NO: 55) and 4 (Adv304-ctac-catgtcttccgttgcttg) (SEQ ID NO: 56) as shown in the FIG. 12. The PCR analysis was performed on the chromosomal DNA isolated from Lmdd and Lm-ddΔactA. The sizes of the DNA fragments after amplification with two different set of primer pairs 1, 2 and 3, 4 in Lm-dd chromosomal DNA was expected to be 3.0 Kb and 3.4 Kb. However, for the Lm-ddΔactA the expected sizes of PCR using the primer pairs 1, 2 and 3, 4 was 1.2 Kb and 1.6 Kb. Thus, PCR analysis in FIG. 12 confirms that 1.8 kb region of actA was deleted in the strain, Lm-ddΔactA. DNA sequencing was also performed on PCR products to confirm the deletion of actA containing region in the strain, Lm-ddΔactA (FIG. 13, SEQ ID NO: 57).

(SEQ ID NO: 57)
gcgccaaatcattggttgattggtgaggatgtctgtgtgcgtgggtcgcg agatgggcgaataagaagcattaaagatcctgacaaatataatcaagcgg ctcatatgaaagattacgaatcgcttccactcacagaggaaggcgactgg ggcggagttcattataatagtggtatcccgaataaagcagcctataatac tatcactaaacttggaaaagaaaaaacagaacagctttattttcgcgcct taaagtactatttaacgaaaaaatcccagtttaccgatgcgaaaaaagcg cttcaacaagcagcgaaagatttatatggtgaagatgcttctaaaaaagt tgctgaagcttgggaagcagttggggttaactgattaacaaatgttagag aaaaattaattctccaagtgatattcttaaaataattcatgaatattttt -continued

```
tcttatattagctaattaagaagataactaactgctaatccaattttta cggaacaaattagtgaaaatgaaggccgaattttccttgttctaaaaagg ttgtattagcgtatcacgaggagggagtataagtgggattaaacagattt atgcgtgcgatgatggtggttttcattactgccaattgcattacgattaa ccccgacgtcgaccatacgacgttaattcttgcaatgttagctattggc gtgttctctttaggggcgtttatcaaaattattcaattaagaaaaaataa ttaaaaacacagaacgaaagaaaaagtgaggtgaatgatatgaaattcaa aaaggtggttctaggtatgtgcttgatcgcaagtgttctagtctttccgg taacgataaaagcaaatgcctgttgtgatgaatacttacaaacacccgca gctccgcatgatattgacagcaaattaccacataaacttagttggtccgc ggataacccgacaaatactgacgtaaatacgcactattggcttttaaac aagcggaaaaaatactagctaaagatgtaaatcatatgcgagctaattta atgaatgaacttaaaaaattcgataaacaaatagctcaaggaatatatga tgcggatcataaaaatccatattatgatactagtacattttatctcatt tttataatcctgatagagataatacttatttgccgggttttgctaatgcg aaaataacaggagcaaagtatttcaatcaatcggtgactgattaccgaga agggaa.
```

Production of Inflammatory Cytokines:

Macrophages such as RAW 264.7 are infected with different *Listeria* backbones such as Lm prfA− (pGG55), Lm dal dat, Lm dal dat actA, Lm dal dat actA Δ inlC and Lm dal dat Δ inlC and supernatant is harvested at different time points to quantify the level of various cytokines using different ELISA based kits. The cytokines that are quantified include IFN-γ, TNF-α and IL-6.

In Vivo Cytokine Production:

To measure the in vivo cytokine production and recruitment of neutrophils, C57BL/6 mice are injected intraperitoneally with different $10^8$ CFU of Lm prfA− (pGG55), Lm dal dat, Lm dal dat actA, Lm dal dat actA Δ inlC and Lm dal dat Δ inlC, *Listeria* control or an equivalent volume of saline. After 12 h mice are killed and peritoneal cavities are washed with 2 mL of PBS. The peritoneal washes are examined for bacterial load after plating on growth medium and analysis of proinflammatory cytokines such as MIP-1α, KC, MCP etc. Using flow cytometry the number of neutrophils and macrophages is determine after staining with markers such as Gr-1, CD11b and F4/80 and further these populations are quantified using CellQuest software.

Transwell Migration Assay:

This assay is done to determine if there is an increase in the migration of neutrophils following infection of bone marrow derived macrophages or dendritic cells with the inlC deletion strain. Bone marrow-derived macrophages or dendritic cells are isolated from mice such as C57BL/6 and are infected with the inlC deletion mutants or control *Listeria*. Using infected cells the transwell assay is set up using corning costar Transwell plates. The assay is initially standardized using 3, 5, or 8 micron pore transwell plates. To test neutrophil migration, plate the infected APCs in the bottom of the plate and the neutrophils in the top of the well in the chamber. At different time points the cells are counted to determine the number of neutrophils that have migrated to the bottom.

Therapeutic Efficacy of the Lm dal dat actA Δ inlC Mutant:

To determine the therapeutic efficacy of inlC mutant, human Prostate specific antigen (PSA) is used as tumor antigen as proof of concept. The backbone Lm dal dat actA inlC are transformed with the plasmid, pAdv142 that contains expression cassette for human PSA resulting in LmddAinlC142. The strain LmddAinlC142 is characterized for the expression and secretion of fusion protein, tLLO-PSA. Further the strain LmddAinlC142 are passaged twice in vivo in mice and the colonies obtained after two in vivo passages are examined for the expression and secretion of fusion protein, tLLO-PSA. The vaccine working stock are prepared from the colonies obtained after second in vivo passage and this are used for the assessment of therapeutic effects and immunogenicity.

Impact on Tumor Microenvironment:

The ability of LmddA, LmddAΔactA, LmddAΔPlcA, LmddAΔPlcB, LmddAΔprfA, LmddAinlC142, LmddA142 and other control strains to cause infiltration of immune cells in the tumor microenvironment are determined. In this study mice are inoculated with $1 \times 10^6$ TPSA23 tumor cells on day 0 and are vaccinated on day 7, 14 and 21 with $10^8$ CFU of LmddAinlC142, LmddA142 and other control strains. Tumors are harvested on day 28 and processed for further staining with different cell surface markers such as Gr-1, CD11b, CD3, CD4, CD8, CD25, Foxp3, NK1.1 and CD62L. Using these markers different cell populations that are examined include macrophages (CD11b$^+$), NK cells (NK1.1$^+$), neutrophils (Gr-1$^+$ CD11b$^+$), myeloid derived suppressor cells (MDSCs) (Gr-1$^+$ CD11b$^+$), regulatory T cells (CD4$^+$ CD25$^+$ Foxp3$^+$) and effector T cells (CD8$^+$ CD3$^+$ CD62L$^{low}$). Further effector T cells are characterized for their functional ability to produce effector cytokines such as IFN-γ, TNF-α and IL-2. The intratumoral regulatory T cells and MDSCs are tested for their ability to cause suppression of T cell proliferation.

Results

Figure 9A:
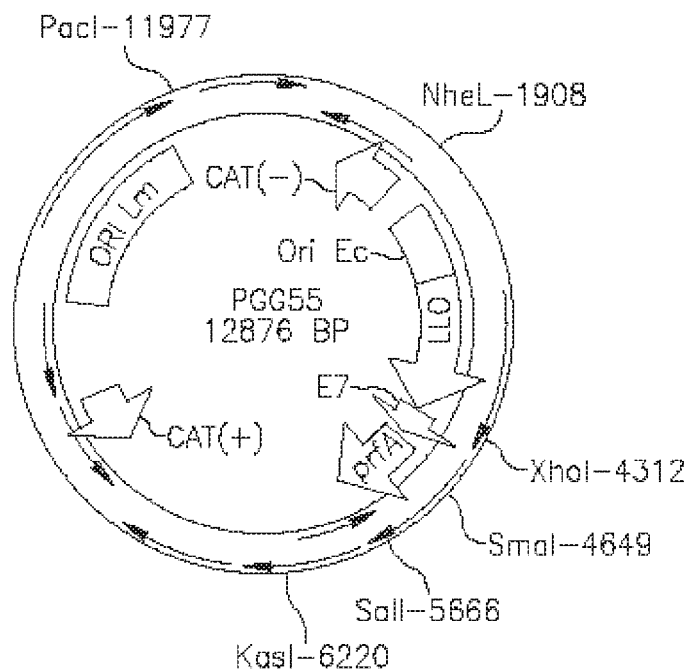
FIG. 9A shows a schematic map of E. coli-Listeria shuttle plasmid pGG55. CAT(-): E. coli chloramphenicol transferase; CAT(+): Listeria chloramphenicol transferase; Ori Lm: replication origin for Listeria; Ori Ec: p15 origin of replication for E. coli; prfA: Listeria pathogenicity regulating factor A; LLO: C-terminally truncated listeriolysin O, including its promoter; E7: HPV E7. Selected restriction sites are also depicted.
Figure 9B:
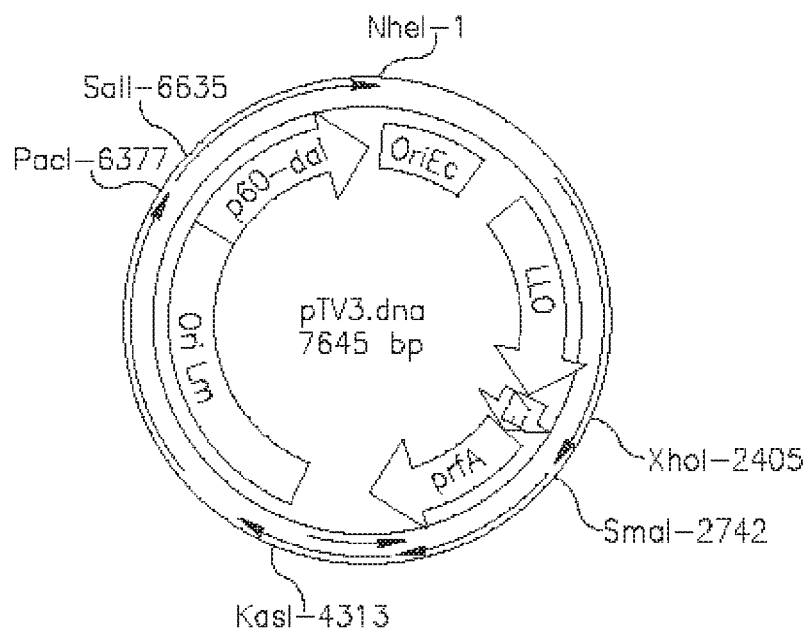
FIG. 9B shows a schematic map of E. coli-Listeria shuttle plasmid pTV3 (below). CAT(-): E. coli chloramphenicol transferase; CAT(+): Listeria chloramphenicol transferase; Ori Lm: replication origin for Listeria; Ori Ec: p15 origin of replication for E. coli; prfA: Listeria pathogenicity regulating factor A; LLO: C-terminally truncated listeriolysin O, including its promoter; E7: HPV E7; p60-dal: expression cassette of p60 promoter and Listeria dal gene. Selected restriction sites are also depicted.

Example 5: A Plasmid Containing an Amino Acid Metabolism Enzyme Instead of an Antibiotic Resistance Gene is Retained in *E. coli* and LM Both In Vitro and In Vivo An auxotroph complementation system based on D-alanine racemase was utilized to mediate plasmid retention in LM without the use of an antibiotic resistance gene. *E. coli* strain MB2159 is an alr (−)/dadX (−) deficient mutant that is not able to synthesize D-alanine racemase. *Listeria* strain Lm dal(−)/dat(−) (Lmdd) similarly is not able to synthesize D-alanine racemase due to partial deletions of the dal and the dat genes. Plasmid pGG55, which is based on *E. coli-Listeria* shuttle vector pAM401, was modified by removing both CAT genes and replacing them with a p60-dal expression cassette under control of the *Listeria* p60 promoter to generate pTV3 (FIG. 9). DNA was purified from several colonies.

Example 6: Plasmids Containing a Metabolic Enzyme do not Increase the Virulence of Bacteria As virulence is linked to LLO function, the hemolytic lysis activity between Lmdd-TV3 and Lm-LLOE7 was compared. This assay tests LLO function by lysis of red blood cells and can be performed with culture supernatant, purified LLO or bacterial cells. Lmdd-TV3 displayed higher hemolytic lysis activity than Lm-LLOE7.

In vivo virulence was also measured by determining $LD_{50}$ values, a more direct, and therefore accurate, means of measuring virulence. The $LD_{50}$ of Lmdd-TV3 ($0.75 \times 10^9$) was very close to that of Lm-LLOE7 ($1 \times 10^9$), showing that plasmids containing a metabolic enzyme do not increase the virulence of bacteria.

Figure 14:
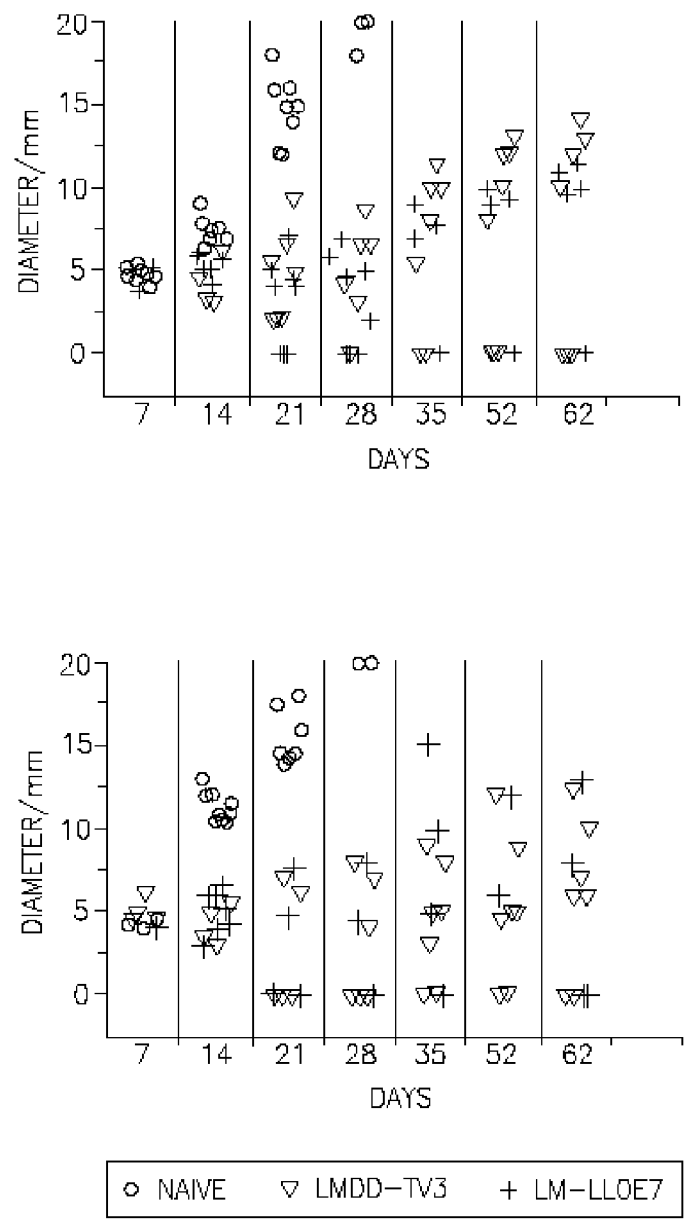
FIG. 14 depicts tumor regression in response to administration of LM vaccine strains (A). Circles represent naive mice, inverted triangles represent mice administered Lmdd-TV3, and crosses represent mice administered Lm-LLOE7.

Example 7: Induction of Anti-Tumor Immunity by Plasmids Containing a Metabolic Enzyme Efficacy of the metabolic enzyme-containing plasmid as a cancer vaccine was determined in a tumor regression model. The TC-1 cell line model, which is well characterized for HPV vaccine development and which allowed for a controlled comparison of the regression of established tumors of similar size after immunization with Lmdd-TV3 or Lm-LLOE7, was used. In two separate experiments, immunization of mice with Lmdd-TV3 and Lm-LLOE7 resulted in similar tumor regression (FIG. 14) with no statistically significant difference ($p<0.05$) between vaccinated groups. All immunized mice were still alive after 63 days, whereas non-immunized mice had to be sacrificed when their tumors reached 20 mm diameter. Cured mice remained tumor-free until the termination of the experiment.

Thus, metabolic enzyme-containing plasmids are efficacious as a therapeutic cancer vaccine. Because immune responses required for a therapeutic cancer vaccine are stronger than those required for a prophylactic cancer vaccine, these results demonstrate utility as well for a prophylactic cancer vaccine.

Example 8: inlC-Deletion Mutant Generate Significantly High Levels of the Chemokines and Cytokines inlC deletion mutant generates significantly high levels of the chemokines such as MIP-1α, KC (mouse homolog of IL-8), MCP resulting in infiltration of neutrophils and leukocytes towards the site of infection. Thus when different *Listeria* strains are administered intraperitoneally, the inlC mutant demonstrate an increase production of these cytokines and chemokines, which attract neutrophils and macrophages in the peritoneal fluid obtained 12 h after injection. Further, inlC deletion mutant generate significantly high levels of the inflammatory cytokines when compared to control strains.

Example 9: inlC-Deletion Mutants Induce Neutrophil Migration

The macrophages infected with inlC deletion mutant show significant increase in the migration of neutrophils at different time points when compared to other control strains. The results of this experiment strongly support the ability of this strain to attract immune cells such as neutrophils during infection.

Example 10: inlC-Deletion Mutants Effect a Therapeutic Anti-Tumor Response

The results of anti-tumor studies using both LmddA142 and LmddAinlC142 are very comparable to each other and therapeutic regression of tumors is observed. Further, two doses of LmddAinlC142 are comparable to three doses of the strain LmddA142 because of its ability to generate high levels of innate responses and increased secretion of proinflammatory cytokines.

Materials and Methods (Examples 11-16)

Oligonucleotides were synthesized by Invitrogen (Carlsbad, Calif.) and DNA sequencing was done by Genewiz Inc, South Plainfield, N.J. Flow cytometry reagents were purchased from Becton Dickinson Biosciences (BD, San Diego, Calif.). Cell culture media, supplements and all other reagents, unless indicated, were from Sigma (St. Louise, Mo.). Her2/neu HLA-A2 peptides were synthesized by EZbiolabs (Westfield, Ind.). Complete RPMI 1640 (C-RPMI) medium contained 2 mM glutamine, 0.1 mM non-essential amino acids, and 1 mM sodium pyruvate, 10% fetal bovine serum, penicillin/streptomycin, Hepes (25 mM). The polyclonal anti-LLO antibody was described previously and anti-Her2/neu antibody was purchased from Sigma.

Mice and Cell Lines

All animal experiments were performed according to approved protocols by IACUC at the University of Pennsylvania or Rutgers University. FVB/N mice were purchased from Jackson laboratories (Bar Harbor, Me.). The FVB/N Her2/neu transgenic mice, which overexpress the rat Her2/neu onco-protein were housed and bred at the animal core facility at the University of Pennsylvania. The NT-2 tumor cell line expresses high levels of rat Her2/neu protein, was derived from a spontaneous mammary tumor in these mice and grown as described previously. DHFR-G8 (3T3/neu) cells were obtained from ATCC and were grown according to the ATCC recommendations. The EMT6-Luc cell line was a generous gift from Dr. John Ohlfest (University of Minnesota, Minn.) and was grown in complete C-RPMI medium. Bioluminescent work was conducted under guidance by the Small Animal Imaging Facility (SAIF) at the University of Pennsylvania (Philadelphia, Pa.).

*Listeria* Constructs and Antigen Expression

Her2/neu-pGEM7Z was kindly provided by Dr. Mark Greene at the University of Pennsylvania and contained the full-length human Her2/neu (hHer2) gene cloned into the pGEM7Z plasmid (Promega, Madison Wis.). This plasmid was used as a template to amplify three segments of hHer-2/neu, namely, EC1, EC2, and IC1, by PCR using pfx DNA polymerase (Invitrogen) and the oligos indicated in Table 1.

TABLE 1

Primers for cloning of Human her-2-Chimera

| | DNA sequence | Base pair region | Amino acid region or junctions |
|---|---|---|---|
| Her-2-Chimera (F) | TGATCTCGAGACCCACCTGGACATGCTC (SEQ ID NO: 58) | 120-510 | 40-170 |

TABLE 1-continued

Primers for cloning of Human her-2-Chimera

| | DNA sequence | Base pair region | Amino acid region or junctions |
|---|---|---|---|
| HerEC1-EC2F (Junction) | CTACCAGGACACGATTTTGTGGAAG-AATATCCA GGAGTTTGCTGGCTGC (SEQ ID NO: 59) | 510/1077 | 170/359 |
| HerEC1-EC2R (Junction) | GCAGCCAGCAAACTCCTGGATATT-CTTCCACAA AATCGTGTCCTGGTAG (SEQ ID NO: 60) | | |
| HerEC2-ICIF (Junction) | CTGCCACCAGCTGTGCGCCCGAGGG-CAGCAGAAGATCCGGAAGTACACGA (SEQ ID NO: 61) | 1554/2034 | 518/679 |
| HerEC2-ICIR (Junction) | TCGTGTACTTCCGGATCTTCTGCTG CCCTCGGGCGCACAGCTGGTGGCAG (SEQ ID NO: 62) | | |
| Her-2-Chimera (R) | GTGGCCCGGGTCTAGATTAGTCTAAGAGGCAGCCAT AGG (SEQ ID NO: 63) | 2034-2424 | 679-808 |

The Her-2/neu chimera construct was generated by direct fusion by the SOEing PCR method and each separate hHer-2/neu segment as templates. Primers are shown in table 2.

TABLE 2

| | DNA sequence | Base pair region | Amino acid region |
|---|---|---|---|
| Her-2-EC1(F) | CCGCCTCGAGGCCGCGAGCACCCAAGTG (SEQ ID NO: 64) | 58-979 | 20-326 |
| Her-2-EC1(R) | CGCGACTAGTTTAATCCTCTGCTGTCACCTC (SEQ ID NO: 65) | | |
| Her-2-EC2(F) | CCGCCTCGAGTACCTTTCTACGGACGTG (SEQ ID NO: 66) | 907-1504 | 303-501 |
| Her-2-EC2(R) | CGCGACTAGTTTACTCTGGCCGGTTGGCAG (SEQ ID NO: 67) | | |
| Her-2-IC1(F) | CCGCCTCGAGCAGCAGAAGATCCGGAAGTAC (SEQ ID NO: 68) | 2034-3243 | 679-1081 |
| Her-2-IC1(R) | CGCGACTAGTTTAAGCCCCTTCGGAGGGTG (SEQ ID NO: 69) | | |

Sequence of primers for amplification of different segments human Her2 regions.

Sequence of primers for amplification of different segments human Her2 regions.

ChHer2 gene was excised from pAdv138 using XhoI and SpeI restriction enzymes, and cloned in frame with a truncated, non-hemolytic fragment of LLO in the Lmdd shuttle vector, pAdv134. The sequences of the insert, LLO and hly promoter were confirmed by DNA sequencing analysis. This plasmid was electroporated into electro-competent actA, dal, dat mutant *Listeria monocytogenes* strain, LmddA and positive clones were selected on Brain Heart infusion (BHI) agar plates containing streptomycin (250 μg/ml). In some experiments similar *Listeria* strains expressing hHer2/neu (Lm-hHer2) fragments were used for comparative purposes. These have been previously described. In all studies, an irrelevant *Listeria* construct (Lm-control) was included to account for the antigen independent effects of *Listeria* on the immune system. Lm-controls were based on the same *Listeria* platform as ADXS31-164, but expressed a different antigen such as HPV16-E7 or NY-ESO-1. Expression and secretion of fusion proteins from *Listeria* were tested. Each construct was passaged twice in vivo.

Cytotoxicity Assay

Groups of 3-5 FVB/N mice were immunized three times with one week intervals with $1\times10^8$ colony forming units (CFU) of Lm-LLO-ChHer2, ADXS31-164, Lm-hHer2 ICI or Lm-control (expressing an irrelevant antigen) or were left naïve. NT-2 cells were grown in vitro, detached by trypsin and treated with mitomycin C (250 μg/ml in serum free C-RPMI medium) at 37° C. for 45 minutes. After 5 washes, they were co-incubated with splenocytes harvested from immunized or naïve animals at a ratio of 1:5 (Stimulator:Responder) for 5 days at 37° C. and 5% $CO_2$. A standard cytotoxicity assay was performed using europium labeled 3T3/neu (DHFR-G8) cells as targets according to the method previously described. Released europium from killed target cells was measured after 4 hour incubation using a spectrophotometer (Perkin Elmer, Victor²) at 590 nm. Percent specific lysis was defined as (lysis in experimental group-spontaneous lysis)/(Maximum lysis-spontaneous lysis).

Interferon-γ Secretion by Splenocytes from Immunized Mice

Groups of 3-5 FVB/N or HLA-A2 transgenic mice were immunized three times with one week intervals with $1\times10^8$ CFU of ADXS31-164, a negative *Listeria* control (expressing an irrelevant antigen) or were left naïve. Splenocytes from FVB/N mice were isolated one week after the last immunization and co-cultured in 24 well plates at 5×10^6 cells/well in the presence of mitomycin C treated NT-2 cells in C-RPMI medium. Splenocytes from the HLA-A2 transgenic mice were incubated in the presence of 1 μM of HLA-A2 specific peptides or 1 μg/ml of a recombinant His-tagged ChHer2 protein, produced in *E. coli* and purified by a nickel based affinity chromatography system. Samples from supernatants were obtained 24 or 72 hours later and tested for the presence of interferon-γ (IFN-γ) using mouse IFN-γ Enzyme-linked immunosorbent assay (ELISA) kit according to manufacturer's recommendations.

Tumor Studies in Her2 Transgenic Animals

Six weeks old FVB/N rat Her2/neu transgenic mice (9-14/group) were immunized 6 times with 5×10^8 CFU of Lm-LLO-ChHer2, ADXS31-164 or Lm-control. They were observed twice a week for the emergence of spontaneous mammary tumors, which were measured using an electronic caliper, for up to 52 weeks. Escaped tumors were excised when they reached a size 1 cm^2 in average diameter and preserved in RNAlater at −20° C. In order to determine the effect of mutations in the Her2/neu protein on the escape of these tumors, genomic DNA was extracted using a genomic DNA isolation kit, and sequenced.

Effect of ADXS31-164 on Regulatory T cells in Spleens and Tumors

Mice were implanted subcutaneously (s.c.) with 1×10^6 NT-2 cells. On days 7, 14 and 21, they were immunized with 1×10^8 CFUs of ADXS31-164, LmddA-control or left naïve. Tumors and spleens were extracted on day 28 and tested for the presence of CD3+/CD4+/FoxP3+ Tregs by FACS analysis. Briefly, splenocytes were isolated by homogenizing the spleens between two glass slides in C-RPMI medium. Tumors were minced using a sterile razor blade and digested with a buffer containing DNase (12 U/ml), and collagenase (2 mg/ml) in PBS. After 60 min incubation at RT with agitation, cells were separated by vigorous pipetting. Red blood cells were lysed by RBC lysis buffer followed by several washes with complete RPMI-1640 medium containing 10% FBS. After filtration through a nylon mesh, tumor cells and splenocytes were resuspended in FACS buffer (2% FBS/PBS) and stained with anti-CD3-PerCP-Cy5.5, CD4-FITC, CD25-APC antibodies followed by permeabilization and staining with anti-Foxp3-PE. Flow cytometry analysis was performed using 4-color FACS calibur (BD) and data were analyzed using cell quest software (BD).

Statistical Analysis

The log-rank Chi-Squared test was used for survival data and student's t-test for the CTL and ELISA assays, which were done in triplicates. A p-value of less than 0.05 (marked as *) was considered statistically significant in these analyzes. All statistical analysis was done with either Prism software, V.4.0a (2006) or SPSS software, V.15.0 (2006). For all FVB/N rat Her2/neu transgenic studies we used 8-14 mice per group, for all wild-type FVB/N studies we used at least 8 mice per group unless otherwise stated. All studies were repeated at least once except for the long term tumor study in Her2/neu transgenic mouse model.

Results

Example 11: Generation of *L. Monocytogenes* Strains that Secrete LLO Fragments Fused to Her-2 Fragments: Construction of Adxs31-164

Figure 15A:
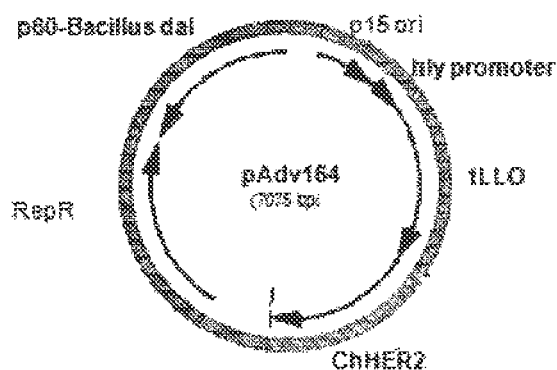
FIGS. 15A-B show (FIG. 15A) Plasmid map of pAdv164, which harbors Bacillus subtilis dal gene under the control of constitutive Listeria p60 promoter for complementation of the chromosomal dal-dat deletion in LmddA strain. It also contains the fusion of truncated LLO$_{(1-441)}$ to the chimeric human Her2/neu gene, which was constructed by the direct fusion of 3 fragments the Her2/neu: EC1 (aa 40-170), EC2 (aa 359-518) and ICI (aa 679-808).
Figure 15B:
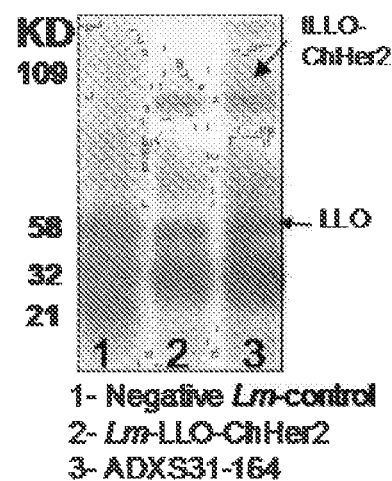

Construction of the chimeric Her2/neu gene (ChHer2) was described previously. Briefly, ChHer2 gene was generated by direct fusion of two extracellular (aa 40-170 and aa 359-433) and one intracellular fragment (aa 678-808) of the Her2/neu protein by SOEing PCR method. The chimeric protein harbors most of the known human MHC class I epitopes of the protein. ChHer2 gene was excised from the plasmid, pAdv138 (which was used to construct Lm-LLO-ChHer2) and cloned into LmddA shuttle plasmid, resulting in the plasmid pAdv164 (FIG. 15A). There are two major differences between these two plasmid backbones. 1) Whereas pAdv138 uses the chloramphenicol resistance marker (cat) for in vitro selection of recombinant bacteria, pAdv164 harbors the D-alanine racemase gene (dal) from *Bacillus subtilis*, which uses a metabolic complementation pathway for in vitro selection and in vivo plasmid retention in LmddA strain which lacks the dal-dat genes. This vaccine platform was designed and developed to address FDA concerns about the antibiotic resistance of the engineered *Listeria* vaccine strains. 2) Unlike pAdv138, pAdv164 does not harbor a copy of the prfA gene in the plasmid (see sequence below and FIG. 15A), as this is not necessary for in vivo complementation of the Lmdd strain. The LmddA vaccine strain also lacks the actA gene (responsible for the intracellular movement and cell-to-cell spread of *Listeria*) so the recombinant vaccine strains derived from this backbone are 100 times less virulent than those derived from the Lmdd, its parent strain. LmddA-based vaccines are also cleared much faster (in less than 48 hours) than the Lmdd-based vaccines from the spleens of the immunized mice. The expression and secretion of the fusion protein tLLO-ChHer2 from this strain was comparable to that of the Lm-LLO-ChHer2 in TCA precipitated cell culture supernatants after 8 hours of in vitro growth (FIG. 15B) as a band of ~104 KD was detected by an anti-LLO antibody using Western Blot analysis. The *Listeria* backbone strain expressing only tLLO was used as negative control.

pAdv164 sequence (7075 base pairs) (see FIG. 15):
(SEQ ID NO: 70)
cggagtgtatactggcttactatgttggcactgatgagggtgtcagtgaa gtgcttcatgtggcaggagaaaaaaggctgcaccggtgcgtcagcagaat atgtgatacaggatatattccgcttcctcgctcactgactcgctacgctc ggtcgttcgactgcggcgagcggaaatggcttacgaacggggcggagatt tcctggaagatgccaggaagatacttaacagggaagtgagagggccgcgg caaagccgttttccataggctccgccccctgacaagcatcacgaaatc tgacgctcaaatcagtggtggcgaaacccgacaggactataaagatacca ggcgtttcccctggcggctccctcgtgcgctctcctgttcctgccttc ggtttaccggtgtcattccgctgttatggccgcgtttgtctcattccacg cctgacactcagttccgggtaggcagttcgctccaagctggactgtatgc acgaaccccccgttcagtccgaccgctgcgccttatccggtaactatcgt cttgagtccaacccggaaagacatgcaaaagcaccactggcagcagccac tggtaattgatttagaggagttagtcttgaagtcatgcgccggttaaggc taaactgaaaggacaagttttggtgactgcgctcctccaagccagttacc tcggttcaaagagttggtagctcagagaaccttcgaaaaaccgccctgca aggcggttttttcgttttcagagcaagagattacgcgcagaccaaaacga tctcaagaagatcatcttattaatcagataaaatatttctagccctcctt tgattagtatattcctatcttaaagttacttttatgtggaggcattaaca -continued tttgttaatgacgtcaaaaggatagcaagactagaataaaagctataaagc
aagcatataatattgcgtttcatctttagaagcgaatttcgccaatatta
taattatcaaaagagaggggtggcaaacggtatttggcattattaggtta
aaaaatgtagaaggagagtgaaacccatgaaaaaaataatgctagttttt
attacacttatattagttagtctaccaattgcgcaacaaactgaagcaaa
ggatgcatctgcattcaataaagaaaattcaatttcatccatggcaccac
cagcatctccgcctgcaagtcctaagacgccaatcgaaaagaaacacgcg
gatgaaatcgataagtatatacaaggattggattacaataaaaacaatgt
attagtataccacggagatgcagtgacaaatgtgccgccaagaaaaggtt
acaaagatggaaatgaatatattgttgtggagaaaaagaagaaatccatc
aatcaaaataatgcagacattcaagttgtgaatgcaatttcgagcctaac
ctatccaggtgctctcgtaaaagcgaattcggaattagtagaaaatcaac
cagatgttctccctgtaaaacgtgattcattaacactcagcattgatttg
ccaggtatgactaatcaagacaataaaatagttgtaaaaaatgccactaa
atcaaacgttaacaacgcagtaaatacattagtggaaagatggaatgaaa
aatatgctcaagcttatccaaatgtaagtgcaaaaattgattatgatgac
gaaatggcttacagtgaatcacaattaattgcgaaatttggtacagcatt
taaagctgtaaataatagcttgaatgtaaacttcggcgcaatcagtgaag
ggaaaatgcaagaagaagtcattagttttaaacaaatttactataacgtg
aatgttaatgaacctacaagaccttccagattttttcggcaaagctgttac
taaagagcagttgcaagcgcttggagtgaatgcagaaaatcctcctgcat
atatctcaagtgtggcgtatggccgtcaagttttatttgaaattatcaact
aattcccatagtactaaagtaaaagctgcttttgatgctgccgtaagcgg
aaaatctgtctcaggtgatgtagaactaacaaatatcatcaaaaattctt
ccttcaaagccgtaatttacggaggttccgcaaaagatgaagttcaaatc
atcgacggcaaccctcggagacttacgcgatattttgaaaaaaggcgctac
ttttaatcgagaaacaccaggagttcccattgcttatacaacaaacttcc
taaaagacaatgaattagctgttattaaaaacaactcagaatatattgaa
acaacttcaaaagcttatacagatggaaaaattaacatcgatcactctgg
aggatacgttgctcaattcaacatttcttgggatgaagtaaattatgatc
tcgagacccacctggacatgctccgccacctctaccagggctgccaggtg
gtgcagggaaacctggaactcacctacctgcccaccaatgccagcctgtc
cttcctgcaggatatccaggaggtgcagggctacgtgctcatcgctcaca
accaagtgaggcaggtcccactgcagaggctgcggattgtgcgaggcacc
cagctctcttgaggacaactatgccctggccgtgctagacaatggagaccc
gctgaacaataccaccccctgtcacaggggcctccccaggaggcctgcggg
agctgcagcttcgaagcctcacagagatcttgaaaggaggggtcttgatc
cagcggaaccccagctctgctaccaggacacgattttgtggaagaatat
ccaggagtttgctggctgcaagaagatctttgggagcctggcatttctgc
cggagagctttgatggggacccagcctccaacactgccccgctccagcca -continued gagcagctccaagtgtttgagactctggaagagatcacaggttacctata
catctcagcatggccggacagcctgcctgacctcagcgtcttccagaacc
tgcaagtaatccggggacgaattctgcacaatggcgcctactcgctgacc
ctgcaagggctgggcatcagctggctggggctgcgctcactgagggaact
gggcagtggactggccctcatccaccataacacccacctctgcttcgtgc
acacggtgccctgggaccagctcttcggaacccgcaccaagctctgctc
cacactgccaaccggccagaggacgagtgtgtgggcgagggcctggcctg
ccaccagctgtgcgcccgagggcagcagaagatccggaagtacacgatgc
ggagactgctgcaggaaacggagctggtggagccgctgacacctagcgga
gcgatgcccaaccaggcgcagatgcggatcctgaaagagacggagctgag
gaaggtgaaggtgcttggatctggcgcttttggcacagtctacaagggca
tctggatccctgatggggagaatgtgaaaattccagtggccatcaaagtg
ttgagggaaaacacatcccccaaagccaacaaagaaatcttagacgaagc
atacgtgatggctggtgtgggctccccatatgtctcccgccttctgggca
tctgcctgacatccacggtgcagctggtgacacagcttatgccctatggc
tgcctcttagactaatctagacccgggccactaactcaacgctagtagtg
gatttaatcccaaatgagccaacagaaccagaaccagaaacagaacaagt
aacattggagttagaaatggaagaagaaaaaagcaatgatttcgtgtgaa
taatgcacgaaatcattgcttatttttttaaaaagcgatatactagatat
aacgaaacaacgaactgaataaagaatacaaaaaaagagccacgaccagt
taaagcctgagaaactttaactgcgagccttaattgattaccaccaatca
attaaagaagtcgagacccaaaatttggtaaagtatttaattactttatt
aatcagatacttaaatatctgtaaacccattatatcgggttttgagggg
attttcaagtcttttaagaagataccaggcaatcaattaagaaaaacttagt
tgattgccttttttgttgtgattcaactttgatcgtagcttctaactaat
taattttcgtaagaaaggagaacagctgaatgaatatccctttgttgta
gaaactgtgcttcatgacggcttgttaaagtacaaatttaaaaatagtaa
aattcgctcaatcactaccaagccaggtaaaagtaaaggggctatttttg
cgtatcgctcaaaaaaagcatgattggcggacgtggcgttgttctgact
tccgaagaagcgattcacgaaaatcaagatacatttacgcattggacacc
aaacgtttatcgttatggtacgtatgcagacgaaaaccgttcatacacta
aaggacattctgaaaacaatttaagacaaatcaataccttctttattgat
tttgatattcacacggaaaaagaaactatttcagcaagcgatattttaac
aacagctattgatttaggttttatgcctacgttaattatcaaatctgata
aaggttatcaagcatattttgttttagaaacgccagtctatgtgacttca
aaaatcagaatttaaatctgtcaaagcagccaaaataatctcgcaaaatat
ccgagaatattttggaaagtctttgccagttgatctaacgtgcaatcatt
ttgggattgctcgtataccaagaacggacaatgtagaatttttgatccc
aattaccgttattctttcaaagaatggcaagattggtctttcaaacaaac
agataataagggctttactcgttcaagtctaacggttttaagcggtacag
aaggcaaaaaacaagtagatgaaccctggtttaatctcttattgcacgaa -continued

```
acgaaattttcaggagaaagggtttagtagggcgcaatagcgttatgtt taccctctctttagcctactttagttcaggctattcaatcgaaacgtgcg aatataatatgtttgagtttaataatcgattagatcaacccttagaagaa aaagaagtaatcaaaattgttagaagtgcctattcagaaaactatcaagg ggctaatagggaatacattaccattctttgcaaagctttgggtatcaagtg atttaaccagtaaagatttatttgtccgtcaagggtggtttaaattcaag aaaaaaagaagcgaacgtcaacgtgttcatttgtcagaatggaaagaaga tttaatggcttatattagcgaaaaaagcgatgtatacaagccttatttag cgacgaccaaaaaagagattagagaagtgctaggcattcctgaacggaca ttagataaattgctgaaggtactgaaggcgaatcaggaaattttctttaa gattaaaccaggaagaaatggtggcattcaacttgctagtgttaaatcat tgttgctatcgatcattaaattaaaaaaagaagaacgagaaagctatata aaggcgctgacagcttcgtttaatttagaacgtacatttattcaagaaac tctaaacaaattggcagaacgccccaaaacggacccacaactcgatttgt ttagctacgatacaggctgaaaataaaacccgcactatgccattacattt atatctatgatacgtgtttgttttctttgctggctagcttaattgctta tatttacctgcaataaaggatttcttacttccattatactcccattttcc aaaaacatacggggaacacgggaacttattgtacaggccacctcatagtt aatggtttcgagccttcctgcaatctcatccatggaaatatattcatccc cctgccggcctattaatgtgacttttgtgcccggcggatattcctgatcc agctccaccataaattggtccatgcaaattcggccggcaattttcaggcg ttttcccttcacaaggatgtcggtccctttcaattttcggagccagccgt ccgcatagcctacaggcaccgtcccgatccatgtgtcttttccgctgtg tactcggctccgtagctgacgctctcgccttttctgatcagtttgacatg tgacagtgtcgaatgcagggtaaatgccggacgcagctgaaacggtatct cgtccgacatgtcagcagacgggcgaaggccatacatgccgatgccgaat ctgactgcattaaaaaagccttttttcagccggagtccagcggcgctgtt cgcgcagtggaccattagattcttttaacggcagcggagcaatcagctctt taaagcgctcaaactgcattaagaaatagcctctttcttttttcatccgct gtcgcaaaatgggtaaatacccctttgcactttaaacgagggttgcggtc aagaattgccatcacgttctgaacttcttcctctgtttttacaccaagtc tgttcatcccgtatcgaccttcagatgaaaatgaagagaaccttattcg tgtggcgggctgcctcctgaagccattcaacagaataacctgttaaggtc acgtcatactcagcagcgattgccacatactccggggaaccgcgccaag caccaatataggcgccttcaatccattttgcgcagtgaaatcgcttcatc caaaatggccacggccaagcatgaagcacctgcgtcaagagcagcctttg ctgtttctgcatcaccatgcccgtaggcgtttgctttcacaactgccatc aagtggacatgttcaccgatatgttttttcatattgctgacattttcctt tatcgcggacaagtcaatttccgcccacgtatctctgtaaaaaggttttg tgctcatggaaaactcctctcttttttcagaaaatcccagtacgtaatta agtatttgagaattaattttatattgataatactaagtttacccagtttt cacctaaaaaacaaatgatgagataatagctccaaaggctaaagaggact ataccaactatttgttaattaa
```

Example 12: ADXS31-164 is as Immunogenic as LM-LLO-ChHER2

Figure 16A:
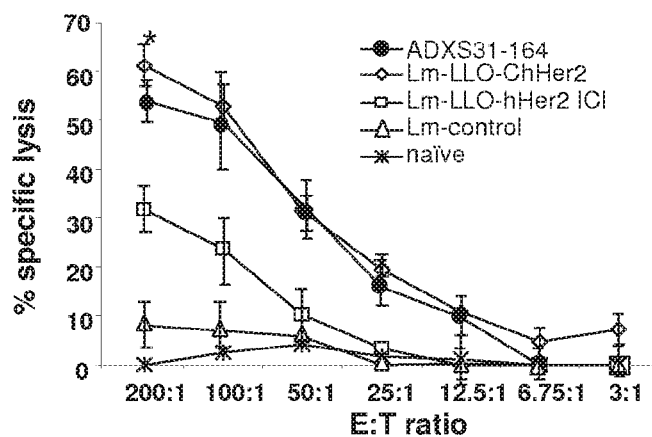
FIGS. 16A-C.
Figure 16B:
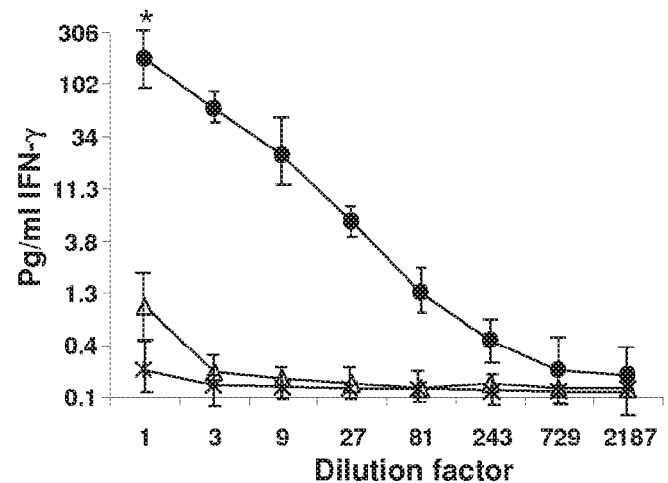

Immunogenic properties of ADXS31-164 in generating anti-Her2/neu specific cytotoxic T cells were compared to those of the Lm-LLO-ChHer2 vaccine in a standard CTL assay. Both vaccines elicited strong but comparable cytotoxic T cell responses toward Her2/neu antigen expressed by 3T3/neu target cells. Accordingly, mice immunized with a *Listeria* expressing only an intracellular fragment of Her2-fused to LLO showed lower lytic activity than the chimeras which contain more MHC class I epitopes. No CTL activity was detected in naïve animals or mice injected with the irrelevant *Listeria* vaccine (FIG. 16A). ADXS31-164 was also able to stimulate the secretion of IFN-γ by the splenocytes from wild type FVB/N mice (FIG. 16B). This was detected in the culture supernatants of these cells that were co-cultured with mitomycin C treated NT-2 cells, which express high levels of Her2/neu antigen (FIG. 19C).

Figure 16C:
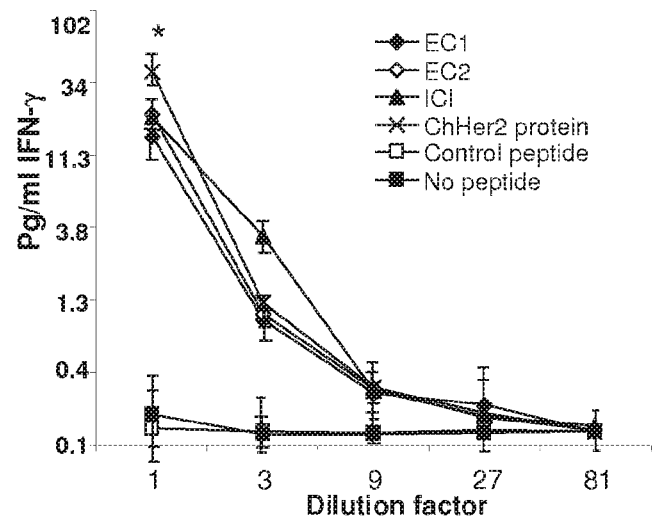

Proper processing and presentation of the human MHC class I epitopes after immunizations with ADXS31-164 was tested in HLA-A2 mice. Splenocytes from immunized HLA-A2 transgenics were co-incubated for 72 hours with peptides corresponding to mapped HLA-A2 restricted epitopes located at the extracellular (HLYQGCQVV SEQ ID NO: 71 or KIFGSLAFL SEQ ID NO: 72) or intracellular (RLLQETELV SEQ ID NO: 73) domains of the Her2/neu molecule (FIG. 16C). A recombinant ChHer2 protein was used as positive control and an irrelevant peptide or no peptide as negative controls. The data from this experiment show that ADXS31-164 is able to elicit anti-Her2/neu specific immune responses to human epitopes that are located at different domains of the targeted antigen.

Figure 17:
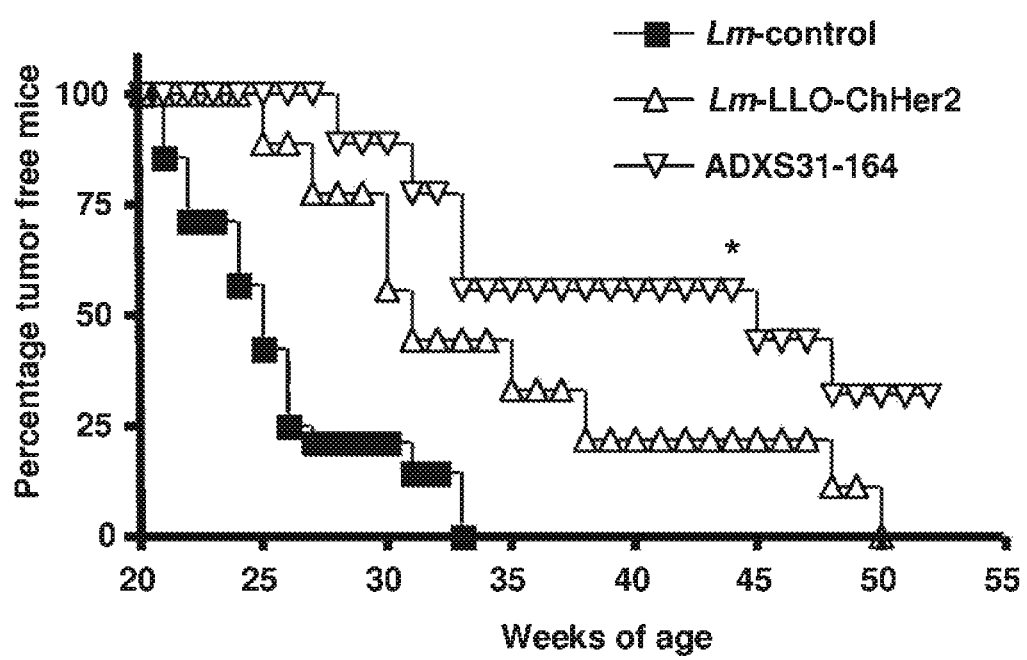
FIG. 17 represents results from Her2/neu transgenic mice that were injected six times with each recombinant Listeria-ChHer2 or a control Listeria vaccine. Immunizations started at 6 weeks of age and continued every three weeks until week 21. Appearance of tumors was monitored on a weekly basis and expressed as percentage of tumor free mice. *p<0.05, N=9 per group.

Example 13: ADXS31-164 was more Efficacious than LM-LLO-ChHER2 in Preventing the Onset of Spontaneous Mammary Tumors Anti-tumor effects of ADXS31-164 were compared to those of Lm-LLO-ChHer2 in Her2/neu transgenic animals which develop slow growing, spontaneous mammary tumors at 20-25 weeks of age. All animals immunized with the irrelevant *Listeria*-control vaccine developed breast tumors within weeks 21-25 and were sacrificed before week 33. In contrast, *Liseria*-Her2/neu recombinant vaccines caused a significant delay in the formation of the mammary tumors. On week 45, more than 50% of ADXS31-164 vaccinated mice (5 out of 9) were still tumor free, as compared to 25% of mice immunized with Lm-LLO-ChHer2. At week 52, 2 out of 8 mice immunized with ADXS31-164 still remained tumor free, whereas all mice from other experimental groups had already succumbed to their disease (FIG. 17). These results indicate that despite being more attenuated, ADXS31-164 is more efficacious than Lm-LLO-ChHer2 in preventing the onset of spontaneous mammary tumors in Her2/neu transgenic animals.

Example 14: Mutations in HER2/NEU Gene uUpon Immunization with ADXS31-164

Mutations in the MHC class I epitopes of Her2/neu have been considered responsible for tumor escape upon immunization with small fragment vaccines or trastuzumab (Herceptin), a monoclonal antibody that targets an epitope in the extracellular domain of Her2/neu. To assess this, genomic material was extracted from the escaped tumors in the transgenic animals and sequenced the corresponding fragments of the neu gene in tumors immunized with the chimeric or control vaccines. Mutations were not observed within the Her-2/neu gene of any vaccinated tumor samples suggesting alternative escape mechanisms (data not shown).

Figure 19A:
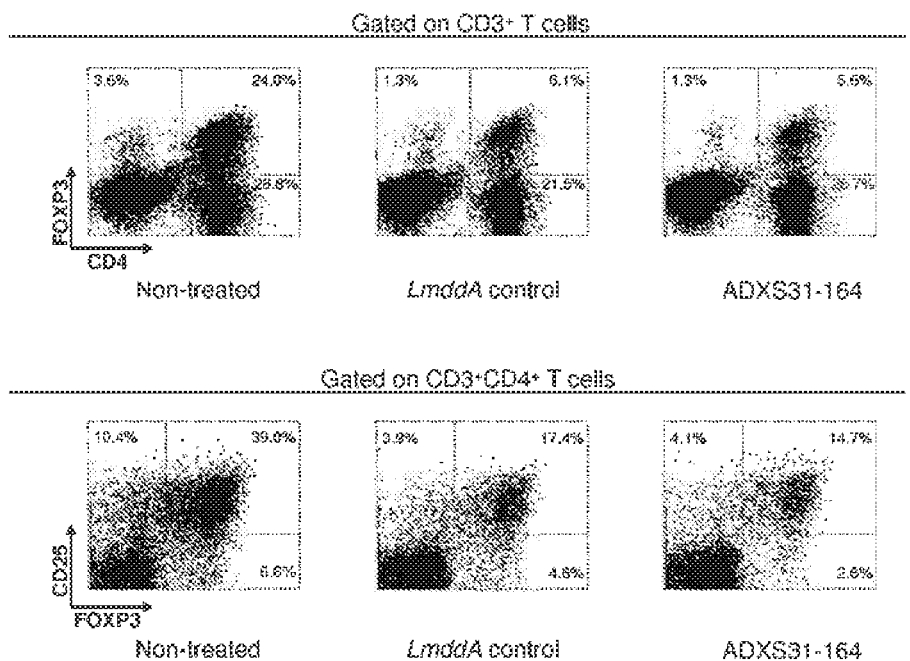
FIGS. 19A-B show FVB/N mice were inoculated s.c. with $1 \times 10^6$ NT-2 cells and immunized three times with each vaccine at one week intervals. Tumors were harvested 7 days after the second immunization. After isolation of the immune cells, they were stained for detection of Tregs by anti CD3, CD4, CD25 and FoxP3 antibodies.
Figure 19B:
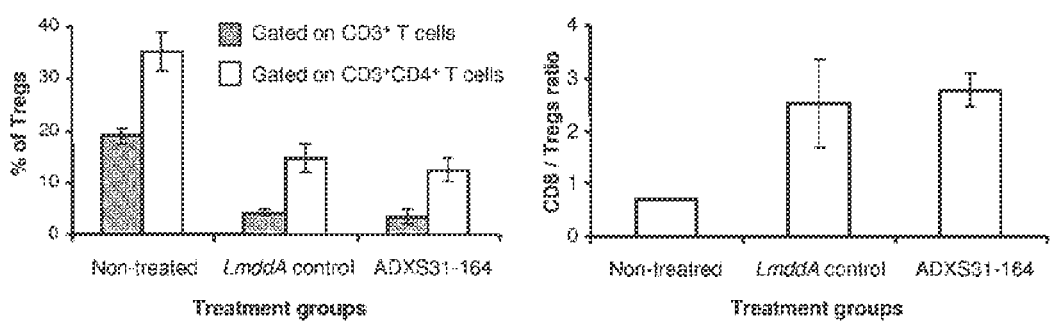
Figure 20A:
FIGS. 20A-C represent a schematic map of a recombinant Listeria protein minigene construct.
Figure 20B:
Figure 20C:

Example 15: ADXS31-164 Causes a Significant Decrease in Intra-Tumoral T Regulatory Cells To elucidate the effect of ADXS31-164 on the frequency of regulatory T cells in spleens and tumors, mice were implanted with NT-2 tumor cells. Splenocytes and intra-tumoral lymphocytes were isolated after three immunizations and stained for Tregs, which were defined as $CD3^+/CD4^+/CD25^+/FoxP3^+$ cells, although comparable results were obtained with either FoxP3 or CD25 markers when analyzed separately. The results indicated that immunization with ADXS31-164 had no effect on the frequency of Tregs in the spleens, as compared to an irrelevant *Listeria* vaccine or the naïve animals (See FIG. 18). In contrast, immunization with the *Listeria* vaccines caused a considerable impact on the presence of Tregs in the tumors (FIG. 19A). Whereas in average 19.0% of all $CD3^+$ T cells in untreated tumors were Tregs, this frequency was reduced to 4.2% for the irrelevant vaccine and 3.4% for ADXS31-164, a 5-fold reduction in the frequency of intra-tumoral Tregs (FIG. 19B). The decrease in the frequency of intra-tumoral Tregs in mice treated with either of the LmddA vaccines could not be attributed to differences in the sizes of the tumors. In a representative experiment, the tumors from mice immunized with ADXS31-164 were significantly smaller [mean diameter (mm)±SD, 6.71±0.43, n=5] than the tumors from untreated mice (8.69±0.98, n=5, p<0.01) or treated with the irrelevant vaccine (8.41±1.47, n=5, p=0.04), whereas comparison of these last two groups showed no statistically significant difference in tumor size (p=0.73). The lower frequency of Tregs in tumors treated with LmddA vaccines resulted in an increased intratumoral CD8/Tregs ratio, suggesting that a more favorable tumor microenvironment can be obtained after immunization with LmddA vaccines. However, only the vaccine expressing the target antigen HER2/neu (ADXS31-164) was able to reduce tumor growth, indicating that the decrease in Tregs has an effect only in the presence on antigen-specific responses in the tumor.

Example 16: Peptide "Minigene" Expression System

Materials and Methods

This expression system is designed to facilitate cloning of panels of recombinant proteins containing distinct peptide moieties at the carboxy-terminus. This is accomplished by a simple PCR reaction utilizing a sequence encoding one of the SS-Ub-Peptide constructs as a template. By using a primer that extends into the carboxy-terminal region of the Ub sequence and introducing codons for the desired peptide sequence at the 3' end of the primer, a new SS-Ub-Peptide sequence can be generated in a single PCR reaction. The 5' primer encoding the bacterial promoter and first few nucleotides of the ActA signal sequence is the same for all constructs. The constructs generated using this strategy are represented schematically in FIG. 1. In this example, two constructs are described. One contains a model peptide antigen presented on mouse MHC class I and the second construct indicates where a therapeutically relevant peptide, such as one derived from a human glioblastoma (GBM) TAA, would be substituted. For clarity, we have designated the constructs diagramed in FIG. 1 as containing an $ActA_{1-100}$ secretion signal. However, an LLO based secretion signal could be substituted equal effect.

One of the advantages of the proposed system is that it will be possible to load cells with multiple peptides using a single *Listeria* vector construct. Multiple peptides will be introduce into recombinant attenuated *Listeria* (e.g. prfA mutant *Listeria* or a dal/dat/actA mutant *Listeria*) using a modification of the single peptide expression system described above. A chimeric protein encoding multiple distinct peptides from sequential SS-Ub-Peptide sequences encoded in one insert. Shine-Dalgarno ribosome binding sites are introduced before each SS-Ub-Peptide coding sequence to enable separate translation of each of the peptide constructs. FIG. 1C demonstrates a schematic representation of a construct designed to express 4 separate peptide antigens from one strain of recombinant *Listeria*. Since this is strictly a representation of the general expression strategy, we have included 4 distinct MHC class I binding peptides derived from known mouse or human tumor associated- or infectious disease antigens.

While certain features of the disclosure have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A recombinant *Listeria* strain comprising a minigene nucleic acid construct, said construct comprising a first open reading frame encoding a chimeric protein, wherein said chimeric protein comprises:
    (a) a bacterial secretion signal sequence,
    (b) a ubiquitin (Ub) protein, and
    (c) a first peptide for direct presentation by MEW class I molecules,
    wherein said signal sequence, said ubiquitin and said first peptide in (a)-(c) are arranged from the amino-terminus to the carboxy-terminus of said chimeric protein, wherein said recombinant *Listeria* comprises a genomic mutation or deletion in each of a D-alanine racemase (dal) gene, a D-amino acid transferase (dat) gene, and an actA gene, wherein said construct further comprising a second open reading frame encoding a metabolic enzyme, and wherein said metabolic enzyme complements said genomic mutation or deletion in the dal and dat genes.

2. The recombinant *Listeria* of claim 1, wherein said first open reading frame encoding the chimeric protein is linked to a third open reading frame by a Shine-Dalgarno ribosome binding site nucleic acid sequence, wherein the third open reading frame encodes a second chimeric protein comprising: (d) a second bacterial secretion signal sequence; (e) a second ubiquitin (Ub) protein; and (f) a second peptide, wherein the second signal sequence, the second ubiquitin, and the second peptide in (d)-(f) are arranged from the amino terminus to the carboxy terminus of the second chimeric protein.

3. The recombinant *Listeria* of claim 2 wherein each of the first and second peptides comprises a different peptide.

4. The recombinant *Listeria* of claim 1, wherein said construct further comprises a 5' bacterial promoter driving expression of said construct.

5. The recombinant *Listeria* of claim 4, wherein said promoter is an actA promoter, an hly promoter, or a p60 promoter.

6. The recombinant *Listeria* of claim 1, wherein said bacterial secretion signal sequence encodes an ActA100 signal sequence comprising the first 100 amino acids of the ActA protein signal sequence or is a secretion signal sequence from a listeriolysin O (LLO) protein.

7. The recombinant *Listeria* of claim 1, wherein said construct is in a plasmid in said recombinant *Listeria* strain, and wherein said plasmid is stably maintained in said recombinant *Listeria* strain in the absence of antibiotic selection.

8. The recombinant *Listeria* of claim 1, wherein said metabolic enzyme is an alanine racemase enzyme or a D-amino acid transferase enzyme.

9. The recombinant *Listeria* of claim 1, wherein said construct is integrated into the *Listeria* genome or is in an extrachromosomal plasmid in said *Listeria*.

10. The recombinant *Listeria* of claim 1, wherein said recombinant *Listeria* is a *Listeria monocytogenes*.

11. A pharmaceutical composition comprising the recombinant *Listeria* of claim 1 and a pharmaceutically acceptable carrier.

12. A method of eliciting an anti-tumor or anti-cancer response in a subject having a tumor or cancer or treating a tumor or cancer in a subject, said method comprising the step of administering to said subject a recombinant *Listeria* comprising a minigene nucleic acid construct, said construct comprising a first open reading frame encoding a chimeric protein, wherein said chimeric protein comprises:
   a. a bacterial secretion signal sequence,
   b. a ubiquitin (Ub) protein, and
   c. a first peptide,
   wherein said signal sequence, said ubiquitin and said first peptide in a.-c. are arranged from the amino-terminus to the carboxy-terminus of said chimeric protein, wherein said recombinant *Listeria* comprises a genomic mutation or deletion in each of a D-alanine racemase (dal) gene, a D-amino acid transferase (dat) gene, and an actA gene, wherein said construct further comprising a second open reading frame encoding a metabolic enzyme, and wherein said metabolic enzyme complements said genomic mutation or deletion in the dal and dat genes.

13. The method of claim 12, wherein the first open reading frame encoding the chimeric protein is linked to a third open reading frame by a Shine-Dalgarno ribosome binding site nucleic acid sequence, wherein the third open reading frame encodes a second chimeric protein comprising: (a) a second bacterial secretion signal sequence; (b) a second ubiquitin (Ub) protein; and (c) a second peptide, wherein the second signal sequence, the second ubiquitin, and the second peptide in (a)-(c) are arranged from the amino terminus to the carboxy terminus of the second chimeric protein.

14. The method of claim 12, wherein said first peptide comprises one or more neoepitopes.

15. The method of claim 13, wherein each of the first and second peptides comprises a different peptide.

16. The method of claim 12, wherein said construct further comprises a 5' bacterial promoter driving expression of said construct.

17. The method of claim 16, wherein said promoter is an actA promoter, an hly promoter, or a p60 promoter.

18. The method of claim 12, wherein said bacterial secretion signal sequence encodes an ActA100 signal sequence comprising the first 100 amino acids of the ActA protein signal sequence or is a secretion signal sequence from listeriolysin O (LLO) protein.

19. The method of claim 12, wherein said construct is in a plasmid in said recombinant *Listeria* strain, and wherein said plasmid is stably maintained in said recombinant *Listeria* strain in the absence of antibiotic selection.

20. The method of claim 12, wherein said metabolic enzyme is an alanine racemase enzyme or a D-amino acid transferase enzyme.

21. The method of claim 12, wherein said construct is integrated into the *Listeria* genome or is in an extrachromosomal plasmid in said *Listeria*.

22. The method of claim 12, wherein said recombinant *Listeria* is a *Listeria monocytogenes*.

23. The method of claim 12, further comprising administration of an independent adjuvant selected from the group consisting of: a granulocyte/macrophage colony-stimulating factor (GM-CSF) protein, a nucleotide molecule encoding a GM-CSF protein, saponin QS21, monophosphoryl lipid A, and an unmethylated CpG-containing oligonucleotide.

24. The method of claim 12, wherein said cancer is a refractory cancer, a lymphoma, a leukemia, a breast cancer, a colorectal cancer, a head and neck squamous carcinoma, a renal cell carcinoma, a pancreatic ductal adenocarcinoma, an osteosarcoma, a gastric cancer, a non-small cell lung cancer, or a bone cancer.

25. The method of claim 24, wherein said lymphoma is Hodgkin's Lymphoma, Non-Hodgkin's Lymphoma, or multiple myeloma.

26. The method of claim 12, wherein said administration comprises at least two administrations of said recombinant *Listeria*.

27. The method of claim 12, further comprising a step of administering said recombinant *Listeria* following a relapse or metastasis of said cancer in said subject.

28. The method of claim 12, further comprising administering a booster shot.

29. The method of claim 12, wherein said immune response is a CD8+ T cell immune response.

30. The method of claim 12, wherein said treating delays metastatic disease, reduces lymph node size, results in progression-free survival, or results in increase of the time to disease progression.

* * * * *

SEQUENCE LISTING

<160> NUMBER OF SEQ ID NOS: 72

<210> SEQ ID NO 1
<211> LENGTH: 529
<212> TYPE: PRT
<213> ORGANISM: Artificial Sequence
<220> FEATURE:
<223> OTHER INFORMATION: LLO protein

<400> SEQUENCE: 1

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys

-continued

```
                  20                  25                  30
Glu Asn Ser Ile Ser Ser Met Ala Pro Pro Ala Ser Pro Ala Ser
                35                  40                  45
Pro Lys Thr Pro Ile Glu Lys Lys His Ala Asp Glu Ile Asp Lys Tyr
 50                  55                  60
Ile Gln Gly Leu Asp Tyr Asn Lys Asn Asn Val Leu Val Tyr His Gly
 65                  70                  75                  80
Asp Ala Val Thr Asn Val Pro Pro Arg Lys Gly Tyr Lys Asp Gly Asn
                 85                  90                  95
Glu Tyr Ile Val Val Glu Lys Lys Lys Ser Ile Asn Gln Asn Asn
                100                 105                 110
Ala Asp Ile Gln Val Val Asn Ala Ile Ser Ser Leu Thr Tyr Pro Gly
                115                 120                 125
Ala Leu Val Lys Ala Asn Ser Glu Leu Val Glu Asn Gln Pro Asp Val
                130                 135                 140
Leu Pro Val Lys Arg Asp Ser Leu Thr Leu Ser Ile Asp Leu Pro Gly
145                 150                 155                 160
Met Thr Asn Gln Asp Asn Lys Ile Val Val Lys Asn Ala Thr Lys Ser
                165                 170                 175
Asn Val Asn Asn Ala Val Asn Thr Leu Val Glu Arg Trp Asn Glu Lys
                180                 185                 190
Tyr Ala Gln Ala Tyr Pro Asn Val Ser Ala Lys Ile Asp Tyr Asp Asp
                195                 200                 205
Glu Met Ala Tyr Ser Glu Ser Gln Leu Ile Ala Lys Phe Gly Thr Ala
                210                 215                 220
Phe Lys Ala Val Asn Asn Ser Leu Asn Val Asn Phe Gly Ala Ile Ser
225                 230                 235                 240
Glu Gly Lys Met Gln Glu Glu Val Ile Ser Phe Lys Gln Ile Tyr Tyr
                245                 250                 255
Asn Val Asn Val Asn Glu Pro Thr Arg Pro Ser Arg Phe Phe Gly Lys
                260                 265                 270
Ala Val Thr Lys Glu Gln Leu Gln Ala Leu Gly Val Asn Ala Glu Asn
                275                 280                 285
Pro Pro Ala Tyr Ile Ser Ser Val Ala Tyr Gly Arg Gln Val Tyr Leu
                290                 295                 300
Lys Leu Ser Thr Asn Ser His Ser Thr Lys Val Lys Ala Ala Phe Asp
305                 310                 315                 320
Ala Ala Val Ser Gly Lys Ser Val Ser Gly Asp Val Glu Leu Thr Asn
                325                 330                 335
Ile Ile Lys Asn Ser Ser Phe Lys Ala Val Ile Tyr Gly Gly Ser Ala
                340                 345                 350
Lys Asp Glu Val Gln Ile Ile Asp Gly Asn Leu Gly Asp Leu Arg Asp
                355                 360                 365
Ile Leu Lys Lys Gly Ala Thr Phe Asn Arg Glu Thr Pro Gly Val Pro
                370                 375                 380
Ile Ala Tyr Thr Thr Asn Phe Leu Lys Asp Asn Glu Leu Ala Val Ile
385                 390                 395                 400
Lys Asn Asn Ser Glu Tyr Ile Glu Thr Thr Ser Lys Ala Tyr Thr Asp
                405                 410                 415
Gly Lys Ile Asn Ile Asp His Ser Gly Gly Tyr Val Ala Gln Phe Asn
                420                 425                 430
Ile Ser Trp Asp Glu Val Asn Tyr Asp Pro Glu Gly Asn Glu Ile Val
                435                 440                 445
```

```
Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
                515                 520                 525

Glu

<210> SEQ ID NO 2
<211> LENGTH: 441
<212> TYPE: PRT
<213> ORGANISM: Artificial Sequence
<220> FEATURE:
<223> OTHER INFORMATION: N-terminal fragment of an LLO protein

<400> SEQUENCE: 2

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
                20                  25                  30

Glu Asn Ser Ile Ser Ser Val Ala Pro Pro Ala Ser Pro Pro Ala Ser
            35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Ser Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270
```

```
Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
                340                 345                 350

Lys Asp Glu Val Gln Ile Ile Asp Gly Asn Leu Gly Asp Leu Arg Asp
                355                 360                 365

Ile Leu Lys Lys Gly Ala Thr Phe Asn Arg Glu Thr Pro Gly Val Pro
        370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
                420                 425                 430

Ile Ser Trp Asp Glu Val Asn Tyr Asp
        435                 440

<210> SEQ ID NO 3
<211> LENGTH: 416
<212> TYPE: PRT
<213> ORGANISM: Artificial Sequence
<220> FEATURE:
<223> OTHER INFORMATION: LLO fragment

<400> SEQUENCE: 3

Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Val Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190
```

```
Tyr Ala Gln Ala Tyr Ser Asn Val Ser Ala Lys Ile Asp Tyr Asp Asp
            195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
            340                 345                 350

Lys Asp Glu Val Gln Ile Ile Asp Gly Asn Leu Gly Asp Leu Arg Asp
        355                 360                 365

Ile Leu Lys Lys Gly Ala Thr Phe Asn Arg Glu Thr Pro Gly Val Pro
    370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

<210> SEQ ID NO 4
<211> LENGTH: 25
<212> TYPE: PRT
<213> ORGANISM: Artificial Sequence
<220> FEATURE:
<223> OTHER INFORMATION: LLO signal peptide

<400> SEQUENCE: 4

Met Lys Lys Ile Met Leu Val Phe Ile Thr Leu Ile Leu Val Ser Leu
1               5                   10                  15

Pro Ile Ala Gln Gln Thr Glu Ala Lys
            20                  25

<210> SEQ ID NO 5
<211> LENGTH: 639
<212> TYPE: PRT
<213> ORGANISM: Artificial Sequence
<220> FEATURE:
<223> OTHER INFORMATION: Sequence ecoding an ActA protein

<400> SEQUENCE: 5

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Lys Thr
        35                  40                  45

Glu Glu Gln Pro Ser Glu Val Asn Thr Gly Pro Arg Tyr Glu Thr Ala
    50                  55                  60
```

```
Arg Glu Val Ser Ser Arg Asp Ile Lys Glu Leu Lys Ser Asn Lys
 65                  70                  75                  80

Val Arg Asn Thr Asn Lys Ala Asp Leu Ile Ala Met Leu Lys Glu Lys
                 85                  90                  95

Ala Glu Lys Gly Pro Asn Ile Asn Asn Asn Ser Glu Gln Thr Glu
            100                 105                 110

Asn Ala Ala Ile Asn Glu Glu Ala Ser Gly Ala Asp Arg Pro Ala Ile
            115                 120                 125

Gln Val Glu Arg Arg His Pro Gly Leu Pro Ser Asp Ser Ala Ala Glu
            130                 135                 140

Ile Lys Lys Arg Arg Lys Ala Ile Ala Ser Ser Asp Ser Glu Leu Glu
145                 150                 155                 160

Ser Leu Thr Tyr Pro Asp Lys Pro Thr Lys Val Asn Lys Lys Val
                165                 170                 175

Ala Lys Glu Ser Val Ala Asp Ala Ser Glu Ser Asp Leu Asp Ser Ser
            180                 185                 190

Met Gln Ser Ala Asp Glu Ser Ser Pro Gln Pro Leu Lys Ala Asn Gln
            195                 200                 205

Gln Pro Phe Phe Pro Lys Val Phe Lys Lys Ile Lys Asp Ala Gly Lys
            210                 215                 220

Trp Val Arg Asp Lys Ile Asp Glu Asn Pro Glu Val Lys Lys Ala Ile
225                 230                 235                 240

Val Asp Lys Ser Ala Gly Leu Ile Asp Gln Leu Leu Thr Lys Lys Lys
                245                 250                 255

Ser Glu Glu Val Asn Ala Ser Asp Phe Pro Pro Pro Thr Asp Glu
            260                 265                 270

Glu Leu Arg Leu Ala Leu Pro Glu Thr Pro Met Leu Leu Gly Phe Asn
            275                 280                 285

Ala Pro Ala Thr Ser Glu Pro Ser Ser Phe Glu Phe Pro Pro Pro Pro
            290                 295                 300

Thr Asp Glu Glu Leu Arg Leu Ala Leu Pro Glu Thr Pro Met Leu Leu
305                 310                 315                 320

Gly Phe Asn Ala Pro Ala Thr Ser Glu Pro Ser Ser Phe Glu Phe Pro
                325                 330                 335

Pro Pro Pro Thr Glu Asp Glu Leu Glu Ile Ile Arg Glu Thr Ala Ser
            340                 345                 350

Ser Leu Asp Ser Ser Phe Thr Arg Gly Asp Leu Ala Ser Leu Arg Asn
            355                 360                 365

Ala Ile Asn Arg His Ser Gln Asn Phe Ser Asp Phe Pro Pro Ile Pro
            370                 375                 380

Thr Glu Glu Glu Leu Asn Gly Arg Gly Arg Pro Thr Ser Glu Glu
385                 390                 395                 400

Phe Ser Ser Leu Asn Ser Gly Asp Phe Thr Asp Asp Glu Asn Ser Glu
                405                 410                 415

Thr Thr Glu Glu Glu Ile Asp Arg Leu Ala Asp Leu Arg Asp Arg Gly
            420                 425                 430

Thr Gly Lys His Ser Arg Asn Ala Gly Phe Leu Pro Leu Asn Pro Phe
            435                 440                 445

Ala Ser Ser Pro Val Pro Ser Leu Ser Pro Lys Val Ser Lys Ile Ser
            450                 455                 460

Asp Arg Ala Leu Ile Ser Asp Ile Thr Lys Lys Thr Pro Phe Lys Asn
465                 470                 475                 480
```

```
Pro Ser Gln Pro Leu Asn Val Phe Asn Lys Lys Thr Thr Thr Lys Thr
                485                 490                 495

Val Thr Lys Lys Pro Thr Pro Val Lys Thr Ala Pro Lys Leu Ala Glu
            500                 505                 510

Leu Pro Ala Thr Lys Pro Gln Glu Thr Val Leu Arg Glu Asn Lys Thr
            515                 520                 525

Pro Phe Ile Glu Lys Gln Ala Glu Thr Asn Lys Gln Ser Ile Asn Met
            530                 535                 540

Pro Ser Leu Pro Val Ile Gln Lys Glu Ala Thr Glu Ser Asp Lys Glu
545                 550                 555                 560

Glu Met Lys Pro Gln Thr Glu Glu Lys Met Val Glu Glu Ser Glu Ser
                565                 570                 575

Ala Asn Asn Ala Asn Gly Lys Asn Arg Ser Ala Gly Ile Glu Glu Gly
            580                 585                 590

Lys Leu Ile Ala Lys Ser Ala Glu Asp Glu Lys Ala Lys Glu Glu Pro
            595                 600                 605

Gly Asn His Thr Thr Leu Ile Leu Ala Met Leu Ala Ile Gly Val Phe
            610                 615                 620

Ser Leu Gly Ala Phe Ile Lys Ile Ile Gln Leu Arg Lys Asn Asn
625                 630                 635

<210> SEQ ID NO 6
<211> LENGTH: 1170
<212> TYPE: DNA
<213> ORGANISM: Artificial Sequence
<220> FEATURE:
<223> OTHER INFORMATION: Recombinant nucleotide encoding a truncated
      ActA protein

<400> SEQUENCE: 6
atgcgtgcga tgatggtggt tttcattact gccaattgca ttacgattaa ccccgacata      60
atatttgcag cgacagatag cgaagattct agtctaaaca cagatgaatg ggaagaagaa     120
aaaacagaag agcaaccaag cgaggtaaat acgggaccaa gatacgaaac tgcacgtgaa     180
gtaagttcac gtgatattaa agaactagaa aaatcgaata agtgagaaa tacgaacaaa     240 gcagacctaa tagcaatgtt gaaagaaaaa gcagaaaaag gtccaaatat caataataac     300
aacagtgaac aaactgagaa tgcggctata aatgaagagg cttcaggagc cgaccgacca     360
gctatacaag tggagcgtcg tcatccagga ttgccatcgg atagcgcagc ggaaattaaa     420
aaaagaagga agccatagc atcatcggat agtgagcttg aaagccttac ttatccggat     480
aaaccaacaa aagtaaataa gaaaaaagtg gcgaaagagt cagttgcgga tgcttctgaa     540
agtgacttag attctagcat gcagtcagca gatgagtctt caccacaacc tttaaaagca     600
aaccaacaac catttttccc taaagtattt aaaaaaataa aagatgcggg gaaatggta     660 cgtgataaaa tcgacgaaaa tcctgaagta agaaagcga ttgttgataa aagtgcaggg     720
ttaattgacc aattattaac caaaagaaa agtgaagagg taaatgcttc ggacttcccg     780
ccaccaccta cggatgaaga gttaagactt gctttgccag agacaccaat gcttcttggt     840
tttaatgctc ctgctacatc agaaccgagc tcattcgaat tccaccacc acctacggat     900 gaagagttaa gacttgcttt gccagagacg ccaatgcttc ttggttttaa tgctcctgct     960
acatcggaac cgagctcgtt cgaatttcca ccgcctccaa cagaagatga actagaaatc    1020
atccgggaaa cagcatcctc gctagattct agttttacaa gaggggattt agctagtttg    1080
agaaatgcta ttaatcgcca tagtcaaaat ttctctgatt tcccaccaat cccaacagaa    1140
```

-continued

```
gaagagttga acgggagagg cggtagacca                                    1170
```

<210> SEQ ID NO 7
<211> LENGTH: 639
<212> TYPE: PRT
<213> ORGANISM: Artificial Sequence
<220> FEATURE:
<223> OTHER INFORMATION: ActA protein

<400> SEQUENCE: 7

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
            20                  25                  30

Ser Glu Asp Ser Ser Leu Asn Thr Asp Glu Trp Glu Glu Glu Lys Thr
        35                  40                  45

Glu Glu Gln Pro Ser Glu Val Asn Thr Gly Pro Arg Tyr Glu Thr Ala
    50                  55                  60

Arg Glu Val Ser Ser Arg Asp Ile Glu Glu Leu Glu Lys Ser Asn Lys
65                  70                  75                  80

Val Lys Asn Thr Asn Lys Ala Asp Leu Ile Ala Met Leu Lys Ala Lys
                85                  90                  95

Ala Glu Lys Gly Pro Asn Asn Asn Asn Asn Asn Gly Glu Gln Thr Gly
            100                 105                 110

Asn Val Ala Ile Asn Glu Glu Ala Ser Gly Val Asp Arg Pro Thr Leu
        115                 120                 125

Gln Val Glu Arg Arg His Pro Gly Leu Ser Ser Asp Ser Ala Ala Glu
    130                 135                 140

Ile Lys Lys Arg Arg Lys Ala Ile Ala Ser Ser Asp Ser Glu Leu Glu
145                 150                 155                 160

Ser Leu Thr Tyr Pro Asp Lys Pro Thr Lys Ala Asn Lys Arg Lys Val
                165                 170                 175

Ala Lys Glu Ser Val Val Asp Ala Ser Glu Ser Asp Leu Asp Ser Ser
            180                 185                 190

Met Gln Ser Ala Asp Glu Ser Thr Pro Gln Pro Leu Lys Ala Asn Gln
        195                 200                 205

Lys Pro Phe Phe Pro Lys Val Phe Lys Lys Ile Lys Asp Ala Gly Lys
    210                 215                 220

Trp Val Arg Asp Lys Ile Asp Glu Asn Pro Glu Val Lys Lys Ala Ile
225                 230                 235                 240

Val Asp Lys Ser Ala Gly Leu Ile Asp Gln Leu Leu Thr Lys Lys Lys
                245                 250                 255

Ser Glu Glu Val Asn Ala Ser Asp Phe Pro Pro Pro Thr Asp Glu
            260                 265                 270

Glu Leu Arg Leu Ala Leu Pro Glu Thr Pro Met Leu Leu Gly Phe Asn
        275                 280                 285

Ala Pro Thr Pro Ser Glu Pro Ser Ser Phe Glu Phe Pro Pro Pro Pro
    290                 295                 300

Thr Asp Glu Glu Leu Arg Leu Ala Leu Pro Glu Thr Pro Met Leu Leu
305                 310                 315                 320

Gly Phe Asn Ala Pro Ala Thr Ser Glu Pro Ser Ser Phe Glu Phe Pro
                325                 330                 335

Pro Pro Pro Thr Glu Asp Glu Leu Glu Ile Met Arg Glu Thr Ala Pro
            340                 345                 350

Ser Leu Asp Ser Ser Phe Thr Ser Gly Asp Leu Ala Ser Leu Arg Ser

```
                355                 360                 365
Ala Ile Asn Arg His Ser Glu Asn Phe Ser Asp Phe Pro Ile Pro
            370                 375                 380

Thr Glu Glu Glu Leu Asn Gly Arg Gly Gly Arg Pro Thr Ser Glu Glu
385                 390                 395                 400

Phe Ser Ser Leu Asn Ser Gly Asp Phe Thr Asp Glu Asn Ser Glu
                405                 410                 415

Thr Thr Glu Glu Glu Ile Asp Arg Leu Ala Asp Leu Arg Asp Arg Gly
                420                 425                 430

Thr Gly Lys His Ser Arg Asn Ala Gly Phe Leu Pro Leu Asn Pro Phe
            435                 440                 445

Ile Ser Ser Pro Val Pro Ser Leu Thr Pro Lys Val Pro Lys Ile Ser
            450                 455                 460

Ala Pro Ala Leu Ile Ser Asp Ile Thr Lys Lys Ala Pro Phe Lys Asn
465                 470                 475                 480

Pro Ser Gln Pro Leu Asn Val Phe Asn Lys Lys Thr Thr Thr Lys Thr
                485                 490                 495

Val Thr Lys Lys Pro Thr Pro Val Lys Thr Ala Pro Lys Leu Ala Glu
            500                 505                 510

Leu Pro Ala Thr Lys Pro Gln Glu Thr Val Leu Arg Glu Asn Lys Thr
            515                 520                 525

Pro Phe Ile Glu Lys Gln Ala Glu Thr Asn Lys Gln Ser Ile Asn Met
            530                 535                 540

Pro Ser Leu Pro Val Ile Gln Lys Glu Ala Thr Glu Ser Asp Lys Glu
545                 550                 555                 560

Glu Met Lys Pro Gln Thr Glu Lys Met Val Glu Ser Glu Ser
                565                 570                 575

Ala Asn Asn Ala Asn Gly Lys Asn Arg Ser Ala Gly Ile Glu Glu Gly
            580                 585                 590

Lys Leu Ile Ala Lys Ser Ala Glu Asp Glu Lys Ala Lys Glu Glu Pro
            595                 600                 605

Gly Asn His Thr Thr Leu Ile Leu Ala Met Leu Ala Ile Gly Val Phe
            610                 615                 620

Ser Leu Gly Ala Phe Ile Lys Ile Ile Gln Leu Arg Lys Asn Asn
625                 630                 635

<210> SEQ ID NO 8
<211> LENGTH: 390
<212> TYPE: PRT
<213> ORGANISM: Artificial Sequence
<220> FEATURE:
<223> OTHER INFORMATION: Truncated ActA protein

<400> SEQUENCE: 8

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
                20                  25                  30

Asn Thr Asp Glu Trp Glu Glu Glu Lys Thr Glu Glu Gln Pro Ser Glu
            35                  40                  45

Val Asn Thr Gly Pro Arg Tyr Glu Thr Ala Arg Glu Val Ser Ser Arg
        50                  55                  60

Asp Ile Lys Glu Leu Glu Lys Ser Asn Lys Val Arg Asn Thr Asn Lys
65                  70                  75                  80

Ala Asp Leu Ile Ala Met Leu Lys Glu Lys Ala Glu Lys Gly Pro Asn
```

-continued

```
                85                  90                  95
Ile Asn Asn Asn Ser Glu Gln Thr Glu Asn Ala Ala Ile Asn Glu
            100                 105                 110
Glu Ala Ser Gly Ala Asp Arg Pro Ala Ile Gln Val Glu Arg Arg His
            115                 120                 125
Pro Gly Leu Pro Ser Asp Ser Ala Ala Glu Ile Lys Lys Arg Arg Lys
    130                 135                 140
Ala Ile Ala Ser Ser Asp Ser Glu Leu Glu Ser Leu Thr Tyr Pro Asp
145                 150                 155                 160
Lys Pro Thr Lys Val Asn Lys Lys Val Ala Lys Glu Ser Val Ala
                165                 170                 175
Asp Ala Ser Glu Ser Asp Leu Asp Ser Ser Met Gln Ser Ala Asp Glu
            180                 185                 190
Ser Ser Pro Gln Pro Leu Lys Ala Asn Gln Gln Pro Phe Phe Pro Lys
        195                 200                 205
Val Phe Lys Lys Ile Lys Asp Ala Gly Lys Trp Val Arg Asp Lys Ile
        210                 215                 220
Asp Glu Asn Pro Glu Val Lys Lys Ala Ile Val Asp Lys Ser Ala Gly
225                 230                 235                 240
Leu Ile Asp Gln Leu Leu Thr Lys Lys Lys Ser Glu Glu Val Asn Ala
                245                 250                 255
Ser Asp Phe Pro Pro Pro Pro Thr Asp Glu Glu Leu Arg Leu Ala Leu
            260                 265                 270
Pro Glu Thr Pro Met Leu Leu Gly Phe Asn Ala Pro Ala Thr Ser Glu
        275                 280                 285
Pro Ser Ser Phe Glu Phe Pro Pro Pro Thr Asp Glu Glu Leu Arg
        290                 295                 300
Leu Ala Leu Pro Glu Thr Pro Met Leu Leu Gly Phe Asn Ala Pro Ala
305                 310                 315                 320
Thr Ser Glu Pro Ser Ser Phe Glu Phe Pro Pro Pro Thr Glu Asp
                325                 330                 335
Glu Leu Glu Ile Ile Arg Glu Thr Ala Ser Ser Leu Asp Ser Ser Phe
            340                 345                 350
Thr Arg Gly Asp Leu Ala Ser Leu Arg Asn Ala Ile Asn Arg His Ser
        355                 360                 365
Gln Asn Phe Ser Asp Phe Pro Pro Ile Pro Thr Glu Glu Leu Asn
        370                 375                 380
Gly Arg Gly Gly Arg Pro
385                 390

<210> SEQ ID NO 9
<211> LENGTH: 100
<212> TYPE: PRT
<213> ORGANISM: Artificial Sequence
<220> FEATURE:
<223> OTHER INFORMATION: Truncated ActA protein

<400> SEQUENCE: 9

Met Gly Leu Asn Arg Phe Met Arg Ala Met Met Val Val Phe Ile Thr
1               5                   10                  15
Ala Asn Cys Ile Thr Ile Asn Pro Asp Ile Ile Phe Ala Ala Thr Asp
                20                  25                  30
Ser Glu Asp Ser Ser Leu Asn Thr Asp Glu Trp Glu Glu Glu Lys Thr
            35                  40                  45
Glu Glu Gln Pro Ser Glu Val Asn Thr Gly Pro Arg Tyr Glu Thr Ala
```

```
                 50                  55                  60

Arg Glu Val Ser Ser Arg Asp Ile Lys Glu Leu Glu Lys Ser Asn Lys
 65                  70                  75                  80

Val Arg Asn Thr Asn Lys Ala Asp Leu Ile Ala Met Leu Lys Glu Lys
                     85                  90                  95

Ala Glu Lys Gly
            100

<210> SEQ ID NO 10
<211> LENGTH: 390
<212> TYPE: PRT
<213> ORGANISM: Artificial Sequence
<220> FEATURE:
<223> OTHER INFORMATION: Truncated ActA protein

<400> SEQUENCE: 10

Met Arg Ala Met Met Val Val Phe Ile Thr Ala Asn Cys Ile Thr Ile
  1               5                  10                  15

Asn Pro Asp Ile Ile Phe Ala Ala Thr Asp Ser Glu Asp Ser Ser Leu
                 20                  25                  30

Asn Thr Asp Glu Trp Glu Glu Glu Lys Thr Glu Glu Gln Pro Ser Glu
             35                  40                  45

Val Asn Thr Gly Pro Arg Tyr Glu Thr Ala Arg Glu Val Ser Ser Arg
 50                  55                  60

Asp Ile Lys Glu Leu Glu Lys Ser Asn Lys Val Arg Asn Thr Asn Lys
 65                  70                  75                  80

Ala Asp Leu Ile Ala Met Leu Lys Glu Lys Ala Glu Lys Gly Pro Asn
                 85                  90                  95

Ile Asn Asn Asn Asn Ser Glu Gln Thr Glu Asn Ala Ala Ile Asn Glu
                100                 105                 110

Glu Ala Ser Gly Ala Asp Arg Pro Ala Ile Gln Val Glu Arg Arg His
            115                 120                 125

Pro Gly Leu Pro Ser Asp Ser Ala Ala Glu Ile Lys Lys Arg Arg Lys
        130                 135                 140

Ala Ile Ala Ser Ser Asp Ser Glu Leu Glu Ser Leu Thr Tyr Pro Asp
145                 150                 155                 160

Lys Pro Thr Lys Val Asn Lys Lys Val Ala Lys Glu Ser Val Ala
                165                 170                 175

Asp Ala Ser Glu Ser Asp Leu Asp Ser Ser Met Gln Ser Ala Asp Glu
                180                 185                 190

Ser Ser Pro Gln Pro Leu Lys Ala Asn Gln Gln Pro Phe Phe Pro Lys
            195                 200                 205

Val Phe Lys Lys Ile Lys Asp Ala Gly Lys Trp Val Arg Asp Lys Ile
        210                 215                 220

Asp Glu Asn Pro Glu Val Lys Lys Ala Ile Val Asp Lys Ser Ala Gly
225                 230                 235                 240

Leu Ile Asp Gln Leu Leu Thr Lys Lys Lys Ser Glu Glu Val Asn Ala
                245                 250                 255

Ser Asp Phe Pro Pro Pro Pro Thr Asp Glu Glu Leu Arg Leu Ala Leu
            260                 265                 270

Pro Glu Thr Pro Met Leu Leu Gly Phe Asn Ala Pro Ala Thr Ser Glu
        275                 280                 285

Pro Ser Ser Phe Glu Phe Pro Pro Pro Thr Asp Glu Glu Leu Arg
        290                 295                 300

Leu Ala Leu Pro Glu Thr Pro Met Leu Leu Gly Phe Asn Ala Pro Ala
```

```
                305                 310                 315                 320
Thr Ser Glu Pro Ser Ser Phe Glu Phe Pro Pro Pro Thr Glu Asp
                325                 330                 335

Glu Leu Glu Ile Ile Arg Glu Thr Ala Ser Ser Leu Asp Ser Ser Phe
                340                 345                 350

Thr Arg Gly Asp Leu Ala Ser Leu Arg Asn Ala Ile Asn Arg His Ser
                355                 360                 365

Gln Asn Phe Ser Asp Phe Pro Pro Ile Pro Thr Glu Glu Glu Leu Asn
                370                 375                 380

Gly Arg Gly Gly Arg Pro
385                 390

<210> SEQ ID NO 11
<211> LENGTH: 100
<212> TYPE: PRT
<213> ORGANISM: Artificial Sequence
<220> FEATURE:
<223> OTHER INFORMATION: Truncated ActA protein

<400> SEQUENCE: 11

Met Gly Leu Asn Arg Phe Met Arg Ala Met Met Val Val Phe Ile Thr
1               5                   10                  15

Ala Asn Cys Ile Thr Ile Asn Pro Asp Ile Ile Phe Ala Ala Thr Asp
                20                  25                  30

Ser Glu Asp Ser Ser Leu Asn Thr Asp Glu Trp Glu Glu Glu Lys Thr
            35                  40                  45

Glu Glu Gln Pro Ser Glu Val Asn Thr Gly Pro Arg Tyr Glu Thr Ala
        50                  55                  60

Arg Glu Val Ser Ser Arg Asp Ile Lys Glu Leu Glu Lys Ser Asn Lys
65                  70                  75                  80

Val Arg Asn Thr Asn Lys Ala Asp Leu Ile Ala Met Leu Lys Glu Lys
                85                  90                  95

Ala Glu Lys Gly
            100

<210> SEQ ID NO 12
<211> LENGTH: 93
<212> TYPE: PRT
<213> ORGANISM: Artificial Sequence
<220> FEATURE:
<223> OTHER INFORMATION: Truncated ActA protein

<400> SEQUENCE: 12

Ala Thr Asp Ser Glu Asp Ser Ser Leu Asn Thr Asp Glu Trp Glu Glu
1               5                   10                  15

Glu Lys Thr Glu Glu Gln Pro Ser Glu Val Asn Thr Gly Pro Arg Tyr
                20                  25                  30

Glu Thr Ala Arg Glu Val Ser Ser Arg Asp Ile Glu Glu Leu Glu Lys
            35                  40                  45

Ser Asn Lys Val Lys Asn Thr Asn Lys Ala Asp Leu Ile Ala Met Leu
        50                  55                  60

Lys Ala Lys Ala Glu Lys Gly Pro Asn Asn Asn Asn Asn Asn Gly Glu
65                  70                  75                  80

Gln Thr Gly Asn Val Ala Ile Asn Glu Glu Ala Ser Gly
                85                  90

<210> SEQ ID NO 13
<211> LENGTH: 124
```

<212> TYPE: PRT
<213> ORGANISM: Artificial Sequence
<220> FEATURE:
<223> OTHER INFORMATION: Truncated ActA protein

<400> SEQUENCE: 13

Met Arg Ala Met Met Val Val Phe Ile Thr Ala Asn Cys Ile Thr Ile
1               5                   10                  15

Asn Pro Asp Ile Ile Phe Ala Ala Thr Asp Ser Glu Asp Ser Ser Leu
            20                  25                  30

Asn Thr Asp Glu Trp Glu Glu Lys Thr Glu Gln Pro Ser Glu
            35                  40                  45

Val Asn Thr Gly Pro Arg Tyr Glu Thr Ala Arg Glu Val Ser Ser Arg
 50                  55                  60

Asp Ile Glu Glu Leu Glu Lys Ser Asn Lys Val Lys Asn Thr Asn Lys
65                  70                  75                  80

Ala Asp Leu Ile Ala Met Leu Lys Ala Lys Ala Glu Lys Gly Pro Asn
                85                  90                  95

Asn Asn Asn Asn Asn Gly Glu Gln Thr Gly Asn Val Ala Ile Asn Glu
            100                 105                 110

Glu Ala Ser Gly Val Asp Arg Pro Thr Leu Gln Val
            115                 120

<210> SEQ ID NO 14
<211> LENGTH: 101
<212> TYPE: PRT
<213> ORGANISM: Artificial Sequence
<220> FEATURE:
<223> OTHER INFORMATION: Truncated ActA protein

<400> SEQUENCE: 14

Ala Thr Asp Ser Glu Asp Ser Ser Leu Asn Thr Asp Glu Trp Glu Glu
1               5                   10                  15

Glu Lys Thr Glu Glu Gln Pro Ser Glu Val Asn Thr Gly Pro Arg Tyr
            20                  25                  30

Glu Thr Ala Arg Glu Val Ser Ser Arg Asp Ile Glu Glu Leu Glu Lys
            35                  40                  45

Ser Asn Lys Val Lys Asn Thr Asn Lys Ala Asp Leu Ile Ala Met Leu
 50                  55                  60

Lys Ala Lys Ala Glu Lys Gly Pro Asn Asn Asn Asn Asn Asn Gly Glu
65                  70                  75                  80

Gln Thr Gly Asn Val Ala Ile Asn Glu Glu Ala Ser Gly Val Asp Arg
                85                  90                  95

Pro Thr Leu Gln Val
            100

<210> SEQ ID NO 15
<211> LENGTH: 200
<212> TYPE: PRT
<213> ORGANISM: Artificial Sequence
<220> FEATURE:
<223> OTHER INFORMATION: Truncated ActA protein

<400> SEQUENCE: 15

Ala Thr Asp Ser Glu Asp Ser Ser Leu Asn Thr Asp Glu Trp Glu Glu
1               5                   10                  15

Glu Lys Thr Glu Glu Gln Pro Ser Glu Val Asn Thr Gly Pro Arg Tyr
            20                  25                  30

Glu Thr Ala Arg Glu Val Ser Ser Arg Asp Ile Glu Glu Leu Glu Lys

```
            35                  40                  45
Ser Asn Lys Val Lys Asn Thr Asn Lys Ala Asp Leu Ile Ala Met Leu
 50                  55                  60

Lys Ala Lys Ala Glu Lys Gly Pro Asn Asn Asn Asn Asn Gly Glu
 65                  70                  75                  80

Gln Thr Gly Asn Val Ala Ile Asn Glu Glu Ala Ser Gly Val Asp Arg
                 85                  90                  95

Pro Thr Leu Gln Val Glu Arg Arg His Pro Gly Leu Ser Ser Asp Ser
                100                 105                 110

Ala Ala Glu Ile Lys Lys Arg Arg Lys Ala Ile Ala Ser Ser Asp Ser
                115                 120                 125

Glu Leu Glu Ser Leu Thr Tyr Pro Asp Lys Pro Thr Lys Ala Asn Lys
                130                 135                 140

Arg Lys Val Ala Lys Glu Ser Val Val Asp Ala Ser Glu Ser Asp Leu
145                 150                 155                 160

Asp Ser Ser Met Gln Ser Ala Asp Glu Ser Thr Pro Gln Pro Leu Lys
                165                 170                 175

Ala Asn Gln Lys Pro Phe Phe Pro Lys Val Phe Lys Lys Ile Lys Asp
                180                 185                 190

Ala Gly Lys Trp Val Arg Asp Lys
                195                 200

<210> SEQ ID NO 16
<211> LENGTH: 303
<212> TYPE: PRT
<213> ORGANISM: Artificial Sequence
<220> FEATURE:
<223> OTHER INFORMATION: Truncated ActA protein

<400> SEQUENCE: 16

Ala Thr Asp Ser Glu Asp Ser Ser Leu Asn Thr Asp Glu Trp Glu Glu
 1               5                  10                  15

Glu Lys Thr Glu Glu Gln Pro Ser Glu Val Asn Thr Gly Pro Arg Tyr
                 20                  25                  30

Glu Thr Ala Arg Glu Val Ser Ser Arg Asp Ile Glu Glu Leu Glu Lys
                 35                  40                  45

Ser Asn Lys Val Lys Asn Thr Asn Lys Ala Asp Leu Ile Ala Met Leu
 50                  55                  60

Lys Ala Lys Ala Glu Lys Gly Pro Asn Asn Asn Asn Asn Gly Glu
 65                  70                  75                  80

Gln Thr Gly Asn Val Ala Ile Asn Glu Glu Ala Ser Gly Val Asp Arg
                 85                  90                  95

Pro Thr Leu Gln Val Glu Arg Arg His Pro Gly Leu Ser Ser Asp Ser
                100                 105                 110

Ala Ala Glu Ile Lys Lys Arg Arg Lys Ala Ile Ala Ser Ser Asp Ser
                115                 120                 125

Glu Leu Glu Ser Leu Thr Tyr Pro Asp Lys Pro Thr Lys Ala Asn Lys
                130                 135                 140

Arg Lys Val Ala Lys Glu Ser Val Val Asp Ala Ser Glu Ser Asp Leu
145                 150                 155                 160

Asp Ser Ser Met Gln Ser Ala Asp Glu Ser Thr Pro Gln Pro Leu Lys
                165                 170                 175

Ala Asn Gln Lys Pro Phe Phe Pro Lys Val Phe Lys Lys Ile Lys Asp
                180                 185                 190

Ala Gly Lys Trp Val Arg Asp Lys Ile Asp Glu Asn Pro Glu Val Lys
```

```
                195                 200                 205
Lys Ala Ile Val Asp Lys Ser Ala Gly Leu Ile Asp Gln Leu Leu Thr
210                 215                 220
Lys Lys Lys Ser Glu Glu Val Asn Ala Ser Asp Phe Pro Pro Pro
225                 230                 235                 240
Thr Asp Glu Glu Leu Arg Leu Ala Leu Pro Glu Thr Pro Met Leu Leu
                245                 250                 255
Gly Phe Asn Ala Pro Thr Pro Ser Glu Pro Ser Ser Phe Glu Phe Pro
                260                 265                 270
Pro Pro Pro Thr Asp Glu Glu Leu Arg Leu Ala Leu Pro Glu Thr Pro
                275                 280                 285
Met Leu Leu Gly Phe Asn Ala Pro Ala Thr Ser Glu Pro Ser Ser
                290                 295                 300
```

<210> SEQ ID NO 17
<211> LENGTH: 370
<212> TYPE: PRT
<213> ORGANISM: Artificial Sequence
<220> FEATURE:
<223> OTHER INFORMATION: Truncated ActA protein

<400> SEQUENCE: 17

```
Ala Thr Asp Ser Glu Asp Ser Ser Leu Asn Thr Asp Glu Trp Glu Glu
1               5                   10                  15
Glu Lys Thr Glu Glu Gln Pro Ser Glu Val Asn Thr Gly Pro Arg Tyr
                20                  25                  30
Glu Thr Ala Arg Glu Val Ser Ser Arg Asp Ile Glu Glu Leu Glu Lys
            35                  40                  45
Ser Asn Lys Val Lys Asn Thr Asn Lys Ala Asp Leu Ile Ala Met Leu
50                  55                  60
Lys Ala Lys Ala Glu Lys Gly Pro Asn Asn Asn Asn Asn Asn Gly Glu
65                  70                  75                  80
Gln Thr Gly Asn Val Ala Ile Asn Glu Glu Ala Ser Gly Val Asp Arg
                85                  90                  95
Pro Thr Leu Gln Val Glu Arg Arg His Pro Gly Leu Ser Ser Asp Ser
                100                 105                 110
Ala Ala Glu Ile Lys Lys Arg Arg Lys Ala Ile Ala Ser Ser Asp Ser
            115                 120                 125
Glu Leu Glu Ser Leu Thr Tyr Pro Asp Lys Pro Thr Lys Ala Asn Lys
130                 135                 140
Arg Lys Val Ala Lys Glu Ser Val Val Asp Ala Ser Glu Ser Asp Leu
145                 150                 155                 160
Asp Ser Ser Met Gln Ser Ala Asp Glu Ser Thr Pro Gln Pro Leu Lys
                165                 170                 175
Ala Asn Gln Lys Pro Phe Phe Pro Lys Val Phe Lys Lys Ile Lys Asp
                180                 185                 190
Ala Gly Lys Trp Val Arg Asp Lys Ile Asp Glu Asn Pro Glu Val Lys
            195                 200                 205
Lys Ala Ile Val Asp Lys Ser Ala Gly Leu Ile Asp Gln Leu Leu Thr
210                 215                 220
Lys Lys Lys Ser Glu Glu Val Asn Ala Ser Asp Phe Pro Pro Pro Pro
225                 230                 235                 240
Thr Asp Glu Glu Leu Arg Leu Ala Leu Pro Glu Thr Pro Met Leu Leu
                245                 250                 255
Gly Phe Asn Ala Pro Thr Pro Ser Glu Pro Ser Ser Phe Glu Phe Pro
```

-continued

```
                260                 265                 270
Pro Pro Pro Thr Asp Glu Glu Leu Arg Leu Ala Leu Pro Glu Thr Pro
            275                 280                 285

Met Leu Leu Gly Phe Asn Ala Pro Ala Thr Ser Glu Pro Ser Ser Phe
            290                 295                 300

Glu Phe Pro Pro Pro Thr Glu Asp Glu Leu Glu Ile Met Arg Glu
305                 310                 315                 320

Thr Ala Pro Ser Leu Asp Ser Ser Phe Thr Ser Gly Asp Leu Ala Ser
                        325                 330                 335

Leu Arg Ser Ala Ile Asn Arg His Ser Glu Asn Phe Ser Asp Phe Pro
            340                 345                 350

Leu Ile Pro Thr Glu Glu Leu Asn Gly Arg Gly Gly Arg Pro Thr
            355                 360                 365

Ser Glu
    370

<210> SEQ ID NO 18
<211> LENGTH: 226
<212> TYPE: PRT
<213> ORGANISM: Artificial Sequence
<220> FEATURE:
<223> OTHER INFORMATION: Truncated ActA fused to hly signal peptide

<400> SEQUENCE: 18

Met Lys Lys Ile Met Leu Val Phe Ile Thr Leu Ile Leu Val Ser Leu
1               5                   10                  15

Pro Ile Ala Gln Gln Thr Glu Ala Ser Arg Ala Thr Asp Ser Glu Asp
            20                  25                  30

Ser Ser Leu Asn Thr Asp Glu Trp Glu Glu Lys Thr Glu Glu Gln
        35                  40                  45

Pro Ser Glu Val Asn Thr Gly Pro Arg Tyr Glu Thr Ala Arg Glu Val
    50                  55                  60

Ser Ser Arg Asp Ile Glu Glu Leu Glu Lys Ser Asn Lys Val Lys Asn
65                  70                  75                  80

Thr Asn Lys Ala Asp Leu Ile Ala Met Leu Lys Ala Lys Ala Glu Lys
                85                  90                  95

Gly Pro Asn Asn Asn Asn Asn Gly Glu Gln Thr Gly Asn Val Ala
            100                 105                 110

Ile Asn Glu Glu Ala Ser Gly Val Asp Arg Pro Thr Leu Gln Val Glu
        115                 120                 125

Arg Arg His Pro Gly Leu Ser Ser Asp Ser Ala Ala Glu Ile Lys Lys
130                 135                 140

Arg Arg Lys Ala Ile Ala Ser Ser Asp Ser Glu Leu Glu Ser Leu Thr
145                 150                 155                 160

Tyr Pro Asp Lys Pro Thr Lys Ala Asn Lys Arg Lys Val Ala Lys Glu
                165                 170                 175

Ser Val Val Asp Ala Ser Glu Ser Asp Leu Asp Ser Ser Met Gln Ser
            180                 185                 190

Ala Asp Glu Ser Thr Pro Gln Pro Leu Lys Ala Asn Gln Lys Pro Phe
        195                 200                 205

Phe Pro Lys Val Phe Lys Lys Ile Lys Asp Ala Gly Lys Trp Val Arg
    210                 215                 220

Asp Lys
225
```

<210> SEQ ID NO 19
<211> LENGTH: 678
<212> TYPE: DNA
<213> ORGANISM: Artificial Sequence
<220> FEATURE:
<223> OTHER INFORMATION: Sequence encoding a truncated ActA fused to hly
      signal peptide

<400> SEQUENCE: 19

```
atgaaaaaaa taatgctagt ttttattaca cttatattag ttagtctacc aattgcgcaa      60
caaactgaag catctagagc gacagatagc gaagattcca gtctaaacac agatgaatgg     120
gaagaagaaa aaacagaaga gcagccaagc gaggtaaata cgggaccaag atacgaaact     180
gcacgtgaag taagttcacg tgatattgag aactagaaa atcgaataa agtgaaaaat      240 acgaacaaag cagacctaat agcaatgttg aaagcaaaag cagagaaagg tccgaataac     300
aataataaca acggtgagca acaggaaat gtggctataa atgaagaggc ttcaggagtc     360
gaccgaccaa ctctgcaagt ggagcgtcgt catccaggtc tgtcatcgga tagcgcagcg     420
gaaattaaaa aagaagaaa agccatagcg tcgtcggata gtgagcttga aagccttact     480
tatccagata aaccaacaaa agcaaataag agaaagtgg cgaaagagtc agttgtggat     540
gcttctgaaa gtgacttaga ttctagcatg cagtcagcag acgagtctac accacaacct     600
ttaaaagcaa atcaaaaacc attttttccct aaagtattta aaaaaataa agatgcgggg     660 aaatgggtac gtgataaa                                                    678
```

<210> SEQ ID NO 20
<211> LENGTH: 1170
<212> TYPE: DNA
<213> ORGANISM: Artificial Sequence
<220> FEATURE:
<223> OTHER INFORMATION: Recombinant nucleotide encoding a truncated
      ActA protein

<400> SEQUENCE: 20

```
atgcgtgcga tgatggtggt tttcattact gccaattgca ttacgattaa ccccgacata      60
atatttgcag cgacagatag cgaagattct agtctaaaca cagatgaatg gaagaagaa     120 aaaacagaag agcaaccaag cgaggtaaat acgggaccaa gatacgaaac tgcacgtgaa     180
gtaagttcac gtgatattaa agaactagaa aaatcgaata agtgagaaa tacgaacaaa     240 gcagacctaa tagcaatgtt gaaagaaaaa gcagaaaaag gtccaaatat caataataac     300
aacagtgaac aaactgagaa tgcggctata aatgaagagg cttcaggagc cgaccgacca     360
gctatacaag tggagcgtcg tcatccagga ttgccatcgg atagcgcagc ggaaattaaa     420 aaagaagga aagccatagc atcatcggat agtgagcttg aaagccttac ttatccggat     480
aaaccaacaa agtaaataa gaaaaagtg gcgaaagagt cagttgcgga tgcttctgaa     540
agtgacttag attctagcat gcagtcagca gatgagtctt caccacaacc tttaaaagca     600
aaccaacaac cattttttccc taaagtattt aaaaaaataa agatgcggg gaaatgggta     660 cgtgataaaa tcgacgaaaa tcctgaagta agaaagcga ttgttgataa agtgcaggg     720 ttaattgacc aattattaac caaaagaaa agtgaagagg taaatgcttc ggacttcccg     780
ccaccaccta cggatgaaga gttaagactt gctttgccag agacaccaat gcttcttggt     840
tttaatgctc ctgctacatc agaaccgagc tcattcgaat tccaccacc acctacggat     900 gaagagttaa gacttgcttt gccagagacg ccaatgcttc ttggttttaa tgctcctgct     960
acatcggaac cgagctcgtt cgaatttcca ccgcctccaa cagaagatga actagaaatc    1020
```

| | |
|---|---|
| atccgggaaa cagcatcctc gctagattct agttttacaa gagggattt agctagtttg | 1080 |
| agaaatgcta ttaatcgcca tagtcaaaat ttctctgatt tcccaccaat cccaacagaa | 1140 |
| gaagagttga acgggagagg cggtagacca | 1170 |

```
<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
```

| | |
|---|---|
| ggctcgagca tggagataca cc | 22 |

```
<210> SEQ ID NO 22
<211> LENGTH: 28
<212> TYPE: DNA
<213> ORGANISM: Artificial Sequence
<220> FEATURE:
<223> OTHER INFORMATION: Primer

<400> SEQUENCE: 22
```

| | |
|---|---|
| ggggactagt ttatggtttc tgagaaca | 28 |

```
<210> SEQ ID NO 23
<211> LENGTH: 31
<212> TYPE: DNA
<213> ORGANISM: Artificial Sequence
<220> FEATURE:
<223> OTHER INFORMATION: Primer

<400> SEQUENCE: 23
```

| | |
|---|---|
| gggggctagc cctcctttga ttagtatatt c | 31 |

```
<210> SEQ ID NO 24
<211> LENGTH: 28
<212> TYPE: DNA
<213> ORGANISM: Artificial Sequence
<220> FEATURE:
<223> OTHER INFORMATION: Primer

<400> SEQUENCE: 24
```

| | |
|---|---|
| ctccctcgag atcataattt acttcatc | 28 |

```
<210> SEQ ID NO 25
<211> LENGTH: 55
<212> TYPE: DNA
<213> ORGANISM: Artificial Sequence
<220> FEATURE:
<223> OTHER INFORMATION: Primer

<400> SEQUENCE: 25
```

| | |
|---|---|
| gactacaagg acgatgaccg acaagtgata acccgggatc taaataaatc cgttt | 55 |

```
<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26
```

| | |
|---|---|
| cccgtcgacc agctcttctt ggtgaag | 27 |

```
<210> SEQ ID NO 27
<211> LENGTH: 25
<212> TYPE: DNA
<213> ORGANISM: Artificial Sequence
<220> FEATURE:
<223> OTHER INFORMATION: Primer

<400> SEQUENCE: 27
gcggatccca tgagataca cctac                                              25

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
gctctagatt atggtttctg ag                                                22

<210> SEQ ID NO 29
<211> LENGTH: 31
<212> TYPE: DNA
<213> ORGANISM: Artificial Sequence
<220> FEATURE:
<223> OTHER INFORMATION: Primer

<400> SEQUENCE: 29
ggggtctaga cctcctttga ttagtatatt c                                      31

<210> SEQ ID NO 30
<211> LENGTH: 45
<212> TYPE: DNA
<213> ORGANISM: Artificial Sequence
<220> FEATURE:
<223> OTHER INFORMATION: Primer

<400> SEQUENCE: 30
atcttcgcta tctgtcgccg cggcgcgtgc ttcagtttgt tgcgc                       45

<210> SEQ ID NO 31
<211> LENGTH: 45
<212> TYPE: DNA
<213> ORGANISM: Artificial Sequence
<220> FEATURE:
<223> OTHER INFORMATION: Primer

<400> SEQUENCE: 31
gcgcaacaaa ctgaagcagc ggccgcggcg acagatagcg aagat                       45

<210> SEQ ID NO 32
<211> LENGTH: 42
<212> TYPE: DNA
<213> ORGANISM: Artificial Sequence
<220> FEATURE:
<223> OTHER INFORMATION: Primer

<400> SEQUENCE: 32
tgtaggtgta tctccatgct cgagagctag gcgatcaatt tc                          42

<210> SEQ ID NO 33
<211> LENGTH: 42
<212> TYPE: DNA
<213> ORGANISM: Artificial Sequence
<220> FEATURE:
<223> OTHER INFORMATION: Primer
```

```
<400> SEQUENCE: 33
ggaattgatc gcctagctct cgagcatgga gatacaccta ca                    42

<210> SEQ ID NO 34
<211> LENGTH: 42
<212> TYPE: DNA
<213> ORGANISM: Artificial Sequence
<220> FEATURE:
<223> OTHER INFORMATION: Primer

<400> SEQUENCE: 34
aaacggattt atttagatcc cgggttatgg tttctgagaa ca                    42

<210> SEQ ID NO 35
<211> LENGTH: 42
<212> TYPE: DNA
<213> ORGANISM: Artificial Sequence
<220> FEATURE:
<223> OTHER INFORMATION: Primer

<400> SEQUENCE: 35
tgttctcaga accataacc cgggatctaa ataaatccgt tt                     42

<210> SEQ ID NO 36
<211> LENGTH: 28
<212> TYPE: DNA
<213> ORGANISM: Artificial Sequence
<220> FEATURE:
<223> OTHER INFORMATION: Primer

<400> SEQUENCE: 36
gggggtcgac cagctcttct tggtgaag                                    28

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
ccatggtgac aggctggcat c                                           21

<210> SEQ ID NO 38
<211> LENGTH: 27
<212> TYPE: DNA
<213> ORGANISM: Artificial Sequence
<220> FEATURE:
<223> OTHER INFORMATION: Primer

<400> SEQUENCE: 38
gctagcctaa tggatgtatt ttctagg                                     27

<210> SEQ ID NO 39
<211> LENGTH: 27
<212> TYPE: DNA
<213> ORGANISM: Artificial Sequence
<220> FEATURE:
<223> OTHER INFORMATION: Primer

<400> SEQUENCE: 39
ttaattaaca aatagttggt atagtcc                                     27

<210> SEQ ID NO 40
<211> LENGTH: 36
```

```
<212> TYPE: DNA
<213> ORGANISM: Artificial Sequence
<220> FEATURE:
<223> OTHER INFORMATION: Primer

<400> SEQUENCE: 40
gacgatgcca gcctgtcacc atggaaaact cctctc                                36

<210> SEQ ID NO 41
<211> LENGTH: 156
<212> TYPE: DNA
<213> ORGANISM: Artificial Sequence
<220> FEATURE:
<223> OTHER INFORMATION: truncated p60 promoter

<400> SEQUENCE: 41
caaatagttg gtatagtcct ctttagcctt tggagtatta tctcatcatt tgttttttag     60
gtgaaaactg ggtaaactta gtattatcaa tataaaatta attctcaaat acttaattac    120
gtactgggat tttctgaaaa aagagaggag ttttcc                              156

<210> SEQ ID NO 42
<211> LENGTH: 25
<212> TYPE: DNA
<213> ORGANISM: Artificial Sequence
<220> FEATURE:
<223> OTHER INFORMATION: Sequence NarI/EheI site was added upstream of

<400> SEQUENCE: 42
ggcgccacta actcaacgct agtag                                           25

<210> SEQ ID NO 43
<211> LENGTH: 27
<212> TYPE: DNA
<213> ORGANISM: Artificial Sequence
<220> FEATURE:
<223> OTHER INFORMATION: Sequence NarI/EheI site was added downstream of

<400> SEQUENCE: 43
gctagccagc aaagaaaaac aaacacg                                         27

<210> SEQ ID NO 44
<211> LENGTH: 38
<212> TYPE: DNA
<213> ORGANISM: Artificial Sequence
<220> FEATURE:
<223> OTHER INFORMATION: Primer

<400> SEQUENCE: 44
gtcgacggtc accggcgcca ctaactcaac gctagtag                             38

<210> SEQ ID NO 45
<211> LENGTH: 35
<212> TYPE: DNA
<213> ORGANISM: Artificial Sequence
<220> FEATURE:
<223> OTHER INFORMATION: Primer

<400> SEQUENCE: 45
ttaattaagc tagccagcaa agaaaaacaa acacg                                35

<210> SEQ ID NO 46
<211> LENGTH: 29
<212> TYPE: DNA
<213> ORGANISM: Artificial Sequence
<220> FEATURE:
```

<223> OTHER INFORMATION: Primer

<400> SEQUENCE: 46
atgaaaaaaa taatgctagt ttttattac                                          29

<210> SEQ ID NO 47
<211> LENGTH: 48
<212> TYPE: DNA
<213> ORGANISM: Artificial Sequence
<220> FEATURE:
<223> OTHER INFORMATION: Primer

<400> SEQUENCE: 47
gcggccgctt aatgatgatg atgatgatgt ggtttctgag aacagatg                     48

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
gcaagtgtga ctctacgctt cg                                                 22

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
tgcccattaa caggtcttcc a                                                  21

<210> SEQ ID NO 50
<211> LENGTH: 32
<212> TYPE: DNA
<213> ORGANISM: Artificial Sequence
<220> FEATURE:
<223> OTHER INFORMATION: Primer

<400> SEQUENCE: 50
tgcgtacaaa gcacacacgt agacattcgt ac                                      32

<210> SEQ ID NO 51
<211> LENGTH: 24
<212> TYPE: DNA
<213> ORGANISM: Artificial Sequence
<220> FEATURE:
<223> OTHER INFORMATION: Primer

<400> SEQUENCE: 51
tgacatcgtt tgtgtttgag ctag                                               24

<210> SEQ ID NO 52
<211> LENGTH: 23
<212> TYPE: DNA
<213> ORGANISM: Artificial Sequence
<220> FEATURE:
<223> OTHER INFORMATION: Primer

<400> SEQUENCE: 52
gcagcgctct ctataccagg tac                                                23

```
<210> SEQ ID NO 53
<211> LENGTH: 38
<212> TYPE: DNA
<213> ORGANISM: Artificial Sequence
<220> FEATURE:
<223> OTHER INFORMATION: Primer

<400> SEQUENCE: 53
ttaatgtcca tgttatgtct ccgttatagc tcatcgta                            38

<210> SEQ ID NO 54
<211> LENGTH: 19
<212> TYPE: DNA
<213> ORGANISM: Artificial Sequence
<220> FEATURE:
<223> OTHER INFORMATION: Primer

<400> SEQUENCE: 54
tgggatggcc aagaaattc                                                 19

<210> SEQ ID NO 55
<211> LENGTH: 22
<212> TYPE: DNA
<213> ORGANISM: Artificial Sequence
<220> FEATURE:
<223> OTHER INFORMATION: Primer

<400> SEQUENCE: 55
ctaccatgtc ttccgttgct tg                                             22

<210> SEQ ID NO 56
<211> LENGTH: 1256
<212> TYPE: DNA
<213> ORGANISM: Artificial Sequence
<220> FEATURE:
<223> OTHER INFORMATION: Lm-dd?actA

<400> SEQUENCE: 56
gcgccaaatc attggttgat tggtgaggat gtctgtgtgc gtgggtcgcg agatgggcga    60
ataagaagca ttaaagatcc tgacaaatat aatcaagcgg ctcatatgaa agattacgaa   120
tcgcttccac tcacagagga aggcgactgg ggcggagttc attataatag tggtatcccg   180
aataaagcag cctataatac tatcactaaa cttggaaaag aaaaaacaga acagctttat   240
tttcgcgcct aaagtactta tttaacgaaa aaatcccagt ttaccgatgc gaaaaaagcg   300
cttcaacaag cagcgaaaga tttatatggt gaagatgctt ctaaaaaagt tgctgaagct   360
tgggaagcag ttggggttaa ctgattaaca aatgttagaa aaaaattaat tctccaagtg   420
atattcttaa aataattcat gaatattttt tcttatatta gctaattaag aagataacta   480
actgctaatc caatttttaa cggaacaaat tagtgaaaat gaaggccgaa ttttccttgt   540
tctaaaaagg ttgtattagc gtatcacgag gagggagtat aagtgggatt aaacagattt   600
atgcgtgcga tgatggtggt tttcattact gccaattgca ttacgattaa ccccgacgtc   660
gacccatacg acgttaattc ttgcaatgtt agctattggc gtgttctctt tagggcgtt    720 tatcaaaatt attcaattaa gaaaaaataa ttaaaaacac agaacgaaag aaaaagtgag   780
gtgaatgata tgaaattcaa aaaggtggtt ctaggtatgt gcttgatcgc aagtgttcta   840
gtctttccgg taacgataaa agcaaatgcc tgttgtgatg aatacttaca acacccgca   900 gctccgcatg atattgacag caaattacca cataaactta gttggtccgc ggataacccg   960
acaaatactg acgtaaatac gcactattgg cttttttaaac aagcggaaaa aatactagct  1020
```

| | | |
|---|---|---|
| aaagatgtaa atcatatgcg agctaattta atgaatgaac ttaaaaaatt cgataaacaa | 1080 | |
| atagctcaag gaatatatga tgcggatcat aaaaatccat attatgatac tagtacattt | 1140 | |
| ttatctcatt tttataatcc tgatagagat aatacttatt tgccgggttt tgctaatgcg | 1200 | |
| aaaataacag gagcaaagta tttcaatcaa tcggtgactg attaccgaga agggaa | 1256 | |

```
<210> SEQ ID NO 57
<211> LENGTH: 28
<212> TYPE: DNA
<213> ORGANISM: Artificial Sequence
<220> FEATURE:
<223> OTHER INFORMATION: Primer

<400> SEQUENCE: 57
```
tgatctcgag acccacctgg acatgctc                                          28

```
<210> SEQ ID NO 58
<211> LENGTH: 49
<212> TYPE: DNA
<213> ORGANISM: Artificial Sequence
<220> FEATURE:
<223> OTHER INFORMATION: Primer

<400> SEQUENCE: 58
```
ctaccaggac acgattttgt ggaagaatat ccaggagttt gctggctgc                   49

```
<210> SEQ ID NO 59
<211> LENGTH: 49
<212> TYPE: DNA
<213> ORGANISM: Artificial Sequence
<220> FEATURE:
<223> OTHER INFORMATION: Primer

<400> SEQUENCE: 59
```
gcagccagca aactcctgga tattcttcca caaaatcgtg tcctggtag                   49

```
<210> SEQ ID NO 60
<211> LENGTH: 50
<212> TYPE: DNA
<213> ORGANISM: Artificial Sequence
<220> FEATURE:
<223> OTHER INFORMATION: Primer

<400> SEQUENCE: 60
```
ctgccaccag ctgtgcgccc gagggcagca gaagatccgg aagtacacga                  50

```
<210> SEQ ID NO 61
<211> LENGTH: 50
<212> TYPE: DNA
<213> ORGANISM: Artificial Sequence
<220> FEATURE:
<223> OTHER INFORMATION: Primer

<400> SEQUENCE: 61
```
tcgtgtactt ccggatcttc tgctgccctc gggcgcacag ctggtggcag                  50

```
<210> SEQ ID NO 62
<211> LENGTH: 39
<212> TYPE: DNA
<213> ORGANISM: Artificial Sequence
<220> FEATURE:
<223> OTHER INFORMATION: Primer

<400> SEQUENCE: 62
```
gtggcccggg tctagattag tctaagaggc agccatagg                              39

<210> SEQ ID NO 63
<211> LENGTH: 28
<212> TYPE: DNA
<213> ORGANISM: Artificial Sequence
<220> FEATURE:
<223> OTHER INFORMATION: Primer

<400> SEQUENCE: 63
ccgcctcgag gccgcgagca cccaagtg                                      28

<210> SEQ ID NO 64
<211> LENGTH: 31
<212> TYPE: DNA
<213> ORGANISM: Artificial Sequence
<220> FEATURE:
<223> OTHER INFORMATION: Primer

<400> SEQUENCE: 64
cgcgactagt ttaatcctct gctgtcacct c                                  31

<210> SEQ ID NO 65
<211> LENGTH: 28
<212> TYPE: DNA
<213> ORGANISM: Artificial Sequence
<220> FEATURE:
<223> OTHER INFORMATION: Primer

<400> SEQUENCE: 65
ccgcctcgag tacctttcta cggacgtg                                      28

<210> SEQ ID NO 66
<211> LENGTH: 30
<212> TYPE: DNA
<213> ORGANISM: Artificial Sequence
<220> FEATURE:
<223> OTHER INFORMATION: Primer

<400> SEQUENCE: 66
cgcgactagt ttactctggc cggttggcag                                    30

<210> SEQ ID NO 67
<211> LENGTH: 31
<212> TYPE: DNA
<213> ORGANISM: Artificial Sequence
<220> FEATURE:
<223> OTHER INFORMATION: Primer

<400> SEQUENCE: 67
ccgcctcgag cagcagaaga tccggaagta c                                  31

<210> SEQ ID NO 68
<211> LENGTH: 30
<212> TYPE: DNA
<213> ORGANISM: Artificial Sequence
<220> FEATURE:
<223> OTHER INFORMATION: Primer

<400> SEQUENCE: 68
cgcgactagt ttaagcccct tcggagggtg                                    30

<210> SEQ ID NO 69
<211> LENGTH: 7075
<212> TYPE: DNA
<213> ORGANISM: Artificial Sequence
<220> FEATURE:

<223> OTHER INFORMATION: pAdv164

<400> SEQUENCE: 69

```
cggagtgtat actggcttac tatgttggca ctgatgaggg tgtcagtgaa gtgcttcatg      60
tggcaggaga aaaaaggctg caccggtgcg tcagcagaat atgtgataca ggatatattc     120
cgcttcctcg ctcactgact cgctacgctc ggtcgttcga ctgcggcgag cggaaatggc     180
ttacgaacgg ggcggagatt tcctggaaga tgccaggaag atacttaaca gggaagtgag     240
agggccgcgg caaagccgtt tttccatagg ctccgccccc ctgacaagca tcacgaaatc     300
tgacgctcaa atcagtggtg gcgaaacccg acaggactat aaagatacca ggcgtttccc     360
cctggcggct ccctcgtgcg ctctcctgtt cctgcctttc ggtttaccgg tgtcattccg     420
ctgttatggc cgcgtttgtc tcattccacg cctgacactc agttccgggt aggcagttcg     480
ctccaagctg gactgtatgc acgaaccccc cgttcagtcc gaccgctgcg ccttatccgg     540
taactatcgt cttgagtcca acccggaaag acatgcaaaa gcaccactgg cagcagccac     600
tggtaattga tttagaggag ttagtcttga agtcatgcgc cggttaaggc taaactgaaa     660
ggacaagttt tggtgactgc gctcctccaa gccagttacc tcggttcaaa gagttggtag     720
ctcagagaac cttcgaaaaa ccgccctgca aggcggtttt ttcgttttca gagcaagaga     780
ttacgcgcag accaaaacga tctcaagaag atcatcttat taatcagata aaatatttct     840
agccctcctt tgattagtat attcctatct taaagttact tttatgtgga ggcattaaca     900
tttgttaatg acgtcaaaag gatagcaaga ctagaataaa gctataaagc aagcatataa     960
tattgcgttt catctttaga agcgaatttc gccaatatta taattatcaa agagagggg    1020
tggcaaacgg tatttggcat tattaggtta aaaaatgtag aaggagagtg aaacccatga    1080
aaaaaataat gctagttttt attacactta tattagttag tctaccaatt gcgcaacaaa    1140
ctgaagcaaa ggatgcatct gcattcaata agaaaattc aatttcatcc atggcaccac    1200
cagcatctcc gcctgcaagt cctaagacgc caatcgaaaa gaaacacgcg gatgaaatcg    1260
ataagtatat acaaggattg gattacaata aaaacaatgt attagtatac cacggagatg    1320
cagtgacaaa tgtgccgcca agaaaaggtt acaaagatgg aaatgaatat attgttgtgg    1380
agaaaaagaa gaaatccatc aatcaaaata atgcagacat tcaagttgtg aatgcaattt    1440
cgagcctaac ctatccaggt gctctcgtaa aagcgaattc ggaattagta gaaaatcaac    1500
cagatgttct ccctgtaaaa cgtgattcat taacactcag cattgatttg ccaggtatga    1560
ctaatcaaga caataaaata gttgtaaaaa atgccactaa atcaaacgtt aacaacgcag    1620
taaatacatt agtggaaaga tggaatgaaa aatatgctca agcttatcca aatgtaagtg    1680
caaaaattga ttatgatgac gaaatggctt acagtgaatc acaattaatt gcgaaatttg    1740
gtacagcatt taaagctgta aataatagct tgaatgtaaa cttcggcgca atcagtgaag    1800
ggaaaatgca agaagaagtc attagtttta aacaaattta ctataacgtg aatgttaatg    1860
aacctacaag accttccaga tttttcggca agctgttac taaagagcag ttgcaagcgc    1920
ttggagtgaa tgcagaaaat cctcctgcat atatctcaag tgtggcgtat ggccgtcaag    1980
tttatttgaa attatcaact aattcccata gtactaaagt aaaagctgct tttgatgctg    2040
ccgtaagcgg aaaatctgtc tcaggtgatg tagaactaac aaatatcatc aaaaattctt    2100
ccttcaaagc cgtaatttac ggaggttccg caaagatga agttcaaatc atcgacggca    2160
acctcggaga cttacgcgat attttgaaaa aaggcgctac ttttaatcga gaacaccag    2220
gagttcccat tgcttataca acaaacttcc taaaagacaa tgaattagct gttattaaaa    2280
```

```
acaactcaga atatattgaa acaacttcaa aagcttatac agatggaaaa attaacatcg    2340
atcactctgg aggatacgtt gctcaattca acatttcttg ggatgaagta aattatgatc    2400
tcgagaccca cctggacatg ctccgccacc tctaccaggg ctgccaggtg gtgcagggaa    2460
acctggaact cacctacctg cccaccaatg ccagcctgtc cttcctgcag gatatccagg    2520
aggtgcaggg ctacgtgctc atcgctcaca accaagtgag gcaggtccca ctgcagaggc    2580
tgcggattgt gcgaggcacc cagctctttg aggacaacta tgccctggcc gtgctagaca    2640
atggagaccc gctgaacaat accacccctg tcacaggggc ctccccagga ggcctgcggg    2700
agctgcagct tcgaagcctc acagagatct tgaaaggagg ggtcttgatc cagcggaacc    2760
cccagctctg ctaccaggac acgattttgt ggaagaatat ccaggagttt gctggctgca    2820
agaagatctt tgggagcctg gcatttctgc cggagagctt tgatggggac ccagcctcca    2880
acactgcccc gctccagcca gagcagctcc aagtgtttga gactctggaa gagatcacag    2940
gttacctata catctcagca tggccggaca gcctgcctga cctcagcgtc ttccagaacc    3000
tgcaagtaat ccggggacga attctgcaca atggcgccta ctcgctgacc ctgcaagggc    3060
tgggcatcag ctggctgggg ctgcgctcac tgagggaact gggcagtgga ctggccctca    3120
tccaccataa cacccacctc tgcttcgtgc acacggtgcc ctgggaccag ctctttcgga    3180
acccgcacca agtctgtctc cacactgcca accggccaga ggacgagtgt gtgggcgagg    3240
gcctggcctg ccaccagctg tgcgcccgag ggcagcagaa gatccggaag tacacgatgc    3300
ggagactgct gcaggaaacg gagctggtgg agccgctgac acctagcgga gcgatgccca    3360
accaggcgca gatgcggatc ctgaaagaga cggagctgag gaaggtgaag gtgcttggat    3420
ctggcgcttt tggcacagtc tacaagggca tctggatccc tgatggggag aatgtgaaaa    3480
ttccagtggc catcaaagtg ttgagggaaa acacatcccc caaagccaac aaagaaatct    3540
tagacgaagc atacgtgatg gctggtgtgg gctccccata tgtctcccgc cttctgggca    3600
tctgcctgac atccacggtg cagctggtga cacagcttat gccctatggc tgcctcttag    3660
actaatctag acccggggcca ctaactcaac gctagtagtg gatttaatcc caaatgagcc    3720
aacagaacca gaaccagaaa cagaacaagt aacattggag ttagaaatgg aagaagaaaa    3780
aagcaatgat ttcgtgtgaa taatgcacga aatcattgct tattttttta aaaagcgata    3840
tactagatat aacgaaacaa cgaactgaat aaagaataca aaaaaagagc cacgaccagt    3900
taaagcctga gaaactttaa ctgcgagcct taattgatta ccaccaatca attaaagaag    3960
tcgagaccca aaatttggta aagtatttaa ttactttatt aatcagatac ttaaatatct    4020
gtaaacccat tatatcgggt ttttgagggg atttcaagtc tttaagaaga taccaggcaa    4080
tcaattaaga aaaacttagt tgattgcctt ttttgttgtg attcaacttt gatcgtagct    4140
tctaactaat taattttcgt aagaaggag aacagctgaa tgaatatccc ttttgttgta    4200
gaaactgtgc ttcatgacgg cttgttaaag tacaaattta aaaatagtaa aattcgctca    4260
atcactacca agccaggtaa aagtaaaggg gctatttttg cgtatcgctc aaaaaaaagc    4320
atgattggcg gacgtggcgt tgttctgact tccgaagaag cgattcacga aaatcaagat    4380
acatttacgc attggacacc aaacgtttat cgttatggta cgtatgcaga cgaaaaccgt    4440
tcatacacta aaggacattc tgaaaacaat ttaagacaaa tcaatacctt ctttattgat    4500
tttgatattc acacggaaaa agaaactatt tcagcaagcg atattttaac aacagctatt    4560
gatttaggtt ttatgcctac gttaattatc aaatctgata aaggttatca agcatatttt    4620
```

```
gttttagaaa cgccagtcta tgtgacttca aaatcagaat ttaaatctgt caaagcagcc    4680
aaaataatct cgcaaaatat ccgagaatat tttggaaagt cttgccagt tgatctaacg    4740 tgcaatcatt ttgggattgc tcgtatacca agaacggaca atgtagaatt ttttgatccc    4800
aattaccgtt attctttcaa agaatggcaa gattggtctt tcaaacaaac agataataag    4860
ggctttactc gttcaagtct aacggtttta agcggtacag aaggcaaaaa acaagtagat    4920
gaaccctggt ttaatctctt attgcacgaa acgaaatttt caggagaaaa gggtttagta    4980
gggcgcaata gcgttatgtt taccctctct ttagcctact ttagttcagg ctattcaatc    5040
gaaacgtgcg aatataatat gtttgagttt aataatcgat tagatcaacc cttagaagaa    5100
aaagaagtaa tcaaaattgt tagaagtgcc tattcagaaa actatcaagg ggctaatagg    5160
gaatacatta ccattctttg caaagcttgg gtatcaagtg atttaaccag taaagattta    5220
tttgtccgtc aagggtggtt taaattcaag aaaaaaagaa gcgaacgtca acgtgttcat    5280
ttgtcagaat ggaagaagaa tttaatgggct tatattagcg aaaaaagcga tgtatacaag    5340
ccttatttag cgacgaccaa aaaagagatt agagaagtgc taggcattcc tgaacggaca    5400
ttagataaat tgctgaaggt actgaaggcg aatcaggaaa ttttctttaa gattaaacca    5460
ggaagaaatg gtggcattca acttgctagt gttaaatcat tgttgctatc gatcattaaa    5520
ttaaaaaaag aagaacgaga aagctatata aaggcgctga cagcttcgtt taatttagaa    5580
cgtacattta ttcaagaaac tctaaacaaa ttggcagaac gccccaaaac ggacccacaa    5640
ctcgatttgt ttagctacga tacaggctga aaataaaacc cgcactatgc cattacattt    5700
atatctatga tacgtgtttg ttttctttg ctggctagct taattgctta tatttacctg    5760
caataaagga tttcttactt ccattatact cccattttcc aaaaacatac ggggaacacg    5820
ggaacttatt gtacaggcca cctcatagtt aatggtttcg agccttcctg caatctcatc    5880
catggaaata tattcatccc cctgccggcc tattaatgtg acttttgtgc ccggcggata    5940
ttcctgatcc agctccacca taaattggtc catgcaaatt cggccggcaa ttttcaggcg    6000
ttttcccttc acaaggatgt cggtcccttt caattttcgg agccagccgt ccgcatagcc    6060
tacaggcacc gtcccgatcc atgtgtcttt ttccgctgtg tactcggctc cgtagctgac    6120
gctctcgcct tttctgatca gtttgacatg tgacagtgtc gaatgcaggg taaatgccgg    6180
acgcagctga acggtatct cgtccgacat gtcagcagac gggcgaaggc catacatgcc    6240
gatgccgaat ctgactgcat taaaaaagcc tttttcagc cggagtccag cggcgctgtt    6300
cgcgcagtgg accattagat tctttaacgg cagcggagca atcagctctt taaagcgctc    6360
aaactgcatt aagaaatagc ctctttcttt ttcatccgct gtcgcaaaat gggtaaatac    6420 cccttttgcac tttaaacgag ggttgcggtc aagaattgcc atcacgttct gaacttcttc    6480
ctctgttttt acaccaagtc tgttcatccc cgtatcgacc ttcagatgaa aatgaagaga    6540 acctttttc gtgtggcggg ctgcctcctg aagccattca acagaataac ctgttaaggt    6600
cacgtcatac tcagcagcga ttgccacata ctccggggga accgcgccaa gcaccaatat    6660
aggcgccttc aatcccttt tgcgcagtga atcgcttca tccaaaatgg ccacggccaa    6720
gcatgaagca cctgcgtcaa gagcagcctt tgctgtttct gcatcaccat gcccgtaggc    6780
gtttgctttc acaactgcca tcaagtggac atgttcaccg atatgttttt tcatattgct    6840 gacatttcc tttatcgcgg acaagtcaat ttccgcccac gtatctctgt aaaaaggttt    6900
tgtgctcatg gaaactcct ctcttttttc agaaaatccc agtacgtaat taagtatttg    6960
agaattaatt ttatattgat taatactaag tttacccagt tttcacctaa aaaacaaatg    7020
```

-continued

```
atgagataat agctccaaag gctaaagagg actataccaa ctatttgtta attaa      7075
```

<210> SEQ ID NO 70
<211> LENGTH: 9
<212> TYPE: PRT
<213> ORGANISM: Artificial Sequence
<220> FEATURE:
<223> OTHER INFORMATION: HLA-A2 restricted epitopes

<400> SEQUENCE: 70

Lys Ile Phe Gly Ser Leu Ala Phe Leu
1               5

<210> SEQ ID NO 71
<211> LENGTH: 2015
<212> TYPE: DNA
<213> ORGANISM: Artificial Sequence
<220> FEATURE:
<223> OTHER INFORMATION: DNA sequence present upstream and downstream of
      the inlC region on the genome of Listeria strain

<400> SEQUENCE: 71

```
atggcgcggg atggtatact atacaagcgt atggttcaaa aagatacttt gaattaagaa      60
gtacaataaa gttaacttca ttagacaaaa agaaaaaaca aggaagaata gtacatagtt     120
ataaatactt ggagagtgag gtgtaatatg ggggcagctg attttggggt tttcatatat     180
gtagtttcaa gattagccat tgttgcggca gtagtttact tcttatactt attgagaaaa     240
attgcaaata aatagaaaaa aagccttgtc aaacgaggct ttttttatgc aaaaaatacg     300
acgaatgaag ccatgtgaga caatttggaa tagcagacaa caaggaaggt agaacatgtt     360
ttgaaaaatt tactgatttt cgattattat taacgcttgt taatttaaac atctcttatt     420
tttgctaaca tataagtata caaagggaca taaaaaggtt aacagcgttt gttaaatagg     480
aagtatatga aaatcctctt ttgtgtttct aaatttattt ttaaggagtg gagaatgttg     540
aaaaaaaata attggttaca aaatgcagta atagcaatgc tagtgttaat tgtaggtctg     600
tgcattaata tgggttctgg aacaaaagta caagctgaga gtattcaacg accaacgcct     660
attaaccaag tttttccaga tcccggccta gcgaatgcag tgaaacaaaa tttagggaag     720
caaagtgtta cagaccttgt atcacaaaag gaactatctg gagtacaaaa tttcaatgga     780
gataatagca acattcaatc tcttgcggga atgcaatttt tcactaattt aaaagaactt     840
catctatccc ataatcaaat aagtgaccct agtcctttaa aggatctaac taagttagaa     900
gagctatctg tgaatagaaa cagactgaaa aatttaaacg gaattccaag tgcttgttta     960
tctcgcttgt ttttagataa caacgaactc agagatactg actcgcttat tcatttgaaa    1020
aatctagaaa tcttatctat tcgtaataat aagttaaaaa gtattgtgat gcttggtttt    1080
ttatcaaaac tagaggtatt agatttgcat ggtaatgaaa taacaaatac aggtggacta    1140
actagattga agaaagttaa ctggatagat ttaactggtc agaaatgtgt gaatgaacca    1200
gtaaaatacc aaccagaatt gtatataaca aatactgtca aagacccaga tggaagatgg    1260
atatctccat attacatcag taatggtggg agttatgtag atggttgtgt cctgtgggaa    1320
ttgccagttt atacagatga agtaagctat aagtttagcg aatatataaa cgttggggag    1380
actgaggcta tatttgatgg aacagttaca caacctatca agaattagga cttgtgcaca    1440
cctgtatact ttgagctctc gtataatcac gagagctttt taaatatgta agtcttaatt    1500
atctcttgac aaaaagaacg tttattcgta taaggttacc aagagatgaa gaaactattt    1560
```

```
tatttacaat tcaccttgac accaaaaact ccatatgata tagtaaataa ggttattaaa    1620
caagaaagaa gaagcaaccc gcttctcgcc tcgttaacac gaacgttttc aggcaaaaaa    1680
ttcaaacttt cgtcgcgtag cttacgcgat tttgaatgtg cgggattgct gaaaagcagc    1740
ccgttttttt atggcctccg aacgaatgag ttagcaggcc gcagatttga acagctattt    1800
tctatcttgt tgtaacaaaa ttaagtggag gtggctcacc attagcaaag acatgttggt    1860
aaacgatggg attcgtgcac gtgaagtaag attgatcgac caagacggtg aacaattagg    1920
cgtgaagagt aaaatcgatg cgcttcaaat tgctgaaaag gctaatcttg atctagtgct    1980
tgttgctcca acagcgaaac cgccagtagc tcgta                              2015

<210> SEQ ID NO 72
<211> LENGTH: 1140
<212> TYPE: DNA
<213> ORGANISM: Artificial Sequence
<220> FEATURE:
<223> OTHER INFORMATION: DNA that is cloned in the temperature sensitive
      plasmid, pKSV7 to create inl C deletion muta

<400> SEQUENCE: 72
gaattcatgg cgcgggatgg tatactatac aagcgtatgg ttcaaaaaga tactttgaat      60
taagaagtac aataaagtta acttcattag acaaaaagaa aaaacaagga agaatagtac     120
atagttataa atacttggag agtgaggtgt aatatggggg cagctgattt ttggggtttc     180
atatatgtag tttcaagatt agccattgtt gcggcagtag tttacttctt atacttattg     240
agaaaaattg caaataaata gaaaaaaagc cttgtcaaac gaggcttttt ttatgcaaaa     300
aatacgacga atgaagccat gtgagacaat ttggaatagc agacaacaag gaaggtagaa     360
catgttttga aaaatttact gattttcgat tattattaac gcttgttaat ttaaacatct     420
cttatttttg ctaacatata agtatacaaa gggacataaa aaggttaaca gcgtttgtta     480
aataggaagt atatgaaaat cctctttttgt gtttctaaat ttattttttaa ggagtggaga     540 ggatccggac ttgtgcacac ctgtatactt tgagctctcg tataatcacg agagcttttt     600
aaatatgtaa gtcttaatta tctcttgaca aaaagaacgt ttattcgtat aaggttacca     660
agagatgaag aaactatttt atttacaatt caccttgaca ccaaaaactc catatgatat     720
agtaaataag gttattaaac aagaaagaag aagcaacccg cttctcgcct cgttaacacg     780
aacgttttca ggcaaaaaat tcaaactttc gtcgcgtagc ttacgcgatt ttgaatgtgc     840
gggattgctg aaaagcagcc cgttttttta tggcctccga acgaatgagt tagcaggccg     900
cagatttgaa cagctatttt ctatcttgtt gtaacaaaat taagtggagg tggctcacca     960
ttagcaaaga catgttggta aacgatggga ttcgtgcacg tgaagtaaga ttgatcgacc    1020
aagacggtga acaattaggc gtgaagagta aaatcgatgc gcttcaaatt gctgaaaagg    1080
ctaatcttga tctagtgctt gttgctccaa cagcgaaacc gccagtagct cgtactgcag    1140
```

UNITED STATES PATENT AND TRADEMARK OFFICE
CERTIFICATE OF CORRECTION

PATENT NO. : 10,900,044 B2
APPLICATION NO. : 15/553507
DATED : January 26, 2021
INVENTOR(S) : Robert Petit et al.

Page 1 of 1

It is certified that error appears in the above-identified patent and that said Letters Patent is hereby corrected as shown below:

In the Claims

In Claim 1,
Column 143, Line 64, delete "MEW" and insert --MHC--

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*